US011906527B2

(12) United States Patent
Lim et al.

(10) Patent No.: US 11,906,527 B2
(45) Date of Patent: Feb. 20, 2024

(54) PHOTOCLEAVABLE MASS-TAGS FOR MULTIPLEXED MASS SPECTROMETRIC IMAGING OF TISSUES USING BIOMOLECULAR PROBES

(71) Applicant: AmberGen, Inc., Watertown, MA (US)

(72) Inventors: Mark J. Lim, Reading, MA (US); Gargey Yagnik, Hopkinton, MA (US); Kenneth J. Rothschild, Newton, MA (US)

(73) Assignee: AMBERGEN, INC., Billerica, MA (US)

( * ) Notice: Subject to any disclaimer, the term of this patent is extended or adjusted under 35 U.S.C. 154(b) by 364 days.

(21) Appl. No.: 17/399,390

(22) Filed: Aug. 11, 2021

(65) Prior Publication Data

US 2022/0137064 A1   May 5, 2022

Related U.S. Application Data

(60) Provisional application No. 63/106,990, filed on Oct. 29, 2020.

(51) Int. Cl.
*G01N 33/68* (2006.01)
*C07C 271/20* (2006.01)
*C12Q 1/6841* (2018.01)

(52) U.S. Cl.
CPC ....... *G01N 33/6851* (2013.01); *C07C 271/20* (2013.01); *C12Q 1/6841* (2013.01); *G01N 2400/00* (2013.01); *G01N 2458/15* (2013.01)

(58) Field of Classification Search
None
See application file for complete search history.

(56) References Cited

U.S. PATENT DOCUMENTS

| 5,643,722 A | 7/1997 | Rothschild et al. ......... 435/6.13 |
| 5,986,076 A | 11/1999 | Rothschild et al. ......... 536/22.1 |

(Continued)

FOREIGN PATENT DOCUMENTS

| WO | WO 2019/103996 | 5/2019 |
| WO | WO 2019/246033 | 12/2019 |

OTHER PUBLICATIONS

Ackerson, et al., "Site-Specific Biomolecule Labeling with Gold Clusters." *Methods Enzymol*, 481:195-230 (2010).

(Continued)

*Primary Examiner* — Karl J Puttlitz
(74) *Attorney, Agent, or Firm* — Medlen & Carroll, LLP

(57) ABSTRACT

The field of this invention relates to immunohistochemistry (IHC) and in situ hybridization (ISH) for the targeted detection and mapping of biomolecules (e.g., proteins and miRNAs) in tissues or cells for example, for research use and for clinical use such by pathologists (e.g., biomarker analyses of a resected tumor or tumor biopsy). In particular, the use of mass spectrometric imaging (MSI) as a mode to detect and map the biomolecules in tissues or cells for example. More specifically, the field of this invention relates to photocleavable mass-tag reagents which are attached to probes such as antibodies and nucleic acids and used to achieve multiplex immunohistochemistry and in situ hybridization, with MSI as the mode of detection/readout. Probe types other than antibodies and nucleic acids are also covered in the field of invention, including but not limited to carbohydrate-binding proteins (e.g., lectins), receptors and ligands. Finally, the field of the invention also encompasses multi-omic MSI procedures, where MSI of photocleavable mass-tag probes is combined with other modes of MSI, such as direct label-free MSI of endogenous biomolecules from the biospecimen (e.g., tissue), whereby said biomolecules (Continued)

can be intact or digested (e.g., chemically digested or by enzyme).

31 Claims, 58 Drawing Sheets
(38 of 58 Drawing Sheet(s) Filed in Color)

(56) References Cited

U.S. PATENT DOCUMENTS

| | | | |
|---|---|---|---|
| 6,218,530 B1 | 4/2001 | Rothschild et al. | 536/25.32 |
| 7,569,392 B2 | 8/2009 | Levy et al. | 436/6 |
| 8,221,972 B2 | 7/2012 | Lemaire et al. | 435/6.1 |
| 8,906,700 B2 | 12/2014 | Lim et al. | 436/518 |
| 9,513,285 B2 | 12/2016 | Lim et al. | |
| 9,523,680 B2 | 12/2016 | Lim et al. | |
| 10,060,912 B2 | 8/2018 | Lim et al. | |
| 2011/0151451 A1 | 6/2011 | Lemaire et al. | 435/6.11 |
| 2017/0107577 A1 | 4/2017 | Al-Ejeh | |

OTHER PUBLICATIONS

Angel, et al., "Advances in MALDI Imaging Mass Spectrometry of Proteins in Cardiac Tissue, Including the Heart Valve." *Biochim Biophys Acta Proteins Proteom*, 1865(7):927-935 (2017).
Arentz, et al., "Applications of Mass Spectrometry Imaging to Cancer." *Adv Cancer Res*, 134:27-66 (2017).
Barrett, et al., "Hydroxylamine Chemical Digestion for Insoluble Extracellular Matrix Characterization." *J Proteome Res*, 16(11):4177-4184 (2017).
Behrendt, et al., "Advances in Fmoc Solid-Phase Peptide Synthesis." *J Pept Sci*, 22(1):4-27 (2016).
Blom, et al., "Systems Pathology by Multiplexed Immunohistochemistry and Whole-Slide Digital Image Analysis." *Sci Rep*, 7(1):15580 (2017).
Buchberger, et al., "Mass Spectrometry Imaging: A Review of Emerging Advancements and Future Insights." *Anal Chem*, 90(1):240-265 (2018).
Caprioli, et al., "Molecular Imaging of Biological Samples: Localization of Peptides and Proteins Using MALDI-TOF MS." *Anal Chem*, 69(23):4751-4760 (1997).
Chacko and Appukuttan, "Peanut (*Arachis hypogaea*) Lectin Recognizes Alpha-Linked Galactose, but Not N-Acetyl Lactosamine in N-Linked Oligosaccharide Terminals." *Int J Biol Macromol*, 28(5):365-371 (2001).
Chaurand, et al., "From Whole-Body Sections Down to Cellular Level, Multiscale Imaging of Phospholipids by Maldi Mass Spectrometry." *Mol Cell Proteomics*, 10(2):O110 004259 (2011).
Chistiakov, et al., "CD68/Macrosialin: Not Just a Histochemical Marker." *Lab Invest*, 97(1):4-13 (2017).
Damm, et al., "Inhibitory Effect of the Lectin Wheat Germ Agglutinin on the Binding of 125I-CCK-8s to the CCK-A and -B Receptors of AR42J Cells." *Pancreas*, 28(1):31-37 (2004).
Darvin, et al., "Immune Checkpoint Inhibitors: Recent Progress and Potential Biomarkers." *Exp Mot Med*, 50(12):1-11 (2018).
Deng, et al., "Detection of Protein Aggregation in Neurodegenerative Diseases." *Methods Mol Biol*, 793:259-272 (2011).
Drake, et al., "In Situ Imaging of N-Glycans by MALDI Imaging Mass Spectrometry of Fresh or Formalin-Fixed Paraffin-Embedded Tissue." *Curr Protoc Protein Sci*, 94(1):e68 (2018).
Duenas, et al., "Matrix Recrystallization for MALDI-MS Imaging of Maize Lipids at High-Spatial Resolution." *J Am Soc Mass Spectrom*, 27(9):1575-1578 (2016).
Dugger and Dickson, "Pathology of Neurodegenerative Diseases." *Cold Spring Harb Perspect Biol*, 9(7) (2017).
Eckhardt, "The Role and Metabolism of Sulfatide in the Nervous System." *Mol Neurobiol*, 37(2-3):93-103 (2008).
El Ayed, et al., "MALDI Imaging Mass Spectrometry in Ovarian Cancer for Tracking, Identifying, and Validating Biomarkers." *Med Sci Monit*, 16(8):BR233-245 (2010).

Enjalbal, et al., "MALDI-TOF MS Analysis of Soluble Peg Based Multi-Step Synthetic Reaction Mixtures with Automated Detection of Reaction Failure." *J Am Soc Mass Spectrom*, 16(5):670-678 (2005).
Franck, et al., "Maldi Imaging Mass Spectrometry: State of the Art Technology in Clinical Proteomics." *Mol Cell Proteomics*, 8(9):2023-2033 (2009).
Gao, et al., "Prognostic Value of Tumor-Infiltrating Lymphocytes in Patients with Triple-Negative Breast Cancer: A Systematic Review and Meta-Analysis." *BMC Cancer*, 20(1):179 (2020).
Geissler, et al., "Functional Characterization of T-Cells from Palatine Tonsils in Patients with Chronic Tonsillitis." *PLoS One*, 12(9):e0183214 (2017).
Gemperline, et al., "Optimization and Comparison of Multiple MALDI Matrix Application Methods for Small Molecule Mass Spectrometric Imaging." *Anal Chem*, 86(20):10030-10035 (2014).
Gerdes, et al., "Highly Multiplexed Single-Cell Analysis of Formalin-Fixed, Paraffin-Embedded Cancer Tissue." *Proc Natl Acad Sci U S A*, 110(29):11982-11987 (2013).
Giesen, et al., "Highly Multiplexed Imaging of Tumor Tissues with Subcellular Resolution by Mass Cytometry." *Nat Methods*, 11(4):417-422 (2014).
Gorris, et al., "Eight-Color Multiplex Immunohistochemistry for Simultaneous Detection of Multiple Immune Checkpoint Molecules within the Tumor Microenvironment." *J Immunol*, 200(1):347-354 (2018).
Goswami, et al., "Tumor Promoting Role of Anti-Tumor Macrophages in Tumor Microenvironment." *Cell Immunol*, 316:1-10 (2017).
Gundry, et al., "Preparation of Proteins and Peptides for Mass Spectrometry Analysis in a Bottom-up Proteomics Workflow." *Curr Protoc Mol Biol*, Chapter 10:Unit10 25 (2009).
Gusel'nikova and Korzhevskiy, "Neun as a Neuronal Nuclear Antigen and Neuron Differentiation Marker." *Acta Naturae*, 7(2):42-47 (2015).
Haanen and Robert, "Immune Checkpoint Inhibitors." *Prog Tumor Res*, 42:55-66 (2015).
Hale and Cooper, "Native Mass Spectrometry Imaging of Proteins and Protein Complexes by Nano-Desi." *Anal Chem*, 93(10):4619-4627 (2021).
Halse, et al., "Multiplex Immunohistochemistry Accurately Defines the Immune Context of Metastatic Melanoma." *Sci Rep*, 8(1):11158 (2018).
Hankin, et al., "Sublimation as a Method of Matrix Application for Mass Spectrometric Imaging." *J Am Soc Mass Spectrom*, 18(9):1646-1652 (2007).
Hirahara, et al., "Sulfatide Species with Various Fatty Acid Chains in Oligodendrocytes at Different Developmental Stages Determined by Imaging Mass Spectrometry." *J Neurochem*, 140(3):435-450 (2017).
Howat and Warford, "Advancing the Boundaries of Molecular Cellular Pathology." *Methods*, 70(1):1-2 (2014).
Hsu, et al., "Tonsil Surface Epithelium Is Ideal for Monitoring Ki-67 Immunohistochemical Staining." *Histopathology*, 63(6):810-816 (2013).
Hsu, et al., "Imaging of Proteins in Tissue Samples Using Nanospray Desorption Electrospray Ionization Mass Spectrometry." *Anal Chem*, 87(22):11171-11175 (2015).
Jensen, et al., "Molecular Mapping to Species Level of the Tonsillar Crypt Microbiota Associated with Health and Recurrent Tonsillitis." *PLoS One*, 8(2):e56418 (2013).
Jin and Hu, "Tumor-Infiltrating CD8 T Cells Predict Clinical Breast Cancer Outcomes in Young Women." *Cancers (Basel)*, 12(5) (2020).
Kalina, et al., "Cd Maps-Dynamic Profiling of CD1-CD100 Surface Expression on Human Leukocyte and Lymphocyte Subsets." *Front Immunol*, 10:2434 (2019).
Kap, et al., "A Monoclonal Antibody Selection for Immunohistochemical Examination of Lymphoid Tissues from Non-Human Primates." *J Histochem Cytochem*, 57(12):1159-1167 (2009).
Karantza, "Keratins in Health and Cancer: More Than Mere Epithelial Cell Markers." *Oncogene*, 30(2):127-138 (2011).
Kasai, et al., "Double in Situ Hybridization for MicroRNAs and mRNAs in Brain Tissues." *Front Mol Neurosci*, 9:126 (2016).

(56) References Cited

OTHER PUBLICATIONS

Katikireddy and O'Sullivan, "Immunohistochemical and Immunofluorescence Procedures for Protein Analysis." *Methods Mol Biol*, 784:155-167 (2011).
Kitada, et al., "Lectins as a Tool for Detecting Neural Stem/Progenitor Cells in the Adult Mouse Brain." *Anat Rec* (Hoboken), 294(2):305-321 (2011).
Kolb, et al., "Click Chemistry: Diverse Chemical Function from a Few Good Reactions." *Angew Chem Int Ed Engl*, 40(11):2004-2021 (2001).
Kompauer, et al., "Atmospheric Pressure MALDI Mass Spectrometry Imaging of Tissues and Cells at 1.4-Mum Lateral Resolution." *Nat Methods*, 14(1):90-96 (2017).
Kulkarni, et al., "Laesi Mass Spectrometry Imaging as a Tool to Differentiate the Root Metabolome of Native and Range-Expanding Plant Species." *Planta*, 248(6):1515-1523 (2018).
Kwok, et al., "Pembrolizumab (Keytruda)." *Hum Vaccin Immunother*, 12(11):2777-2789 (2016).
Lanni, et al., "Mass Spectrometry Imaging and Profiling of Single Cells." *J Proteomics*, 75(16):5036-5051 (2012).
Lazova, et al., "Histopathology-Guided Mass Spectrometry Differentiates Benign Nevi from Malignant Melanoma." *J Cutan Pathol*, 47(3):226-240 (2020).
Lei, et al., "Mmish: Multicolor MicroRNA in Situ Hybridization for Paraffin Embedded Samples." *Biotechnol Rep* (Amst), 18:e00255 (2018).
Lemaire, et al., "Tag-Mass: Specific Molecular Imaging of Transcriptome and Proteome by Mass Spectrometry Based on Photocleavable Tag." *J Proteome Res*, 6(6):2057-2067 (2007).
Li, et al., "A One-Step Matrix Application Method for MALDI Mass Spectrometry Imaging of Bacterial Colony Biofilms." *J Mass Spectrom*, 51(11):1030-1035 (2016).
Lim and Rothschild, "Photocleavage-Based Affinity Purification and Printing of Cell-Free Expressed Proteins: Application to Proteome Microarrays." *Anal Biochem*, 383(1):103-115 (2008).
Lim, et al., "Correlated Matrix-Assisted Laser Desorption/Ionization Mass Spectrometry and Fluorescent Imaging of Photocleavable Peptide-Coded Random Bead-Arrays." *Rapid communications in mass spectrometry : RCM*, 28(1):49-62 (2014).
MacLennan, "Germinal Centers." *Annu Rev Immunol*, 12:117-139 (1994).
Martinez, et al., "Single-Stranded Antisense siRNAs Guide Target Rna Cleavage in RNAi." *Cell*, 110(5):563-574 (2002).
Mason, "Axon Development in Mouse Cerebellum: Embryonic Axon Forms and Expression of Synapsin I." *Neuroscience*, 19(4):1319-1333 (1986).
McKay and Finn, "Click Chemistry in Complex Mixtures: Bioorthogonal Bioconjugation." *Chem Biol*, 21(9):1075-1101 (2014).
Menger, et al., "MALDI Mass Spectrometric Imaging of the Nematode *Caenorhabditis Elegans.*" *Current Metabolomics*, 3(2):130-137 (2015).
Mitra, et al., "Fluorescent in Situ Sequencing on Polymerase Colonies." *Anal Biochem*, 320(1):55-65 (2003).
Morpurgo, et al., "N-Hydroxysuccinimide Carbonates and Carbamates Are Useful Reactive Reagents for Coupling Ligands to Lysines on Proteins." *J Biochem Biophys Methods*, 38(1):17-28 (1999).
Mueller, et al., "Determination of the No. Of E-Amino Groups Available for Conjugation of Effector Molecules to Monoclonal Antibodies." *Hybridoma*, 7(5):453-456 (1988).
Mueller, et al., "Protein Biomarkers for Subtyping Breast Cancer and Implications for Future Research." *Expert Rev Proteomics*, 15(2):131-152 (2018).
Nave, et al., "Morphology and Immunology of the Human Palatine Tonsil." *Anat Embryol* (Berl), 204(5):367-373 (2001).
Niehaus, et al., "Transmission-Mode MALDI-2 Mass Spectrometry Imaging of Cells and Tissues at Subcellular Resolution." *Nat Methods*, 16(9):925-931 (2019).
Nielsen, et al., "The Solution Structure of a Locked Nucleic Acid (LNA) Hybridized to DNA." *J Biomol Struct Dyn*, 17(2):175-191 (1999).
Nielsen, "MicroRNA in Situ Hybridization." *Methods Mol Biol*, 822:67-84 (2012).
Olejnik, et al., "Photocleavable Biotin Derivatives: a Versatile Approach for the Isolation of Biomolecules." *Proc. Natl. Acad. Sci. USA*, 92:7590-7594 (1995).
Olejnik, "Photocleavable Biotin Phosphoramidite for 5'-End-Labeling, Affinity Purification and Phosphorylation of Synthetic Oligonucleotides." *Nucl. Acids Res.*, 24:361-366 (1996).
Olejnik, et al., "Photocleavable Aminotag Phosphoramidites for 5'-Termini DNA/RNA Labeling." *Nucleic Acids Res*, 26(15):3572-3576 (1998).
Olejnik, et al., "Photocleavable Peptide-DNA Conjugates: Synthesis and Applications to DNA Analysis Using MALDI MS." *Nucleic Acids Res*, 27(23):4626-4631 (1999).
Oviano and Bou, "Matrix-Assisted Laser Desorption Ionization-Time of Flight Mass Spectrometry for the Rapid Detection of Antimicrobial Resistance Mechanisms and Beyond." *Clin Microbiol Rev*, 32(1) (2019).
Pandori, et al., "Photochemical Control of the Infectivity of Adenoviral Vectors Using a Novel Photocleavable Biotinylation Reagent." *Chem Biol*, 9(5):567-573 (2002).
Parra, et al., "Validation of Multiplex Immunofluorescence Panels Using Multispectral Microscopy for Immune-Profiling of Formalin-Fixed and Paraffin-Embedded Human Tumor Tissues." *Sci Rep*, 7(1):13380 (2017).
Poh and Ernst, "Targeting Macrophages in Cancer: From Bench to Bedside." *Front Oncol*, 8:49 (2018).
Poiroux, et al., "Plant Lectins Targeting O-Glycans at the Cell Surface as Tools for Cancer Diagnosis, Prognosis and Therapy." *Int J Mol Sci*, 18(6) (2017).
Qin, et al., "Two Methods for Glass Surface Modification and Their Application in Protein Immobilization." *Colloids Surf B Biointerfaces*, 60(2):243-249 (2007).
Renwick, et al., "Multicolor MicroRNA Fish Effectively Differentiates Tumor Types." *J Clin Invest*, 123(6):2694-2702 (2013).
Renwick, et al., "Multiplexed MiRNA Fluorescence in Situ Hybridization for Formalin-Fixed Paraffin-Embedded Tissues." *Methods Mol Biol*, 1211:171-187 (2014).
Rieth, et al., "Prevalence of High-Risk Human Papillomavirus in Tonsil Tissue in Healthy Adults and Colocalization in Biofilm of Tonsillar Crypts." *JAMA Otolaryngol Head Neck Surg*, 144(3):231-237 (2018).
Roach, et al., "Nanospray Desorption Electrospray Ionization: An Ambient Method for Liquid-Extraction Surface Sampling in Mass Spectrometry." *Analyst*, 135(9):2233-2236 (2010).
Robertson and Thach, "LNA Flow-Fish: A Flow Cytometry-Fluorescence in Situ Hybridization Method to Detect Messenger RNA Using Locked Nucleic Acid Probes." *Anal Biochem*, 390(2):109-114 (2009).
Rogakou, et al., "DNA Double-Stranded Breaks Induce Histone H2ax Phosphorylation on Serine 139." *J Biol Chem*, 273(10):5858-5868 (1998).
Sada-Ovalle, et al., "Functionality of CD4+ and CD8+ T Cells from Tonsillar Tissue." *Clin Exp Immunol*, 168(2):200-206 (2012).
Schubert, et al., "Analyzing Proteome Topology and Function by Automated Multidimensional Fluorescence Microscopy." *Nat Biotechnol*, 24(10):1270-1278 (2006).
Sempere, et al., "Altered MicroRNA Expression Confined to Specific Epithelial Cell Subpopulations in Breast Cancer." *Cancer Res*, 67(24):11612-11620 (2007).
Sharma and Allison, "The Future of Immune Checkpoint Therapy." *Science*, 348(6230):56-61 (2015).
Shirasaki, et al., "Expression of Steroid Receptors in Palatine Tonsils." *International Congress Series*, 1257:115-118 (2003).
Siuzdak, "Cover Feature: Book Preview: An Introduction to Mass Spectrometry Ionization: An Excerpt from the Expanding Role of Mass Spectrometry in Biotechnology, 2nd Ed.; MCC Press: San Diego, 2005." *JALA*, 9(2):50-63 (2004).
Smith, et al., "METLIN: A Metabolite Mass Spectral Database." *Ther Drug Monit*, 27(6):747-751 (2005).

(56) References Cited

OTHER PUBLICATIONS

Stack, et al., "Multiplexed Immunohistochemistry, Imaging, and Quantitation: A Review, with an Assessment of Tyramide Signal Amplification, Multispectral Imaging and Multiplex Analysis." *Methods*, 70(1):46-58 (2014).

Stawikowski and Fields, "Introduction to Peptide Synthesis." *Curr Protoc Protein Sci*, Chapter 18:Unit 18 11 (2012).

Takats, et al., "Mass Spectrometry Sampling under Ambient Conditions with Desorption Electrospray Ionization." *Science*, 306(5695):471-473 (2004).

Takats, et al., "In Situ Desorption Electrospray Ionization (Desi) Analysis of Tissue Sections." *CSH Protoc*, 2008:pdb prot4994 (2008).

Tang, et al., "Brain Microvasculature Defects and Glut1 Deficiency Syndrome Averted by Early Repletion of the Glucose Transporter-1 Protein." *Nat Commun*, 8:14152 (2017).

Thiery, et al., "Multiplex Target Protein Imaging in Tissue Sections by Mass Spectrometry—Tamsim." *Rapid Commun Mass Spectrom*, 21(6):823-829 (2007).

Thiery, et al., "Improvements of Targeted Multiplex Mass Spectrometry Imaging." *Proteomics*, 8(18):3725-3734 (2008).

Towers, et al., "Optimised Desorption Electrospray Ionisation Mass Spectrometry Imaging (Desi-Msi) for the Analysis of Proteins/Peptides Directly from Tissue Sections on a Travelling Wave Ion Mobility Q-TOF." *J Am Soc Mass Spectrom*, 29(12):2456-2466 (2018).

Trauger, et al., "High Sensitivity and Analyte Capture with Desorption/Ionization Mass Spectrometry on Silylated Porous Silicon." *Anal Chem*, 76(15):4484-4489 (2004).

Tsaneva and Van Damme, "130 Years of Plant Lectin Research." *Glycoconj J*, 37(5):533-551 (2020).

Tsurui, et al., "Seven-Color Fluorescence Imaging of Tissue Samples Based on Fourier Spectroscopy and Singular Value Decomposition." *J Histochem Cytochem*, 48(5):653-662 (2000).

Vaddepally, et al., "Review of Indications of FDA-Approved Immune Checkpoint Inhibitors Per NCCN Guidelines with the Level of Evidence." *Cancers* (Basel), 12(3) (2020).

Van Meer, et al., "Membrane Lipids: Where They Are and How They Behave." *Nat Rev Mol Cell Biol*, 9(2):112-124 (2008).

Van Tilborg, et al., "A Quantitative Method for Microstructural Analysis of Myelinated Axons in the Injured Rodent Brain." *Sci Rep*, 7(1):16492 (2017).

Vester and Wengel, "LNA (Locked Nucleic Acid): High-Affinity Targeting of Complementary RNA and DNA." *Biochemistry*, 43(42):13233-13241 (2004).

Vihervuori, et al., "Tumor-Infiltrating Lymphocytes and CD8(+) T Cells Predict Survival of Triple-Negative Breast Cancer." *J Cancer Res Clin Oncol*, 145(12):3105-3114 (2019).

Wahlby, et al., "Sequential Immunofluorescence Staining and Image Analysis for Detection of Large Numbers of Antigens in Individual Cell Nuclei." *Cytometry*, 47(1):32-41 (2002).

Wei, et al., "Fundamental Mechanisms of Immune Checkpoint Blockade Therapy." *Cancer Discov*, 8(9):1069-1086 (2018).

Wiche, et al., "Differential Distribution of Microtubule-Associated Proteins Map-1 and Map-2 in Neurons of Rat Brain and Association of Map-1 with Microtubules of Neuroblastoma Cells (Clone N2a)." *EMBO J*, 2(11):1915-1920 (1983).

Wilkinson and Saldova, "Current Methods for the Characterization of O-Glycans." *J Proteome Res*, 19(10):3890-3905 (2020).

Wilschefski and Baxter, "Inductively Coupled Plasma Mass Spectrometry: Introduction to Analytical Aspects." *Clin Biochem Rev*, 40(3):115-133 (2019).

Wisztorski, et al., "MALDI Direct Analysis and Imaging of Frozen Versus FFPE Tissues: What Strategy for Which Sample?". *Methods Mol Biol*, 656:303-322 (2010).

Yalcinde la Monte, "Review of Matrix-Assisted Laser Desorption Ionization-Imaging Mass Spectrometry for Lipid Biochemical Histopathology." *J Histochem Cytochem*, 63(10):762-771 (2015).

Yang and Caprioli, "Matrix Pre-Coated Targets for High Throughput MALDI Imaging of Proteins." *J Mass Spectrom*, 49(5):417-422 (2014).

Yao, et al., "Importance of Matrix: Analyte Ratio for Buffer Tolerance Using 2,5-Dihydroxybenzoic Acid as a Matrix in Matrix-Assisted Laser Desorption/Ionization-Fourier Transform Mass Spectrometry and Matrix-Assisted Laser Desorption/Ionization-Time of Flight." *J Am Soc Mass Spectrom*, 9(8):805-813 (1998).

Zaha, "Significance of Immunohistochemistry in Breast Cancer." *World J Clin Oncol*, 5(3):382-392 (2014).

Zavalin, et al., "Direct Imaging of Single Cells and Tissue at Sub-Cellular Spatial Resolution Using Transmission Geometry MALDI MS." *J Mass Spectrom*, 47(11):1-17 (2012).

Zhou, et al., "Proteome-Wide Drug Screening Using Mass Spectrometric Imaging of Bead-Arrays." *Sci Rep*, 6:26125 (2016).

Zupancic, et al., "Combined Lectin- and Immuno-Histochemistry (CLIH) for Applications in Cell Biology and Cancer Diagnosis: Analysis of Human Urothelial Carcinomas." *Eur J Histochem*, 64(3) (2020).

Cummings, et al., Glycan-Recognizing Probes as Tools. In rd, et al., (Eds.), *Essentials of Glycobiology* (pp. 611-625). Cold Spring Harbor (NY). (2015).

Micheel, et al., "Evolution of Translational Omics: Lessons Learned and the Path Forward." The National Academies Press, Washington (DC). (2012).

"The Path of Biomolecular Mass Spectrometry into Open Research." *Nat Commun*, 10(1):4029 (2019).

Fluidigm, Quick Reference: "Maxpar X8 Antibody Labeling", accessed Sep. 2020, www.fluidigm.com/binaries/content/documents/fluidigm/resources/maxpar-x8-antibody-labeling-quick-reference-fldm-00015-rev01/maxpar-x8-antibody-labeling-quick-reference-fldm-00015-rev01/fluidigm%3Afile].

Casadonte, et al., Proteomic analysis of formalin-fixed paraffin embedded tissue by MALDI imaging mass spectrometry. Nat Protoc., vol. 6, No. 11, pp. 1695-1709. 2011.

IHC Ventana Protocol (2017) [online]. [Retrieved on Oct. 25, 2021]. Retrieved from the Internet Oct. 25, 2021 CURL: www.atlasantibodies.com/globalassets/protocols/ihcventanaprotocol.pdf.

Fig. 5B
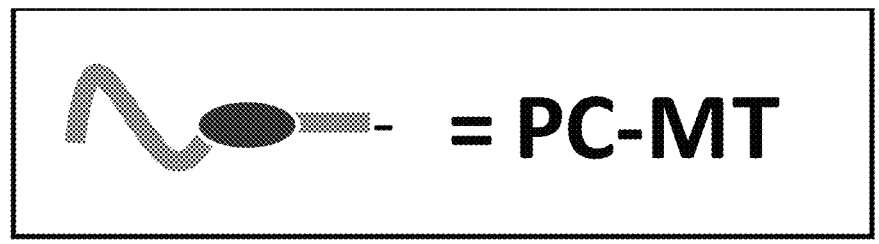
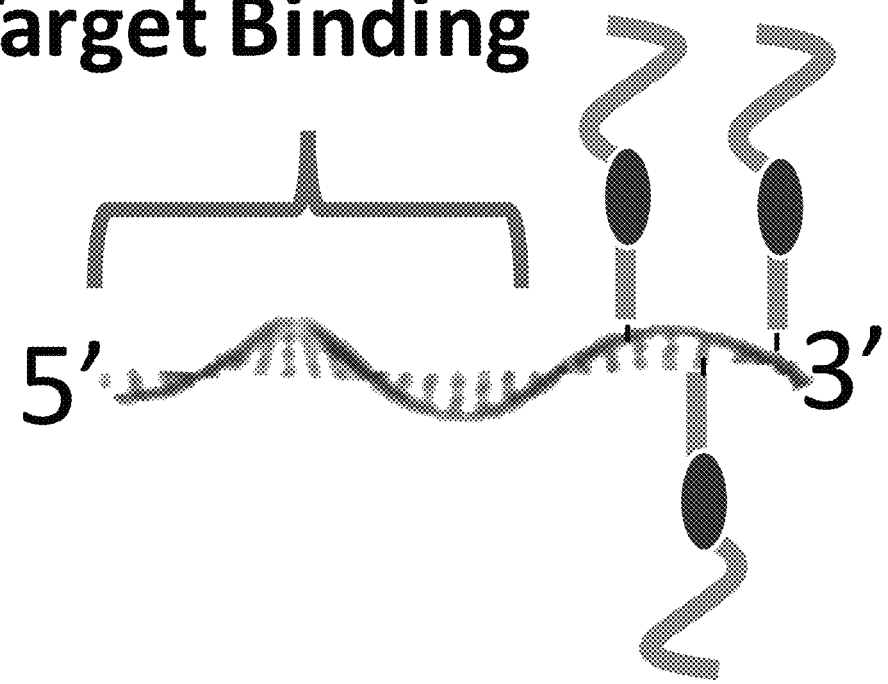

Mass Unit 1, 5 min UV

Mass Unit 3, 5 min UV

Mass Unit 3, 25 min UV

Mass Unit 4, 5 min UV

Mass Unit 4, 25 min UV

Anti-Myelin, Mass Unit 1, 5 min UV

Anti-Myelin, Mass Unit 1, 25 min UV

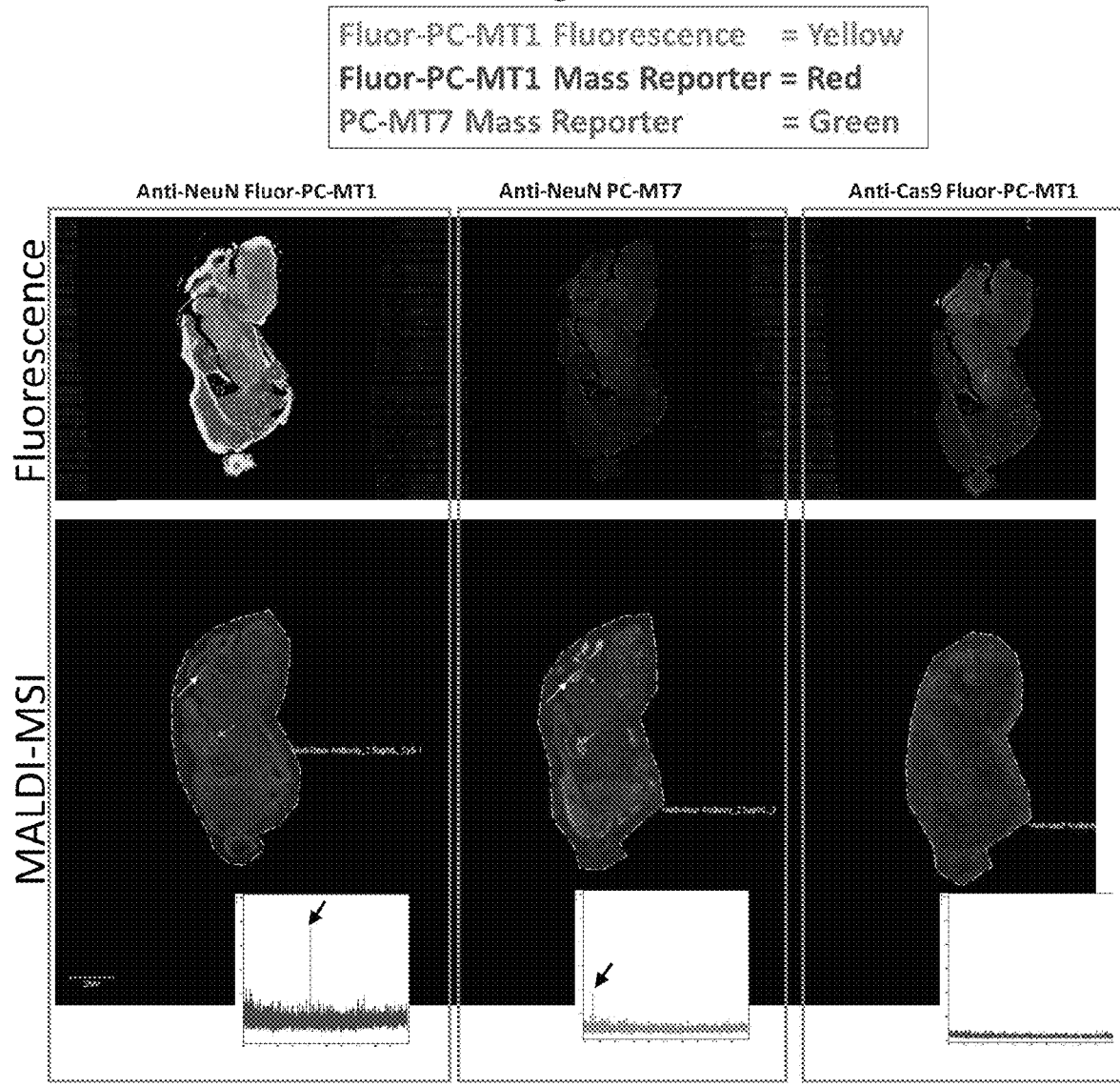

Fig. 18
Matrix Sublimation with Recrystallization
Matrix Sublimation without Recrystallization
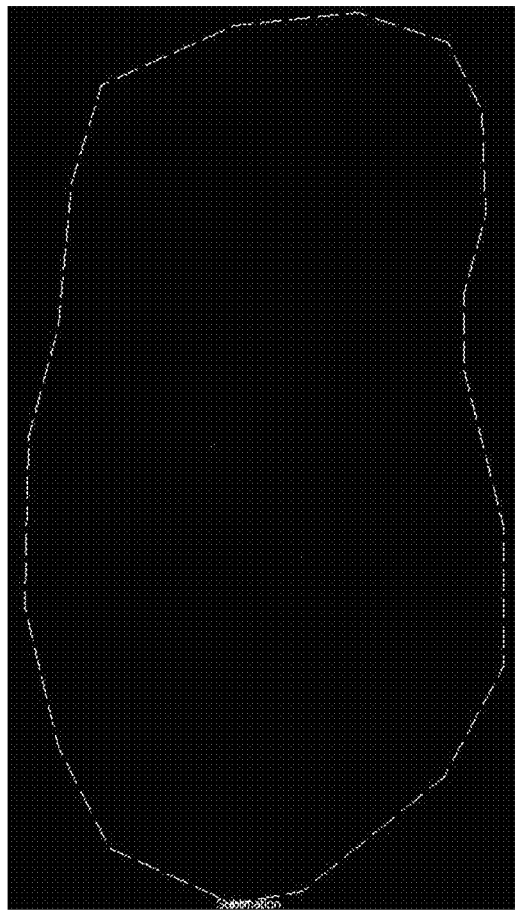

MSI-1 (Direct Label-Free Lipid MSI)

MSI-2 (MIHC)

Merge

PHOTOCLEAVABLE MASS-TAGS FOR MULTIPLEXED MASS SPECTROMETRIC IMAGING OF TISSUES USING BIOMOLECULAR PROBES

CROSS-REFERENCE TO RELATED APPLICATIONS

This application claims priority to U.S. Provisional Application Ser. No. 63/106,990 entitled "Novel Photocleavable Mass-Tags for Multiplexed Mass Spectrometric Imaging of Tissues using Antibody and Nucleic Acid Probes", filed Nov. 29, 2020, hereby incorporated by reference in its entirety.

STATEMENT REGARDING FEDERALLY SPONSORED RESEARCH OR DEVELOPMENT

This invention was made with government support under Grant No. CA236097 awarded by the National Cancer Institute. The government has certain rights in the invention.

FIELD OF THE INVENTION

The field of this invention relates to immunohistochemistry (IHC) and in situ hybridization (ISH) for the targeted detection and mapping of biomolecules (e.g., proteins and miRNAs) in tissues or cells for example, for research use and for clinical use such by pathologists (e.g., biomarker analyses of a resected tumor or tumor biopsy). In particular, the use of mass spectrometric imaging (MSI) as a mode to detect and map the biomolecules in tissues or cells for example. More specifically, the field of this invention relates to photocleavable mass-tag reagents which are attached to probes such as antibodies and nucleic acids and used to achieve multiplex immunohistochemistry and in situ hybridization, with MSI as the mode of detection/readout. Probe types other than antibodies and nucleic acids are also covered in the field of invention, including but not limited to carbohydrate-binding proteins (e.g., lectins), receptors and ligands. Finally, the field of the invention also encompasses multi-omic MSI procedures, where MSI of photocleavable mass-tag probes is combined with other modes of MSI, such as direct label-free MSI of endogenous biomolecules from the biospecimen (e.g., tissue), whereby said biomolecules can be intact or digested (e.g., chemically digested or by enzyme).

BACKGROUND OF THE INVENTION

Immunohistochemistry (IHC) and in situ hybridization (ISH) are widely used to determine the structural organization of biomolecules at the tissue, cellular and subcellular level [Katikireddy and O'Sullivan (2011) Methods Mol Biol 784: 155-67; Howat and Warford (2014) Methods 70: 1-2; Stack, Wang et al. (2014) Methods 70: 46-58]. For example, IHC is the preferred method for studying extracellular amyloid plaques and intracellular tau-based neurofibrillary tangles in neurodegenerative disorders [Deng, Bigio et al. (2011) Methods Mol Biol 793: 259-72; Dugger and Dickson (2017) Cold Spring Harb Perspect Biol 9]. In oncology, IHC and ISH can be used to diagnose, classify into subtypes and determine optimal treatment of various cancers [Renwick, Cekan et al. (2013) J Clin Invest 123: 2694-702; Zaha (2014) World J Clin Oncol 5: 382-92], including the evaluation of tumor infiltrating lymphocytes (TILs) which are of prognostic value [Halse, Colebatch et al. (2018) Sci Rep 8: 11158]. IHC and ISH analyses are generally performed on tissue samples, for example collected by biopsy or surgical resection of a tumor. Typically, tissue samples are fresh frozen (FF) or formalin-fixed and paraffin embedded (FFPE), and then thin-sectioned (e.g., 10 µm) and mounted onto glass microscope slides. Fluorophores or chromogenic agents conjugated to antibody or nucleic acid probes are the most common methods of visualizing the spatial distribution of targeted biomolecules using microscopy (e.g., protein antigens or genetic material such as miRNA) [Katikireddy and O'Sullivan (2011) Methods Mol Biol 784: 155-67].

It is often vital to simultaneously determine the localization and potential co-localization of a number of biomarkers. This is critical in order to map, for example, the location of the hundreds of possible proteins and/or miRNAs involved in cell regulation and dysregulation in a highly heterogeneous tissue [Renwick, Cekan et al. (2014) Methods Mol Biol 1211: 171-87; Blom, Paavolainen et al. (2017) Sci Rep 7: 15580]. However, fluorescence microscopy is limited to the simultaneous detection of only a few biomarkers, since molecular fluorophores exhibit relatively broad excitation and emission bands, resulting in spectral overlap [Stack, Wang et al. (2014) Methods 70: 46-58]. The multiplexing limit of standard fluorescence microscopy is generally 3-5, while hyperspectral/multispectral methods are limited to 8 [Tsurui, Nishimura et al. (2000) J Histochem Cytochem 48: 653-62; Stack, Wang et al. (2014) Methods 70: 46-58; Parra, Uraoka et al. (2017) Sci Rep 7: 13380; Gorris, Halilovic et al. (2018) J Immunol 200: 347-354]. Furthermore, these multiplexing methods often require cycling strategies (e.g., Perkin Elmer's OPAL multispectral platform) such as iterative staining followed by photobleaching or probe removal/denaturation [Wahlby, Erlandsson et al. (2002) Cytometry 47: 32-41; Schubert, Bonnekoh et al. (2006) Nat Biotechnol 24: 1270-8; Gerdes, Sevinsky et al. (2013) Proc Natl Acad Sci USA 110: 11982-7; Blom, Paavolainen et al. (2017) Sci Rep 7: 15580]. Such methods are complex, laborious and incomplete cycling can confound the results [Giesen, Wang et al. (2014) Nat Methods 11: 417-22; Blom, Paavolainen et al. (2017) Sci Rep 7: 15580].

In contrast, mass spectrometric imaging (MSI) facilitates a high level of multiplexing without the limitations of the aforementioned optical methods (limited only by mass resolution which is typically less than 1 Da). Briefly (see FIG. 1 for details), these methods scan the tissue specimen with a mass spectrometer, generating a full mass spectrum at each "pixel" thereby allowing the simultaneous imaging of any given mass species within the spectra [Arentz, Mittal et al. (2017) Adv Cancer Res 134: 27-66]. The Caprioli group first introduced this technique based on matrix-assisted laser desorption ionization mass spectrometry (MALDI-MS) [Caprioli, Farmer et al. (1997) Anal Chem 69: 4751-60] which has since been widely adopted for the direct label-free imaging of biomolecules including proteins, nucleic acids, lipids, metabolites and even small drug compounds in complex tissues [Buchberger, DeLaney et al. (2018) Anal Chem 90: 240-265]. This technique has also been extended to other mass spectrometry (MS) approaches such as ESI-based DESI-MS imaging [Takats, Wiseman et al. (2004) Science 306: 471-3]. While MALDI and DESI MSI approaches do not currently match the spatial resolution of optical methods (e.g., 10 µm laser focus with the newer Bruker rapifleX MALDI-MS instruments), it is possible to obtain improved resolution using innovative designs such as transmission geometry (2 µm) [Zavalin, Todd et al. (2012) J Mass Spectrom 47: i] or atmospheric pressure MALDI-MSI with laser focusing objectives (1.4 µm) [Kompauer, Heiles et al. (2017) Nat Methods 14: 90-96].

However, MSI of intact macromolecules such as proteins is typically not possible due to insufficient mass resolution and poor sensitivity [Buchberger, DeLaney et al. (2018) Anal Chem 90: 240-265]. Identification of a particular biomolecule requires tandem MS/MS fragmentation, ultra-high mass resolution instruments and/or bottom-up proteomic approaches (e.g., in situ proteolysis of the tissue). To overcome this limitation, a few targeted MSI approaches have been introduced which allow multiplex workflows similar to conventional IHC and ISH using labeled antibody and nucleic acid probes. TAMSIM (targeted multiplex mass spectrometric imaging) is a matrix-free laser desorption ionization (LDI) method which uses antibodies conjugated to small organic photocleavable mass-tags which are cleaved and ionized during MSI [Thiery, Shchepinov et al. (2007) Rapid Commun Mass Spectrom 21: 823-9]. However, the mass-tags are not readily synthesized and only 3-plex imaging has been shown [Thiery, Anselmi et al. (2008) Proteomics 8: 3725-34]. Furthermore, those skilled in the art will recognize that analyte co-crystallization with an excess of exogenously added matrix compound, which facilitates absorption of the mass spectrometer's laser energy and transfer to the analyte, is required for efficient analyte vaporization/ionization and detection, termed matrix-assisted laser desorption ionization (MALDI) mass spectrometry [Yao, Scott et al. (1998) J Am Soc Mass Spectrom 9: 805-13; Duenas, Carlucci et al. (2016) J Am Soc Mass Spectrom 27: 1575-8], thus, the TAMSIM method will lack sensitivity.

In contrast, peptide mass-tags are easily produced using standard solid-phase synthesis, the masses are readily tuned by altering the sequence, and peptides generally ionize with high efficiency. Lemaire et al. first introduced a photocleavable peptide-based MSI method for targeted imaging of tissue termed Tag-Mass [Lemaire, Stauber et al. (2007) J Proteome Res 6: 2057-67]. However, the mass-tagging of the probe (e.g., antibody) is a complex multi-step process involving an intermediate chemical linker. Moreover, the photocleavable nucleus used in the peptides provides sub-optimal sensitivity. These drawbacks have thus far limited the general utilization of Tag-Mass and consequently only 2-plex MSI has been achieved to date [Lemaire, Stauber et al. (2007) J Proteome Res 6: 2057-67; Franck, Arafah et al. (2009) Mol Cell Proteomics 8: 2023-33; El Ayed, Bonnel et al. (2010) Med Sci Monit 16: BR233-45].

Imaging mass cytometry uses antibodies tagged with rare earth metals combined with inductively coupled plasma mass spectrometry (ICP-MS) [Giesen, Wang et al. (2014) Nat Methods 11: 417-22]. This approach has achieved the highest multiplexing level to date with at least 32-plex tissue staining. However, this method requires specialized MS instrumentation and is a destructive approach which reduces molecules to elements (atomization) for detection and analysis, and is therefore not compatible with performing untargeted direct MSI analysis of biomolecules (in conjunction with targeted MSI using mass-tagged probes as in Experimental Example 4 of the Present Invention). See Wilschefski et al. for an example review of ICP-MS [Wilschefski and Baxter (2019) Clin Biochem Rev 40: 115-133].

Further drawbacks of the imaging mass cytometry approach include that the probe labeling process is also highly complex, involving pre-loading a polymer with metal ion, partially reducing the antibody and coupling of the two together, with multiple purifications of the polymer and antibody [Fluidigm, Quick Reference: "Maxpar X8 Antibody Labeling", accessed September 2020, www.fluidigm.com/binaries/content/documents/fluidigm/resources/max-par-x8-antibody-labeling-quick-reference-fldm-00015-rev01/maxpar-x8-antibody-labeling-quick-reference-fldm-00015-rev01/fluidigm%3Afile].

SUMMARY OF THE INVENTION

This invention relates to immunohistochemistry (IHC) and in situ hybridization (ISH) for the targeted detection and mapping of biomolecules (e.g. proteins and miRNAs) in tissues or cells for example, for research use and for clinical use such by pathologists (e.g. biomarker analyses of a resected tumor or tumor biopsy). In particular, the use of mass spectrometric imaging (MSI) as a mode to detect and map the biomolecules in tissues or cells for example. More specifically, the field of this invention relates to photocleavable mass-tag reagents which are attached to probes such as antibodies and nucleic acids and used to achieve multiplex immunohistochemistry and in situ hybridization, with MSI as the mode of detection/readout.

In one embodiment, the present invention provides a multiplex method for co-detecting 5 or more different types of biomarkers in a tissue sample on a single slide, said method comprising: a) providing a tissue sample on a single slide; b) contacting said tissue sample with 5 or more different antibodies to effect binding of the antibodies to the tissue sample, each of said antibodies reactive with a different biomarker, and each of said antibodies conjugated to a unique mass-tag; and c) detecting, using mass spectrometric imaging, said mass-tags, or fragments thereof, as molecular ions. In one embodiment, wherein said method further comprising performing, after step a) but before step b), direct mass spectrometric imaging on said tissue sample (i.e. tissue imaging is achieved on a single specimen). In one embodiment, wherein said 5 or more antibodies are in a mixture and said tissue sample in step b) is contacted with said mixture. In one embodiment, wherein said mass-tags are non-rare-earth-metal mass-tags. In one embodiment, wherein said mass-tags comprise a plurality of amino acids. In one embodiment, wherein said tissue sample was fresh frozen and thin-sectioned prior to being mounted on said single slide. In one embodiment, wherein said slide comprises gold. In one embodiment, wherein said slide is a glass slide with a gold layer. In one embodiment, wherein said tissue sample was formalin-fixed and paraffin embedded and thin-sectioned prior to being mounted on said single slide. In one embodiment, wherein the tissue sample is subjected to a treatment prior to the steps of contacting the sample with antibody, said treatment comprising deparaffinization. In one embodiment, wherein said deparaffinization is performed with xylene. In one embodiment, wherein the tissue sample is further subjected to a treatment, said treatment comprising rehydration. In one embodiment, wherein said rehydration is performed with a series of ethanol/water mixtures and aqueous saline buffers. In one embodiment, wherein the tissue sample is further subjected to a treatment, said treatment comprising antigen retrieval. In one embodiment, wherein said antigen retrieval is performed by heating in citrate buffer, pH 6. In one embodiment, wherein said antigen retrieval is performed with the use of formic acid. In one embodiment, wherein said antibodies conjugated to a mass-tag have the following general structure, wherein X is a spacer:

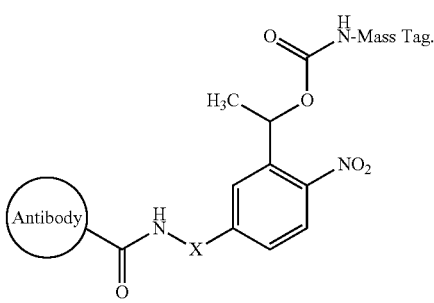

In one embodiment, wherein a matrix compound is applied to said mass-tags before step c). In one embodiment, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid). In one embodiment, wherein said matrix compound is applied by sublimation. In one embodiment, wherein the tissue sample is subjected to a treatment after the steps of contacting the sample with a matrix compound, said treatment comprising matrix recrystallization. In one embodiment, wherein said mass-tags are photocleavable. In one embodiment, wherein the method further comprises illuminating said mass-tags with light so as to photocleave at least a portion of said mass-tags prior to step c). In one embodiment, wherein said tissue is from a tumor. In one embodiment, wherein said tumor is a breast tumor. In one embodiment, wherein at least one of said 5 or more antibodies comprises a fluorescent moiety in addition to said mass-tag. In one embodiment, wherein the number of said different antibodies is 8 or more. In one embodiment, wherein a subset of said different antibodies reacts with i) the estrogen receptor (ER), ii) the progesterone receptor (PR), iii) human epidermal growth factor receptor 2 (HER2), and iv) Ki67. In one embodiment, wherein a subset of said different antibodies reacts with T-cell biomarkers i) CD3 (T-cells), ii) CD4 (T-helper), iii) CD8 (cytotoxic T-cells), and iv) CD45RO (memory T-cells). In one embodiment, wherein one of said different antibodies reacts with the B-cell biomarker CD20. In one embodiment, wherein one of said different antibodies reacts with the macrophage biomarker CD68. In one embodiment, wherein one of said different antibodies reacts with an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a multiplex method for co-detecting human epidermal growth factor receptor 2 (HER2) protein and estrogen receptor (ER) protein in a tissue sample on a single slide, said method comprising: a) providing a tissue sample on a single slide; b) contacting the tissue sample with a HER2 protein-specific antibody, said antibody conjugated to a first non-rare-earth-metal mass-tag, said mass-tag comprising a plurality of amino acids; c) contacting the sample with an ER-specific antibody, said antibody conjugated to a second non-rare-earth-metal mass-tag, said mass-tag comprising a second plurality of amino acids, wherein said second plurality has a different mass from said first plurality of amino acids; and d) detecting, using mass spectrometric imaging, said mass-tags, or fragments thereof, as molecular ions. In one embodiment, wherein steps b) and c) are performed simultaneously. In one embodiment, further comprising performing, after step a) but before step b), direct mass spectrometric imaging on said tissue sample. In one embodiment, wherein said tissue sample was fresh frozen and thin-sectioned prior to being mounted on said single slide. In one embodiment, wherein said slide comprises gold. In one embodiment, wherein said slide is a glass slide with a gold layer. In one embodiment, wherein said tissue sample was formalin-fixed and paraffin embedded and thin-sectioned prior to being mounted on said single slide. In one embodiment, wherein the tissue sample is subjected to a treatment prior to the steps of contacting the sample with antibody, said treatment comprising deparaffinization. In one embodiment, wherein said deparaffinization is performed with xylene. In one embodiment, wherein the tissue sample is further subjected to a treatment, said treatment comprising rehydration. In one embodiment, wherein said rehydration is performed with a series of ethanol/water mixtures and aqueous saline buffers. In one embodiment, wherein the tissue sample is further subjected to a treatment, said treatment comprising antigen retrieval. In one embodiment, wherein said antigen retrieval is performed by heating in citrate buffer, pH 6. In one embodiment, wherein said antigen retrieval is performed with the use of formic acid. In one embodiment, wherein said antibodies conjugated to a mass-tag have the following general structure, wherein X is a spacer:

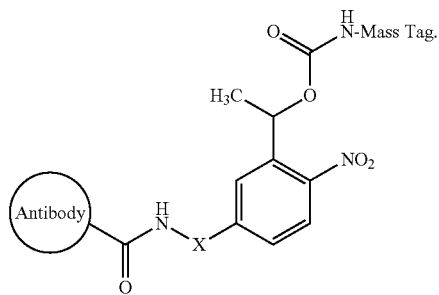

In one embodiment, wherein a matrix compound is applied to said mass-tags before step d). In one embodiment, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid). In one embodiment, wherein said matrix compound is applied by sublimation. In one embodiment, wherein the tissue sample is subjected to a treatment after the steps of contacting the sample with a matrix compound, said treatment comprising matrix recrystallization. In one embodiment, wherein said mass-tags are photocleavable. In one embodiment, wherein the method further comprises illuminating said mass-tags with light so as to photocleave at least a portion of said mass-tags prior to step d). In one embodiment, wherein said tissue is from a tumor. In one embodiment, wherein said tumor is a breast tumor. In one embodiment, further comprising contacting said tissue with additional different antibodies prior to step d), each of said additional different antibodies conjugated to a non-rare-earth-metal mass-tag, said mass-tag comprising a plurality of amino acids. In one embodiment, wherein the number of said different antibodies is 8 or more. In one embodiment, wherein one of said different antibodies reacts with the progesterone receptor (PR). In one embodiment, wherein a subset of said different antibodies reacts with T-cell biomarkers i) CD3 (T-cells), ii) CD4 (T-helper), iii) CD8 (cytotoxic T-cells), and iv)

CD45RO (memory T-cells). In one embodiment, wherein one of said different antibodies reacts with the B-cell biomarker CD20. In one embodiment, wherein one of said different antibodies reacts with the macrophage biomarker CD68. In one embodiment, wherein one of said different antibodies reacts with an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a multiplex method for co-detecting different types of tumor infiltrating immune cells in tumors on a single slide, said method comprising: a) providing a tumor tissue sample on a single slide; b) contacting said tissue sample with a first antibody specific to first type of tumor infiltrating immune cell to effect binding of the antibody to the tissue sample, said antibody conjugated to a first non-rare-earth-metal mass-tag, said mass-tag comprising a plurality of amino acids; c) contacting the tissue sample with a second antibody specific to a second type of tumor infiltrating immune cell to effect binding of the antibody to the tissue sample, said antibody conjugated to a second non-rare-earth-metal mass-tag, said mass-tag comprising a plurality of amino acids; and d) detecting, using mass spectrometric imaging, said mass-tags, or fragments thereof, as molecular ions. In one embodiment, wherein steps b) and c) are performed simultaneously. In one embodiment, further comprising performing, after step a) but before step b), direct mass spectrometric imaging on said tissue sample. In one embodiment, wherein said tissue sample was fresh frozen and thin-sectioned prior to being mounted on said single slide. In one embodiment, wherein said slide comprises gold. In one embodiment, wherein said slide is a glass slide with a gold layer. In one embodiment, wherein said tissue sample was formalin-fixed and paraffin embedded and thin-sectioned prior to being mounted on said single slide. In one embodiment, wherein the tissue sample is subjected to a treatment prior to the steps of contacting the sample with antibody, said treatment comprising deparaffinization. In one embodiment, wherein said deparaffinization is performed with xylene. In one embodiment, wherein the tissue sample is further subjected to a treatment, said treatment comprising rehydration. In one embodiment, wherein said rehydration is performed with a series of ethanol/water mixtures and aqueous saline buffers. In one embodiment, wherein the tissue sample is further subjected to a treatment, said treatment comprising antigen retrieval. In one embodiment, wherein said antigen retrieval is performed by heating in citrate buffer, pH 6. In one embodiment, wherein said antigen retrieval is performed with the use of formic acid. In one embodiment, wherein said antibodies conjugated to a mass-tag have the following general structure, wherein X is a spacer:

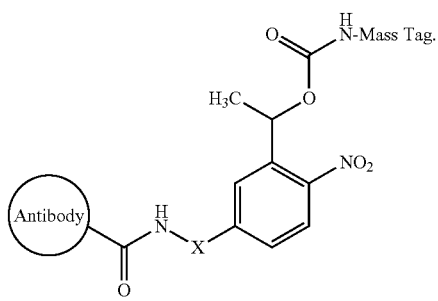

In one embodiment, wherein a matrix compound is applied to said mass-tags before step d). In one embodiment, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid). In one embodiment, wherein said matrix compound is applied by sublimation. In one embodiment, wherein the tissue sample is subjected to a treatment after the steps of contacting the sample with a matrix compound, said treatment comprising matrix recrystallization. In one embodiment, wherein said mass-tags are photocleavable. In one embodiment, wherein the method further comprises illuminating said mass-tags with light so as to photocleave at least a portion of said mass-tags prior to step d). In one embodiment, wherein said tumor is lung tumor. In one embodiment, wherein said tumor is a breast tumor. In one embodiment, wherein first antibody is specific for CD3 and said second antibody is specific for CD8. In one embodiment, further comprising contacting said tissue with additional different antibodies prior to step d), each of said additional different antibodies conjugated to a non-rare-earth-metal mass-tag, said mass-tag comprising a plurality of amino acids. In one embodiment, wherein one of said additional different antibodies reacts with CD4. In one embodiment, wherein one of said additional different antibodies reacts with the macrophage biomarker CD68. In one embodiment, wherein one of said additional different antibodies reacts with an immune checkpoint molecule. In one embodiment, wherein said immune checkpoint molecule is selected from the group consisting of PD-1, PD-L1, PD-L2, CTLA-4, OX40, CD27, and TIM3. In one embodiment, the present invention provides a composition comprising an antibody conjugated to i) a mass-tag through a photocleavable linker, and ii) a fluorophore. In one embodiment, wherein said antibody reacts with a biomarker selected from the group consisting of i) the estrogen receptor (ER), ii) the progesterone receptor (PR), iii) human epidermal growth factor receptor 2 (HER2), and iv) Ki67. In one embodiment, wherein said antibody reacts with T-cell biomarkers selected from the group consisting of i) CD3 (T-cells), ii) CD4 (T-helper), iii) CD8 (cytotoxic T-cells), and iv) CD45RO (memory T-cells). In one embodiment, wherein said antibody reacts with an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a multiplex method of detecting immune checkpoint molecules on tumor tissue on a single slide, said method comprising: a) providing a tumor tissue sample on a single slide; b) contacting said tissue sample with a mixture comprising a plurality of different antibodies, each different antibody reactive with different immune checkpoint molecule, each of said antibodies conjugated to a non-rare-earth-metal mass-tag, said mass-tag comprising a plurality of amino acids; and c) detecting, using mass spectrometric imaging, said mass-tags, or fragments thereof, as molecular ions. In one embodiment, wherein one of said plurality of different antibodies reacts with an immune checkpoint molecule selected from the group consisting of PD-1, PD-L1, PD-L2, CTLA-4, OX40, CD27, and TIM3. In one embodiment, wherein said tumor tissue comprises a biopsy from a human patient. In one embodiment, wherein said biopsy tumor tissue reacts with an antibody to PD-L1. In one embodiment, further comprising treating said human patient with an immune checkpoint inhibitor specific for PD-L1. In one embodiment, wherein said checkpoint inhibitor specific for PD-L1 is selected from the group consisting of atezolizumab, avelumab, and durvalumab.

In one embodiment, the present invention provides a multiplex method for co-detecting 3 or more (and more preferably 5 or more) different biomarkers in a tissue sample, said method comprising: a) providing a tissue sample; b) contacting said tissue sample with 3 or more (and more preferably 5 or more) different probes to create a probed tissue sample, each of said probes conjugated to a unique mass-tag and at least 3 or more (and more preferably 5 or more) of said probes each binding to a different biomarker in said tissue sample; and c) detecting, using mass spectrometric imaging of said probed tissue sample (e.g. tissue imaging is achieved on a single specimen), said unique mass-tags, or fragments thereof, from the at least 3 or more (and preferably 5 or more) of said bound probes, wherein said mass-tags are detected as molecular ions. In one embodiment, wherein said tissue sample is a thin tissue section. In one embodiment, wherein said tissue sample was frozen and thin-sectioned before step b). In one embodiment, where said tissue sample was formalin-fixed and thin-sectioned before step b). In one embodiment, wherein said tissue sample was formalin-fixed, paraffin embedded and thin-sectioned before step b). In one embodiment, wherein said tissue sample is mounted on a slide before step b). In one embodiment, wherein said slide comprises gold. In one embodiment, wherein said slide is a glass slide with a gold layer. In one embodiment, wherein said tissue sample is mounted on a slide before step c). In one embodiment, wherein said slide comprises gold. In one embodiment, wherein said slide is a glass slide with a gold layer. In one embodiment, wherein said tissue sample is from a tumor. In one embodiment, wherein said tumor is a breast tumor. In one embodiment, wherein said 5 or more probes are in a mixture and said tissue sample in step b) is contacted with said mixture to create said probed tissue sample. In one embodiment, wherein said probes conjugated to a mass-tag have the following general structure, wherein X is a spacer:

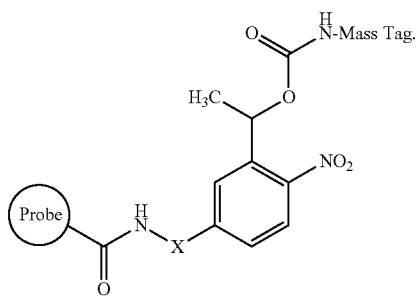

In one embodiment, wherein at least 1 of said 5 or more probes comprises a fluorescent moiety in addition to said mass-tag. In one embodiment, wherein said probes are selected from the group consisting of proteins and nucleic acids. In one embodiment, wherein at least 1 of said probes is an antibody. In one embodiment, wherein said antibody is selected from the group consisting of recombinant antibodies, nanobodies, single-chain fragment variable (scFv) antibodies, single domain antibodies, and VHH single domain antibodies. In one embodiment, wherein at least 1 of said probes is selected from the group consisting of affibodies, receptors and ligands. In one embodiment, wherein at least 1 of said probes is an aptamer. In one embodiment, wherein at least 1 of said probes binds to RNA targets. In one embodiment, wherein at least 1 of said probes binds to miRNA targets. In one embodiment, wherein at least 1 of said probes binds to DNA targets. In one embodiment, wherein said mass-tags are non-rare-earth-metal mass-tags. In one embodiment, wherein said mass-tags comprise a plurality of amino acids. In one embodiment, wherein said mass-tags are photocleavable. In one embodiment, wherein the method further comprises illuminating said mass-tags with light so as to photocleave at least a portion of said mass-tags before step c). In one embodiment, further comprising performing, after step a) but before step b), mass spectrometric imaging on said tissue sample. In one embodiment, wherein a matrix compound is applied to said probed tissue sample before step c). In one embodiment, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid). In one embodiment, wherein said matrix compound is applied by sublimation. In one embodiment, wherein said probed tissue sample is subjected to a treatment after the steps of applying said matrix compound to said probed tissue sample, said treatment comprising matrix recrystallization. In one embodiment, wherein said tissue sample is subjected to a treatment after said paraffin embedding and before step b), said treatment comprising deparaffinization. In one embodiment, wherein said deparaffinization is performed with xylene. In one embodiment, wherein said tissue sample is further subjected to a treatment, said treatment comprising rehydration. In one embodiment, wherein said rehydration is performed with a series of ethanol/water mixtures and aqueous saline buffers. In one embodiment, wherein said tissue sample is further subjected to a treatment, said treatment comprising antigen retrieval. In one embodiment, wherein said antigen retrieval is performed by heating in citrate buffer, pH 6. In one embodiment, wherein said antigen retrieval is performed with the use of formic acid. In one embodiment, wherein the number of said different probes is 10 or more. In one embodiment, wherein a subset of said different probes is capable of binding to i) the estrogen receptor (ER), ii) the progesterone receptor (PR), iii) human epidermal growth factor receptor 2 (HER2), and iv) Ki67. In one embodiment, wherein a subset of said different probes is capable of binding to T-cell biomarkers i) CD3 (T-cells), ii) CD4 (T-helper), iii) CD8 (cytotoxic T-cells), and iv) CD45RO (memory T-cells). In one embodiment, wherein 1 of said different probes is capable of binding to the B-cell biomarker CD20. In one embodiment, wherein 1 of said different probes is capable of binding to the macrophage biomarker CD68. In one embodiment, wherein 1 of said different probes is capable of binding to an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a multiplex method for co-detecting different hormone receptors in a tissue sample on a single slide, said method comprising: a) providing a tissue sample mounted on a single slide; b) contacting said tissue sample with a first probe which is capable of binding to a first hormone receptor, said probe conjugated to a first non-rare-earth-metal mass-tag, said mass-tag comprising a plurality of amino acids; c) contacting said tissue sample with a second probe which is capable of binding to a second hormone receptor, said probe conjugated to a second non-rare-earth-metal mass-tag, said mass-tag comprising a second plurality of amino acids, wherein said second hormone receptor is different from said first hormone receptor and said second plurality of amino acids has a different mass from said first plurality of amino acids, and wherein steps b) and c) together create a probed tissue sample; and d) detecting, using mass spectrometric imaging, at least 1 said mass-tags, or fragments thereof, as molecular ions. In one embodiment, wherein said tissue sample is a thin tissue section. In one embodiment, wherein said tissue sample was frozen and thin-sectioned before mounting on said slide. In one embodiment, where said tissue sample was formalin-fixed and thin-sectioned before mounting on said slide. In one embodiment, wherein said tissue sample was formalin-fixed, paraffin embedded and thin-sectioned before mounting on said slide. In one embodiment, wherein said slide comprises gold. In one embodiment, wherein said slide is a glass slide with a gold layer. In one embodiment, wherein said tissue sample is from a tumor. In one embodiment, wherein said tumor is a breast tumor. In one embodiment, wherein said probes conjugated to a non-rare-earth-metal mass-tag have the following general structure, wherein X is a spacer:

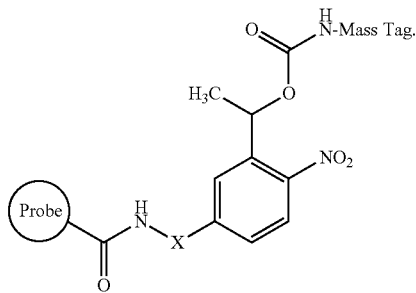

In one embodiment, wherein at least 1 of said probes comprises a fluorescent moiety in addition to said non-rare-earth-metal mass-tag. In one embodiment, wherein said probes are selected from the group consisting of proteins and nucleic acids. In one embodiment, wherein at least 1 of said probes is an antibody. In one embodiment, wherein said antibody is selected from the group consisting of recombinant antibodies, nanobodies, single-chain fragment variable (scFv) antibodies, single domain antibodies, and VHH single domain antibodies. In one embodiment, wherein at least 1 of said probes is selected from the group consisting of affibodies, receptors and ligands. In one embodiment, wherein at least 1 of said probes is an aptamer. In one embodiment, wherein at least 1 of said probes is capable of binding to RNA targets. In one embodiment, wherein at least 1 of said probes is capable of binding to miRNA targets. In one embodiment, wherein at least 1 of said probes is capable of binding to DNA targets. In one embodiment, wherein said non-rare-earth-metal mass-tags are photocleavable. In one embodiment, wherein the method further comprises illuminating said non-rare-earth-metal mass-tags with light so as to photocleave at least a portion of said non-rare-earth-metal mass-tags before step d). In one embodiment, wherein steps b) and c) are performed simultaneously to create said probed tissue sample. In one embodiment, further comprising performing, after step a) but before step b), mass spectrometric imaging on said tissue sample. In one embodiment, wherein a matrix compound is applied to said probed tissue sample before step d). In one embodiment, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid). In one embodiment, wherein said matrix compound is applied by sublimation. In one embodiment, wherein said probed tissue sample is subjected to a treatment after the steps of applying said matrix compound to said probed tissue sample, said treatment comprising matrix recrystallization. In one embodiment, wherein said tissue sample is subjected to a treatment after said paraffin embedding and before step b), said treatment comprising deparaffinization. In one embodiment, wherein said deparaffinization is performed with xylene. In one embodiment, wherein the tissue sample is further subjected to a treatment, said treatment comprising rehydration. In one embodiment, wherein said rehydration is performed with a series of ethanol/water mixtures and aqueous saline buffers. In one embodiment, wherein the tissue sample is further subjected to a treatment, said treatment comprising antigen retrieval. In one embodiment, wherein said antigen retrieval is performed by heating in citrate buffer, pH 6. In one embodiment, wherein said antigen retrieval is performed with the use of formic acid. In one embodiment, wherein said first probe is capable of binding to the estrogen receptor (ER) and said second probe is capable of binding to the progesterone receptor (PR). In one embodiment, further comprising contacting said tissue sample with additional different probes prior to step d), each of said additional different probes conjugated to a different non-rare-earth-metal mass-tag, said mass-tag comprising a plurality of amino acids and wherein the mass of each mass-tag is different. In one embodiment, wherein the number of said probes is 10 or more. In one embodiment, wherein a subset of said additional different probes is capable of binding to i) human epidermal growth factor receptor 2 (HER2) and ii) Ki67. In one embodiment, wherein a subset of said additional different probes is capable of binding to T-cell biomarkers i) CD3 (T-cells), ii) CD4 (T-helper), iii) CD8 (cytotoxic T-cells), and iv) CD45RO (memory T-cells). In one embodiment, wherein 1 of said additional different probes is capable of binding to the B-cell biomarker CD20. In one embodiment, wherein 1 of said additional different probes is capable of binding to the macrophage biomarker CD68. In one embodiment, wherein 1 of said additional different probes is capable of binding to an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a multiplex method for co-detecting different types of tumor infiltrating immune cells in tumor tissue on a single slide, said method comprising: a) providing a tumor tissue sample mounted on a single slide; b) contacting said tumor tissue sample with a first probe which is capable of binding to a first tumor infiltrating immune cell type, said probe conjugated to a first non-rare-earth-metal mass-tag, said mass-tag comprising a plurality of amino acids; c) contacting said tumor tissue sample with a second probe which is capable of binding to a second tumor infiltrating immune cell type, said probe conjugated to a second non-rare-earth-metal mass-tag, said mass-tag comprising a second plurality of amino acids, wherein said second tumor infiltrating immune cell is a different type from said first tumor infiltrating immune cell and said second plurality of amino acids has a different mass from said first plurality of amino acids, and wherein steps b) and c) together create a probed tumor tissue sample; and d) detecting, using mass spectrometric imaging, at least 1 of said mass-tags, or fragments thereof, as molecular ions. In one embodiment, wherein said tumor tissue sample is a thin tissue section. In one embodiment, wherein said tumor tissue sample was frozen and thin-sectioned before mounting on said slide. In one embodiment, where said tumor tissue sample was formalin-fixed and thin-sectioned before mounting on said slide. In one embodiment, wherein said tumor tissue sample was formalin-fixed, paraffin embedded and thin-sectioned before mounting on said slide. In one embodiment, wherein said slide comprises gold. In one embodiment, wherein said slide is a glass slide with a gold layer. In one embodiment, wherein said tumor tissue sample is from a breast tumor. In one embodiment, wherein said probes conjugated to a non-rare-earth-metal mass-tag have the following general structure, wherein X is a spacer:

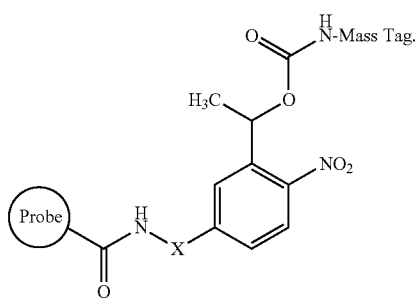

In one embodiment, wherein at least 1 of said probes comprises a fluorescent moiety in addition to said non-rare-earth-metal mass-tag. In one embodiment, wherein said probes are selected from the group consisting of proteins and nucleic acids. In one embodiment, wherein at least 1 of said probes is an antibody. In one embodiment, wherein said antibody is selected from the group consisting of recombinant antibodies, nanobodies, single-chain fragment variable (scFv) antibodies, single domain antibodies, and VHH single domain antibodies. In one embodiment, wherein at least 1 of said probes is selected from the group consisting of affibodies, receptors and ligands. In one embodiment, wherein at least 1 of said probes is an aptamer. In one embodiment, wherein at least 1 of said probes is capable of binding to RNA targets. In one embodiment, wherein at least 1 of said probes is capable of binding to miRNA targets. In one embodiment, wherein at least 1 of said probes is capable of binding to DNA targets. In one embodiment, wherein said non-rare-earth-metal mass-tags are photocleavable. In one embodiment, wherein the method further comprises illuminating said non-rare-earth-metal mass-tags with light so as to photocleave at least a portion of said non-rare-earth-metal mass-tags before step d). In one embodiment, wherein steps b) and c) are performed simultaneously to create said probed tumor tissue sample. In one embodiment, further comprising performing, after step a) but before step b), mass spectrometric imaging on said tumor tissue sample. In one embodiment, wherein a matrix compound is applied to said probed tumor tissue sample before step d). In one embodiment, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid). In one embodiment, wherein said matrix compound is applied by sublimation. In one embodiment, wherein said probed tumor tissue sample is subjected to a treatment after the steps of applying said matrix compound to said probed tumor tissue sample, said treatment comprising matrix recrystallization. In one embodiment, wherein said tumor tissue sample is subjected to a treatment after said paraffin embedding and before step b), said treatment comprising deparaffinization. In one embodiment, wherein said deparaffinization is performed with xylene. In one embodiment, wherein the tumor tissue sample is further subjected to a treatment, said treatment comprising rehydration. In one embodiment, wherein said rehydration is performed with a series of ethanol/water mixtures and aqueous saline buffers. In one embodiment, wherein the tumor tissue sample is further subjected to a treatment, said treatment comprising antigen retrieval. In one embodiment, wherein said antigen retrieval is performed by heating in citrate buffer, pH 6. In one embodiment, wherein said antigen retrieval is performed with the use of formic acid. In one embodiment, wherein said first probe is capable of binding to CD4 and said second probe is capable of binding to CD8. In one embodiment, further comprising contacting said tumor tissue sample with additional different probes prior to step d), each of said additional different probes conjugated to a different non-rare-earth-metal mass-tag, said mass-tag comprising a plurality of amino acids and wherein the mass of each mass-tag is different. In one embodiment, wherein the number of said probes is 10 or more. In one embodiment, wherein 1 of said additional different probes is capable of binding to the T-cell biomarker CD3. In one embodiment, wherein 1 of said additional different probes is capable of binding to the macrophage biomarker CD68. In one embodiment, wherein 1 of said additional different probes is capable of binding to an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a composition comprising a probe conjugated to i) a mass-tag through a photocleavable linker, and ii) a fluorophore. In one embodiment, wherein said probe is capable of binding to a biomarker selected from the group consisting of i) the estrogen receptor (ER), ii) the progesterone receptor (PR), iii) human epidermal growth factor receptor 2 (HER2), and iv) Ki67. In one embodiment, wherein said probe is capable of binding to a T-cell biomarker selected from the group consisting of i) CD3 (T-cells), ii) CD4 (T-helper), iii) CD8 (cytotoxic T-cells), and iv) CD45RO (memory T-cells). In one embodiment, wherein said probe is capable of binding to an immune checkpoint molecule. In one embodiment, wherein said immune checkpoint molecule is selected from the group consisting of PD-1, PD-L1, PD-L2, CTLA-4, OX40, CD27, and TIM3.

In one embodiment, the present invention provides a multiplex method of detecting different immune checkpoint molecules in tumor tissue on a single slide, said method comprising: a) providing a tumor tissue sample on a single slide; b) contacting said tumor tissue sample with a mixture comprising a plurality of different probes, each different probe capable of binding to a different immune checkpoint molecule, each of said probes conjugated to a non-rare-earth-metal mass-tag, said mass-tag comprising a plurality of amino acids; and c) detecting, using mass spectrometric imaging, at least 1 of said mass-tags, or fragments thereof, as molecular ions. In one embodiment, wherein 1 of said plurality of different probes is capable of binding to an immune checkpoint molecule selected from the group consisting of PD-1, PD-L1, PDL2, CTLA-4, OX40, CD27, and TIM3. In one embodiment, wherein said tumor tissue sample comprises a biopsy from a human patient. In one embodiment, wherein said tumor tissue biopsy binds to a mass-tagged probe for PD-L1. In one embodiment, further comprising treating said human patient with an immune checkpoint inhibitor specific for PD-L1. In one embodiment, wherein said checkpoint inhibitor specific for PD-L1 is selected from the group consisting of atezolizumab, avelumab, and durvalumab. In one embodiment, wherein at least 1 of said probes is an antibody. In one embodiment, wherein said antibody is selected from the group consisting of recombinant antibodies, nanobodies, single-chain fragment variable (scFv) antibodies, single domain antibodies, and VHH single domain antibodies.

In one embodiment, the present invention provides a multiplex method for co-detecting 3 or more (and more preferably 5 or more) different types of carbohydrates in a tissue sample, said method comprising: a) providing a tissue sample; b) contacting said tissue sample with 3 or more (and more preferably 5 or more) different carbohydrate-binding proteins to effect binding of said carbohydrate-binding proteins to said tissue sample to create a probed tissue sample, each of said carbohydrate-binding proteins reactive with a different carbohydrate, and each of said carbohydrate-binding proteins conjugated to a unique mass-tag; and c) detecting, using mass spectrometric imaging of said probed tissue sample, said mass-tags, or fragments thereof, as molecular ions. In one embodiment, wherein said tissue sample is a thin tissue section. In one embodiment, wherein said tissue sample was frozen and thin-sectioned before step b). In one embodiment, where said tissue sample was formalin-fixed and thin-sectioned before step b). In one embodiment, wherein said tissue sample was formalin-fixed, paraffin embedded and thin-sectioned before step b). In one embodiment, wherein said tissue sample is mounted on a slide before step b). In one embodiment, wherein said slide comprises gold. In one embodiment, wherein said slide is a glass slide with a gold layer. In one embodiment, wherein said tissue sample is mounted on a slide before step c). In one embodiment, wherein said slide comprises gold. In one embodiment, wherein said slide is a glass slide with a gold layer. In one embodiment, wherein said tissue sample is from a tumor. In one embodiment, wherein said tumor is a breast tumor. In one embodiment, wherein said carbohydrate-binding proteins conjugated to a mass-tag have the following general structure, wherein X is a spacer and CBP is a carbohydrate-binding protein:

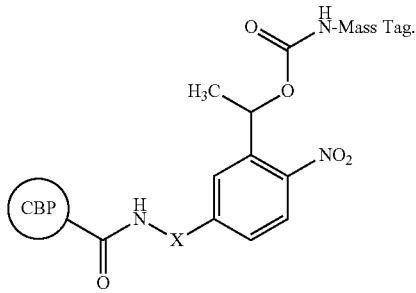

In one embodiment, wherein said 3 or more (and more preferably 5 or more) carbohydrate-binding proteins are in a mixture and said tissue sample in step b) is contacted with said mixture to create said probed tissue sample. In one embodiment, wherein said mixture additionally contains 1 or more probes, each of said probes reactive with a different target within said tissue, and each of said probes conjugated to a unique mass-tag. In one embodiment, wherein at least 1 of said 5 or more carbohydrate-binding proteins comprises a fluorescent moiety in addition to said mass-tag. In one embodiment, wherein at least 1 of said 5 or more carbohydrate-binding proteins is a lectin. In one embodiment, wherein said mass-tags are non-rare-earth-metal mass-tags. In one embodiment, wherein said mass-tags comprise a plurality of amino acids. In one embodiment, wherein said mass-tags are photocleavable. In one embodiment, wherein the method further comprises illuminating said mass-tags with light so as to photocleave at least a portion of said mass-tags before step c).

In one embodiment, the present invention provides a multi-omic method for detecting different biomolecules, or fragments thereof, in the same tissue sample, said method comprising: a) providing a tissue sample; b) applying a digesting agent to at least a portion of said tissue sample; c) performing mass spectrometric imaging on said tissue sample; d) contacting said tissue sample with 3 or more (and more preferably 5 or more) different probes to effect binding of said probes to said tissue sample to create a probed tissue sample, each of said probes reactive with a different target within said tissue sample, and each of said probes conjugated to a unique mass-tag; and e) detecting, using mass spectrometric imaging of said probed tissue sample, said mass-tags, or fragments thereof, as molecular ions. In one embodiment, wherein said digesting agent is an enzyme. In one embodiment, wherein said enzyme is selected from the group consisting of nucleases, proteases, kinases, phosphatases and glycosidases. In one embodiment, wherein said digesting agent is a chemical. In one embodiment, wherein said chemical is selected from the group consisting of cyanogen bromide (CNBr) and hydroxylamine. In one embodiment, wherein a mixture of different digesting agents is instead applied at step b). In one embodiment, wherein steps b) and c) are instead performed, respectively, after step e). In one embodiment, wherein said tissue sample is further subjected to a treatment after step e), before said step of applying said digesting agent to said tissue sample, said treatment comprising detachment of said bound probes from said tissue sample. In one embodiment, wherein said detachment of said bound probes comprises subjecting said tissue sample to a denaturing treatment. In one embodiment, wherein said denaturing treatment is selected from the group consisting of chaotropic agents, solutions of pH ≤5, solutions of pH ≥10, reducing agents, oxidizing agents, heat, organic solvents, and detergents. In one embodiment, wherein said tissue sample is a thin tissue section. In one embodiment, wherein said tissue sample was frozen and thin-sectioned before step b). In one embodiment, where said tissue sample was formalin-fixed and thin-sectioned before step b). In one embodiment, wherein said tissue sample was formalin-fixed, paraffin embedded and thin-sectioned before step b). In one embodiment, wherein said tissue sample is mounted on a slide before step b). In one embodiment, wherein said slide comprises gold. In one embodiment, wherein said slide is a glass slide with a gold layer. In one embodiment, wherein said tissue sample is from a tumor. In one embodiment, wherein said tumor is a breast tumor. In one embodiment, wherein said probes conjugated to a mass-tag have the following general structure, wherein X is a spacer:

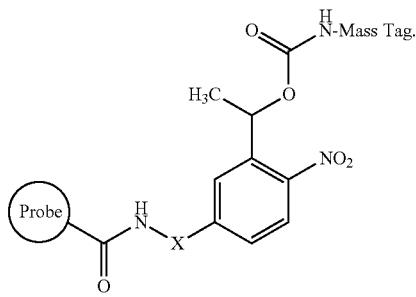

wherein said probes are selected from the group consisting of proteins and nucleic acids. In one embodiment, wherein at least 1 of said protein probes is selected from the group consisting of antibodies, recombinant antibodies, affibodies, nanobodies, single-chain fragment variable (scFv) antibodies, single domain antibodies, VHH single domain antibodies, receptors, ligands, and carbohydrate-binding proteins. In one embodiment, wherein at least 1 of said nucleic acid probes is an aptamer. In one embodiment, wherein at least 1 of said nucleic acid probes binds to RNA targets. In one embodiment, wherein at least 1 of said nucleic acid probes binds to miRNA targets. In one embodiment, wherein at least 1 of said nucleic acid probes binds to DNA targets. In one embodiment, wherein said mass-tags are non-rare-earth-metal mass-tags. In one embodiment, wherein said mass-tags comprise a plurality of amino acids. In one embodiment, wherein said mass-tags are photocleavable. In one embodiment, wherein the method further comprises illuminating said mass-tags with light so as to photocleave at least a portion of said mass-tags before step e).

In one embodiment, the present invention provides a composition comprising the general chemical structure:

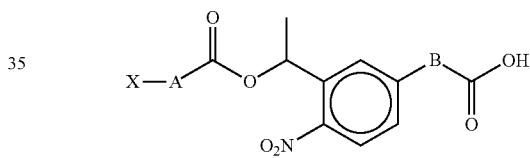

wherein A is a first linker unit (also called a first spacer unit) comprising at least 1 amine, X is a protecting group covalently bonded to the nitrogen atom of said amine, and B is a second linker unit (also called a second spacer unit). In one embodiment, wherein said protected amine is an Fmoc-protected amine. In one embodiment, the composition has the following chemical structure:

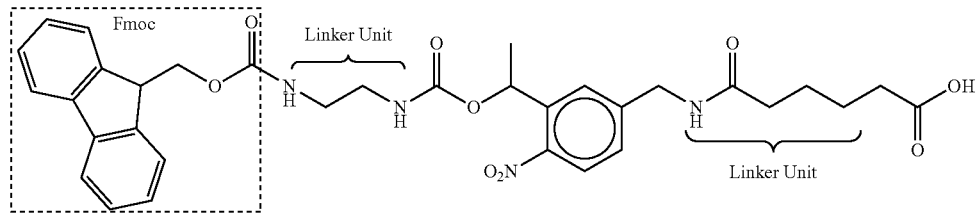

In one embodiment, wherein said 3 or more (and more preferably 5 or more) probes are in a mixture and said tissue sample in step d) is contacted with said mixture to create said probed tissue sample. In one embodiment, wherein at least 1 of said 5 or more probes comprises a fluorescent moiety in addition to said mass-tag. In one embodiment, In one embodiment, said first and/or second linker (or first and/or second spacer unit) comprises polyethylene glycol. In one embodiment, said first and/or second linker (or first and/or second spacer unit) comprises 2,2'-(ethylenedioxy)-bis-(ethylamine) chemical linker.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 2A) The preferred peptide-based PC-MTs. Curved lines are the peptide-based mass units, ovals are the photocleavable linker (PC-Linker) and "NHS" is the probe-reactive moiety, shown in this example as a primary amine reactive NHS-ester leaving group. Note that the peptide-based PC-MTs are N-terminal blocked/protected (e.g., acetylated—not depicted) to prevent self-reaction/polymerization of the PC-MTs in the case where the probe-reactive moiety is primary amine reactive (and internal primary amines such as the ε-amine on lysine amino acids are either avoided or also protected/blocked). Mass-coding of the mass units is achieved using different amino acids (or isotopes, analogs, derivatives or modifications thereof, including natural and unnatural amino acids). Note that a fluorophore (starburst with "F") is optionally included on the PC-MT which can assist in method development by allowing direct comparison of mass spectrometric imaging (MSI) results to conventional fluorescence imaging. (FIG. 2B) PC-MTs are attached to probes such as antibodies or amine-modified nucleic acids for example, to create the PC-MT-Probes. This is typically achieved in a 1-step chemical reaction between the probe-reactive moiety of the PC-MT (e.g., NHS-ester leaving group which is lost in this case) and the probe, with or without purification of the PC-MT-Probe afterwards. (FIG. 2C) PC-MT-Probes are then used to "stain" tissues (i.e., PC-MT-Probes are bound to targets in tissues) in a procedure analogous to conventional immunohistochemistry (IHC) or in situ hybridization (ISH), followed by MSI. Photocleavage, which liberates the mass reporters, can be achieved by exogenous UV treatment before MSI or can be achieved in-line with matrix-assisted laser desorption ionization MSI (MALDI-MSI) using the instrument's laser beam. Note that the mass reporters in some embodiments can contain portions of the photocleaved PC-Linker attached.

FIG. 5A-B. Example Methods of PC-MT Signal Amplification. (FIG. 5A) Multiple PC-MTs for example with NHS-ester based probe-reactive moieties can be conjugated to the surface of amine-terminated gold nanoparticles ("NP"; shown) or dendrimers (not shown). The dendrimers or NPs can then be conjugated to probes (an "Antibody Probe" is depicted). (FIG. 5B) For nucleic acid probes, primary amine modified nucleic acid sequences, which are preferably not part of the "Target Binding" sequence (i.e., target hybridization sequence), can be used to facilitate attachment of many PC-MTs per each probe molecule (e.g., again where the probe-reactive moiety is primary amine reactive).

(FIG. 7A) Color-coded 5-plex overlaid MALDI-MSI "mass-image" of synapsin (blue), MAP-2 (orange), NeuN (green), myelin (red), and Glut-1 (cyan). The different colors pertain to the different m/z values of the monoisotopic PC-MT mass reporter mass-spectral peaks. Among other structures, the hippocampus (*) and cerebellum (⸸) are observed. (FIG. 7B) Colorized immunofluorescence overlay of the cerebellum for synapsin (blue), NeuN (green) and myelin (red). Immunofluorescence was performed in "single-plex" mode on adjacent tissue sections and images overlaid. (FIG. 7C) A standalone MALDI-MS mass-image (sub-region) of the less prominent Glut-1 biomarker is shown (magenta in this case), which detects primarily blood capillaries (cross-sections) of the brain. (FIG. 7D) Corresponding immunofluorescence of Glut-1 (green in this case). (FIG. 7E) Color-coded overlaid MALDI-MS spectra are shown for selected pixels from the 5-plex mass-image (from the pixels denoted with color-coded arrows in panel a.). Black arrows in the spectra denote the PC-MT mass reporter m/z peaks. Note that while 1 Da separated natural isotopes of the peptide PC-MTs are easily resolved by the MALDI-MS, they are not visible in the spectra provided due to the compact X-axis scaling.

(FIG. 9A) Direct untargeted MALDI-MSI on an unfixed fresh-frozen mouse brain sagittal tissue section was first performed. Three well-known lipid species (sulfatide, m/z 888.7; phosphatidylinositol, m/z 885.4; and phosphatidylethanolamine, m/z 790.5) are shown in the colorized MALDI-MS image (red, green and blue, respectively). (FIG. 9B-FIG. 9C) The same tissue section was then processed for a second round of MALDI-MSI. To do so, the matrix was washed away, the tissue fixed and targeted multiplex MALDI-MSI of macromolecular antigens using PC-MT-Abs was performed. For demonstration purposes, images of selected biomolecules from the first and second rounds of MALDI-MSI were overlaid. (FIG. 9B) Sulfatide (red) from the first round of MALDI-MSI (direct small molecule detection) is overlaid with the image of NeuN (green) from the second round of MALDI-MSI (multiplex MIHC). (FIG. 9C) Sulfatide (red) from the first round of MALDI-MSI (direct small molecule detection) is overlaid with the image of myelin basic protein (green) from the second round of MALDI-MSI (multiplex MIHC). (FIG. 9D) Example overlaid spectra from the first round of MALDI-MSI (direct small molecule detection) are shown, color-coded to match the image in FIG. 9A (the three lipid masses are indicated). The color-coded arrows in FIG. 9A indicate the regions from which the MALDI-MS spectra were derived.

(FIG. 10A) Two configurations of attachment of the mass unit ultimately to the phenyl ring of the PC-Nucleus are shown (depicted in this case after photocleavage—see FIG. 3 Step 2 for an example of Configuration 1 before photocleavage). In this example, photocleavable peptides were used and were ultimately attached to a surface as shown (analogous to a PC-MT probe attached ultimately to the surface of a tissue). In preferred Configuration 1, the photocleaved phenyl ring (denoted with *) of the PC-Nucleus does not remain attached to the photocleaved mass reporter which is measured by mass spectrometry (MS), while in Configuration 2, it does. (FIG. 10B) Resultant overlaid mass spectra of the mass reporters after photocleavage from the surface for the two configurations. The expected monoisotopic peaks of the mass reporters are labeled with their respective m/z values for both configurations.

(FIG. 11A) Example MALDI-MSI mass-image of a bead-array, whereby beads were double-labeled with a PC-MT (red) and PC-MT-L (green) both comprised of mass unit 1 (but mass reporters are distinguishable by a difference of 43 m/z due to only the PC-MT leaving a small residual portion of the photocleaved PC-Linker attached to the mass reporter). (FIG. 11B-FIG. 11I) 4 different bead species were made, each double-labeled with a PC-MT and PC-MT-L having the same mass unit (mass units 1-4 from Table 1). 4 separate bead-arrays were formed from each of these bead species (1 bead-array per bead species) and each bead-array subjected to pre-UV illumination for 5 min for photocleavage. Another 4 bead-arrays were formed and subjected to pre-UV illumination for 25 min. The 8 separate bead-arrays total were then subjected to MALDI-MSI. Representative spectra are shown from a single pixel from a bead from each of the bead-arrays (each of the 8 spectra contains peaks corresponding to the mass reporters from both a PC-MT and PC-MT-L comprised of the same mass unit). (FIG. 11J) An anti-myelin antibody probe was double-labeled with a PC-MT and PC-MT-L both comprised of mass unit 1. The probe was used to immunostain mouse brain tissue sections followed by MALDI-MSI. The color-coded mass-image of the tissue is shown. The PC-MT is color-coded red and the PC-MT-L green. 0, 5 and 25 min pre-UV conditions were tested, whereby pre-UV is performed just before matrix application and before the MALDI-MSI analysis. In the case of 0 min pre-UV, photocleavage can only occur during the MALDI-MSI analysis by the instrument's laser beam. Spectra from representative pixels are shown in FIG. 11K and FIG. 11L.

FIG. 12. Fluorescent PC-MTs for Mass Spectrometry Based Immunohistochemistry. The "Fluorescence" panel shows fluorescence images (yellow) of 3 sagittal mouse brain tissue sections probed with the fluorescent Anti-NeuN Fluor-PC-MT1, the non-fluorescent Anti-NeuN PC-MT7 and the negative control fluorescent Anti-Cas9 Fluor-PC-MT1, respectively. The "MALDI-MSI" panel shows MALDI-MS images of the same probed tissue sections (red for mass reporter from Fluor-PC-MT1 and green for mass reporter from PC-MT7). The blue arrows denote the hippocampus and the white arrows the cerebellum. The inset spectra are from representative single pixels within the hippocampus and the corresponding mass reporter peaks, when detected, are denoted with black arrows.

(FIG. 13A) MALDI-MSI mass-image of Bead Pool 1. Mass spectral peak intensities of the various PC-MTs are colorized as indicated above the image. Beads having Bead ID-Tags 9, 10 and 15 were loaded with rAnti-MBP1, Anti-MBP1 and rAnti-AB2, respectively (note, numbers indicate mass units from Table 1 in a particular PC-MT). (FIG. 13B) 3 Overlaid spectra taken from 3 single pixels within the 3 beads circled in (FIG. 13A). Spectra are color-coded according to the bead colors observed in (FIG. 13A). (FIG. 13C) MALDI-MSI mass-image of Bead Pool 2. Mass spectral peak intensities of the various PC-MTs are colorized as indicated above the image. Beads having Bead ID-Tags 9, 10 and 15 were loaded with rAnti-NeuN7, Anti-NeuN7 and rAnti-AB2, respectively (note, numbers indicate mass units from Table 1 in a particular PC-MT). (FIG. 13D) 3 Overlaid spectra taken from 3 single pixels within the 3 beads circled in (FIG. 13C). Spectra are color-coded according to the bead colors observed in (FIG. 13C). (FIG. 13E) Separately, mouse brain sagittal tissue sections were stained with Anti-NeuN7 and rAnti-NeuN7 and subjected to MALDI-MSI. PC-MT7 from the antibodies is colorized as green in the images. White arrow indicates the cerebellum, blue arrow the hippocampus and yellow arrow the speckled nuclear staining pattern. In the spectra provided, chosen from the strongest pixels in the hippocampus of both images, the red trace shows PC-MT7 from the "Recombinant" rAnti-NeuN7 antibody probe and the blue trace shows PC-MT7 from the "Regular" non-recombinant Anti-NeuN7 antibody probe.

(FIG. 14A) CK immunofluorescence image of the whole tonsil tissue section taken at 5 micron resolution using a GenePix 4200A fluorescence microarray scanner. (FIG. 14B) MALDI-MS image of the same tissue section showing an intensity map of the monoisotopic m/z value for the PC-MT from the CK antibody (all MALDI-MS images are 10 micron spatial resolution). (FIG. 14C) Multi-color MALDI-MS image overlay of selected biomarkers from the whole tissue section which show differential structural patterns. Color-coding is indicated in the key underneath the image. (FIG. 14D) Individual MALDI-MS images of all 12 biomarkers shown as gradient color for a representative sub-region of the tissue section (biomarker identities indicated by the labels). The "Blank" is also shown which is an adjacent tissue section stained with an isotype control IgG bearing a PC-MT (same PC-MT as CD3). The gradient color scale is shown at the bottom. For comparison, the display scale of all biomarkers is set to a full intensity threshold of 25 (arbitrary peak intensity units) and a minimum display intensity of 2.5, except CK, CD20, and Ki67 which produced exceptionally strong signals and were therefore set to 50 and 5, respectively.

(FIG. 15A) Multi-color MALDI-MS image overlay of a breast cancer tissue section showing an intensity map of the monoisotopic m/z values for the PC-MTs from selected antibodies which show differential structural patterns (all MALDI-MS images are 10 micron spatial resolution). Color-coding is indicated in the key above the image. The clinical annotations for this biospecimen according to the pathology report provided by the biospecimen vendor (OriGene) were as follows: adenocarcinoma of breast (ductal), TNM staging of pT1cpN3apMX, minimum stage grouping IIIC, 75% tumor, and PR−/ER−/HER2+ according to traditional IHC. (FIG. 15B) Individual MALDI-MS images of all 12 biomarkers shown as gradient color for the entire tissue section (biomarker identities indicated by the labels). The "Blank" is also shown which is an adjacent tissue section stained with an isotype control IgG bearing a PC-MT (same PC-MT as CD3). The gradient color scale is also shown. For comparison, the display scale of all biomarkers is set to a full intensity threshold of 20 (arbitrary peak intensity units) and a minimum display intensity of 2, except CK, CD3, CD4, CD68, and Ki67 which produced exceptionally strong signals and were therefore set to 50 and 5, respectively. (FIG. 15C) Multi-color MALDI-MS image overlay of the same breast cancer tissue section, in this case for simplicity showing only CK, HER2 and ER (color-coding above image) to allow visual discrimination of the relative distribution of these three important biomarkers. (FIG. 15D) Multi-color MALDI-MS image overlay (top panel; color-coding below image) and individual MALDI-MS images (gradient scale; bottom panels) of selected biomarkers on a different breast cancer tissue section. In this case the clinical annotations for this biospecimen according to the pathology report provided by the biospecimen vendor (OriGene) were as follows: adenocarcinoma of breast, ductal, lobular, metastatic. TNM staging of T2N2aMX, minimum stage grouping IIIA, 95% tumor, and PR+/ER+/HER2− according to traditional IHC (i.e., the PR/ER/HER2 profile is the inverse of the previous tissue). For comparison, the display scale of the gradient color images is set to a full intensity threshold of 20 (arbitrary peak intensity units) and a minimum display intensity of 2, except CK which produced an exceptionally strong signal and was therefore set to 100 and 10, respectively.

FIG. 16 shows only common essential elements of the protocols.

FIG. 18. Comparison of MIHC Results for Anti-NeuN Antibody Detection on Mouse Brain FFPE Tissue Sections Using DHB Matrix Sublimation With and Without Matrix Recrystallization.

(FIG. 19A & FIG. 19B) Colorized mass-images of PC-MTs corresponding to 3 lectins, PHA-E4 (red), PNA (green) and WGA (blue). (FIG. 19B) Competitive inhibition (blocking) to show specificity of lectin binding (of WGA in this case). The mixture of PC-MT lectin probes was pre-incubated with the soluble sugar N,N',N"-Triacetylchitotriose (TCT) which specifically binds WGA (and the soluble sugar remained present during the tissue staining/probing step). As a control, the TCT blocking was omitted. (FIG. 19C) An overall average spectrum from the entirety of each mass-image in panel b. was taken. The monoisotopic PC-MT peaks for three lectins are labeled (WGA, PNA and PHA-E4). The orange trace is the tissue processed with TCT blocking and the purple trace is the tissue processed without TCT blocking. 70% reduction in peak intensity of the WGA PC-MT is observed with TCT blocking while the other 2 lectins are unchanged.

(FIG. 20A) MSI-1. Initial direct label-free MALDI-MSI of endogenous lipids (see key in image for which example lipids are displayed). (FIG. 20B) MSI-2. Subsequent MIHC, showing selected antibody PC-MTs (see key in image for which antibody PC-MTs are displayed). (FIG. 20C) Merge. Image merge of selected analytes from the MSI-1 and MSI-2 (see key in image for which analytes). The expected co-localization of the lipid sulfatide (ST) with myelin but not between ST and NeuN is explained in Example 4.

(FIG. 21B) The ratio of the photo-released PC-MT to control peptide monoisotopic peak intensities was taken and plotted as a function of the PC-MT-Ab concentration that was added to the Protein G beads.

Figure 1:
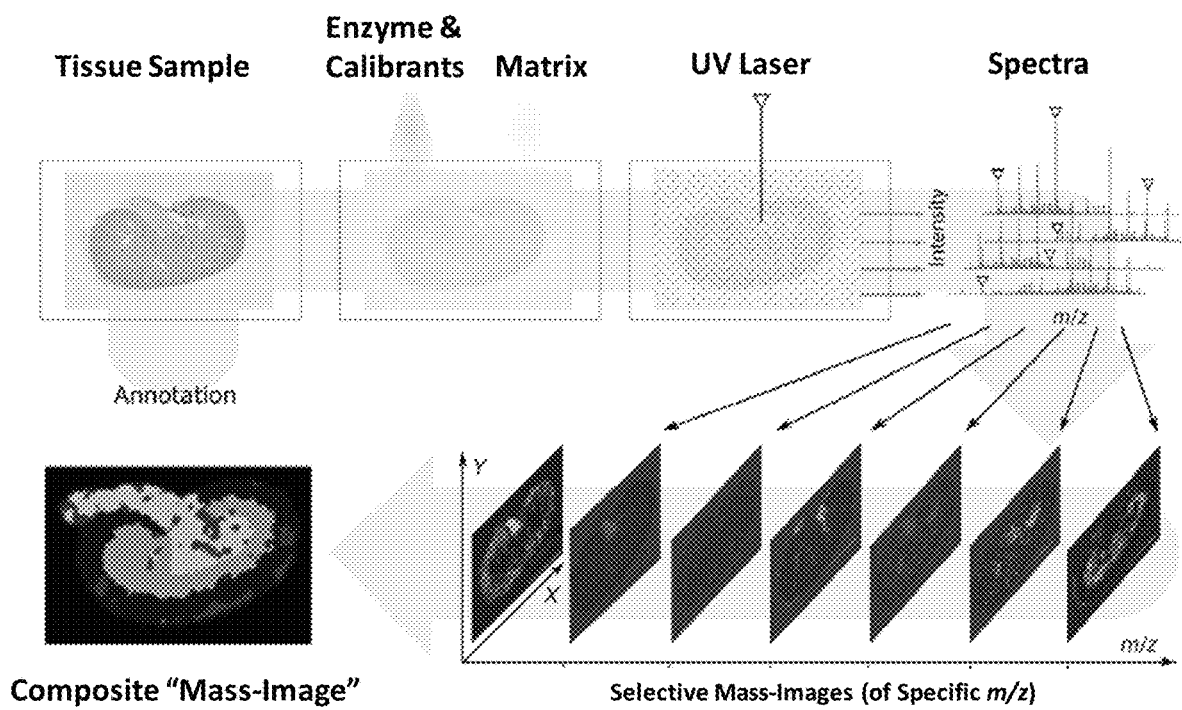
FIG. 1. Bottom-Up Application of Mass Spectrometric Imaging (MSI) for Multiplex Direct Label-Free Mapping of Analytes in Tissue Samples. Adapted from [Arentz, Mittal et al. (2017) Adv Cancer Res 134: 27-66]. This existing approach is multiplexed but inherently untargeted as it does not use labeled probes such as photocleavable mass-tagged probes (PC-MT-Probes) and therefore requires complex methods of identification of the analytes detected, which in some cases also degrades the spatial resolution of the image (e.g., since in situ tissue proteolysis is required for protein detection and identification).

Table 1. Mass Unit Sequences for PC-MTs and Mass Reporter Masses (See FIG. 3 for Example PC-MT Structure).

Table 1.1. Amino Acid Isotopes.

DESCRIPTION OF THE INVENTION

This invention relates to immunohistochemistry (IHC) and in situ hybridization (ISH) for the targeted detection and mapping of biomolecules (e.g., proteins and miRNAs) in tissues or cells for example, for research use and for clinical use such by pathologists (e.g., biomarker analyses of a resected tumor or tumor biopsy). In particular, the use of mass spectrometric imaging (MSI) as a mode to detect and map the biomolecules in tissues or cells for example. More specifically, the field of this invention relates to photocleavable mass-tag reagents which are attached to probes such as antibodies and nucleic acids and used to achieve multiplex immunohistochemistry and in situ hybridization, with MSI as the mode of detection/readout.

Current tissue imaging methods such as fluorescence IHC lack the level of multiplexity and/or multi-omics needed to unravel complex biological systems and human disease. Mass spectrometry imaging (MSI) is generally limited to untargeted analysis of small molecules and peptides and lacks the ability to target specific intact molecules such as proteins, post-translational modifications such as glycans and nucleic acids such as DNA and RNA. We have developed methods utilizing novel photocleavable peptide mass-tags (PC-MTs) for facile labeling of probes including antibodies, lectins and nucleic acids for highly multiplexed MSI of targeted macromolecules in tissues. When combined with untargeted MSI, both high multiplexity and multiomic tissue imaging is achieved on a single specimen. Combined multimodal fluorescence and MS IHC imaging is also achieved on a single tissue specimen by using dual labeled antibody probes. What is needed are novel photocleavable mass-tags (PC-MTs) and MALDI-MSI procedures which overcome these aforementioned limitations.

Here we report novel photocleavable mass-tags (PC-MTs) and MALDI-MSI procedures which overcome these aforementioned limitations. PC-MTs are modified polypeptides comprising: a mass unit, a high efficiency photocleavable linker (PC-Linker) incorporated into the peptide through the solid-phase synthesis, a spacer, and an NHS-ester probe-reactive moiety near the C-terminal. PC-MT antibody probes are produced in a 1-step reaction. The fast and efficient photo-nucleus [Olejnik, Sonar et al. (1995) Proceedings of the National Academy of Science (USA) 92: 7590-7594] used in the novel PC-Linker provides robust sensitivity in practice, allowing high-plex MSI of a wide range of biomarkers in a variety of tissues, including mouse brain (Experimental Example 2), human tonsil and breast cancer (Experimental Example 9), as shown here. Furthermore, novel dual-labeled antibodies, combining both PC-MTs and fluorophores, allowed direct correlation of MSI with conventional immunofluorescence (Experimental Example 9). Finally, the versatility of the approach is shown through the ability to perform on the same tissue section both label-free untargeted small molecule MSI (of lipids), not possible by standard IHC, and multiplex PC-MT-based targeted MSI of macromolecular biomarkers (Experimental Example 4).

This invention entails compositions as well as methods of production and use of novel photocleavable linkers (PC-Linkers), photocleavable mass-tags (PC-MTs) and photocleavable mass-tagged probes (PC-MT-Probes) which overcome the aforementioned limitations of earlier targeted mass spectrometric imaging (MSI) methods, to enable highly multiplexed MSI of targeted biomolecules in biological specimens such as tissues and cells, using probes such as antibodies and nucleic acids.

The basic design of the peptide-based PC-MTs as well as the resultant PC-MT-Probes and their use are depicted in FIG. 2.

Figure 2A:
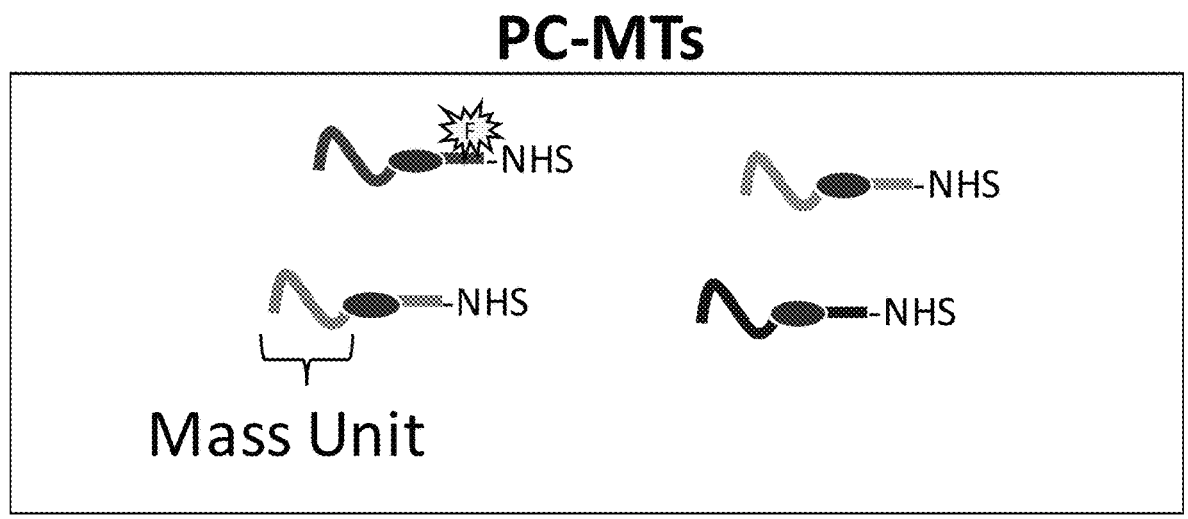
FIG. 2A-C. Basic Design & Use of the Preferred Photocleavable Mass-Tags (PC-MTs) and Photocleavable Mass-Tagged Probes (PC-MT-Probes).

As shown in FIG. 2a, the peptide-based PC-MTs comprise: i) a probe-reactive moiety, for example an amine-reactive NHS-ester leaving group is shown (N-hydroxysuccinimidyl ester); ii) an internal PC-Linker (ovals in FIG. 2a) which is introduced into the peptide chain during solid-phase peptide synthesis (SPPS); iii) a selectively detectable mass unit (curved lines in FIG. 2a) comprising amino acids or isotopes or analogs/derivatives thereof which can be incorporated using SPPS chemistry; and iv) an optional fluorophore (starburst with "F" in FIG. 2a).

Figure 2B:
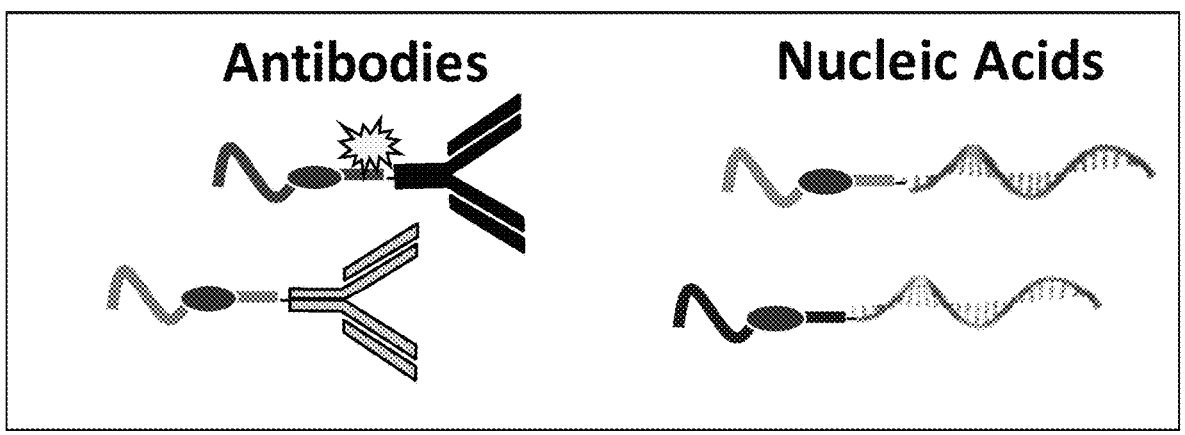

PC-MTs are covalently attached to probes by chemical reaction of the probe-reactive moiety of the PC-MT with the probe, to create the PC-MT-Probes (FIG. 2b). Probes can for example be proteins such as antibodies or nucleic acids such as amine-modified oligonucleotides or aptamers.

Figure 2C:
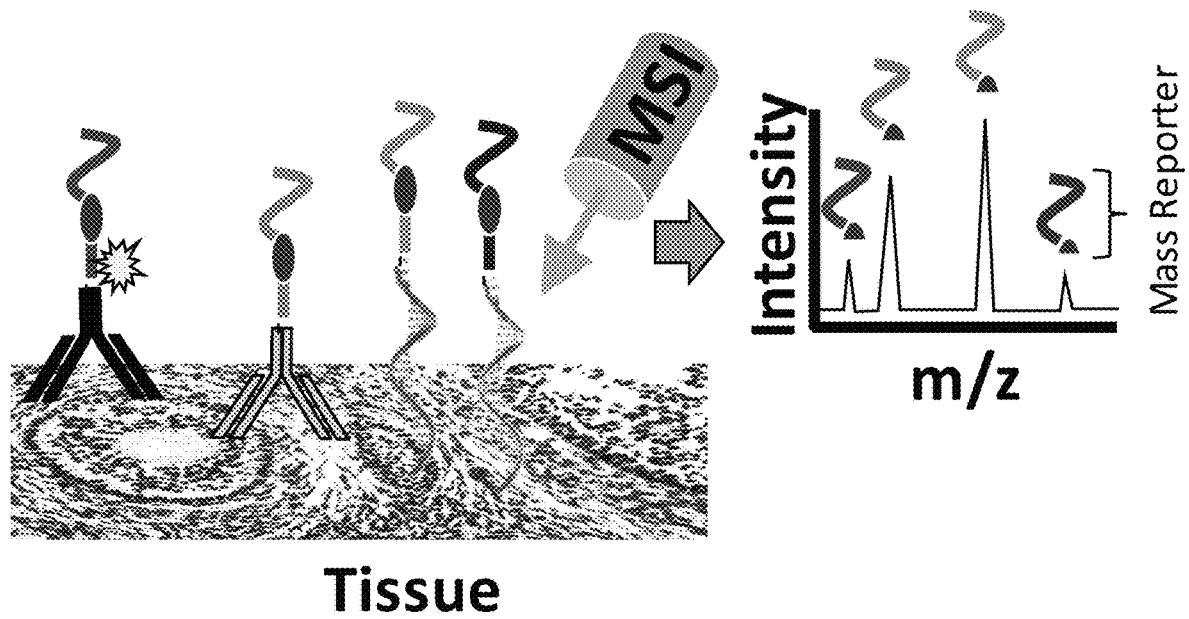

Cells/tissues are "stained" with the PC-MT-Probes (i.e., PC-MT-Probes are bound to their targets in the cells/tissues) and upon photocleavage, the mass reporter region is liberated (photo-released) for detection by MSI (FIG. 2c; note the mass reporter comprises the mass unit and in some embodiments also a portion of the photocleaved PC-Linker). Note that photocleavage may be achieved by a MALDI-MS laser beam and/or by any light, for example UV or near-UV light having a wavelength in the range of 200 nm and 400 nm.

Improvements in the PC-MTs, the resultant PC-MT-Probes and their use, are summarized as follows: i) a fast and efficient photocleavable nucleus (PC-Nucleus; see FIG. 3 Step 1) which has been previously demonstrated in a range of other applications when incorporated into other compounds such as photocleavable biotins (PC-Biotins) and photocleavable phosphoramidites (PC-Phosphoramidites) [Olejnik, Sonar et al. (1995) Proceedings of the National Academy of Science (USA) 92: 7590-7594; Olejnik (1996) Nucleic Acids Research 24: 361-366; Olejnik, Krzymanska-Olejnik et al. (1998) Nucleic Acids Res 26: 3572-6; Martinez, Patkaniowska et al. (2002) Cell 110: 563-74; Pandori, Hobson et al. (2002) Chem Biol 9: 567-73; Mitra, Shendure et al. (2003) Anal Biochem 320: 55-65; Lim and Rothschild (2008) Anal Biochem 383: 103-115; Lim, Liu et al. (2014) Rapid communications in mass spectrometry: RCM 28: 49-62; Zhou, Liu et al. (2016) Sci Rep 6: 26125] [see also U.S. Pat. Nos. 5,643,722; 5,986,076; 6,218,530; 8,906,700; and 10,060,912 which are hereby incorporated by reference]; ii) a novel Fmoc-protected photocleavable linker (Fmoc-PC-Linker; see FIG. 3) comprising said PC-Nucleus and which can be incorporated into a peptide chain using standard Fmoc-based SPPS chemistry (see FIG. 3); iii) facile 1-step probe labeling using the probe-reactive moiety of the PC-MT (e.g., an NHS-ester probe-reactive moiety; see FIG. 3 Steps 1-2); iv) a built-in optional fluorescent label on the PC-MT (see FIG. 2a) to assist in method development by allowing conventional fluorescence imaging in addition to MSI; and v) the ability to perform untargeted label-free small molecule MSI and multiplex PC-MT-based targeted MSI of macromolecules on the same tissue section (see Experimental Example 4).

The Present Invention is not intended to be limited to tissues alone. For example, digested tissue can be used. Moreover, the compositions and methods described in the Present Invention can be applied to cells grown or deposited on surface or biofilms grown or deposited on surface. For example, there has been rapid growth in the use of MSI for rapid identification of microorganisms in clinical microbiology [(2019) Nat Commun 10: 4029; Oviano and Bou (2019) Clin Microbiol Rev 32]. Bacterial cells are grown or deposited on substrates and then MALDI-MSI performed. In an additional example, cells derived from a cancer biopsy and deposited on a surface can be analyzed using the compositions and methods described in the Present Invention. An additional example, are bacteria both of a single species or multiple species grown on a surface to form a complex heterogeneous pattern. An additional example is the MALDI-MSI of biofilms. Recent progress has been made in applying this method to Bacillus subtilis biofilms grown on agar by using a sprayer to deposit specific matrix compounds compatible with MALDI-MSI such as 2,5-dihydroxybenzoin acid solutions [Li, Comi et al. (2016) J Mass Spectrom 51: 1030-1035]. The method could also be applied to complex multicellular whole organisms deposited on a surface. For example, C. elegans is a free-living, transparent nematode, about 1 mm in length, that lives in temperate soil environments. MSI has been previously applied to C. elegans demonstrating the feasibility of applying the compositions and methods described in the Present Invention [Menger, Clendinen et al. (2015) Current Metabolomics 3: 130-137]. The compositions and methods described in the Present Invention can also be applied to subcellular or molecular assemblies that are grown or deposited on a surface including both organic and nonorganic nanostructures. Examples of MSI profiling of single cells and subcellular structures are described in a recent review by Lanni et al. [Lanni, Rubakhin et al. (2012) J Proteomics 75: 5036-5051]. Recently, subcellular resolution has been obtained with MALDI-MSI by using specialized techniques such as transmission-mode geometry [Niehaus, Soltwisch et al. (2019) Nat Methods 16: 925-931] that are compatible with the compositions and methods described in the Present Invention.

In another embodiment, the PC-MTs and PC-MT probes may be used for encoding and/or detection in microarrays and bead-arrays (e.g., U.S. Pat. Nos. 9,523,680, 9,513,285, and 10,060,912 which are hereby incorporated by reference).

DETAILED DESCRIPTION OF THE INVENTION

Photocleavable Mass-Tags (PC-MTs)

Figure 3:
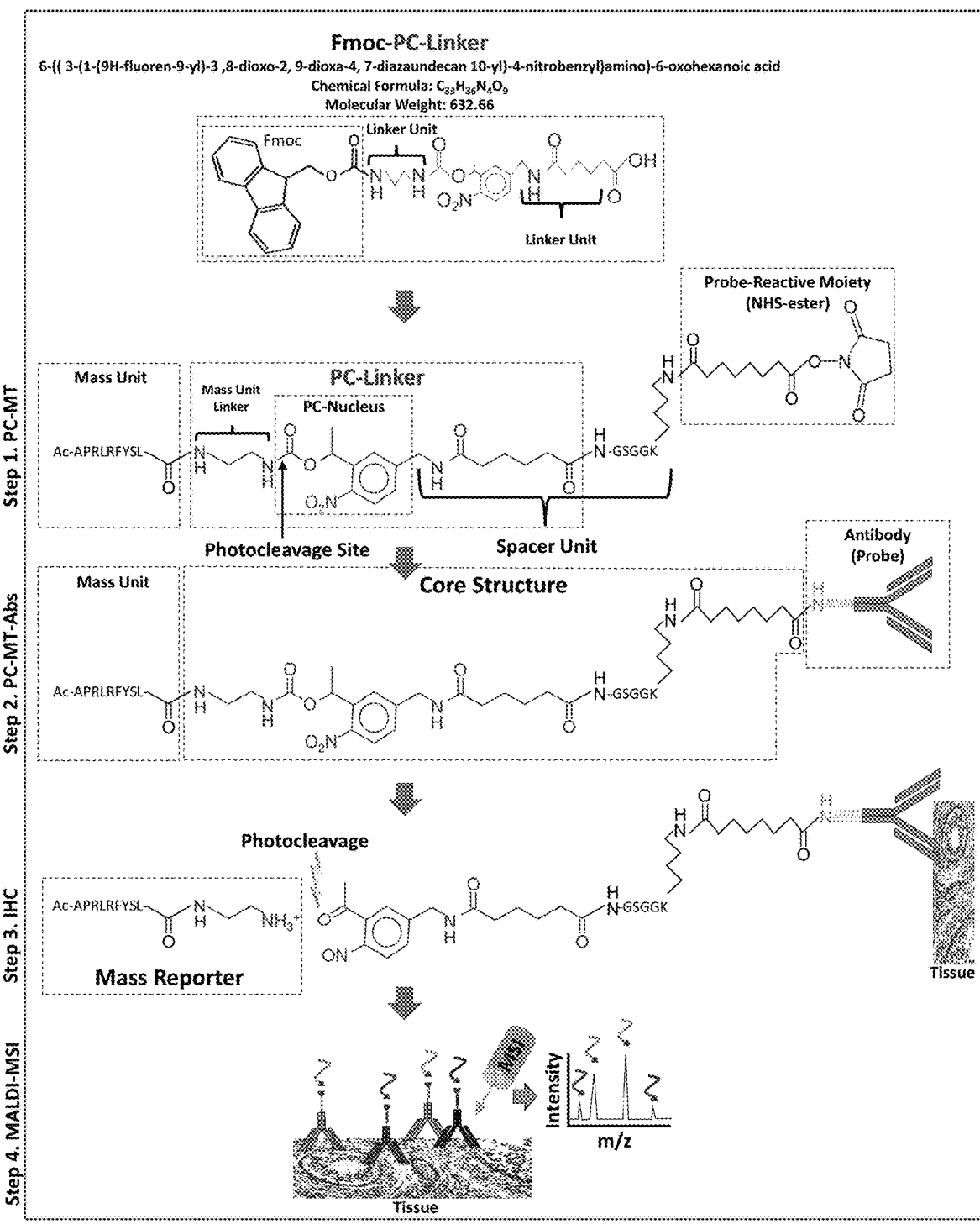
FIG. 3. Detailed Chemical Structures & Use of the Preferred Photocleavable Linker (PC-Linker), Photocleavable Mass-Tags (PC-MTs) and Photocleavable Mass-Tagged Probes (PC-MT-Probes). The Fmoc-PC-Linker is (Step 1) incorporated into a peptide-based PC-MT during conventional Fmoc-based solid-phase peptide synthesis (SPPS), along with the other amino acids (or isotopes, analogs, derivatives or modifications thereof, including natural and unnatural amino acids). The Fmoc-PC-Linker contains optional linker units which can be a variety of chemical compositions. The example PC-MT shown is oriented with the N-terminal on the left and the C-terminal on the right. "APRLRFYSL" is an example amino acid sequence of a mass unit. PC-MTs contain an optional spacer unit, shown as a portion of the PC-Linker plus the GSGGK amino acid sequence as an example. PC-MTs also contain an optional mass unit linker. The spacer unit and mass unit linker can be a variety of chemical compositions. The photocleavable nucleus (PC-Nucleus) of the PC-Linker is a fast and efficient 1-(2-nitrophenyl)-ethyl based moiety. The probe-reactive moiety (e.g., shown as an NHS-ester leaving group) can for example be generated on the ε-amine of an included lysine amino acid as shown (or could for example be generated on the carboxylic acid group of the C-terminal—not depicted). "Ac" is the N-terminal acetylation of the α-amine used to prevent self-reaction/polymerization of the PC-MT shown. (Step 2) the PC-MT is reacted with probes such as antibodies (shown) or amine-modified nucleic acids (not shown) to form PC-MT-Probes. In the example depicted, the NHS-ester leaving group (probe-reactive moiety) of the PC-MT reacts with primary amines on the antibody (the NHS-ester is lost and an amide bond formed). The core structure of the PC-MT-Probe is defined as the portion of the PC-MT which links the mass unit to the probe. This is typically a common structure in all PC-MT-Probe species corresponding to a common structure of all PC-MT species. (Step 3) Finally, the PC-MT-Probes are bound to targets in tissues followed by photocleavage (to liberate the mass reporter) and mass spectrometric imaging (MSI) (MSI not depicted). Note that a small residual portion of the PC-Linker (the mass unit linker) remains as part of the photocleaved mass reporter in this example, generating a primary amine group in this example which may assist with ionization in positive mode MSI.

The chemical structure of the preferred Fmoc-protected photocleavable linker (Fmoc-PC-Linker) is shown in FIG. 3 and is a key building block in the synthesis of PC-MTs. The compound minimally contains an Fmoc-protected primary amine terminal, a free carboxyl terminal and a 1-(2-nitrophenyl)-ethyl based photocleavable nucleus (PC-Nucleus) in between. Optionally, the Fmoc-PC-Linker also contains linker units as denoted in FIG. 3, which link the 1-(2-nitrophenyl)-ethyl based photocleavable nucleus to the fmoc-protected primary amine and to the carboxyl moiety. Overall, the minimal configuration of the Fmoc-PC-Linker allows incorporation of the PC-Linker into a peptide to create a photocleavable mass-tag (PC-MT) (FIG. 3 Step 1). The PC-Linker is incorporated in the same manner as the amino acids using standard Fmoc-based solid-phase peptide synthesis (SPPS), currently the preferred mode of chemical peptide synthesis [Behrendt, White et al. (2016) J Pept Sci 22: 4-27]. However, it is to be understood that other protecting groups and other methods of peptide synthesis are possible, such as Boc protecting groups and the associated peptide synthesis chemistries [Stawikowski and Fields (2012) Cun Protoc Protein Sci Chapter 18: Unit 18 1].

Figure 4:
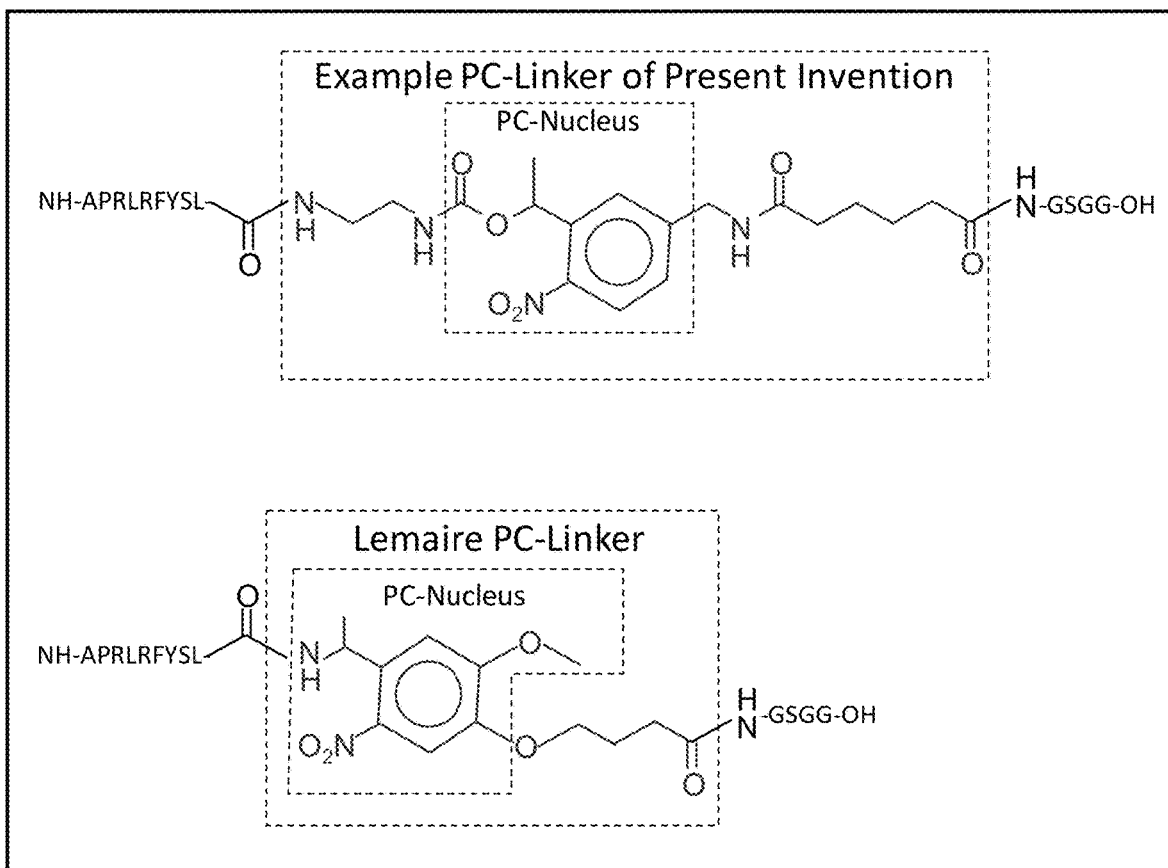
FIG. 4. Comparison of Structures of Example PC-Linker of Present Invention and PC-Linker Used in Work of Lemaire et al. See [Lemaire, Stauber et al. (2007) J Proteome Res 6: 2057-67] and U.S. Pat. No. 8,221,972 for the work of Lemaire et al. The PC-Linkers are shown as incorporated into example peptide sequences.

As shown in FIG. 3, the resultant PC-MTs are comprised of but not limited to the following features:

i) a 1-(2-nitrophenyl)-ethyl based PC-Nucleus is disclosed in FIG. 3 Step 1. The photocleavage site is indicated by the black arrow in FIG. 3 Step 1 and the photocleavage reaction shown in FIG. 3 Step 3. Note that this PC-Nucleus used in the PC-Linker of the Present Invention provides fast and efficient photocleavage and is shown in the Present Specification (Experimental Example 6) to provide superior sensitivity in mass spectrometry in comparison to the PC-Linker used in the aforementioned work of Lemaire et al., which contains an additional methoxy moiety on the nitrophenyl ring of the PC-Nucleus (see FIG. 4 for comparison of PC-Linker structures). For the prior work of Lemaire et al. see [Lemaire, Stauber et al. (2007) J Proteome Res 6: 2057-67] and U.S. Pat. No. 8,221,972.

ii) a probe-reactive moiety, such as a primary amine reactive N-hydroxysuccinimidyl ester (NHS-ester) leaving group. The NHS-ester for example can be created on the ε-amine of a lysine (K) side chain (see FIG. 3 Step 1, NHS-ester) using for example N,N'-Disuccinimidyl Carbonate (DSC) for conversion [Morpurgo, Bayer et al. (1999) J Biochem Biophys Methods 38: 17-28] or DSS (disuccinimidyl suberate). The probe-reactive moiety may also be created for example, by chemical conversion/modification of the carboxylic acid functionality on the C-terminal end of the peptide-based PC-MT (not shown in FIG. 3). The probe-reactive moiety allows facile attachment of the PC-MTs to targeted probes such as antibodies or nucleic acids. It is to be understood that a variety of probe-reactive moieties can be used, including but not limited to amine-reactive N-hydroxysuccinimidyl (NHS) esters, sulfo-N-hydroxysuccinimidyl (sulfo-NHS) esters, succinimidyl esters (SE), sulfo-succinimidyl esters (SSE), aldehydes or tetrafluorophenyl (TFP) esters; sulfhydryl-reactive maleimides or iodoacetamides; or poly-reactive epoxy moieties for example. Azides and alkynes such as used in copper-containing or copper-free Click Chemistry are also possible [McKay and Firm (2014) Chem Biol 21: 1075-101].

iii) an optional spacer unit which links the PC-Nucleus to the probe-reactive moiety, shown for example as a portion of the PC-Linker plus the GSGGK amino acid sequence in FIG. 3 Step 1. It is to be understood this spacer unit is not required, since the probe-reactive moiety can be attached to the 1-(2-nitrophenyl)-ethyl based PC-Nucleus at the same position but without the spacer unit. It is also to be understood that this spacer unit can be of a variety of chemical structures, for example a polyethylene glycol (PEG) spacer to promote hydrophilic/water soluble properties.

iv) a selectively detectable mass unit, shown as the APRLRFYSL amino acid (peptide) sequence in FIG. 3 as an example. It is to be understood that any amino acids used can be natural and unnatural amino acids as well as modified amino acids, isotopic amino acids, amino acid analogs/derivatives and any combination thereof, for example. While peptide-based mass units are a preferred embodiment due to ease of synthesis, robust performance in mass spectrometry and the ability to gain further specificity in mass spectrometric identification using established methods of tandem-MS based fragmentation analysis (e.g., MS/MS), the selectively detectable mass units need not be a peptide, and can for example be any chemical entity which can be detected by mass spectrometry. Polymeric mass units are preferred due to a general ease of synthesis and the ability to readily modulate the mass by simply altering the number and type of monomeric subunits. While peptides are considered to be a form of biopolymer (in addition to nucleic acids for example), polymers other than peptides may be used, such as polyethylene glycols which are readily synthesized and detected by MALDI-MS for example [Enjalbal, Ribiere et al. (2005) J Am Soc Mass Spectrom 16: 670-8].

v) an optional mass unit linker, shown in FIG. 3 Step 1, which links the PC-Nucleus to the mass unit. It is to be understood that this mass unit linker is not required, since the mass unit can be attached to the 1-(2-nitrophenyl)-ethyl based PC-Nucleus at the same position but without the mass unit linker. It is also to be understood that this mass unit linker can be of a variety of chemical structures, for example a polyethylene glycol (PEG) linker to promote hydrophilic/water soluble properties.

vi) a blocking group may be used on the α-amine of the N-terminal of a peptide-based PC-MT, e.g., acetylation ("Ac" in FIG. 3), in cases where the probe-reactive moiety is primary amine-reactive, to avoid self-reaction or polymerization of the PC-MTs. Internal amino acids with free primary amines (e.g., lysine with an ε-amine) may be avoided in these cases, or may also be blocked/protected. In cases where the probe-reactive moiety reacts with different functionalities, such as sulfhydryls, any such functionalities present on the peptide (e.g., from cysteine) may also be blocked/protected to prevent self-reaction or polymerization of the PC-MTs.

vii) a fluorophore or other detectable label (e.g., chromophore or affinity ligand such as biotin) is optionally included on the PC-MT in addition to the selectively detectable mass unit (fluorophore not depicted in FIG. 3, see FIG. 2a for one embodiment). This can assist in method development for example by allowing conventional fluorescence imaging in addition to MSI on the same cell/tissue sample. The fluorophore may be attached for example to the PC-MT on an ε-amine of an included lysine, using a range of commercially available amine-reactive dyes (e.g., Cy5-NHS or Sulfo-Cy5-NHS). This attachment may be achieved during or after SPPS. Fluorophore attachment is also possible with other chemistries such as Click Chemistry [McKay and Finn (2014) Chem Biol 21: 1075-101]. In a preferred embodiment, the fluorophore is attached to the spacer unit. In other embodiments, the fluorophore may be attached to the mass unit or mass unit linker. However, the fluorophore may be attached to any part of the PC-MT structure as long as it does not interfere with the reaction of the probe-reactive moiety with the probe, the photocleavage reaction or the MSI detection of the mass unit, and as long as it does not impair the solubility of the PC-MT labeling reagent in the solvent environment chosen for probe labeling. This approach has the advantage that the mass reporter and fluorophore are part of the same PC-MT labeling reagent, thereby allowing, for example, assessment of PC-MT probe labeling success by fluorescence means (in addition to mass spectrometric means). Alternatively, PC-MTs lacking any fluorescent labels (or other detectable labels such as chromophores or affinity ligands such as biotin) may be attached to the probe and additionally, the fluorescent labels (or other detectable labels such as chromophores or affinity ligands such as biotin) may instead be attached to the same probe at different sites than the PC-MTs. This can be readily achieved for example by labeling the probe (e.g., antibody) both with a PC-MT having an NHS-ester probe-reactive moiety as well as with the aforementioned NHS-activated fluorophores. The labeling of the probe with the PC-MTs and fluorophores can be performed simultaneously or in sequence (either PC-MT first followed by fluorophore, or fluorophore followed by PC-MT). In this embodiment of using primary amine reactive NHS groups for probe labeling, since there are a multitude of primary amines in antibody probes for example, labeling with both the PC-MT and fluorophore is readily possible. Overall, this approach may have advantages over fluorescent PC-MTs, since it may avoid any detrimental effects of the fluorophore on the PC-MT labeling reaction or on the PC-MT solubility during probe labeling, which is typically done under aqueous conditions; it may also avoid detrimental effects of the fluorophore in the mass spectrometric readout (e.g., such as potentially poor ionization efficiency in cases where the fluorophore is attached to the mass reporter). Furthermore, this alternative approach will allow the fluorescent and PC-MT labeling ratios to be adjusted independently.

Finally, it is to be understood that the optional chemical linkers shown in FIG. 3, that is the linker units, the mass unit linker and the spacer unit, are not meant to limit the scope of the Present Invention. These serve as bridges between the PC-Nucleus and important moieties such as the probe-reactive moiety and the mass unit for example. These chemical linkers can be of a variety of chemical compositions. For example, the chemical linkers could simply be hydrocarbon chains, or alternatively for example, a 2,2'-(ethylenedioxy)-bis-(ethylamine) chemical linker could be used for better solubility in an aqueous environment [Pandori, Hobson et al. (2002) Chem Biol 9: 567-73]. Polyethylene glycols (PEGs) are another example, and will be recognized by those skilled in the art as excellent chemical linkers which are relatively stable, water soluble and biocompatible.

PC-MT-Probes

As shown in FIG. 3 Step 2, the PC-MTs are attached to probes through the probe-reactive moiety. In the example shown, the NHS-ester leaving group of the PC-MT is lost after reaction with a primary amine on the antibody, forming an amide bond between the PC-MT and antibody. While an antibody is depicted, the probes can be of any kind such as proteins including but not limited to antibodies, recombinant antibodies, affibodies, nanobodies, single-chain fragment variable (scFv) antibodies, single domain antibodies, VHH single domain antibodies (e.g., camelid single domain VHH antibodies), receptors, carbohydrate-binding proteins (e.g., lectins [Tsaneva and Van Damme (2020) Glycoconj J 37: 533-551]) or ligands for example, or fragments thereof. Probes may also be nucleic acids such as DNA, RNA or Locked Nucleic Acids (LNA) [Nielsen, Singh et al. (1999) J Biomol Struct Dyn 17: 175-91] such as in oligonucleotide hybridization probes or DNA/RNA aptamers for example. Probes may also be other organic molecules or biomolecules such as lipids, carbohydrates, steroids or drugs for example. The labeling of the probe with the PC-MT may be at random sites (e.g., non-specifically at any primary amine sites of a protein, as would occur with PC-MTs comprising an NHS-ester as the probe-reactive moiety) or the labeling may be site-specific (e.g., the carbohydrate region present at specific sites on the heavy chain of some antibodies). In some cases, it may be necessary to use modified probes to facilitate PC-MT labeling, such as primary amine modified nucleic acid probes (e.g., in the case where the probe-reactive moiety is an NHS-ester).

Probes may have a variety of targets with a tissue, that is, the moieties (molecular structures) to which the probes bind. The following examples are not intended to limit the types of probe targets: Different probes may target different biomolecules or biomarkers (e.g., different proteins), or they may target different binding sites within the same biomolecule or biomarker (e.g., different binding sites within the same protein). Probe targets include but are not limited to biomolecules, or complexes or portions thereof, including proteins, post-translational modifications of proteins, glycoproteins, nucleic acids, lipids and derivatives thereof, drugs, metabolites, carbohydrates, glycans, proteoglycans, gangliosides, and organic compounds.

In the PC-MT-Probes, the core structure is defined as the structure which links the mass unit to the probe (see "Core Structure" in FIG. 3 Step 2 for example). The core structure is comprised of but not limited to the PC-Nucleus, the optional spacer unit, and the optional mass unit linker, and is typically a common structure in all PC-MT-Probe species. In a preferred embodiment, the core structure is a non-neutral structure (e.g., contains ionizable groups such as sulfonates, phosphates, amines or carboxylic acids for example). This improves the water solubility of the PC-MT labeling reagents and hence improves the probe labeling reaction which is typically carried out in an aqueous environment. This can also improve the water solubility of the PC-MT-Probes. In one embodiment, a sulfonated fluorophore is included on the core structure (e.g., Sulfo-Cy5 such as used in Experimental Example 7). The sulfonated version of the fluorophore is used since fluorophores are typically poly-cyclic compounds and not water soluble without such sulfonate moieties. In another embodiment, aspartic and/or glutamic acids are included in the amino acid portion of the spacer unit of the PC-MT, to improve the water solubility of the PC-MT labeling reagent and/or the PC-MT-Probe.

Figure 5A:
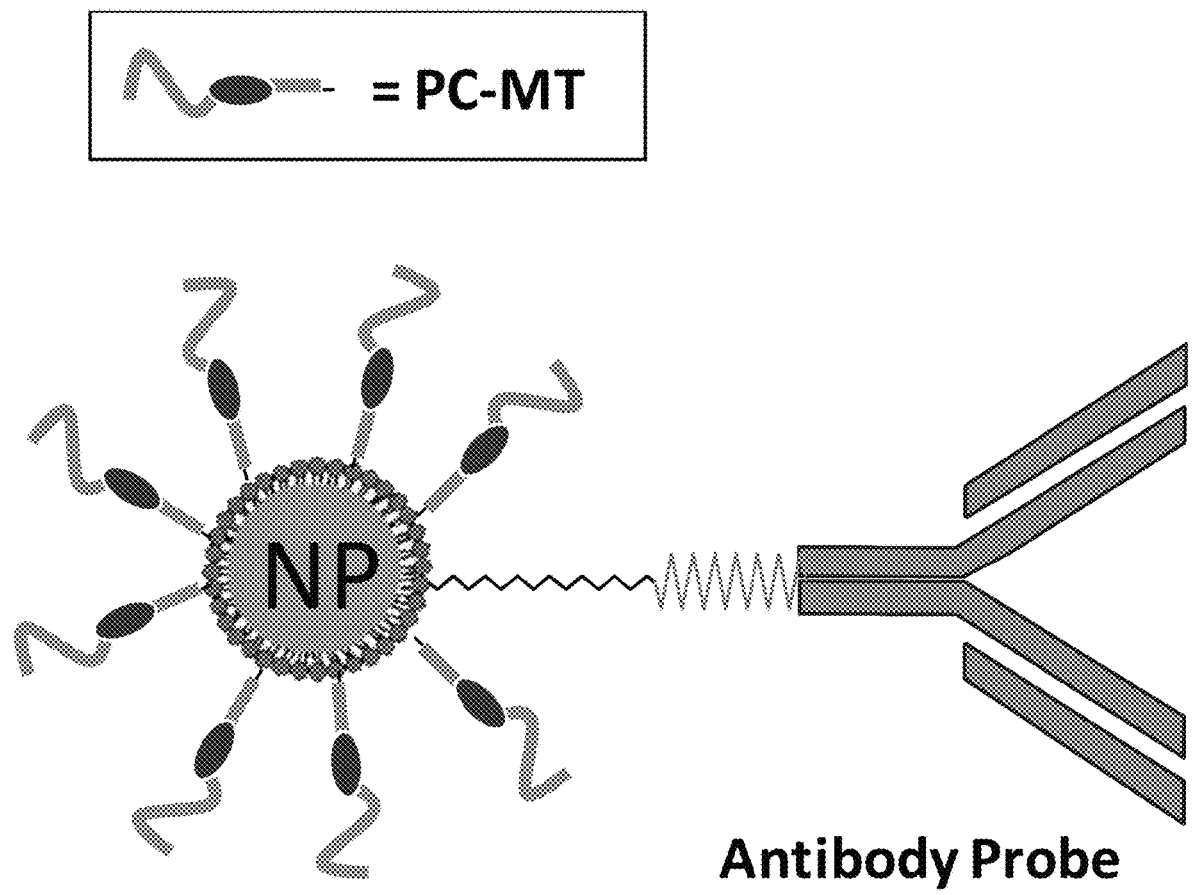

In a preferred embodiment, multiple PC-MT molecules are attached to each probe molecule to facilitate increased sensitivity in the mass spectrometry step. Carriers may be added to the probes to further increase the number of PC-MT labels and thereby facilitate further signal amplification: In one embodiment, poly-amine modified dendrimers or nanoparticles (NPs) are labeled with PC-MTs and then attached to probes (e.g., antibodies) to increase the number of PC-MT labels (FIG. 5a). Gold NPs are particularly attractive since they are as small as 13 nm and routinely used for example with electron microscopy for immunolabeling of target biomolecules [Ackerson, Powell et al. (2010) Methods Enzymol 481: 195-230]. In one example, polyamine-terminated gold NPs or branched dendrimers are commercially available (e.g., from Dendritech and Nanovex Biotechnologies) and can be conjugated to PC-MTs (through the amine-reactive NHS-ester probe-reactive moiety). Alkyne groups can also be introduced into the polyamine dendrimers or NPs using available NHS-activated reagents (e.g., NHS-DIBO-Alkyne from Thermo Scientific [Waltham, MA]). Likewise, antibody or amine-modified nucleic acid probes can be modified with azide groups also using commercial NHS-activated reagents (e.g., NHS-PEG4-Azide from Thermo Scientific [Waltham, MA]). Finally, using well-established, highly selective, gentle and bio-orthogonal Click Chemistry [Kolb, Finn et al. (2001) Angew Chem Int Ed Engl 40: 2004-2021], the PC-MT/alkyne modified dendrimers or NPs can be linked with the azide modified probes (azide and alkyne will spontaneously and selectively form a covalent bond under physiological aqueous conditions even in complex mixtures—in some cases, depending on the type of alkyne used, a copper catalyst is required).

In another embodiment, multiple primary amine modifications are introduced into nucleic acid probes to increase the number of PC-MT labeling sites. In some cases, it may be desirable to use nucleic acid "tails" which are not part of the target binding (hybridization) sequence of a nucleic acid probe, whereby these "tails" carry multiple amine modifications to provide an increased number of PC-MT labeling sites (FIG. 5b). This configuration reduces potential interference from the PC-MTs with the target binding region of a nucleic acid probe. Amine modifications may be introduced into nucleic acid probes using modified nucleotides for example. Such as 5'-Dimethoxytrityl-5-[N-(trifluoro-acetylaminohexyl)-3-acrylimido]-Uridine, 2'-O-triisopropy-lsilyloxymethyl-3'-[(2-cyanoethyl)-(N,N-diisopropyl)]-phosphoramidite, commonly known as Amino-Modifier C6-U Phosphoramidite, which is introduced during phosphoramidite based chemical DNA synthesis. Modified nucleotides may also be introduced enzymatically (e.g., by DNA polymerase) into nucleic acid probes using for example 5-[3-aminoallyl]-2'-deoxyuridine-5'-triphosphate, commonly referred to as Aminoallyl-dUTP. Modifications other than amines for use as sites of PC-MT labeling may be introduced into nucleic acid probes in a similar manner.

In a preferred embodiment, PC-MTs are attached to probes in a 1-step chemical reaction between the PC-MT and probe (e.g., by mixing a PC-MT comprising an NHS-ester as the probe-reactive moiety with a probe such as an antibody or amine-modified nucleic acid). The labeling of probes with PC-MTs in the Present Invention importantly differs from the complex multi-step process in the prior work of Lemaire et al. [Lemaire, Stauber et al. (2007) J Proteome Res 6: 2057-67] [see also U.S. Pat. No. 8,221,972], wherein the probe (e.g., antibody) must first be conjugated to the non-photocleavable heterobifunctional cross-linker MBS (3-maleimidobenzoic acid N-hydroxysuccinimide ester) by reaction with the NHS-ester moiety of the MBS, the antibody then purified by desalting column chromatography (to remove unreacted MBS linker), and the sulfhydryl-reactive maleimide moiety generated on the antibody by the attached MBS linker is subsequently reacted with a peptide containing an internal photocleavage site and a cysteine amino acid (whereby the cysteine on the photocleavable peptide provides a free sulfhydryl moiety for reaction with the maleimide on the antibody-attached MBS linker). Likewise, the aforementioned imaging mass cytometry approach [Giesen, Wang et al. (2014) Nat Methods 11: 417-22] also uses a highly complex multi-step probe (i.e., antibody) labeling procedure, involving pre-loading a polymer with metal ion, partially reducing the antibody and coupling of the two together, with multiple purifications of the polymer and antibody [Fluidigm, Quick Reference: "Maxpar X8 Antibody Labeling", accessed September 2020, www.fluidigm.com/binaries/content/documents/fluidigm/resources/maxpar-x8-antibody-labeling-quick-reference-fldm-00015-rev01/maxpar-x8-antibody-labeling-quick-reference-fldm-00015-rev01/fluidigm%3Afile].

In one embodiment of the Present Invention, it may be possible to avoid further purification of the probe after the PC-MT labeling reaction for simplicity (so as to not remove unreacted PC-MTs) and in other embodiments, removal of unreacted PC-MT by size exclusion (gel filtration) chromatography or ultra-filtration (e.g., using Amicon Ultra-0.5 Centrifugal Filter Units with an appropriate molecular weight cutoff to retain the labeled probe), for example, may be desirable to avoid background in the downstream biomarker detection.

Treating Tissues with PC-MT-Probes and Mass Spectrometry Imaging (MSI)

Figure 16:
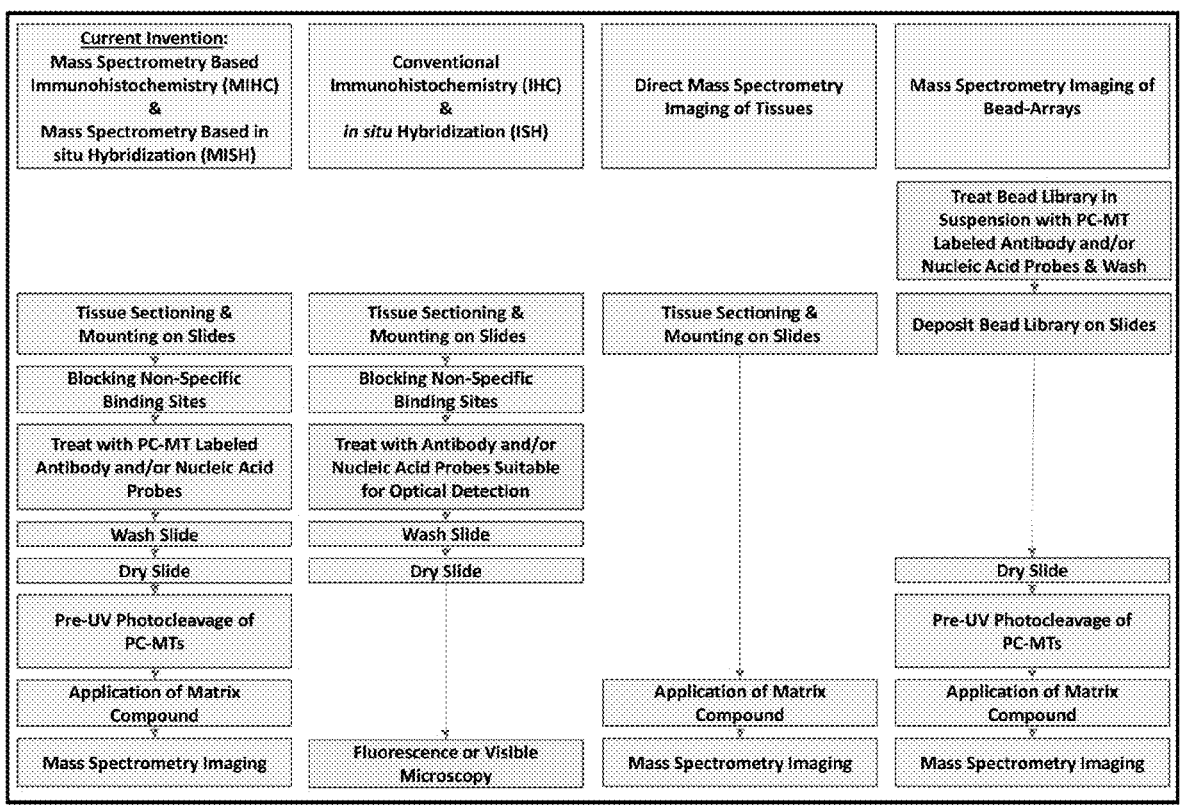
FIG. 16. Comparison of common elements of the protocol for the Present Invention (MIHC and MISH) to that of conventional IHC (e.g., [Katikireddy and O'Sullivan (2011) Methods Mol Biol 784: 155-67]) and conventional ISH (e.g., [Renwick, Cekan et al. (2014) Methods Mol Biol 1211: 171-87]), as well as to conventional direct MSI (e.g., [Caprioli, Farmer et al. (1997) Anal Chem 69: 4751-60]) and to MSI of bead-arrays (e.g., U.S. Pat. No. 9,523,680 which is hereby incorporated by reference). Note that many protocol variations are possible for example depending on whether FF or FFPE tissues are used, whether it is IHC/MIHC or ISH/MISH based protocol, and/or what types of optical detection methods are used for conventional IHC or ISH (such as directly labeled primary antibodies or secondary detection methods; and colorimetric versus fluorescence readout), therefore

The final step in the process is the utilization of the PC-MT-Probes to treat ("stain") cells or tissues (i.e., PC-MT-Probes are bound to targets in the cells/tissues) followed by MSI to image the photocleaved mass reporters (see FIG. 2c and FIG. 3 Step 3). Two example embodiments, termed in the Present Invention as mass spectrometry based immunohistochemistry (MIHC) and mass spectrometry in situ hybridization (MISH), where antibody and nucleic acid probes are used, respectively, are analogous to traditional immunohistochemistry (IHC) and in situ hybridization (ISH). In essence, MIHC and MISH differ in the use of PC-MT labeled probes instead of probes labeled with fluorophores or chromogenic agents, and the use of MSI instead of optical imaging (e.g., microscopy). The MIHC and MISH process, which is exemplified in detail later in the Experimental Examples, typically involves the basic steps described in the following paragraphs (although as is the case with standard IHC and ISH, many protocol variations are possible as will be recognized by those skilled in the art). See also FIG. 16 for comparison of essential common elements of the protocol for the Present Invention (MIHC and MISH) to that of conventional IHC (e.g., [Katikireddy and O'Sullivan (2011) Methods Mol Biol 784: 155-67]) and conventional ISH (e.g., [Renwick, Cekan et al. (2014) Methods Mol Biol 1211: 171-87]), as well as to conventional direct MSI (e.g., [Caprioli, Farmer et al. (1997) Anal Chem 69: 4751-60]) and to MSI of bead-arrays (e.g., U.S. Pat. No. 9,523,680 which is hereby incorporated by reference). Note that many protocol variations are possible for example depending on whether FF or FFPE tissues are used, whether it is IHC/MIHC or ISH/MISH based protocol, and/or what types of optical detection methods are used for conventional IHC or ISH (such as directly labeled primary antibodies or secondary detection methods; and colorimetric versus fluorescence readout), therefore FIG. 16 shows only common essential elements of the protocols:

Basic Steps for MIHC: i) Mounting thin FFPE or fresh frozen tissue sections (e.g., 5-10 μm thick by microtome or cryostat from FFPE or fresh frozen tissue blocks) onto conductive slides (e.g., metal-coated glass slides); note that although indium tin oxide (ITO) coated glass slides as the conductive surface are almost universally used in MSI (e.g., see [Yalcin and de la Monte (2015) J Histochem Cytochem 63: 762-71; Angel, Baldwin et al. (2017) Biochim Biophys Acta Proteins Proteom 1865: 927-935]), in this invention it was found that given the extensive processing steps of MIHC and MISH described below, gold-coated glass slides are beneficial to avoid tissue lifting off the slide during processing and/or tissue damage, while still providing the necessary conductive surface for MSI (e.g., glass slides with a 10 nm gold layer and 2 nm titanium adhesion underlayer as from Platypus Technologies LLC, Madison, WI, or a 50 nm gold layer and 5 nm chromium adhesion underlayer as from Substrata Thin Film Solutions/Angstrom Engineering Inc., ON, Canada); tissue mounting is followed by ii) deparaffinization (e.g., with xylene) in the case of FFPE; iii) rehydration (if deparaffinization was performed) typically with a series of ethanol/water mixtures and aqueous saline buffers; iv) fixation in formalin or paraformaldehyde in the case of fresh frozen tissues; v) antigen retrieval to reverse some of the detrimental effects of formalin/paraformaldehyde fixation (e.g., heating in citrate buffer, pH 6, or the use of formic acid); vi) treatment with blocking buffer to reduce background (typically saline buffer with non-ionic detergent such as Tween-20 as well as protein blockers such as bovine serum albumin [BSA] and animal serum); vii) staining simultaneously with a mixture of different PC-MT antibodies (PC-MT-Abs) for multiplexing (typically diluted in blocking buffer); viii) washing in saline buffer with non-ionic detergent such as Tween-20 to remove any unbound PC-MT-Abs followed by washing in volatile aqueous buffers such as ammonium bicarbonate to remove non-volatile salts which can interfere with some forms of mass spectrometry; and ix) drying of the tissue slides prior to MSI. It was discovered that, with an immunohistochemistry-style mass spectrometry imaging (MSI) protocol (flowchart in FIG. 16), tissues mounted on gold slides (e.g. slides with a gold layer) had better results. More specifically, mounting on gold slides helped to avoid tissue damage or loss during the required slide processing steps (conductive slides for MSI). Prior use of gold slides in tissue MSI has been for direct MSI which lacks all the processing steps of the present invention (see flowchart in FIG. 16) and thus does not have a problem with tissue loss/damage. The present invention uses of gold slides for improved tissue adhesion (more commonly, ITO conductive slides are used for direct MSI but showed poor results in our protocol, see Example 10). Tissue damage and loss can occur at any of the liquid-phase processing steps of the slides.

Steps for MISH: i) Tissue mounting, ii) deparaffinization, iii) rehydration and iv) formalin/paraformaldehyde fixation are performed as described for MIHC; this is typically followed by v) partial protein digestion with Proteinase K; vi) fixation of nucleic acids with EDC (1-Ethyl-3-(3-dimethylaminopropyl)carbodiimide); vii) tissue acetylation to cap free amines and reduce background (caused by non-specific binding of probes); viii) treatment with blocking buffer typically containing at least irrelevant nucleic acids (e.g., yeast tRNA and/or salmon sperm DNA) to reduce background; ix) staining (hybridization) simultaneously with a mixture of different PC-MT nucleic acids (PC-MT-NAs) for multiplexing (typically diluted in blocking buffer or similar); x) washing in saline buffer to remove any unbound PC-MT-NAs followed by washing in volatile aqueous buffers such as ammonium bicarbonate to remove non-volatile salts which can interfere with some forms of mass spectrometry; and xi) drying of the tissue slides prior to MSI.

However, as discussed earlier, probes of the Present Invention need not be restricted to antibodies (used for MIHC) and nucleic acids (used for MISH), and can for example be lectins, receptors or ligands. Therefore, the Present Invention is not restricted to MIHC and MISH methodologies, but other embodiments where tissues are treated ("stained") with PC-MT conjugated lectins, receptors or ligands for example, or any probe type or combination thereof.

Mass Spectrometry Imaging (MSI) (and embodiments including MIHC and MISH): Following the procedures as outlined above, MSI is performed, in one embodiment using MALDI-MSI:

For MALDI-MSI, matrix compound is applied to the tissue typically in a thin and uniform layer. Example matrix compounds include alpha-cyano-4-hydroxycinnamic acid (CHCA), 2,5-Dihydroxybenzoic acid (DHB), 1,5-Diaminonaphthalene (DAN) or 3,5-Dimethoxy-4-hydroxycinnamic acid (sinapinic acid). In a preferred embodiment, matrix sublimation followed by recrystallization [Hankin, Barkley et al. (2007) J Am Soc Mass Spectrom 18: 1646-52; Duenas, Carlucci et al. (2016) J Am Soc Mass Spectrom 27: 1575-8] is used to achieve both excellent spatial resolution (i.e., provided by the sublimation which limits analyte delocalization during matrix application) and high sensitivity (i.e., provided by the recrystallization which allows the mass reporters to sufficiently co-crystallize with matrix, but without significant analyte delocalization). Other methods of matrix application may be used, such as by using a commercially available sprayer (e.g., HTX TM-Sprayer, HTX Technologies, LLC, Chapel Hill, NC).

A variety of mass spectrometry technologies and instrumentation may be used for the MSI step, not just MALDI-MSI. Other MSI methods include, but are not limited to, desorption electrospray ionization mass spectrometry imaging (DESI-MSI) [Takats, Wiseman et al. (2004) Science 306: 471-3], laser ablation electrospray ionization mass spectrometry imaging (LAESI-MSI) [Kulkarni, Wilschut et al. (2018) Planta 248: 1515-1523], and atmospheric pressure (AP) matrix-assisted laser desorption/ionization (MALDI) mass spectrometry imaging (AP-MALDI-MSI) [Kompauer, Heiles et al. (2017) Nat Methods 14: 90-96]. DESI-MSI for example, which was originally best suited for small molecules such as metabolites and lipids, has since been adapted for protein/peptide detection as well [Takats, Wiseman et al. (2004) Science 306: 471-3; Takats, Wiseman et al. (2008) CSH Protoc 2008: pdb prot4994; Hsu, Chou et al. (2015) Anal Chem 87: 11171-5; Towers, Karancsi et al. (2018) J Am Soc Mass Spectrom 29: 2456-2466; Hale and Cooper (2021) Anal Chem 93: 4619-4627]. In its basic form, DESI-MSI works by directing electrosprayed charged solvent droplets onto the surface (e.g., tissue) to extract (desorb) and ionize analytes from the surface which are then taken into the inlet (e.g., transfer capillary) of the mass analyzer of the mass spectrometer [Takats, Wiseman et al. (2004) Science 306: 471-3]. However, variations of DESI-MSI also exist, such as nano-DESI-MSI, which allows separation of the desorption and ionization events [Roach, Laskin et al. (2010) Analyst 135: 2233-6]). DESI-MSI can be readily done under ambient conditions rather than under vacuum, and as such requires minimal sample preparation and is amenable to automation. Moreover, as an ESI (electrospray ionization) based method, DESI-MSI does not require matrix application as MALDI-MSI does. MALDI-MSI matrix application is not only an added difficult and cumbersome step that can lead to reproducibility problems, it also risks analyte delocalization.

Regardless of the type of MSI technology and instrumentation, PC-MTs are photocleaved to liberate the mass reporter from the PC-MT-Probes for MSI analysis (see FIG. 2c and FIG. 3 Step 3). Note that as exemplified in FIG. 3 Step 3, the mass reporter is comprised of the mass unit and in some cases a portion of the photocleaved PC-Linker (in other cases, not depicted in FIG. 3, the mass reporter may contain no portion of the photocleaved PC-Linker and therefore the mass reporter and mass unit are equivalent). PC-MTs may be pre-photocleaved by UV treatment prior to MSI, preferably also before matrix application in the case of MALDI-MSI, to avoid matrix absorption of the incident UV. Photocleavage is also preferably performed on dried slides to prevent delocalization of the photocleaved mass reporters by diffusion. Pre-photocleavage can be achieved for example by using a model XX-15 self-filtering 365 nm peak lamp (UVP/Analytik Jena US LLC, Upland, CA), but many other light sources are possible. In a preferred embodiment, pre-photocleavage is achieved in a short time (e.g., 5 min) with relatively low intensity UV light (e.g., 3-10 mW/cm$^2$). PC-MTs may alternatively be photocleaved in-line with the MALDI-MSI analysis by the instrument's laser beam (or by the laser beam of any other laser-based mass spectrometers, such as in LAESI-MSI). This alternative approach may be expected to improve spatial resolution of the MSI, since the mass reporters are not photocleaved prior to matrix application in the case of MALDI-MSI (whereby matrix application could otherwise cause diffusion of pre-photocleaved mass reporters). However, results in the Present Specification indicate that this approach of in-line photocleavage provides poor sensitivity in the case of MALDI-MSI (Experimental Example 6). Superiority of pre-photocleavage, before matrix application and before MALDI-MSI, may be explained as follows: i) pre-photocleavage avoids the light blocking effects of the matrix compound (it is in fact the function of the matrix to absorb the impinging UV laser light during MALDI-MSI, converting it to heat such that the mass reporters are vaporized and ionized for analysis); and ii) having the mass reporter pre-photocleaved will allow the freed mass reporter to co-crystallize with the subsequently-applied matrix (those skilled in the art will recognize that co-crystallization of analytes with matrix is important for efficient desorption/ionization of the analyte in MALDI-MS), conversely, photocleavage in-line with the MALDI-MSI analysis by the instrument's laser beam necessarily occurs after matrix application/crystallization, likely not allowing for efficient co-crystallization of the matrix and the mass reporter (since at the time of matrix application/crystallization, the mass reporter is still attached to the probe which may be still attached to the tissue). However, other laser-based MSI methods and instrumentation, for example those that do not require matrix compound, may be expected to provide efficient in-line photocleavage and sufficient sensitivity, presuming the laser wavelength is sufficiently matched to the photocleavage wavelength.

Note that with the preferred PC-Linker (FIG. 3), photocleavage leaves a small residual portion of the PC-Linker attached to the mass reporter thereby generating a free primary amine on the mass reporter upon photocleavage (see FIG. 3 Step 3), which may assist in mass reporter ionization in positive mode MALDI-MSI and therefore this design may increase sensitivity.

Note also that FIG. 3 depicts the mass reporter of the PC-MT as linked (prior to photocleavage) to the phenyl ring of the PC-Nucleus through the photocleavage site (see FIG. 3 Step 3 for photocleavage site denoted by the lightning bolt), and the probe ultimately linked to the phenyl ring of the PC-Nucleus at a position different from the photocleavage site. This is the preferred embodiment of the Present Invention since importantly, the photocleaved 1-(2-nitrophenyl)-ethyl moiety of the PC-Linker does not remain attached to the mass reporter upon photocleavage as shown in FIG. 3 Step 3 (instead remains attached to the probe). Conversely, it is possible to entirely reverse this orientation as taught by Olejnik et al. [Olejnik, Ludemann et al. (1999) Nucleic Acids Res 27: 4626-31] and by Levy and Caprioli (U.S. Pat. No. 7,569,392). However, in this configuration the photocleaved 1-(2-nitrophenyl)-ethyl moiety of the PC-Linker remains attached to the mass reporter (not depicted in FIG. 3), and as a result, highly complicated mass spectra containing multiple peaks pertaining to the mass reporter attached to various side-reaction byproducts of the photocleaved 1-(2-nitrophenyl)-ethyl moiety are observed (see Experimental Example 5). This will reduce sensitivity in MSI (by dividing signal for a single mass reporter among many mass spectral peaks, i.e., said byproducts) and will confound discrimination of different mass reporters (e.g., by peak overlap).

Note that in cases where a fluorophore is optionally used on the PC-MT, it is preferably not placed on the mass reporter region. This avoids any potential interference from the fluorophore with the mass spectrometry detection of the mass reporter (e.g., the fluorophore could become structurally altered by the photocleavage light, thereby confounding the analysis). However, in some cases it may be useful to place the fluorophore on the mass reporter, such as to quantify by fluorescence the photocleavage efficiency of the PC-MT.

Finally, overall, as discussed in the preceding paragraphs, the Present Invention is not restricted to the types of probes nor the types of mass spectrometry used for MSI. Therefore, more generically, the PC-MT-Probe based MSI technique of the Present Invention is referred to as PC-MT-MSI (of which the aforementioned methods of mass spectrometry based immunohistochemistry [MIHC] and mass spectrometry based in situ hybridization [MISH] are some of the many possible methodological subtypes).

Multi-Omic Tissue Imaging Using PC-MT-Probes

A key advantage of the Present Invention is the ability to perform multi-omic imaging of tissue specimens, whereby "omics" is the measurement of some characteristic of a large family of cellular molecules, such molecules including, but not limited to, genes (genomics), proteins (proteomics), small metabolites (metabolomics), glycans (glycomics) or RNA (transcriptomics) [(2012) Evolution of Translational Omics: Lessons Learned and the Path Forward]. In the case of tissue imaging, this measured "characteristic" for example can be the spatial mapping, morphological analysis, and co-localization analysis of these cellular molecules, and may also include quantification (e.g., quantifying biomarker levels or scoring the number of biomarker-positive cells). Multi-omics is therefore the combined measurement and analysis of different omic groups (e.g., combined proteomics and glycomics). In the Present Invention in the context of tissue imaging, multi-omics can be achieved by using for example, a) different PC-MT-Probe types or classes (e.g., antibodies and lectins) and/or b) different MSI "modes" (e.g., untargeted direct MSI of endogenous tissue biomolecules as well as MSI of biomolecules targeted by specific PC-MT-Probes). In a preferred embodiment, the different omic measurements are made on the same tissue section. However, it is also possible to make these measurements on separate, preferably sequential/adjacent tissue sections sliced from the same tissue specimen/block. Moreover, the different omic measurements may be performed simultaneously on the tissue section/specimen (e.g., by treating the tissue with a mixture of different PC-MT-Probe classes, such as antibodies and lectins) or in sequence (one omic measurement followed by another). For example, with fluorescence imaging, this has been done with various methodological permutations using lectins and antibodies [Zupancic, Kreft et al. (2020) Eur J Histochem 64]. In the case where the different omic measurements are performed in sequence on the tissue specimen, the Present Invention is not intended to be limited to the order in which these measurements are performed, since many permutations could produce useful results as will be apparent in the following paragraphs.

Finally, it should be noted that in the case where carbohydrate-binding probes such as lectin probes are combined with antibody probes for simultaneous treatment of the tissue, it may be important to use antibody probes which lack glycosylation, so as to avoid cross-reaction of the lectin probes with the antibody probes, which could confound the tissue imaging results (e.g., produce artifacts that don't represent the true endogenous biomarker pattern of the tissue). This could be done for example using antibodies which lack the glycosylated Fc domain, including but not limited to Fab fragment antibodies, F(ab')2 fragment antibodies, nanobodies, single-chain fragment variable (scFv) antibodies, and VHH single domain antibodies (e.g., camelid single domain VHH antibodies). Whole antibody probes containing the Fc domain may still be used simultaneously with carbohydrate-binding probes such as lectins, as long as antibody glycosylation is lacking, including but not limited to the use of recombinant antibodies (e.g., as produced in a prokaryotic expression system) or antibodies which have been chemically or enzymatically de-glycosylated (e.g., using the enzyme PNGase F). More broadly, when different probe classes are combined for simultaneous tissue treatment, it will be important to take measures to avoid cross-reaction of the probes with each other to avoid artifacts in the tissue imaging.

Multi-omics in the Present Invention is facilitated by the use of MSI methods that employ "soft" ionization for molecular analysis, since these methods generally cause no or limited molecular fragmentation and more specifically, do not atomize molecules for detection (allowing for example the detection of intact peptide or polymeric based mass-tags as well as intact endogenous biomolecules in the tissues such as lipids, drugs, or metabolites). Soft ionization methods include but are not limited to laser desorption ionization (LDI), matrix-assisted laser desorption ionization (MALDI), desorption/ionization on silicon (DIOS), fast atom/ion bombardment (FAB) and electrospray ionization (ESI) [Siuzdak (2004) JALA 9: 50-63] including derivatives of ESI as discussed earlier such as DESI and LAESI. The aforementioned list is not intended to limit the Present Invention to any particular type of "soft" ionization mass spectrometry. For the purposes of the Present Invention, "soft" ionization based methods are defined as those which ionize and detect molecular ions, that is, electrically charged molecules comprised of 2 or more atoms held together by chemical bonds.

Double Sequential MSI: In a simple multi-omic embodiment, it is useful to first perform label-free direct MSI of endogenous small biomolecules (e.g., metabolomics), followed by MSI of targeted biomolecules using PC-MT-MSI (e.g., protein targets such as in proteomics), preferably on the same tissue section. The targeted PC-MT-MSI is necessary to detect biomolecules that are generally not accessible to direct MSI, such as macromolecular targets which themselves do not ionize well, are not detected well, may fragment in undesirable fashion even with soft ionization, and/or are not resolved well in the mass spectrometer, for example. Including PC-MT-MSI in the multi-omic workflow is also important where targeting at least some known biomarkers is desired or necessary. Overall, this embodiment of multi-omic tissue imaging may be important for example to co-localize drug compounds (small molecule detection by direct label-free MSI) and drug targets (macromolecule detection by PC-MT-MSI, since drug targets are typically proteins). In a preferred embodiment, label-free direct MALDI-MSI is performed first, and uses fresh frozen (FF) tissue sections so that the tissues have not yet undergone tissue fixation (more ideal for direct label-free MSI of endogenous molecules; although the use of formalin-fixed paraffin embedded [FFPE] is possible [Wisztorski, Franck et al. (2010) Methods Mol Biol 656: 303-22]). In a preferred embodiment, tissue sections are then washed, fixed if not previously done, and then PC-MT-MSI methods are employed such as MIHC and/or MISH which includes another cycle of MSI, on the same tissue section.

In some embodiments, it is useful to first perform label-free direct MSI on tissue sections, e.g. to directly detect small biomolecules, followed by targeted MIHC and/or MISH on the same tissue section to detect macromolecular targets and/or nucleic acid targets. This may be important for example to co-localize drug compounds (small molecule detection by direct label-free MSI) and drug targets (macromolecule detection by targeted PCMT-Probe based MSI). In a preferred embodiment, label-free direct MALDI-MSI is performed first, and uses fresh frozen tissue sections so that the tissues have not yet undergone tissue fixation (more ideal for direct label-free MSI of endogenous molecules; although FFPE is possible [Wisztorski, Franck et al. (2010) Methods Mol Biol 656: 303-22]). In a preferred embodiment, tissue sections are then washed (e.g. in organic solvent) for removal of any remaining matrix compound and then MIHC and/or MISH followed by another cycle of MALDI-MSI is performed as described above, on the same tissue section. See Experimental Example 4 for more detail.

It should be noted that the present invention is facilitated by the use of mass spectrometry methods that employ "soft" ionization for molecular analysis, since these methods generally cause no or limited molecular fragmentation and more specifically, do not atomize molecules for detection (allowing for example the detection of peptide or polymeric based mass-tags as well as endogenous biomolecules in tissues). Such methods include but are not limited to laser desorption ionization (LDI), matrix-assisted laser desorption ionization (MALDI), desorption/ionization on silicon (DIOS), fast atom/ion bombardment (FAB) and electrospray ionization (ESI) mass spectrometry [Siuzdak (2004) JALA 9: 50-63]. The aforementioned list is not intended to limit the present invention to any particular type of "soft" ionization mass spectrometry. For the purposes of this invention, "soft" ionization based methods are defined as those which are able to detect molecular ions, that is, electrically charged molecules comprised of 2 or more atoms held together by chemical bonds.

In another preferred multi-omic embodiment, the targeted PC-MT-MSI method is combined with untargeted "bottom-up" omics methods.

Figure 22:
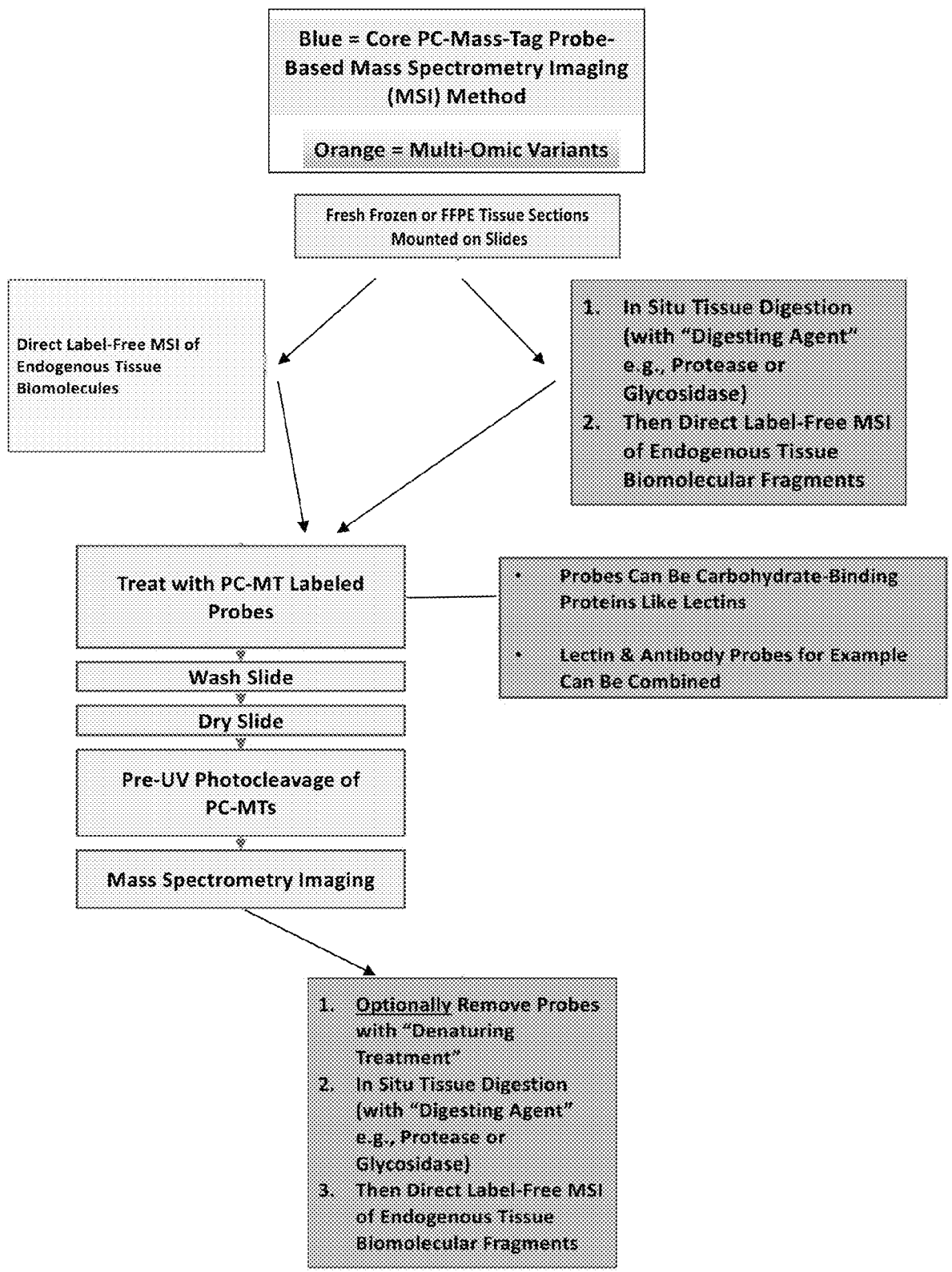
FIG. 22 shows an exemplary schematic illustrating the parallel between working with undigested vs. digested tissue. FFPE=formalin-fixed and paraffin embedded (FFPE).

Bottom-up omics refers to the fact that biomolecules are first broken down (digested) into smaller fragments that are more accessible to mass spectrometry. The identity and structure of the whole biomolecules may be subsequently deduced from the mass spectrometry analysis. In other bottom-up scenarios, the identities of the biomolecules need not be known, since merely a fingerprint of various mass species (measured with high precision) may be correlated with a disease state or stage for example. In the context of bottom-up tissue MSI, the tissue is treated with a digesting agent to liberate biomolecular fragments which are more accessible to mass spectrometry. See for example, FIG. 22. Typically the digesting agents are sprayed onto the tissue in a thin film so as to facilitate digestion without analyte delocalization, so-called in situ digestion. However, it is a challenge to achieve a balance between sufficient digestion and minimal delocalization, and likely no perfect balance exists. These digesting agents may be enzymes, such as nucleases (e.g., restriction enzymes), proteases (e.g., chymotrypsin, trypsin, LysC, or AspN), kinases (e.g., PKC), phosphatases (e.g., alkaline phosphatase), or glycosidases (e.g., Peptide N-Glycosidase F [PNGase F]) or they may be chemical agents such as cyanogen bromide (CNBr) or hydroxylamine [Gundry, White et al. (2009) Curr Protoc Mol Biol Chapter 10: Unit10 25; Barrett, Wither et al. (2017) J Proteome Res 16: 4177-4184]. In situ tissue digestion followed by MSI has been previously reported. For example, Drake et al. [Drake, Powers et al. (2018) Curr Protoc Protein Sci 94: e68], sprayed the glycosidase PNGase F onto FF and FFPE tissues to enzymatically cleave N-linked glycans from proteins in the tissues, followed by MALDI-MSI of the liberated glycans. Other examples, in this case using proteases as the digesting agent, include the use of collagenase to digest a specific protein type or trypsin to achieve general protein digestion [Angel, Schwamborn et al. (2019) Proteomics Clin Appl 13: e1700152; Lazova, Smoot et al. (2020) J Cutan Pathol 47: 226-240].

When bottom-up MSI is combined with PC-MT-MSI for a multi-omic tissue imaging approach, the Present Invention is not intended to be limited to a particular order of operations. For example, the PC-MT-MSI may be performed before the bottom-up MSI, or after (both options requiring 2 rounds of MSI). Conversely, the tissue may be stained with PC-MT-Probes and then in situ digestion performed followed by only a single round of MSI. In cases where PC-MT-MSI is performed first, it may be desirable to subsequently remove the PC-MT-Probes in the case where the probes may interfere with the subsequent bottom-up MSI. To do so, probes may be first detached from the tissues by a denaturing treatment and the probes then washed away. Such denaturing treatments can include, but are not limited to, chaotropic agents, solutions of pH ≤5, solutions of pH ≥10, reducing agents, oxidizing agents, heat, organic solvents, and/or detergents (e.g., ionic detergents such as SDS, non-ionic detergents such as Triton X-100, or zwitterionic detergents such as CHAPS). See for example, FIG. 22.

Note that while the aforementioned covers a wide range of multi-omic methodological permutations, two specific examples using in situ protease or glycosidase digestion are provided in Experimental Example 15.

TABLE 1

Mass Unit Sequences for PC-MTs and Mass Reporter Masses (See FIG. 3 for Example PC-MT Structure).

| Mass Unit ID | Mass Unit Amino Acid Sequence* | Mass Reporter Mass (Monoisotopic)* | Antibody |
|---|---|---|---|
| 1 | APRLRFYSL | 1,206.72 | Myelin, CK, Streptavidin |
| Iso-1.1 | (A)PRLRFYSL | 1,210.74 | CD3 |
| Iso-1.2 | (AP)RLRFYSL | 1,216.75 | CD4 |
| Iso-1.3 | A(P)R(L)RFYSL | 1,222.79 | CD8 |
| Iso-1.4 | (AP)R(L)RFYSL | 1,226.82 | CD20 |
| Iso-1.5 | A(P)R(L)R(F)YSL | 1,230.84 | CD45RO |
| Iso-1.6 | (AP)R(L)R(F)YSL | 1,234.87 | — |
| Iso-1.7 | A(P)R(L)R(F)YS(L) | 1,240.91 | ER |
| Iso-1.8 | (AP)R(L)R(F)YS(L) | 1,244.93 | PR |
| 1.1 | APRLRFYSLG | 1,263.74 | — |
| 1.2 | SAPRLRFYSL | 1,293.75 | HER2 |
| 1.3 | GAPRLRFYSLG | 1,320.76 | Histone H2A.X |
| 1.4 | SAPRLRFYSLG | 1,350.76 | CD68 |
| 1.5 | GAPRLRFYSLGG | 1,377.78 | Ki67 |
| 2 | RPPGFSFFR | 1,194.67 | NeuN, Streptavidin |
| 3 | IPSINVHHY | 1,163.65 | Streptavidin |
| 4 | YHWYGYTPQNVI | 1,624.80 | GLUT-1 |
| 5 | APLFYSL | 894.52 | Synapsin-2, Streptavidin |
| 6 | PPGFSFF | 882.46 | MAP-2, Streptavidin |
| 7 | LRRASLG | 856.56 | Streptavidin, PD-1 |
| 8 | PPGASPFR | 912.52 | Streptavidin, PD-L1 |
| 9 | RYPFPGP | 917.51 | Streptavidin, PD-L2 |
| 10 | SFLLRNP | 930.57 | Streptavidin, CTLA-4 |
| 11 | PPGPSPFR | 938.53 | Streptavidin, OX40 |
| 12 | RPPGFSPL | 954.57 | Streptavidin, CD27 |
| 13 | PPGESPFR | 970.52 | Streptavidin, CD28 |
| 14 | PPGFSPFR | 988.55 | Streptavidin, TIM3 |

TABLE 1-continued

Mass Unit Sequences for PC-MTs and Mass Reporter Masses (See FIG. 3 for Example PC-MT Structure).

| Mass Unit ID | Mass Unit Amino Acid Sequence* | Mass Reporter Mass (Monoisotopic)* | Antibody |
|---|---|---|---|
| 15 | RGYGYQGL | 997.54 | Streptavidin |
| 16 | RGYAYQGL | 1,011.55 | Streptavidin |

Shaded (Bold text) rows are mass unit 1 or variations of mass unit 1 used to minimize variable MALDI-MS ionization efficiency. The letters in parenthesis represent stable isotopic amino acids shown in Table 1.1.

*Mass units are N-terminal acetylated on the α-amine; the mass reporter masses include this acetylation plus the mass unit and a small portion of the photocleaved PC-Linker (see FIG. 3 Step 3).

TABLE 1.1

Amino Acid Isotopes.

| 1-Letter | Isotopic Amino Acid | FMOC-Isotopic Amino Acid |
|---|---|---|
| A | L-ALANINE (2,3,3,3-D4, 98%) | L-ALANINE-N-FMOC (2,3,3,3-D4, 98%) |
| P | L-PROLINE (13C5, 99%; 15N, 99%) | L-PROLINE-N-FMOC (13C5, 99%; 15N, 99%) |
| L | L-LEUCINE (D10, 98%) | L-LEUCINE-N-FMOC (D10, 98%) |
| F | L-PHENYLALANINE (D8, 98%) | L-PHENYLALANINE-N-FMOC (D8, 98%) |

EXPERIMENTAL

Materials for Experimental Examples.

Water (LCMS grade) and xylene (semiconductor grade) were from Acros Organics (Pittsburgh, PA). Methanol (LCMS grade) was from J. T. Baker (Avantor, Radnor, PA). Ethanol (bioreagent for molecular biology), acetone (HPLC grade), N,N dimethyl formamide (anhydrous, ≥99.8%), 1,5-diaminonaphthalene (DAN, 97%), 2,5-dihydroxybenzoic acid (DHB, 98.0%), isopropyl alcohol (bioreagent for molecular biology), sodium chloride (BioXtra, ≥99.5%), sodium bicarbonate (99.7%-100.3%, molecular biology tested), ammonium bicarbonate (BioUltra, ≥99.5%), bovine serum albumin (heat shock fraction, protease free, fatty acid free, essentially globulin free, pH 7, ≥98%), phosphate buffered saline (PBS) (BioPerformance Certified, pH 7.4, P5368), glycine (ultra for molecular biology, ≥99%, Fluka Biochemika), paraformaldehyde (powder, 95%), Citrate Buffer (pH 6.0, 10×, Antigen Retriever), 5-(ethylthio)-1H-tetrazole (5-ETT, 95%), 1-methylimidazole (ReagentPlus, 99%), formamide (BioReagent for molecular biology, ≥99.5%), RNA, tRNA from baker's yeast, Denhardt's Solution (50×5 mL), Atto-647N-NHS Ester and Octyl ß-D-Glucopyranoside (OBG) (50% [w/v] stock solution) were from Sigma Aldrich (St. Louis, MO). 1-ethyl-3-[3-dimethylaminopropyl] carbodiimide hydrochloride (EDC), DyLight 650 NHS Ester, anti-streptavidin antibody clone S3E11, hydroxylamine, the Slide-A-Lyzer™ 0.1 mL MINI Dialysis Devices with 20 kDa Membrane and Biotinylated Protein G were from Thermo Fisher Scientific (Waltham, MA). CHAPS (powder, ≥98%, MP Biomedicals), Invitrogen UltraPure Salmon Sperm DNA Solution and Electron Microscopy Sciences Secure-Seal Hybridization Chambers (1 well, 22 mm×53 mm×0.6 mm deep) were from Fisher Scientific (Hampton, NH). Tris HCl and Tris base (molecular biology grade), 5N sodium chloride (molecular biology grade), 0.5 M EDTA (pH 8; molecular biology grade), Tween-20 (molecular biology grade), SSC buffer 20× (molecular biology grade) and nuclease-free water were from Promega (Madison, WI). Antigen Retrieval Reagent-Basic (CTS013) was obtained from R&D Systems/BioTechne (Minneapolis, MN). Gold coated microscope slides (Au-500 Å) were from Angstrom Engineering Inc. (Kitchener, ON, Canada). Mouse C57 brain sagittal FFPE sections (5 µm thickness) and mouse C57 brain sagittal Fresh Frozen (FF) sections (embedded in 2% w/v CMC, 10 µm thickness) were obtained from Zyagen (San Diego, CA). FFPE human tonsil tissue blocks were from amsbio LLC (Cambridge, MA) and FFPE human breast cancer tissue blocks were from OriGene (Rockville, MD). FFPE tissue blocks were sent to Zyagen (San Diego, CA) for thin sectioning (5 µm thickness) and mounting on slides. Antibodies for multiplex imaging of mouse brain sections were obtained from various suppliers as follows: Anti-Myelin Basic Protein Antibody (MAB42282) from R&D Systems/BioTechne (Minneapolis, MN); Anti-NeuN Antibody (MAB377) and Anti-Synapsin-2 Antibody (MABN1573) from Millipore Sigma (Burlington, MA); Anti-GLUT1 Antibody (PA146152) from Fisher Scientific (Hampton, NH); and the Anti-MAP2 Antibody (ab11268), recombinant anti-NeuN antibody (ab209898) and recombinant anti-Cas9 (ab218654; BSA and azide free), recombinant anti-pan Cytokeratin antibody [C-11]—BSA and Azide free (ab264485), recombinant anti-CD3 repsilon antibody [CAL57]—BSA and Azide free (ab251607), recombinant anti-CD4 antibody [EPR6855]—BSA and Azide free (ab181724), recombinant anti-CD8 alpha antibody [CAL66]—BSA and Azide free (ab251596), recombinant anti-CD20 antibody [EP459Y]—BSA and Azide free (ab214282), anti-CD45RO antibody [UCH-L1] (ab23), recombinant anti-Estrogen Receptor alpha antibody [SP1]—BSA and Azide free (ab187260), recombinant anti-Progesterone Receptor antibody [YR85]—BSA and Azide free (ab206926), recombinant anti-ErbB 2 antibody [CAL27]—BSA and Azide free (ab251602), recombinant anti-Histone H2A.X antibody [EPR22820-23]—ChIP Grade—BSA and Azide free (ab256544), recombinant anti-CD68 antibody [EPR20545]—BSA and Azide free (ab227458), and recombinant anti-Ki67 antibody [EPR3610]—BSA and Azide free (ab209897) were from Abcam (Cambridge, MA). Mouse IgG whole molecule (015-000-003), normal mouse serum (015-222-001), rabbit IgG whole molecule (011-000-003) and normal rabbit serum (011-000-001) were from Jackson ImmunoResearch Laboratories, Inc. (West Grove, PA). For certain bead-array experiments, the Recombinant Anti-Beta Amyloid 1-42 antibody (ab224275) and Recombinant Anti-Myelin Basic Protein antibody (ab230378), both BSA and azide free, were from Abcam (Cambridge, MA). U6-Amine Custom LNA Oligonucleotide (339406 YCO0191704), Sense miR-159-Amine Custom LNA Oligonucleotide (339406 YCO0191705) and the miRCURY LNA miRNA ISH Buffer Set for FFPE were from Qiagen (Germantown, MD). Streptavidin-coated 20 μm and 37 μm PMMA beads (microspheres) were from PolyAn GmbH (Berlin, Germany). 0.5 mL Ultrafree-MC Centrifugal 0.45 μm Filter Devices were from Millipore Sigma (Burlington, MA). NAP-5 Sephadex G-25 Columns and PD SpinTrap G-25 Columns were from GE Healthcare Life Sciences (Pittsburgh, PA); 4-[4-[1-(9-Fluorenylmethyloxycarbonylamino) ethyl]-2-methoxy-5-nitrophenoxy]butanoic acid, referred to from here forward as 4-[4-[1-(9-Fmoc-amino)ethyl]-2-methoxy-5-nitrophenoxy]butanoic acid, was from Santa Cruz Biotechnology (Dallas, TX). FlexWell™ 16-Chamber Self-Adhesive Gaskets (204916) were from Grace Bio-Labs (Bend, Oregon).

Example 1

15-Plex PC-MT-Ab Based MSI Using Bead-Arrays as a Model System

PC-MTs.

The peptide based PC-MTs were produced using standard Fmoc amino acid solid-phase peptide synthesis (SPPS) [Behrendt, White et al. (2016) J Pept Sci 22: 4-27]. An Fmoc-protected photocleavable amino acid linker (see Fmoc-PC-Linker in FIG. 3) was introduced into the peptide chain in the same manner as the other amino acids and the N-terminal α-amine of the peptide was acetylated with acetic anhydride using standard procedures. The NHS-ester probe-reactive moiety was created on the ε-amine of a lysine (K) included in the spacer unit (see FIG. 3 Step 1, NHS-ester). Conversion of the ε-amine of the lysine (K) to an NHS-ester was achieved using disuccinimidyl suberate (DSS). The use of bifunctional succinimidyl esters such as DSS or DSC (disuccinimidyl carbonate) has been previously reported for conversion of primary amines to NHS-esters [Morpurgo, Bayer et al. (1999) J Biochem Biophys Methods 38: 17-28]. PC-MTs were HPLC purified after synthesis using an Onyx Monolithic C18 column and a 0.05% TFA in $H_2O$/0.05% TFA in Acetonitrile solvent system. The chemical structure of an exemplary PC-MT is shown in FIG. 3. 15 different PC-MTs were made, differing only from that shown in FIG. 3 by the amino acid sequence of the mass unit. The 15 different mass unit sequences are listed in Table 1 (IDs 1, 2-3 and 5-16) as well as the monoisotopic mass of the mass reporter, which as shown in FIG. 3 (Step 3) includes the N-terminal acetylation, the peptide mass unit and a small portion of the photocleaved PC-Linker.

In some cases, an additional lysine was included in the spacer unit of the PC-MT and modified with fluorophores using commercially available amine-reactive reagents (e.g., Sulfo-Cy5-NHS from Lumiprobe, Hunt Valley, Maryland). In this case, the amino acid sequence of the spacer unit was GS[K-Sulfo-Cy5]GG[K-NHS] instead of GSGG[K-NHS] in the non-fluorescent PC-MTs.

Preparation of PC-MT Antibodies (PC-MT-Abs)

100 μL of antibody solution (1 μg/μL in PBS) was supplemented with $⅑^{th}$ volume of 1M sodium bicarbonate followed by sufficient PC-MT added from a 1 mM stock in anhydrous DMF for a 10-fold molar excess relative to the antibody. The reaction was carried out for 1 hr protected from light and with gentle mixing. The reaction was then quenched by $⅑^{th}$ volume of 1M glycine followed by mixing for 15 min, protected from light. Finally, $1/199^{th}$ volume of a 10% (w/v) BSA carrier stock in water was added for 0.05% BSA (w/v) final. To remove unreacted PC-MT, the resultant PC-MT antibody (PC-MT-Ab) was processed on PD Spin-Trap G-25 Columns according to the manufacturer's instructions using TBS (50 mM Tris, pH 7.5, 200 mM NaCl) as the pre-equilibration buffer. The resultant PC-MT-Ab was further supplemented with $⅑^{th}$ volume of 10× TBS. In some cases, the PC-MT-Ab was purified by dialysis extensively against TBS using Slide-A-Lyzer™ 0.1 mL MINI Dialysis Devices with 20 kDa Membrane.

Bead-Arrays

Streptavidin-coated 20 micron PMMA beads were processed in 0.5 mL Ultrafree-MC Centrifugal 0.45 μm Filter Devices unless otherwise noted (washing was performed by 3 s vortex mixing of bead suspensions in the Filter Devices and filtration to separate the beads from the solutions was performed for 5 s at 15,000 rpm on a standard microcentrifuge). For each PC-MT-Ab version, 10,000 beads were used and processed separately unless otherwise noted. Beads were first washed 4×400 μL with Bead Block Buffer (1% BSA [w/v] in TBS-T; note TBS-T is TBS supplemented with 0.05% [v/v] Tween-20). Beads were then probed separately with 15 different versions of an anti-streptavidin PC-MT-Ab, each PC-MT-Ab version carrying a different PC-MT species (i.e., different mass unit—see Table 1 for mass units having IDs 1, 2-3 and 5-16). PC-MT-Abs were diluted to 1 μg/mL in Bead Block Buffer and probing was performed using 100 μL for 1 hr with gentle mixing. Beads were then washed 4×400 μL with TBS-T followed by pooling all 15 different bead versions. Pooled beads were then washed further 4×400 μL with mass spectrometry grade water (MS-Water). Bead-Array formation on indium tin oxide (ITO) coated microwell substrates having the footprint of a standard microscope slide was performed as previously reported [Lim, Liu et al. (2014) Rapid communications in mass spectrometry: RCM 28: 49-62; Zhou, Liu et al. (2016) Sci Rep 6: 26125].

Photocleavage

Substrates were ultimately dried for 45 min in a vacuum desiccation chamber and illuminated with 365 nm light at a 5 cm distance for ~3 $mW/cm^2$ using model XX-15 lamp (UVP/Analytik Jena US LLC, Upland, CA). Alternatively, substrates were illuminated with 365 nm light using a LED Cube 100 IC (Honle UV Technology, Marlboro, MA) for ~30 $mW/cm^2$. 5 min light treatment was used unless otherwise noted.

Matrix Application

Next, DHB or DAN matrices were applied to the dried substrates by sublimation followed by recrystallized according to published reports [Hankin, Barkley et al. (2007) J Am Soc Mass Spectrom 18: 1646-52; Duenas, Carlucci et al. (2016) J Am Soc Mass Spectrom 27: 1575-8].

MALDI-MS Imaging (MALDI-MSI)

MALDI-MS imaging (MALDI-MSI) was achieved with a rapifleX MALDI-TOF-MS instrument (Bruker Daltonics, Billerica, MA) using the following parameters: reflector mode; laser spot size 10 or 20 μM with 10 or 20 μm continuous raster scanning, respectively; 300-500 laser shots/pixel; and normalization to total ion count (TIC) in some cases. Image and spectral analysis were performed using flexImaging and flexAnalysis software (Bruker Daltonics, Billerica, MA).

Results

Figure 6:
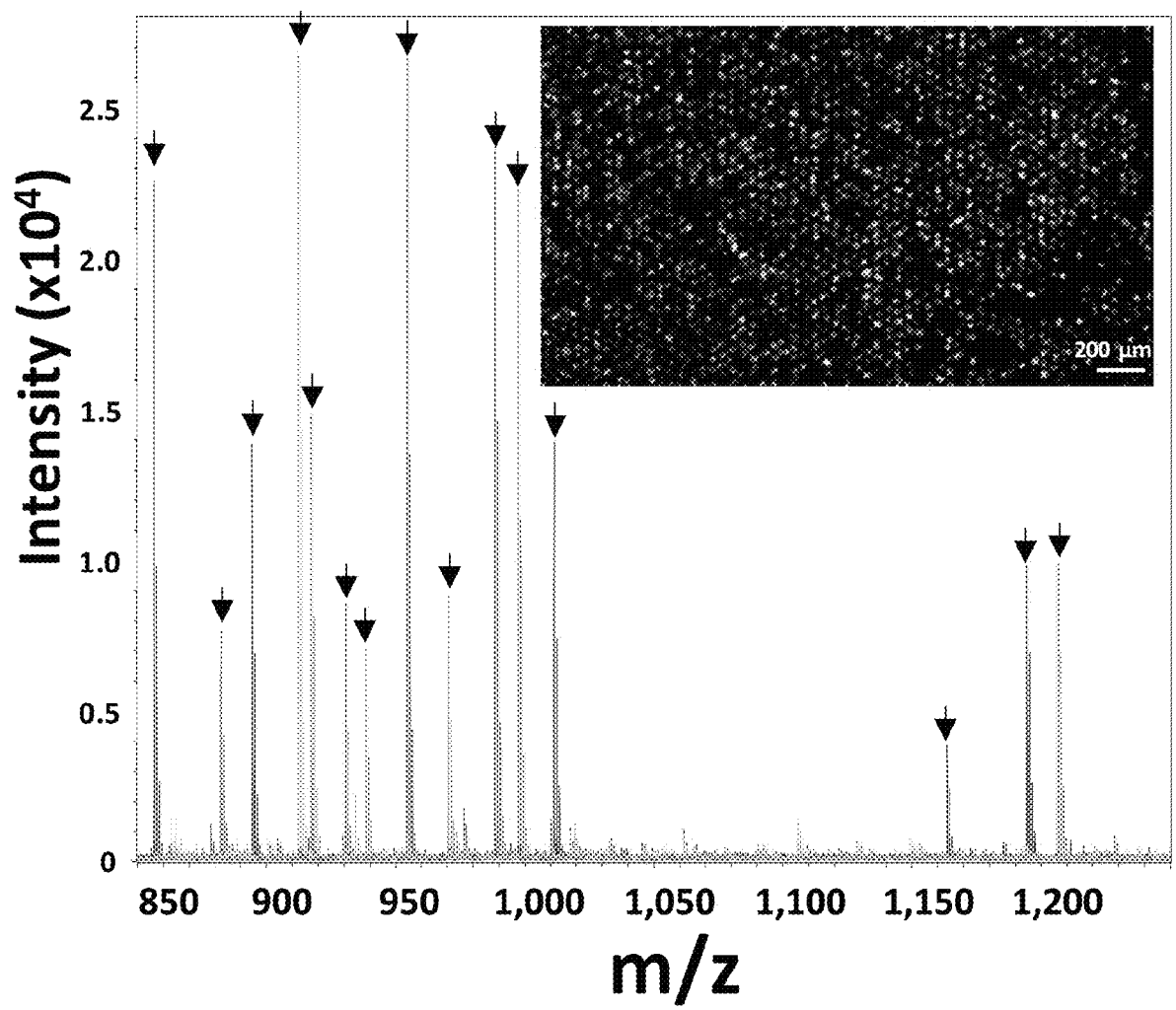
FIG. 6. 15-Plex PC-MT-Ab Based MSI using Bead-Arrays as a Model System. 15 different versions of an anti-streptavidin PC-MT-Ab were created by direct 1-step labeling with 15 novel amine-reactive NHS-activated PC-MT reagents. PC-MT-Ab were used separately to probe 20 µm polymer streptavidin beads. The beads were then pooled and used to form an array in the footprint of a microscope slide, which was then subjected to MALDI-MSI. The inset is a color-coded 15-plex MALDI-MS "mass-image" of a representative region of the bead-array. The color-coded overlaid spectra are from representative single beads within the mass-image for each of the 15 different PC-MT-Ab-probed bead versions (black arrows indicate the different PC-MT mass reporter peaks). Note that while 1 Da separated natural isotopes of the peptide PC-MTs are easily resolved by the MALDI-MS, they are not visible in the spectra provided due to the compact X-axis scaling.

Results in FIG. 6 (inset image) show a MALDI-MS "mass-image" of the bead-array. The different colors in the inset image correspond to the different m/z values of the monoisotopic mass-spectral peak for a particular PC-MT mass reporter (see Table 1 for expected masses of mass reporters having IDs 1, 2-3 and 5-16). 15 different and mass-resolvable mass reporter species derived from the PC-MT-Ab probes bound to distinct 20 μm beads in the array are observed. Color-coded overlaid MALDI-MSI spectra (FIG. 6; black arrows) from representative single beads within the array show no bead-to-bead "cross-talk".

Example 2

5-Plex MIHC Using PC-MT-Abs on Mouse Brain Sagittal FFPE Tissue Sections

Immunostaining with PC-MT-Abs

PC-MTs and PC-MT-Abs were prepared as in Example 1 and used as follows in MIHC: For deparaffinization and hydration, FFPE tissue sections were treated as follows (each treatment step in separate staining jars): 3× with xylene for 5 min each; 1× with xylene:ethanol (1:1) for 3 min; and then hydrate 2× with 100% ethanol for 2 min each, 2× with 95% ethanol for 3 min each, 1× with 70% ethanol for 3 min, 1× with 50% ethanol for 3 min and 1× with TBS for 10 min.

Antigen retrieval was achieved in 200 mL of 1× Citrate Buffer (pH 6.0; see Materials) in a beaker preheated in a water bath at 95° C. for 1 hr and cooled in the same beaker for 30 min at room temperature. Slides were then blocked in a staining jar for 1 hr with 50 mL Tissue Blocking Buffer (2% [v/v] normal serum [rabbit and mouse] and 5% (w/v) BSA in TBS-T; note TBS-T is TBS supplemented with 0.05% [v/v] Tween-20). For PC-MT-Ab staining, slides were treated at 4° C. for overnight with 200 μL/section of a solution containing 2.5 μg/mL of each antibody diluted in Tissue Blocking Buffer (incubation was performed protected from light, in a humidified chamber to avoid evaporation and with each tissue section surrounded by hydrophobic barrier pen to retain the fluid).

The slides were next washed as follows: Wash 3×5 min each with TBS followed by 3×2 min each with 50 mM ammonium bicarbonate (note, all solutions were in LCMS grade water and all washes were performed using excess solution and with the slides placed horizontally in a petri dish with gentle shaking).

Finally, photocleavage, matrix application and MALDI-MSI were performed as in Example 1.

Note that in some cases, immunofluorescence was performed instead of staining with PC-MT-Ab. In these cases, antibodies labeled with a 15-fold molar excess of a DyLight 650 NHS Ester reagent (added from a 5 mM stock in DMF) were used instead of antibodies labeled with PC-MTs (otherwise using the same labeling procedure described earlier for PC-MT-Ab in Example 1). Furthermore, photocleavage, matrix application and MALDI-MSI were not performed, instead, imaging of dried slides was performed on a GenePix 4200A fluorescence scanner at 5 μm resolution (Molecular Devices, San Jose, CA). All other procedures were the same as described for MIHC in this Example.

Results

Figure 7A:
FIG. 7A-E. 5-Plex MIHC using PC-MT-Abs on Mouse Brain FFPE Tissue Sections. FFPE tissue sections were stained simultaneously with PC-MT-Abs against five different protein targets and then subjected to MALDI-MSI. For MSI, matrix application was by sublimation followed by recrystallization (MSI in positive ion reflection mode). Standard immunofluorescence staining was also performed on adjacent tissue sections.
Figure 7B:
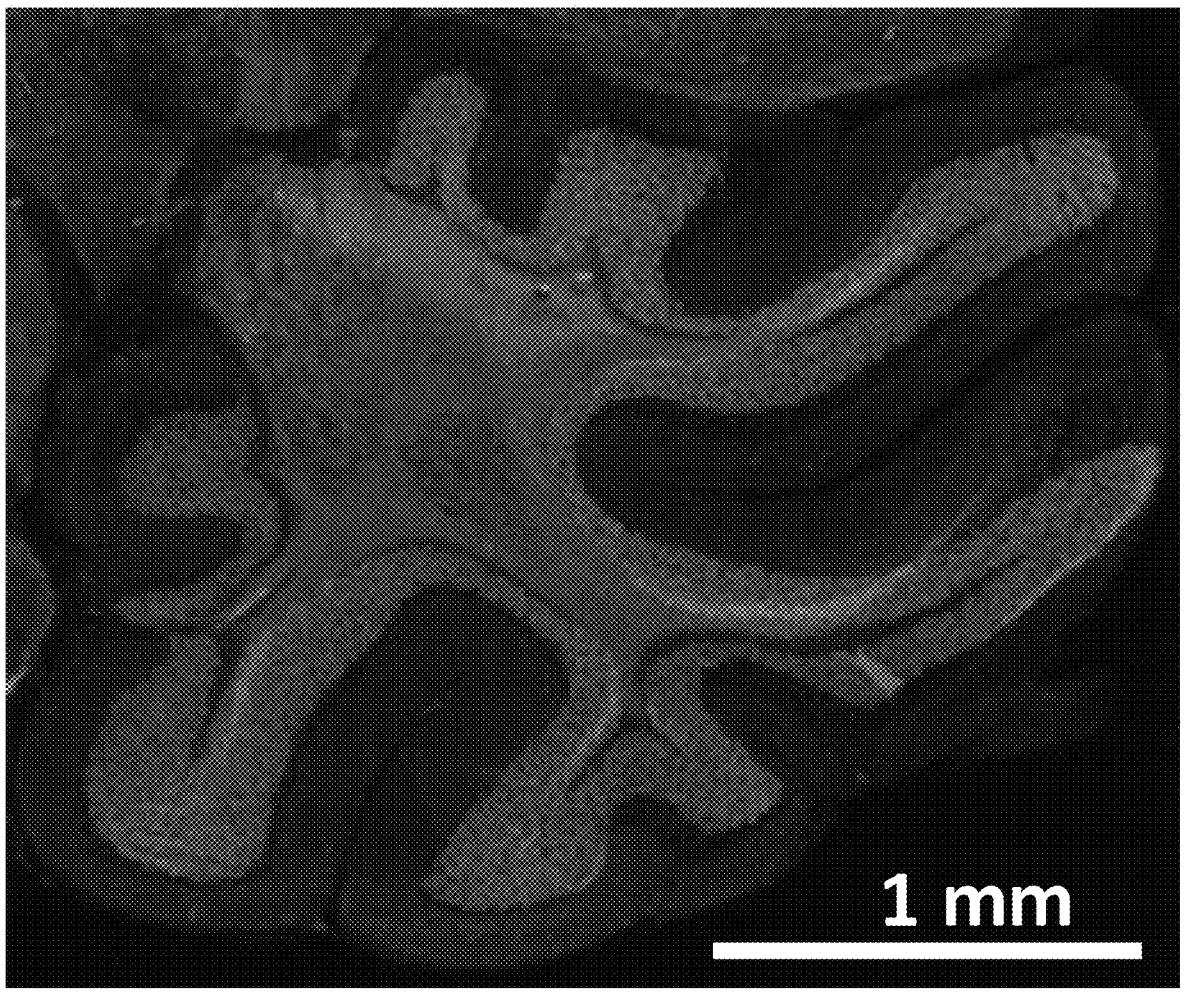
Figure 7C:
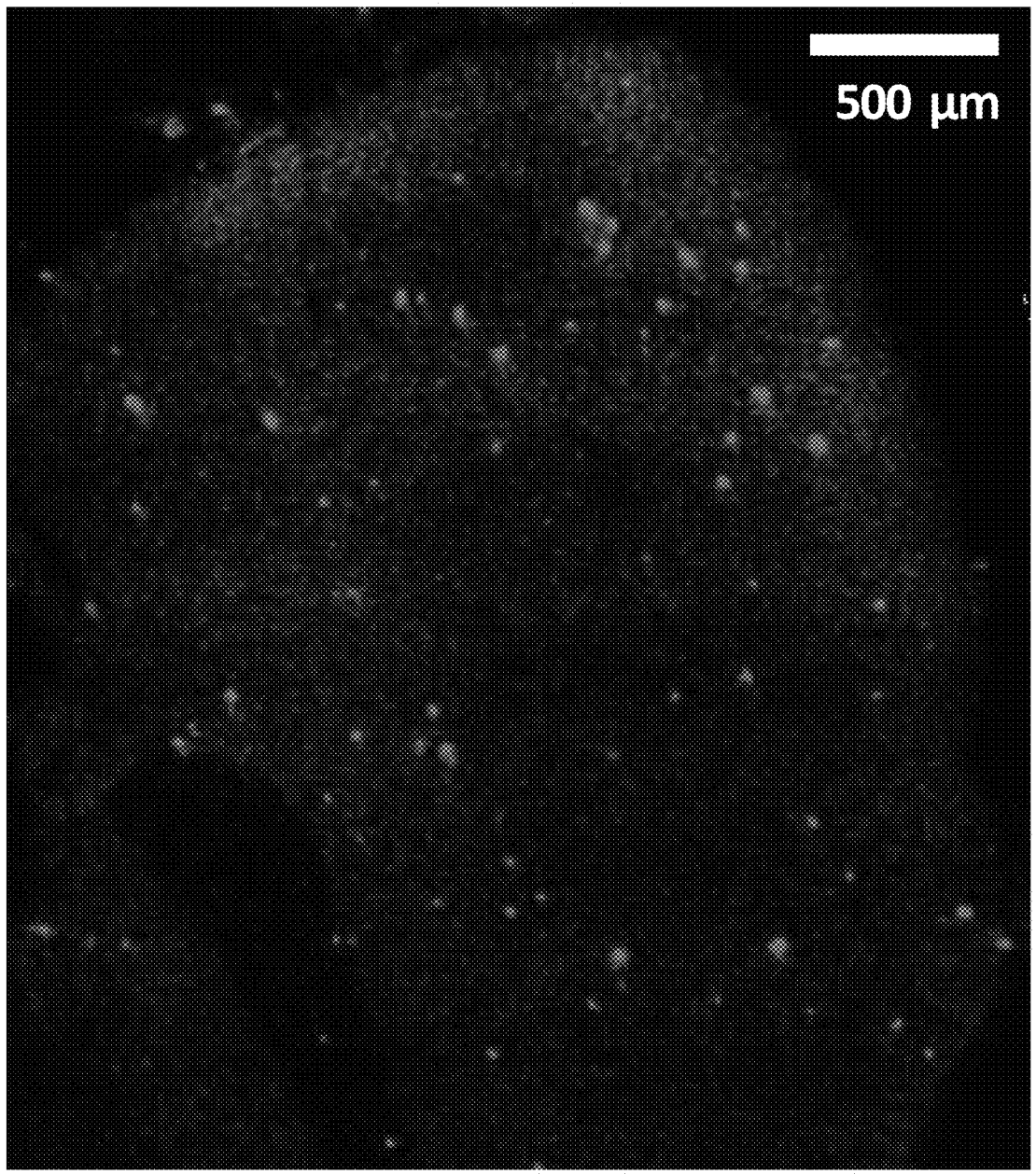
Figure 7D:
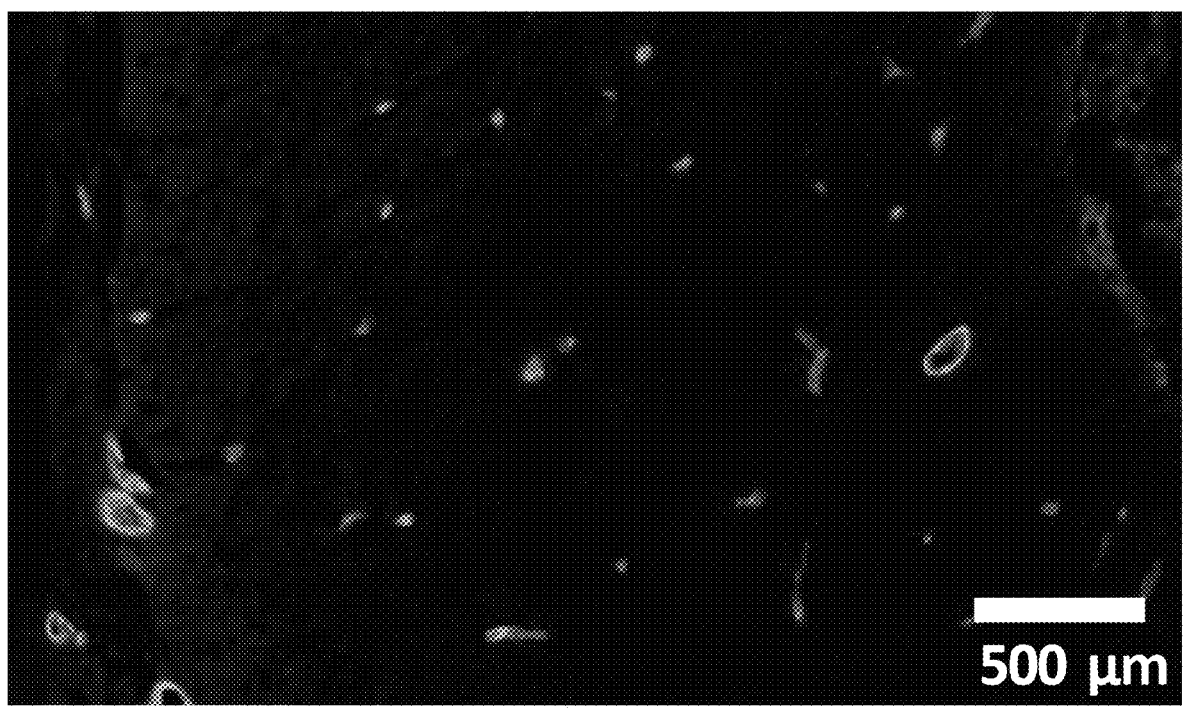
Figure 7E:
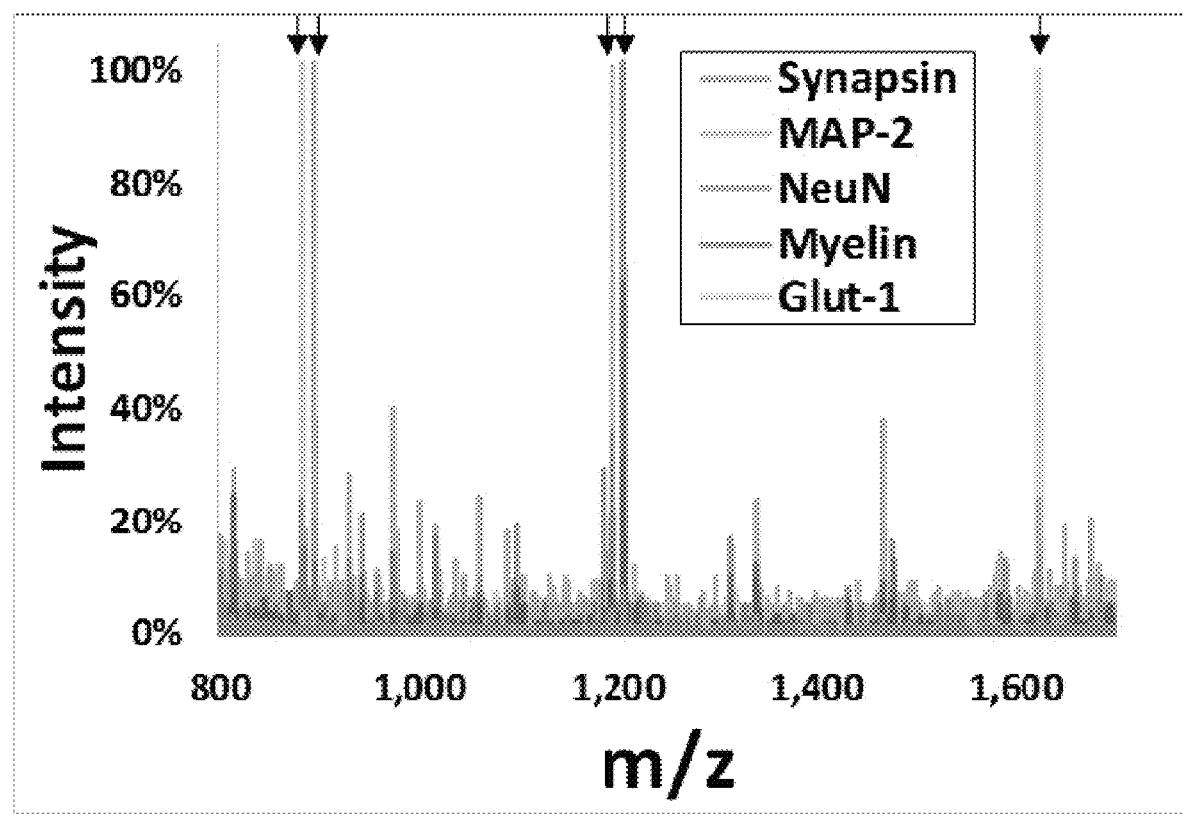

5-Plex MIHC was performed on an FFPE sagittal section of mouse brain. For this purpose, different PC-MTs were directly conjugated in 1-step to antibodies. The five antibodies were targeted to myelin basic protein (a well-known axonal sheath marker, e.g., [van Tilborg, van Kammen et al. (2017) Sci Rep 7: 16492]), NeuN (neuronal nuclear marker, e.g., [Gusel'nikova and Korzhevskiy (2015) Acta Naturae 7: 42-7]), synapsin (a synaptic protein, e.g., [Mason (1986) Neuroscience 19: 1319-33]), Glut-1 (enriched in the blood capillaries of brain tissue [Tang. Gao et al. (2017) Nat Commun 8: 14152]) and MAP-2 (a microtubule associated protein present in nervous tissue, e.g., [Wiche, Briones et al. (1983) EMBO J 2: 1915-20]). MALDI-MSI was achieved on an in-house Bruker rapifleX MSI instrument at 10 μm spatial resolution. FIG. 7a shows the 5-color MALDI-MS "mass-image" of the whole brain section. The different colors correspond to the different m/z values of the monoisotopic mass-spectral peak for a particular PC-MT. Myelin (red), NeuN (green) and synapsin (blue) are the most predominant and produce the most distinct structural patterns. For instance, NeuN produces the distinct "swirl" pattern of the hippocampus (denoted with *). Furthermore, myelin, NeuN and synapsin highlight three distinct layers of the cerebellum (denoted with ╪). Less distinct biomarkers which are hidden in the composite color image can best be seen as single-color images. For example, FIG. 7c shows a single-color standalone MALDI-MS image of the Glut-1 biomarker (showing predominantly cross-sections of the blood capillaries of the brain). MAP-2 produces a fairly uniform staining of the brain sections (not shown as a standalone image). Moreover, species-matched non-immune isotype control immunoglobulins carrying the same PC-MT show no MALDI-MS signals (not shown). Color-coded overlaid mass spectra are shown (FIG. 7e) for selected pixels of the MALDI-MS image (those pixels marked with arrows in FIG. 7a). Finally, the MIHC results clearly match conventional immunofluorescence. For example, using myelin, NeuN and synapsin antibodies, directly labeled with fluorophore only, produces the same pattern in the cerebellum (FIG. 7b) as MIHC. The Glut-1 MALDI-MS pattern is also matched by immunofluorescence (FIG. 7d).

Example 3

MISH Using PC-MT-NA miRNA Hybridization Probes on FFPE Tissue Sections

Preparation of PC-MT Nucleic Acids (PC-MT-NAs)

Amine-modified Locked Nucleic Acid (LNA) probes (see Materials) were labeled with PC-MT as follows: To 100 μL of LNA probe solution (10 μM in 200 mM sodium chloride and 200 mM sodium bicarbonate) sufficient PC-MT was added from a 10 mM stock in anhydrous DMF for a 200-fold molar excess relative to the LNA probe (2 μL of 10 mM stock added every 30 min for a total of 5 additions). The reaction was carried out for total 2.5 hr protected from light and with gentle mixing. To remove unreacted PC-MT, the resultant PC-MT-NA was processed on NAP-5 Sephadex G-25 Columns according to the manufacturer's instructions using TE-150 mM NaCl (10 mM Tris, pH 8.0, 1 mM EDTA and 150 mM NaCl) as the pre-equilibration buffer.

In Situ Hybridization with PC-MT-NAs

For deparaffinization and hydration, FFPE tissue sections were processed in the same manner as Example 2. The following procedure was adapted from Renwick et al. [Renwick, Cekan et al. (2013) J Clin Invest 123: 2694-702]: Tissue sections were prepared for in situ hybridization by proteinase K digestion, EDC fixation and acetylation. For proteinase K digestion, 1.5 μL of Proteinase K Stock Solution from the miRCURY LNA miRNA ISH Buffer Set for FFPE (see Materials) was diluted to 2.0 mL in proteinase K buffer (5 mM Tris-HCl pH 7.4, 1 mM EDTA, 1 mM NaCl) and 300 μL was incubated with each tissue section for 10 min at 37° C. After proteinase K digestion, the tissue sections were washed 2×10 min each with 0.2% (w/v) glycine in PBS. For EDC fixation, tissue sections were pretreated 2×3 min each in 0.1M 1-Methylimidazole Solution and then treated with 200 μL of EDC Fixative Solution for 1 hr (freshly prepared by adding 1.0 mL of 0.1 M 5-ETT and 0.1M 1-methylimidazole to a 10 mg EDC HCl vial; adjust pH to 8.0 with 10M NaOH). After EDC fixation, the tissue sections were washed for 10 min with 0.2% (w/v) glycine in PBS. For acetylation, Acetylation Solution was freshly prepared by adding 149 μL triethanolamine, 2 μL of HCl (37%) and 5 μL acetic anhydride to 846 μL of nuclease-free water and 200 μL was incubated with each tissue section for 10 min. After acetylation, tissue sections were washed in excess PBS for 3 min. Next, sections were pre-hybridized in a humidified chamber at 25° C. for 1 hr in 150 μL of Hybridization Buffer composed of 50% formamide, 1.0 M NaCl, 75 mM Tris-HCl (pH 8.5), 1×Denhardt's solution, 250 μg/mL baker's yeast tRNA, 500 μg/mL salmon sperm DNA, 5 mM CHAPS, and 0.1% Tween-20. After pre-hybridization, self-adhesive hybridization chambers were placed on the slides (22 mm×53 mm×0.6 mm deep per chamber). For hybridization, the PC-MT U6 and 159 LNA probes were diluted to 200 nM in Hybridization Buffer and the tissue sections were incubated overnight at 55° C. in a humidified chamber (protected from light). Tissue sections were then washed 1×5 min in 5×SSC Buffer, 2×5 min each in 1×SSC Buffer and 1×5 min in 0.2×SSC Buffer at 55° C., and 1×5 min in 0.2×SSC Buffer at room temperature.

The slides were next washed as follows: Wash 3×5 min each with TBS followed by 3×2 min each with 50 mM ammonium bicarbonate (note, all solutions were in LCMS grade water and all washes were performed using excess solution and with the slides placed horizontally in a petri dish with gentle shaking).

Finally, photocleavage, matrix application and MALDI-MSI were performed as in Example 1.

Note that in some cases, FISH was performed instead of staining with PC-MT-NAs. In these cases, nucleic acids labeled with an Atto-647N-NHS Ester reagent were used instead of nucleic acids labeled with PC-MTs (otherwise using the same labeling procedure described earlier in this Example for PC-MT-NA). Furthermore, photocleavage, matrix application and MALDI-MSI were not performed, instead, imaging of dried slides was performed on a GenePix 4200A fluorescence scanner at 5 μm resolution (Molecular Devices, San Jose, CA). All other procedures were the same as described for MISH in this Example.

Results

Figure 8:
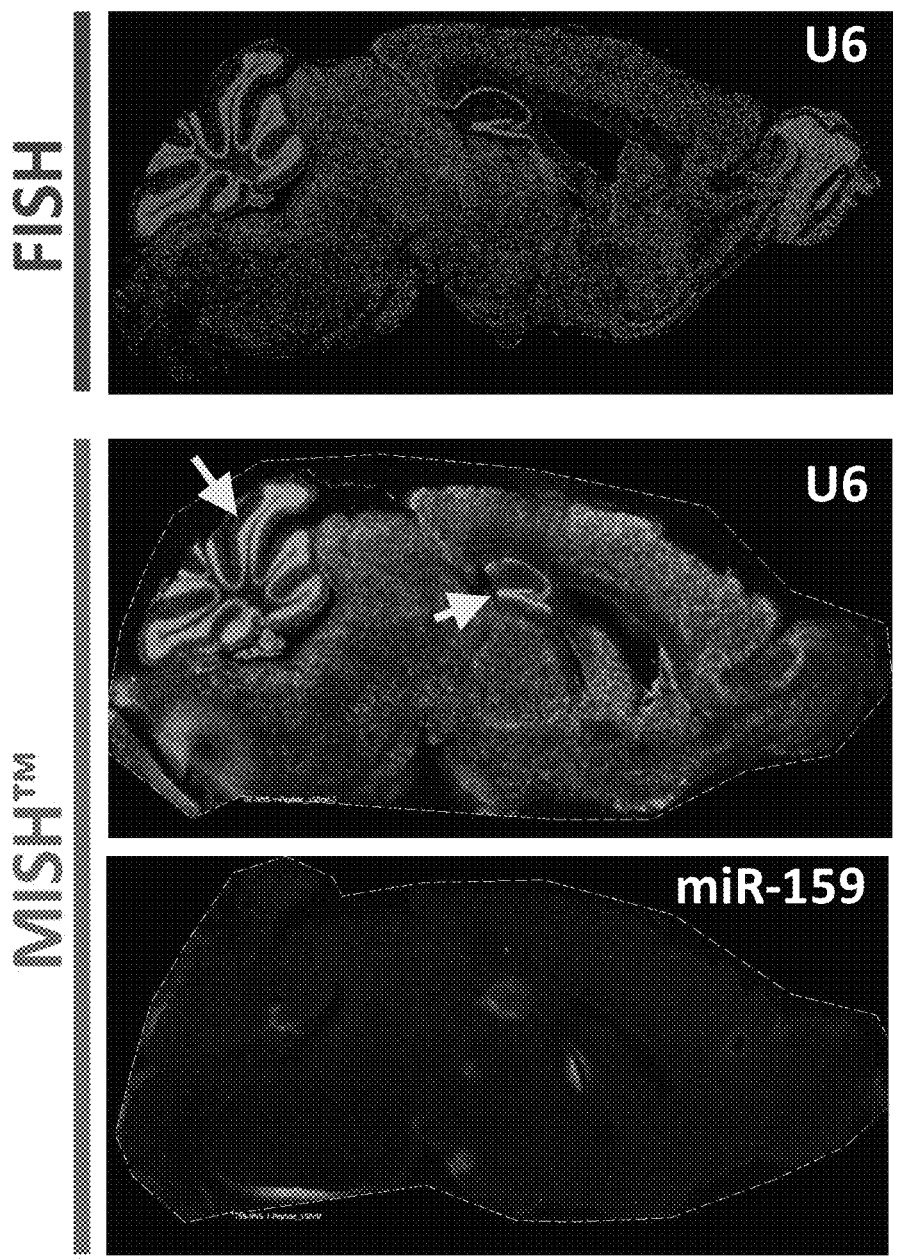
FIG. 8. MISH using PC-MTs Directly Conjugated to Oligonucleotide Probes. U6 snRNA probes (positive control) and plant-specific miR-159 probes (negative control) were used to perform in situ hybridization on mouse brain sagittal tissue sections. To compare conventional "FISH" to "MISH", fluorescence images (red) as well as mass-images corresponding to the m/z values of the monoisotopic PC-MT mass reporter mass-spectral peaks (green) are shown. Yellow arrows highlight the cerebellum and hippocampus features detected with U6.

In order to demonstrate MISH, amine-reactive NHS-activated PC-MT labeling reagents were directly conjugated to 5' amine-terminated LNA hybridization probes (LNA=Locked Nucleic Acids for better affinity [Vester and Wengel (2004) Biochemistry 43: 13233-41; Sempere, Christensen et al. (2007) Cancer Res 67: 11612-20; Robertson and Thach (2009) Anal Biochem 390: 109-14; Nielsen (2012) Methods Mol Biol 822: 67-84; Renwick, Cekan et al. (2013) J Clin Invest 123: 2694-702; Kasai, Kakihara et al. (2016) Front Mol Neurosci 9: 126; Lei, van Mil et al. (2018) Biotechnol Rep (Amst) 18: e00255]). The probes were then used to stain mouse brain sagittal tissue sections and MALDI-MSI was performed. Probes were U6, an snRNA commonly used as a positive control in miRNA FISH, and miR-159, a negative control plant-specific sequence [Lei, van Mil et al. (2018) Biotechnol Rep (Amst) 18: e00255]. Results in FIG. 8 show that MISH with the U6 probe produces a similar tissue staining pattern as conventional FISH methods, while the negative control miR-159 probe produces no appreciable staining pattern.

Example 4

Multi-Omic MSI: Untargeted Label-Free MSI of Lipids and Targeted MIHC on the Same FF Tissue Section Untargeted Label-Free Direct MSI on FF Tissue Section Unprocessed fresh frozen (FF) tissue sections were first directly analyzed in an untargeted manner by MALDI-MSI (after thawing the tissue sections and performing only matrix application as in Example 2 [DAN matrix in this case]).

MIHC on the Same FF Tissue Section

Next, deparaffinization was not necessary with the FF tissue sections, however, paraformaldehyde (PFA) fixation was performed as follows (each treatment step in separate staining jars): pre-wash 2× with cold acetone for 3 min each (note, serves to remove any remaining matrix compound from the prior MALDI-MSI while providing solvent fixation) and air dry for 10 min; 10 min fixation using 1% PFA in PBS, pH 7.4 (note this solution was prepared fresh by dissolving 1.0 g of PFA in 60 mL of PBS with 1.0 mL 1 M NaOH on a heating block at ~60° C. under constant stirring, followed by adjusting the pH to 7.4 with 1 M HCl [~1 mL] and adjusting the final volume to 100 mL with PBS); wash 1× with PBS for 10 min. The remaining steps for PC-MT-Ab based MIHC were performed as in Example 2 starting with the antigen retrieval step to the end.

Results

Figure 9A:
FIG. 9A-D. Untargeted small molecule MALDI-MSI and targeted PC-MT-Ab-based macromolecule MALDI-MSI on the same tissue section.
Figure 9B:
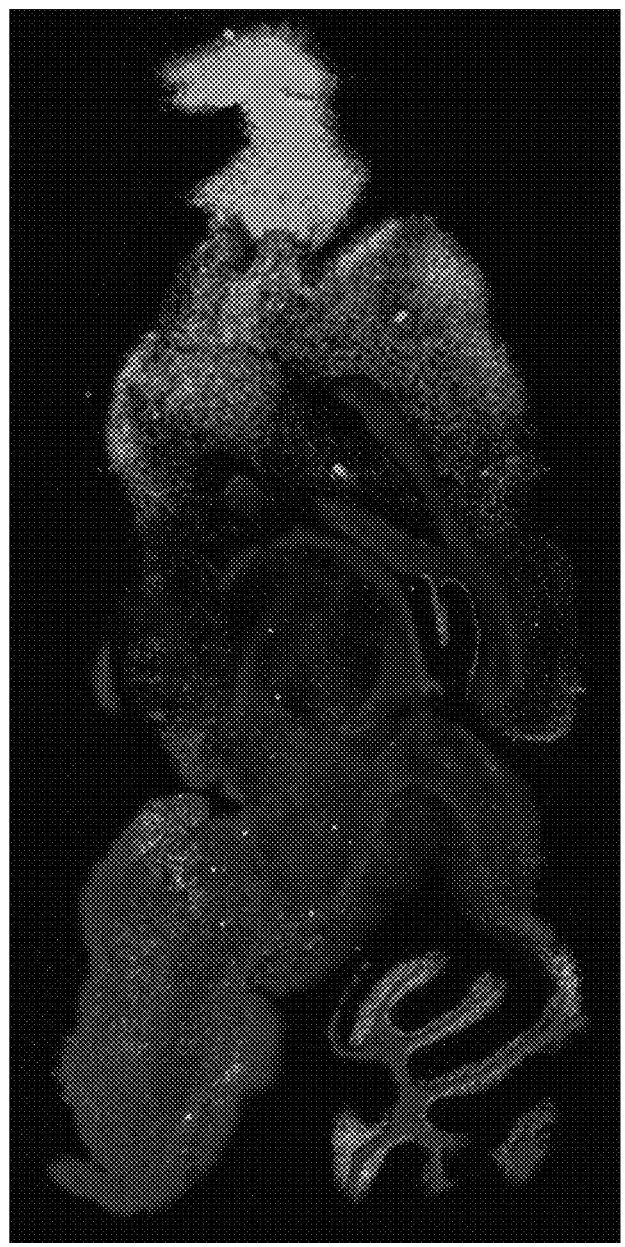
Figure 9C:
Figure 9D:
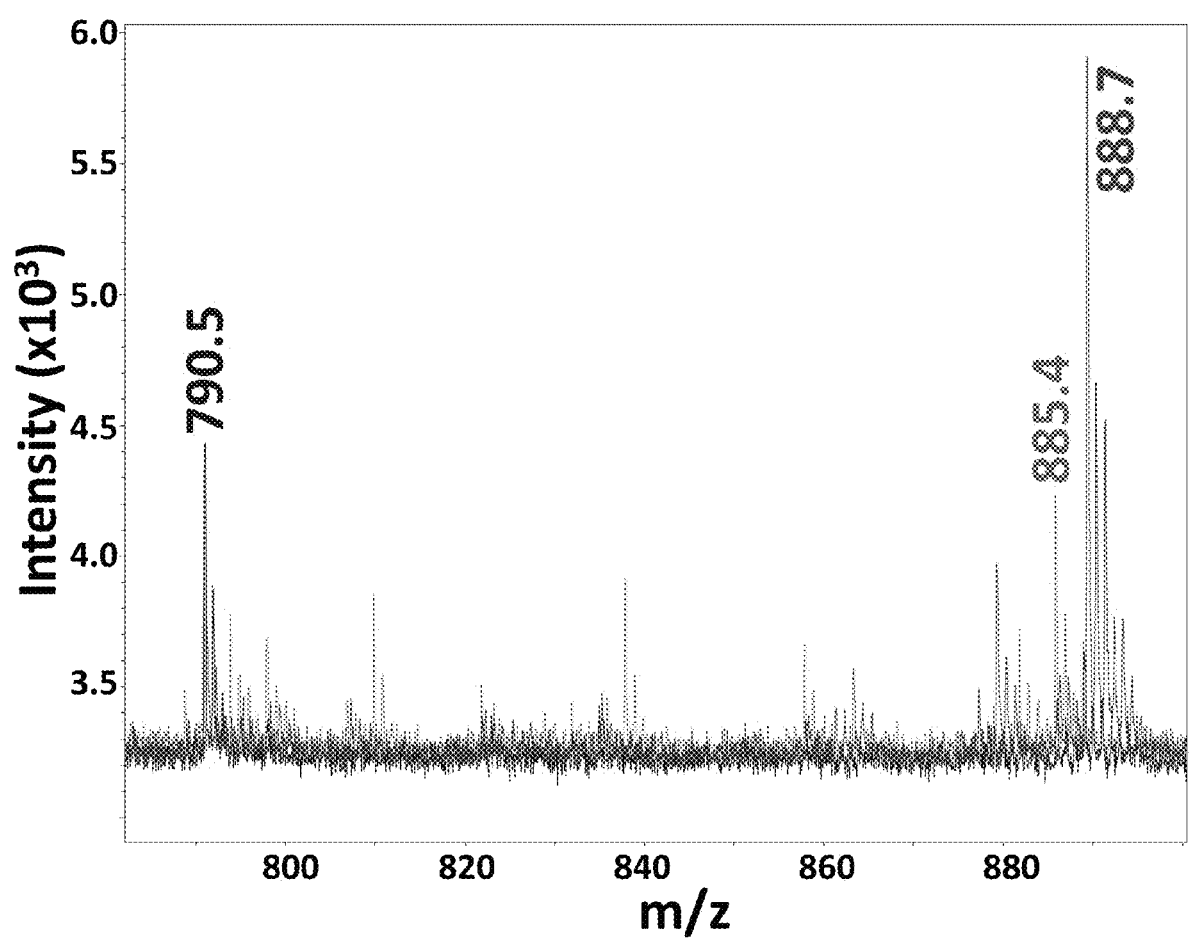

It would be highly advantageous to be able to detect both untargeted label-free small molecules and PC-MT-Ab-targeted macromolecules on the same tissue section. For example this would allow co-localization of small molecule drugs and drug-targets such as their receptors, as well as associated biomolecules involved in the cellular response to the drug. To demonstrate the basic feasibility of this capability, we first performed direct MALDI-MSI analysis on fresh frozen mouse brain sagittal tissue sections (fresh frozen is optimal instead of FFPE to facilitate small molecule detection without tissue fixation or prior washing). Negative ion mode MALDI-MSI with DAN matrix was used. Next, the tissue was washed/fixed with cold acetone to remove the MALDI-MS matrix compound and then fixed further with paraformaldehyde. MIHC was then performed, constituting of a second round of MALDI-MSI (so-called Dual-MSI). The result of the first round of direct MALDI-MSI is shown in FIG. 9a, with the image color-coded for the m/z values of three well-known lipids identified from the METLIN database of the Scripps Center for Metabolomics [Smith, O'Maille et al. (2005) Ther Drug Monit 27: 747-51] and in agreement with prior MALDI-MSI analysis of lipids from mouse brain tissue sections [Wang, Wang et al. (2018) Anal Chim Acta 1000: 155-162] (sulfatide [N24:1], red, observed m/z 888.7; phosphatidylethanolamine [40:6], blue, observed m/z 790.5; and phosphatidylinositol [38:4], green, observed m/z 885.4). These three lipids are clearly enriched in different structures of the brain, in particular, sulfatide (red) shows a distinct pattern from the other two lipids. However, there is also significant co-localization of phosphatidylethanolamine (blue) and phosphatidylinositol (green), as would be expected as two of the major structural lipids of eukaryotic cellular membranes [van Meer, Voelker et al. (2008) Nat Rev Mol Cell Biol 9: 112-24] (co-localized blue and green appears as cyan in FIG. 9a). For demonstration purposes, FIG. 9b and FIG. 9c show 2-color overlays of the sulfatide lipid, detected in the first round of direct MALDI-MSI, with selected macromolecular biomarkers, detected by MIHC in the second round of MALDI-MSI. FIG. 9b shows sulfatide (red), overlaid with the neuronal nuclear biomarker NeuN (green), detected as demonstrated earlier in Example 2 with a PC-MT-Ab. These two biomolecules generally do not co-localize. Conversely, FIG. 9c shows the same lipid, sulfatide (red), overlaid with myelin basic protein (green), again detected with a PC-MT-Ab in the multiplex MIHC analysis. In this case, there is a strong co-localization of sulfatide and myelin (evidenced by the yellow occurring from co-localization of the green and red colors). The co-localization of sulfatide and myelin agrees with previous literature which indicates sulfatide is predominantly found in myelin sheath (Schwann cells/oligodendrocytes) of neuronal axons [Eckhardt (2008) Mol Neurobiol 37: 93-103; Hirahara, Wakabayashi et al. (2017) J Neurochem 140: 435-450]. Conversely, sulfatide would not be expected to co-localize with the neuronal nuclear biomarker NeuN, as was observed here (note that as shown earlier in Example 2, myelin and NeuN also generally do not co-localize). Finally, example spectra from the first round of direct MALDI-MSI are shown in FIG. 9d. These spectra are from selected image pixels chosen from the three different colored "layers" observed in the olfactory bulb/nerve layer of the mouse brain (see colored arrows in FIG. 9a for these layers). In the future, the utilization of MS/MS or higher resolution FTICR mass spectrometers will provide for more accurate small molecule identification.

Example 5

Preferred Attachment Site of Mass Unit to PC-Nucleus

Figure 10A:
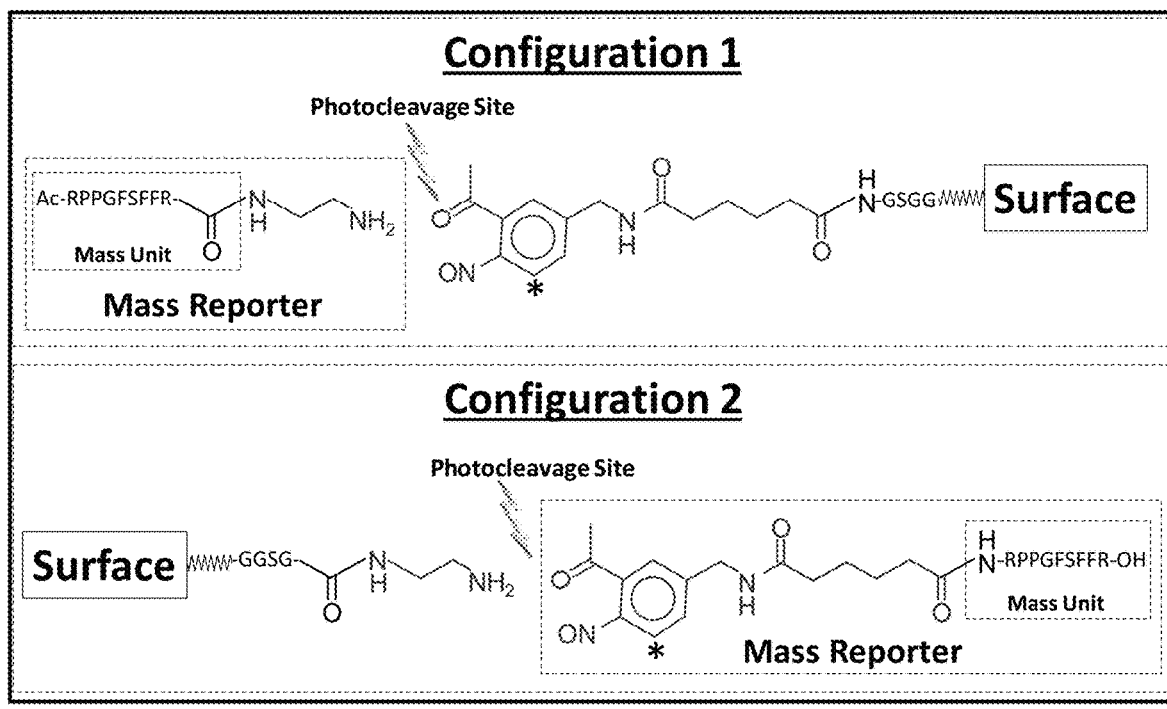
FIG. 10A-B. Preferred Attachment Site of Mass Unit to PC-Nucleus.

In the Present Invention, the preferred mode of attachment of the mass unit to the phenyl ring of the PC-Nucleus (see FIG. 3 for PC-Nucleus) is ultimately through the photocleavage site (see FIG. 10a, Configuration 1; see also FIG. 3). In this configuration, the photocleaved phenyl ring of the PC-Nucleus does not remain attached to the photocleaved mass reporter that is detected by mass spectrometry (MS). While it is possible to instead attach the mass unit ultimately to the phenyl ring of the PC-Nucleus through a site other than the photocleavage site, as taught by Olejnik et al. [Olejnik, Ludemann et al. (1999) Nucleic Acids Res 27: 4626-31] and by Levy and Caprioli (U.S. Pat. No. 7,569, 392), this is not preferred since the photocleaved phenyl ring of the PC-Nucleus remains attached to the photocleaved mass reporter detected by MS (see FIG. 10a, Configuration 2).

Figure 10B:
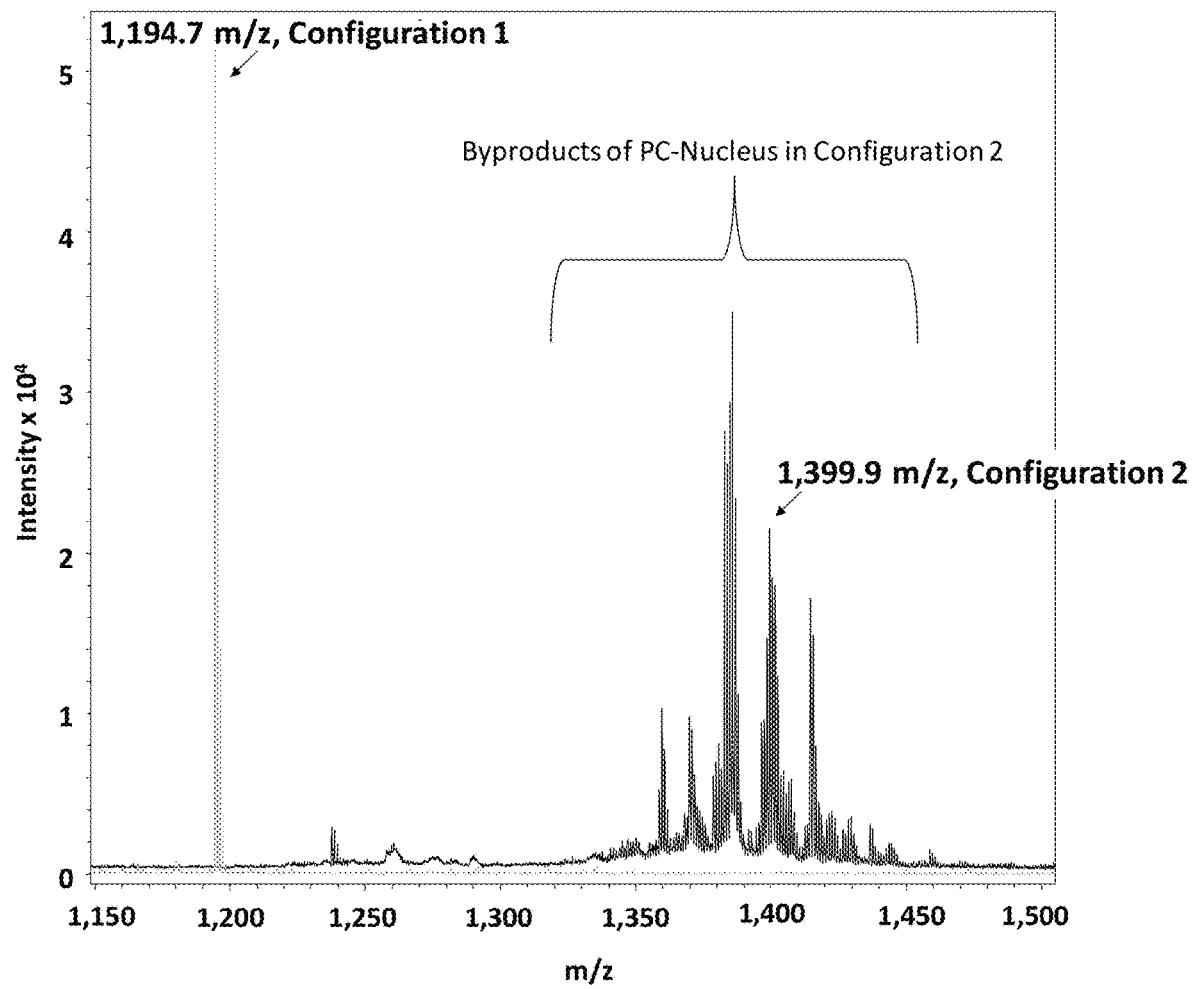

To demonstrate the benefits of preferred Configuration 1, photocleavable peptides having the same mass unit peptide sequence were attached to surfaces according to the two configurations shown in FIG. 10a. (see FIG. 10a also for the structure and sequence of the photocleavable peptides). Mass reporters were then photocleaved from the surfaces and measured by mass spectrometry. Preferred Configuration 1 provides a clean monoisotopic peak at the expected mass of the mass reporter (light gray trace in FIG. 10b; 1,194.7 m/z; Configuration 1) and only the accompanying peak cluster corresponding to the natural isotopes of the mass reporter separated by 1 m/z (present but not discernable in FIG. 10b due to the X-axis scaling). With Configuration 2, the photocleaved mass reporter does provide the expected monoisotopic mass reporter peak (black trace in FIG. 10b; 1,399.9 m/z; Configuration 2), but also produces a highly complex mass spectrum likely resulting from side-reaction byproducts of the photocleaved phenyl ring of the PC-Nucleus which remains attached to the mass reporter (see FIG. 10b "Byproducts of PC-Nucleus in Configuration 2"). These byproducts may in part include oxygen adducts and losses resulting from the oxygen radical chemistry involved. Ultimately, this will degrade sensitivity (by dividing the mass reporter signal into a multitude of mass spectral peaks) and will confound mass reporter identification in multiplex analyses (by peak overlap).

Example 6

Comparison of Different PC-Linkers and Comparison of Pre-Photocleavage Versus In-Line Photocleavage with the MALDI-MS Laser Beam

PC-MT

PC-MTs having the structural configuration depicted in FIG. 3 were produced as in Example 1 (4 PC-MTs in this Example, comprised of mass units 1 and 2-4 listed in Table 1).

Additionally, so-called PC-MTs-L were produced in the same manner, differing only by the use of the PC-Linker from Lemaire et al. ([Lemaire, Stauber et al. (2007) J Proteome Res 6: 2057-67] [see also U.S. Pat. No. 8,221,972] instead of the PC-Linker depicted in FIG. 3. To achieve this, 4-[4-[1-(9-Fmoc-amino)ethyl]-2-methoxy-5-nitrophenoxy] butanoic acid (see Materials) was used to introduce the PC-Linker into the PC-MTs-L during peptide synthesis (see FIG. 4 "Lemaire PC-Linker" for this PC-Linker as incorporated into a plain peptide—note in FIG. 4 a plain peptide is depicted to show the PC-Linker itself, however, the plain peptide lacks other features of the PC-MTs and PC-MTs-L). Importantly, while the PC-Linker of the PC-MTs-L was that used by Lemaire et al., the other features of the PC-MTs-L, which are the same as the PC-MT features depicted in FIG. 3, are not taught by Lemaire et al. These features (FIG. 3) include, but are not limited to, the probe-reactive moiety (NHS-ester in this case), the N-terminal blocking of the peptide based PC-MT (N-terminal acetylation in this case), the peptide sequences of the mass unit (Table 1) and in the spacer unit, and the specific attachment of the mass unit to the phenyl ring of the PC-Nucleus through the photocleavage site.

Bead-Arrays

The PC-MTs-L were used at equimolar concentration along with the PC-MTs to simultaneously double-label streptavidin-coated 37 micron PMMA beads. To achieve this, in 4 separate reactions, 4 bead species were created by simultaneously double-labeling each with a PC-MT-L and a PC-MT comprised of the same mass unit. This is possible since the PC-MTs leave a small residual portion of the PC-Linker attached to the photocleaved mass reporter (see FIG. 3 Step 3) while the PC-MTs-L do not (thus, even though the mass units are the same on each bead species, the masses of the photocleaved mass reporters are distinguishable in the mass spectrometer).

Mass-Tag labeling of the beads was performed as follows: Streptavidin-coated 37 micron PMMA beads were processed in 0.5 mL Ultrafree-MC Centrifugal 0.45 µm Filter Devices unless otherwise noted (washing was performed by 3 s vortex mixing of bead suspensions in the Filter Devices and filtration to separate the beads from the solutions was performed for 5 s at 15,000 rpm on a standard microcentrifuge). For each of the 4 bead species (processed separately unless otherwise noted), 100,000 beads were used. Beads were washed 4×400 μL with Conjugation Buffer (200 mM sodium bicarbonate with 200 mM NaCl). Each bead pellet was then re-suspended in 100 μL of Conjugation Buffer followed by addition of 2 μL containing 500 μM each of the PC-MT-L and the PC-MT (in DMF). The reaction was mixed for 30 min and the beads then washed 3×15 min each with 400 μL of Glycine-Hydroxylamine Quench (1M glycine and 100 mM hydroxylamine in 10× concentrated TBS; prepared fresh). Beads were then washed 4×15 min each with 400 μL of OBG Saline (25 mM Ammonium Bicarbonate, 0.05% (w/v) octyl-ß-D-glucopyranoside and 50 mM NaCl) and re-suspended to 250 beads/μL in the same buffer.

Finally, bead-arrays were formed as follows: Beads were washed 4×400 μL and re-suspended (20,000 beads/100 μL) with mass spectrometry grade purified water. Then, using FlexWell™ 16-Chamber Self-Adhesive Gaskets (see Materials) affixed to gold-coated microscope slides (see Materials), beads were dried overnight in a chemical fume hood at a density of 400 beads/mm$^2$. Following drying, the slide was washed gently in a tray with excess mass spectrometry grade purified water (beads remain adherent to the slide) and the slide then dried again for 45 min in a vacuum desiccation chamber.

Photocleavage, Matrix Application and MALDI-MSI of Bead-Arrays

Performed as in Example 1 (note that the beads, which were mass-tagged directly as detailed above, were not probed with PC-MT-Abs as done in Example 1). In some cases, UV illumination was increased to 25 min.

C-MT-Ab

Prepared as in Example 1 except that an anti-myelin antibody was simultaneously dual-labeled with equimolar concentration of a PC-MT-L and a PC-MT, each comprised of mass unit 1 listed in Table 1 (i.e., both the PC-MT-L and PC-MT labeling reagents were pre-mixed in equimolar concentrations [1 mM each in DMF] and the mixture then added to the same antibody for dual-labeling [10-fold molar excess of each compared to antibody for labeling]).

Tissue Immunostaining with PC-MT-Abs, Photocleavage, Matrix Application and MALDI-MSI Performed as in Example 2. In some cases, UV illumination was increased to 25 min. In other cases, UV illumination was not performed, allowing only in-line photocleavage during MALDI-MSI, using the instrument's laser beam.

Results

Figure 11A:
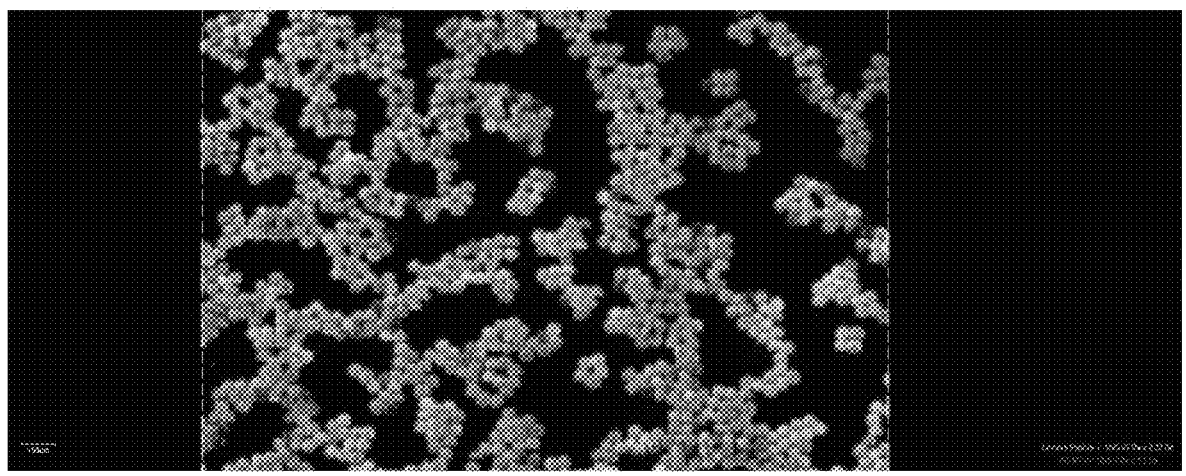
FIG. 11A-L. Comparison of Different PC-Linkers and Comparison of Pre-Photocleavage versus In-Line Photocleavage with the MALDI-MS Laser Beam.
Figure 11B:
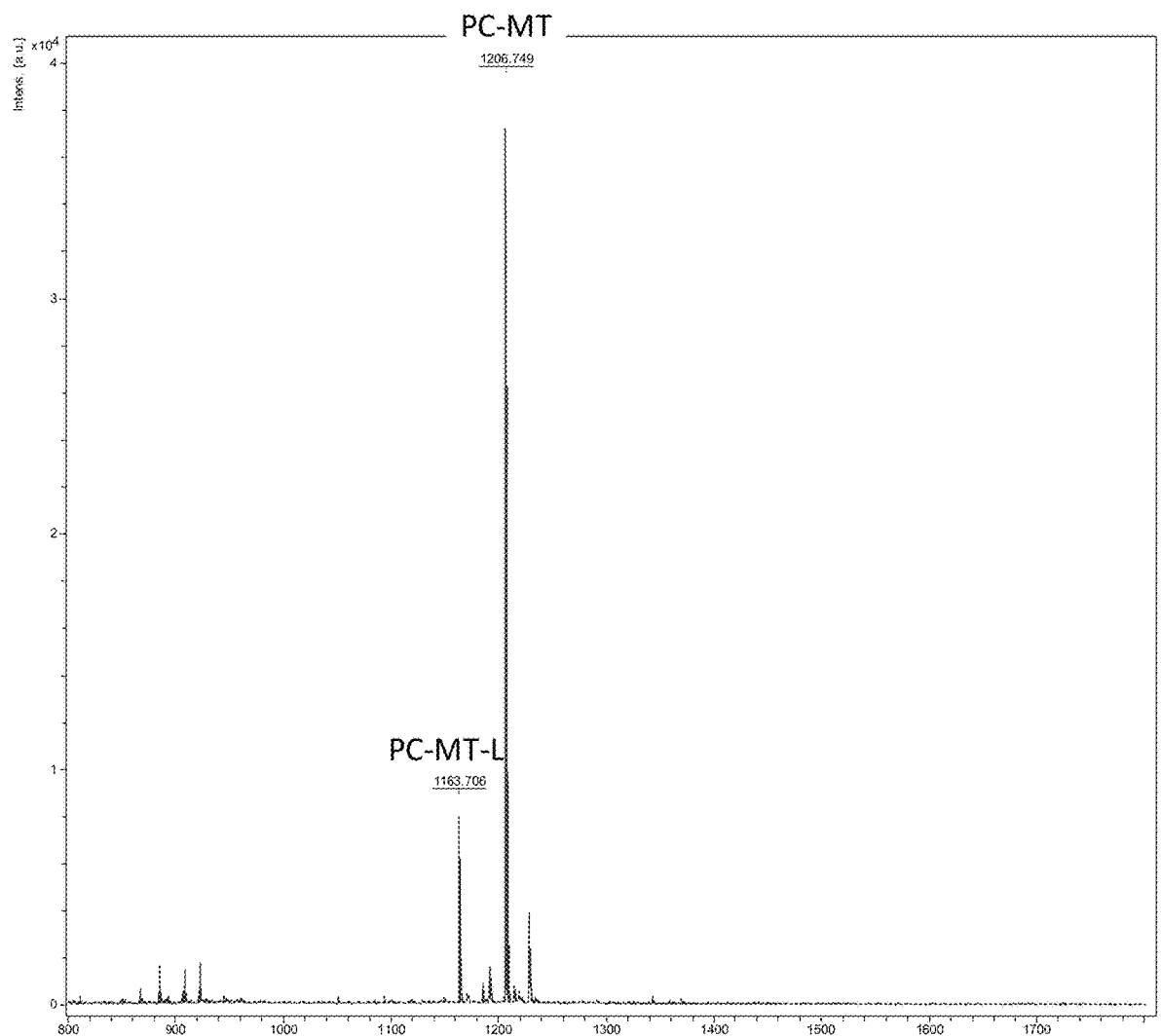
Figure 11C:
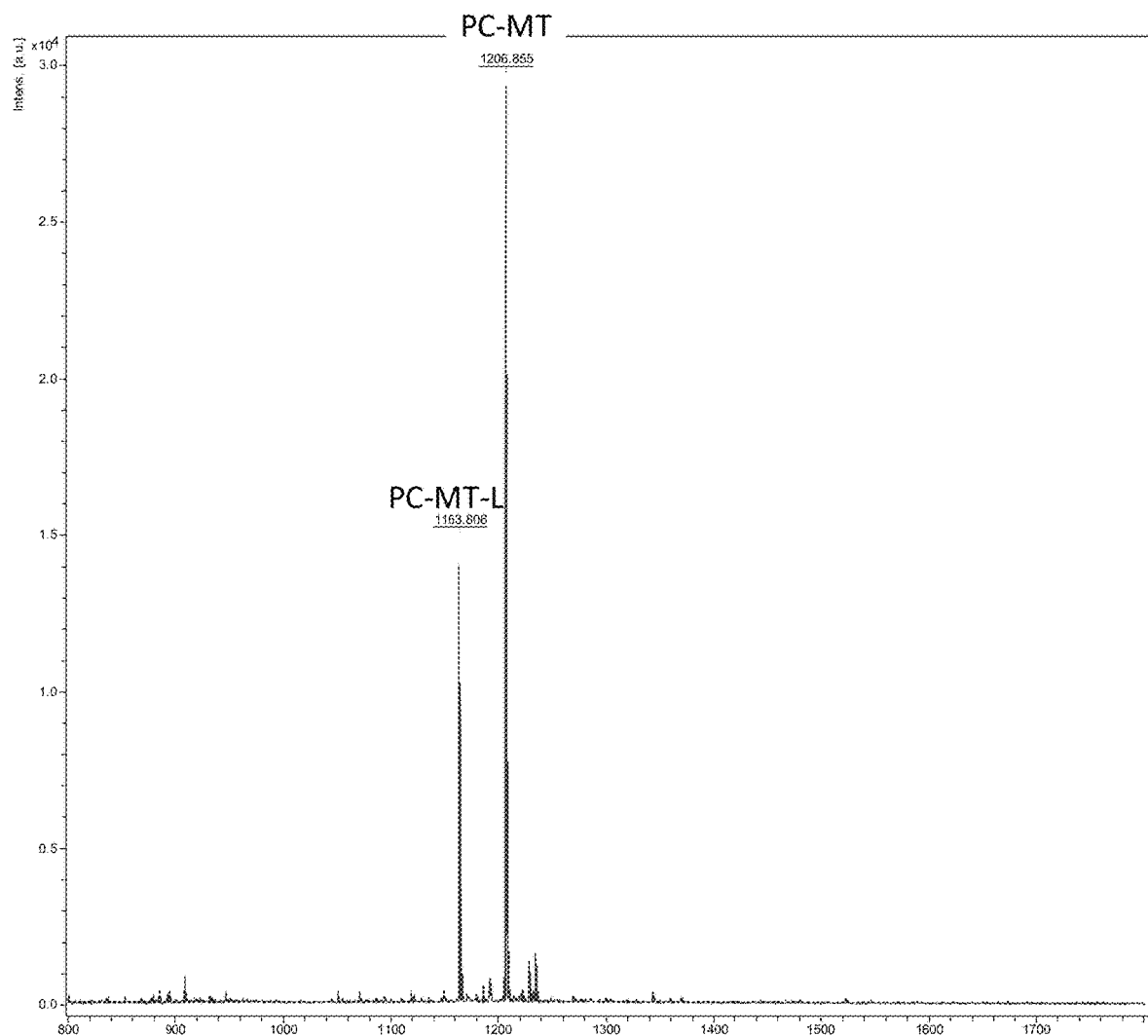
Figure 11D:
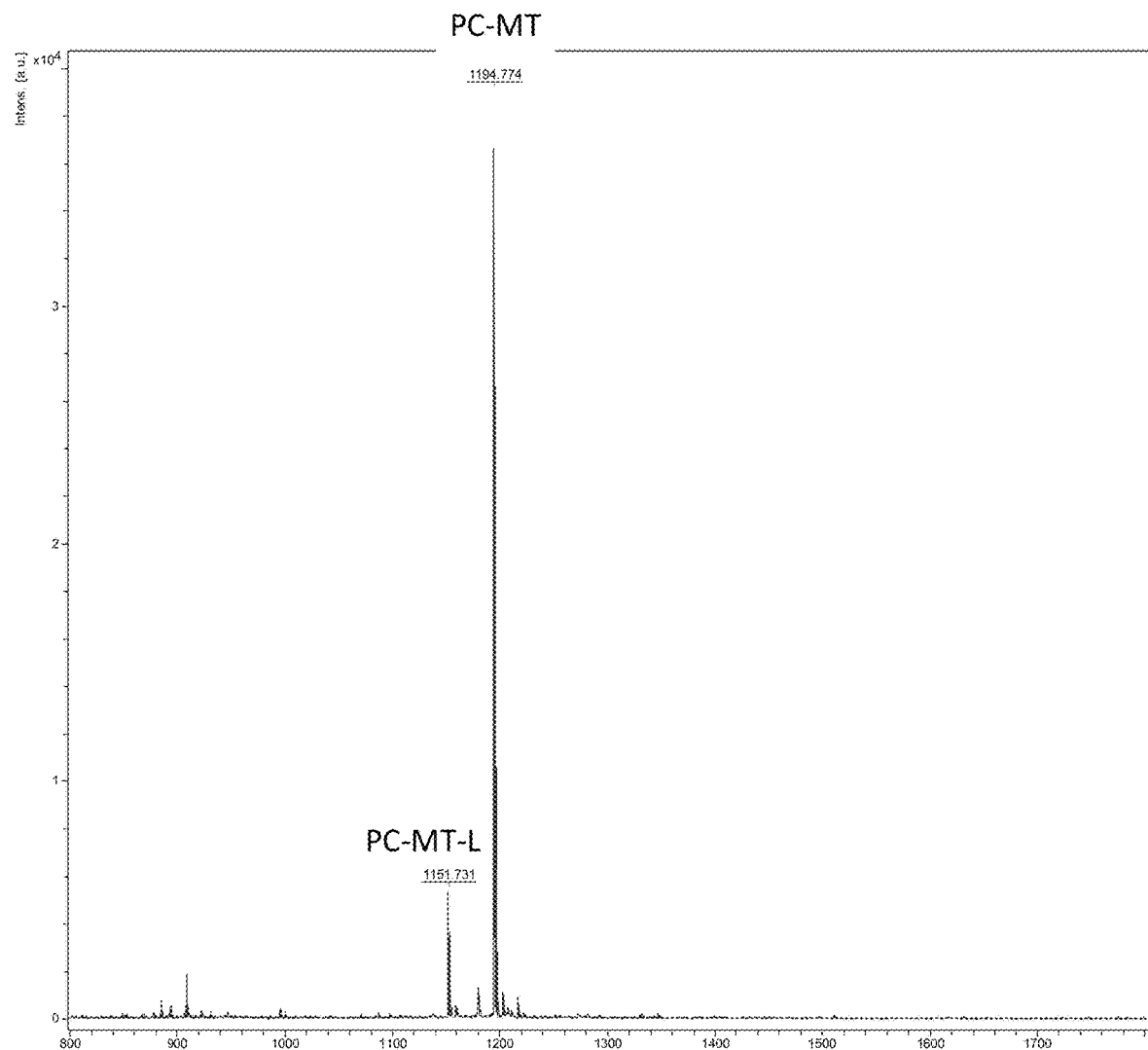
Figure 11E:
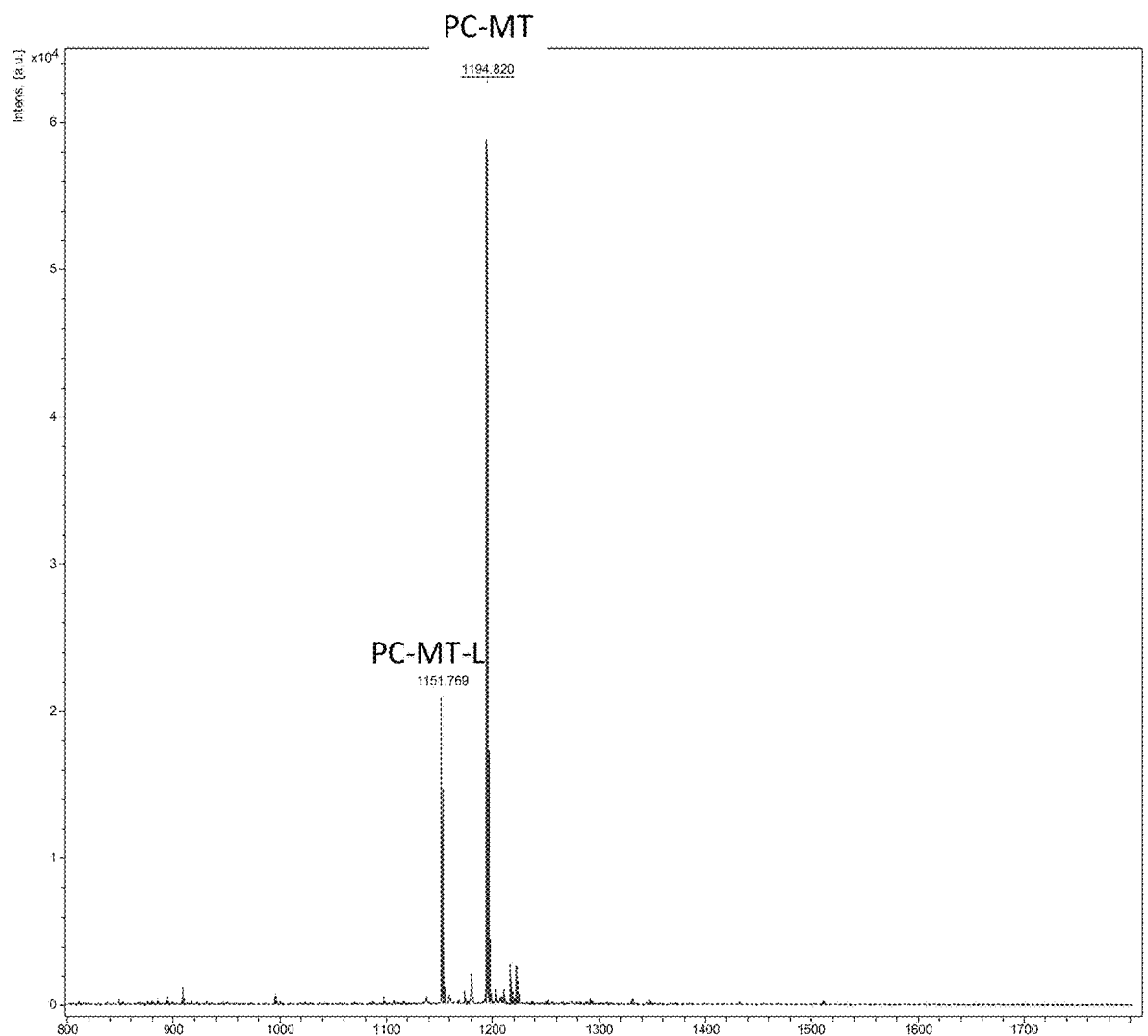
Figure 11F:
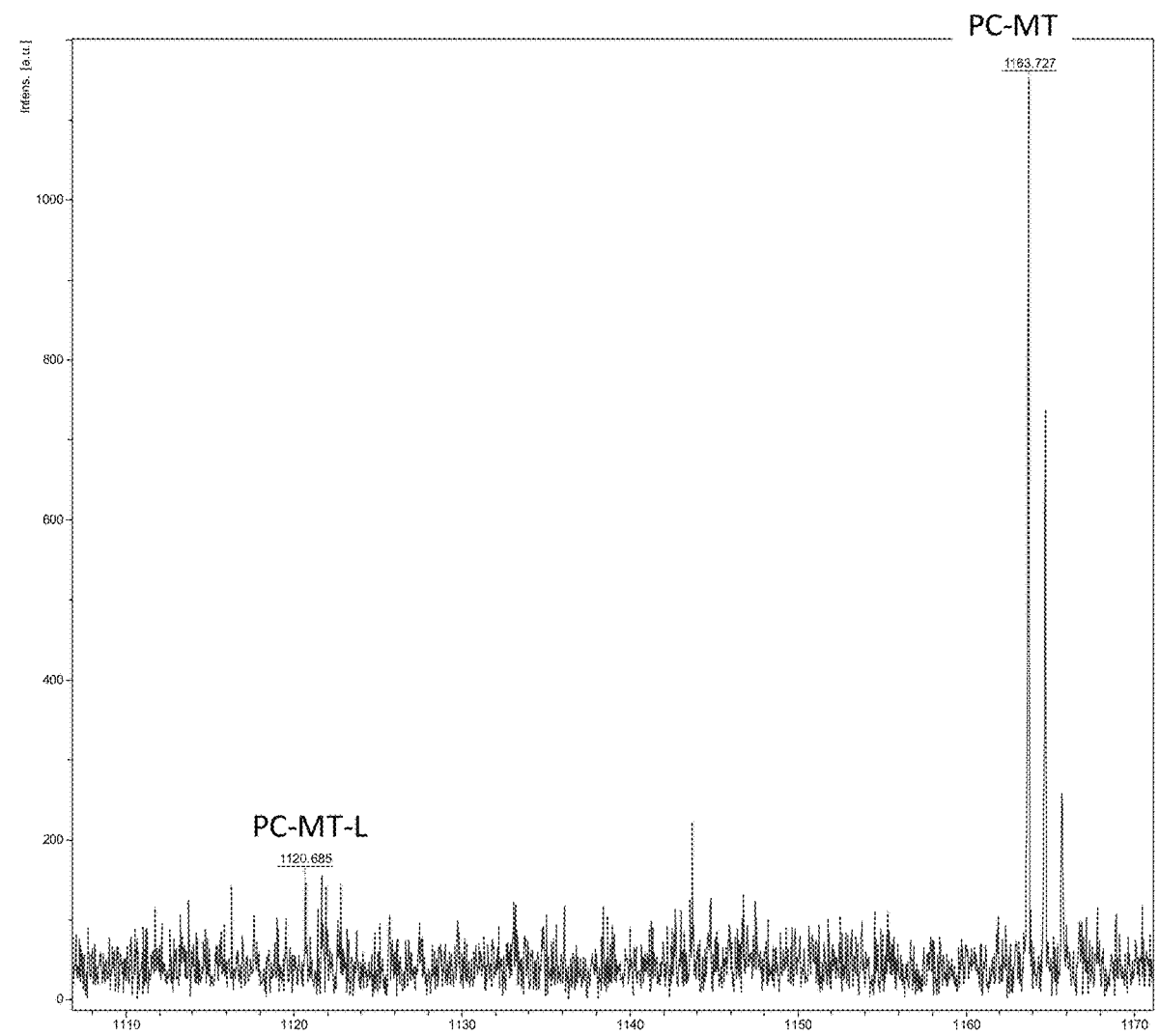
Figure 11G:
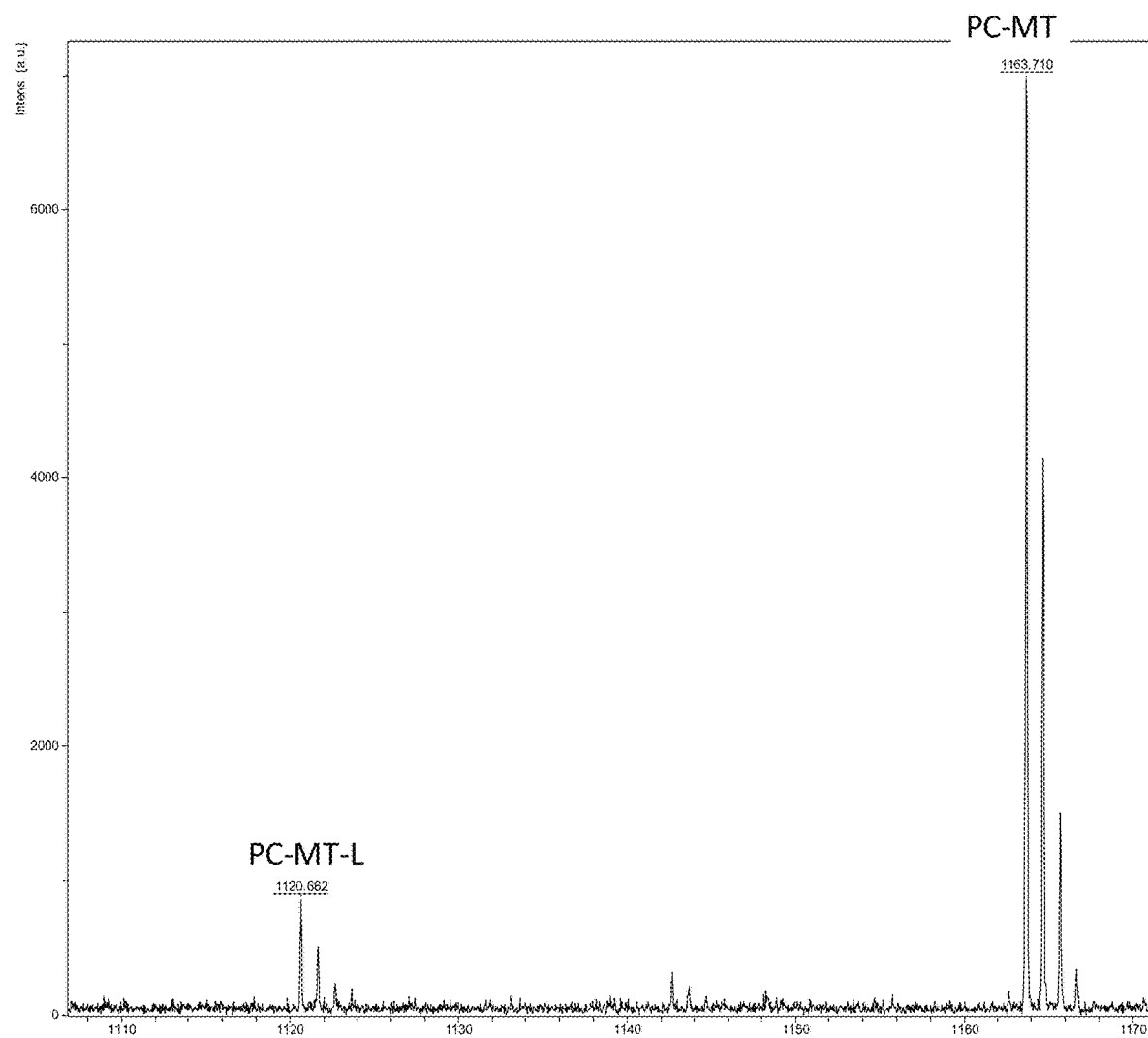
Figure 11H:
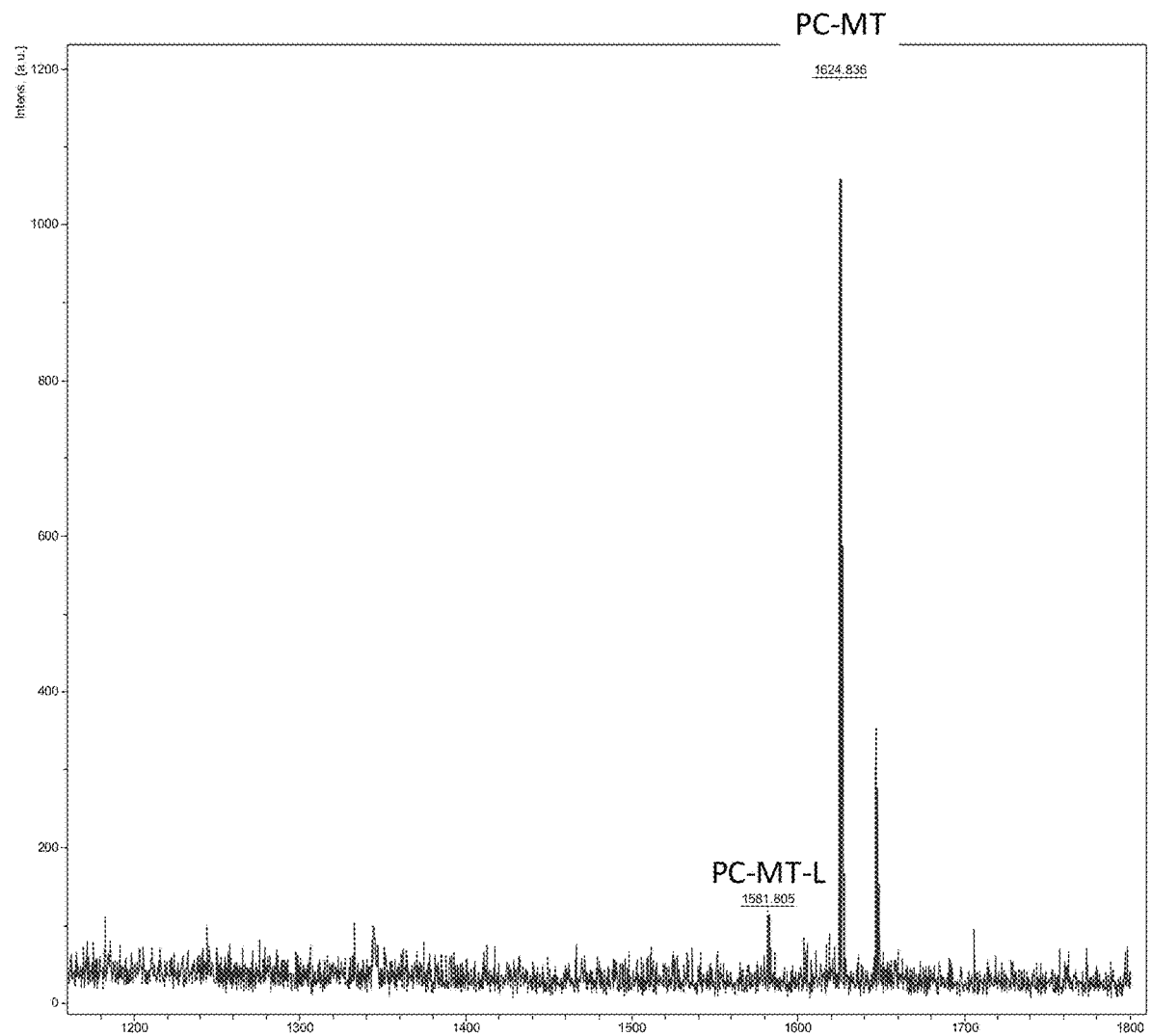
Figure 11I:
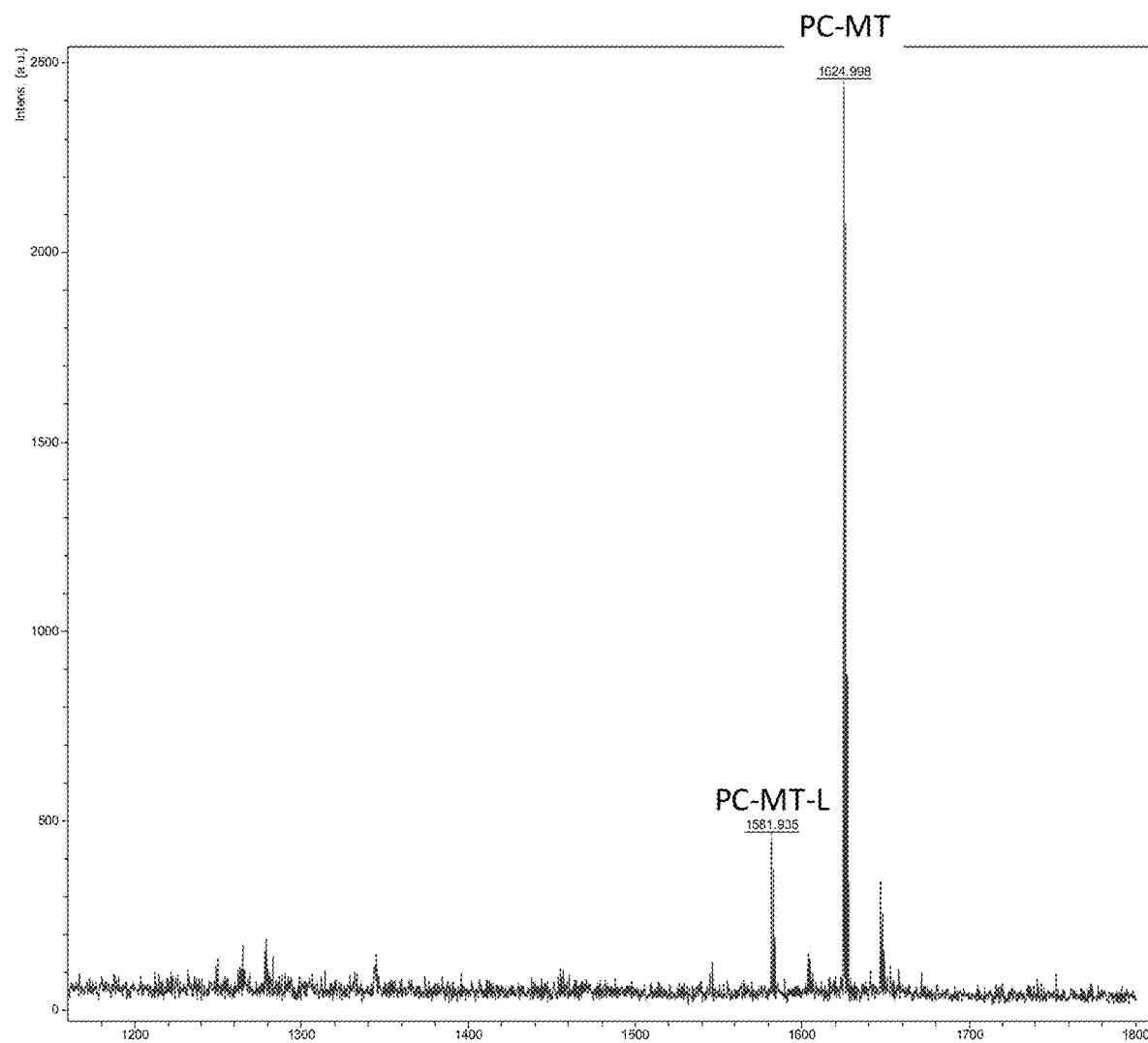

First, using the bead-arrays, PC-MTs were compared to PC-MTs-L for mass units 1 and 2-4 listed in Table 1. FIG. 11a shows an example mass-image of a bead array, for mass unit 1, representing a pixel map of the mass reporter mass spectral peak intensities at 1,206.7 m/z (PC-MT with mass unit 1) and 1,163.7 m/z (PC-MT-L with mass unit 1). The PC-MT is color coded red and the PC-MT-L is color-coded green in the image. The 2-color overlay would be expected to produce a yellow color if the peaks were of similar intensity, however, since the PC-MT yields a much stronger signal, the beads appear red-orange. Representative mass spectra from single pixels from beads in the arrays are shown in FIGS. 11b-i for all 4 mass units at 5 and 25 min pre-UV illumination (i.e., UV photocleavage before matrix application and before MALDI-MSI). Note that since each of the 4 bead species were double-labeled, each spectra contains peaks for both the PC-MT and PC-MT-L for a given mass unit (PC-MTs yield an m/z of +43 compared to the equivalent mass unit from PC-MT-L, since PC-MTs leave a small residual portion of the photocleaved PC-Linker attached to the mass reporter while PC-MTs-L do not). PC-MT to PC-MT-L ratios of the mass spectral peak intensities were then calculated for each mass unit and for each pre-UV time point, averaged from 5 pixels (5 spectra) for each permutation. These ratios were 5:1, 8:1, 10:1, and 6:1 for the 5 min pre-UV, for mass units 1 and 2-4, respectively, thus showing a 5-10 fold higher signal of the PC-MTs compared to PC-MTs-L. While the relative PC-MT-L signals improved modestly at 25 min UV, yielding ratios of 2:1, 3:1, 7:1 and 5:1, there were diminishing returns as the improvement was never commensurate with increase in pre-UV time (5-fold increase in pre-UV time) and the PC-MTs always remained superior to PC-MTs-L.

Figure 11J:
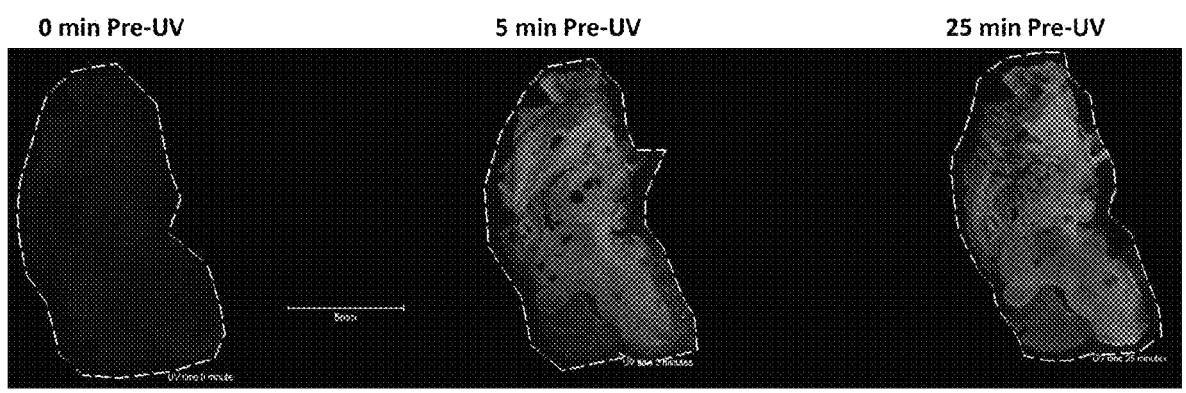
Figure 11K:
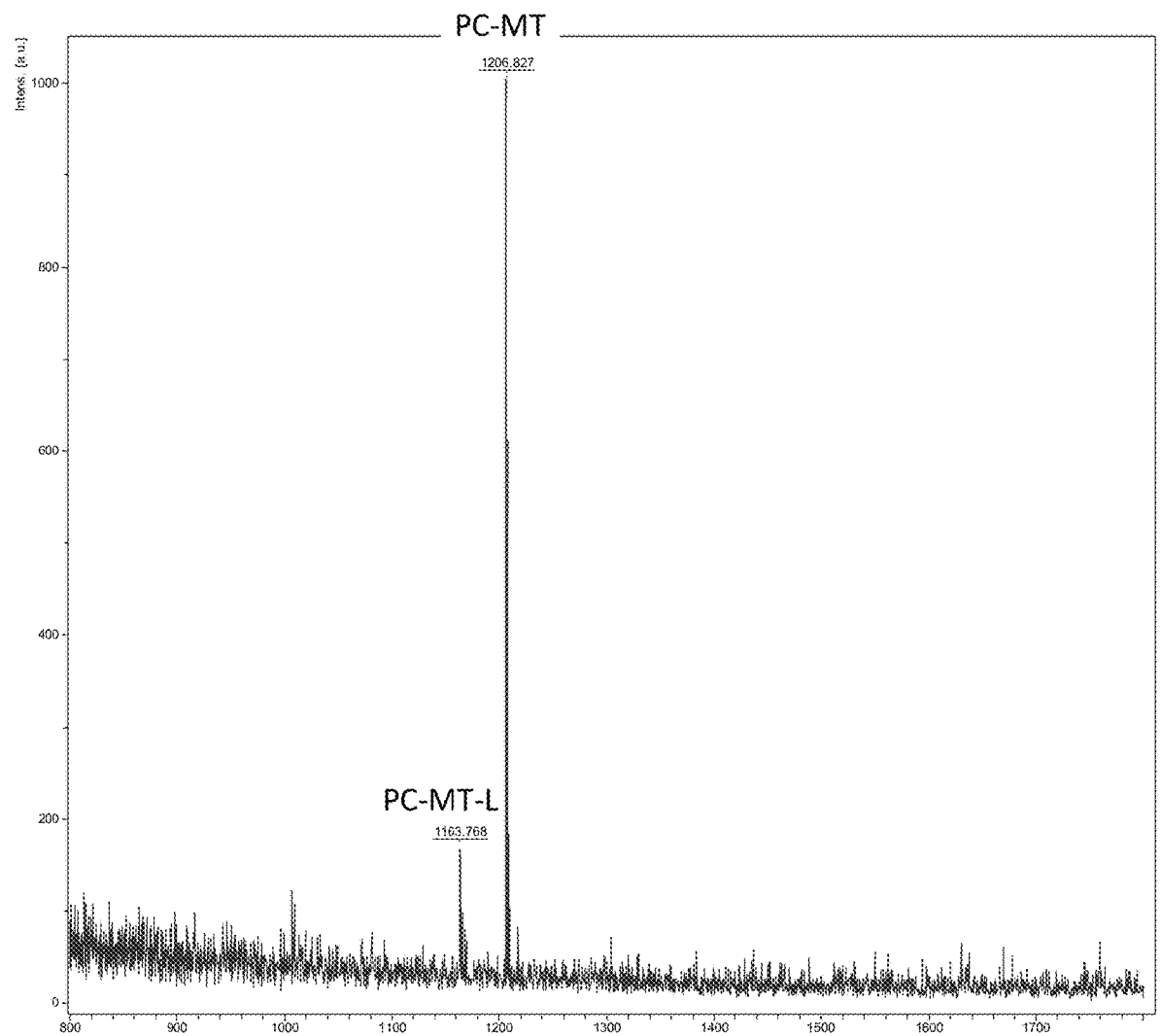
Figure 11L:
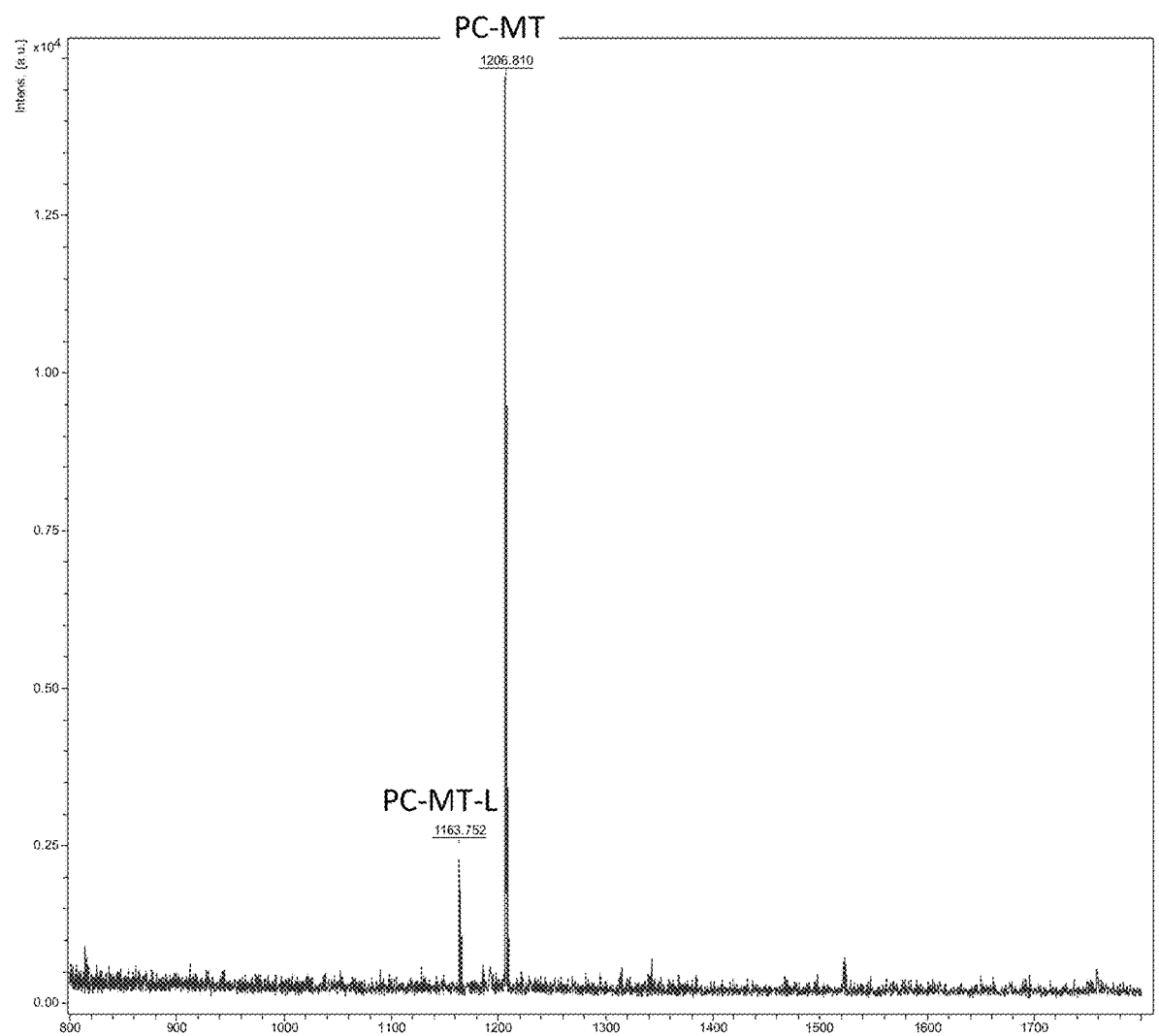

Second, using MIHC (mass spectrometry based immunohistochemistry), a PC-MT and PC-MT-L for mass unit 1 were compared using a double-labeled antibody probe against myelin to stain mouse brain tissue sections. In this case, in addition to 5 and 25 min pre-UV treatment of the tissues (just before matrix application and before MALDI-MSI), 0 min pre-UV was also tested, in which case photocleavage is only in-line with the MALDI-MSI analysis using the instrument's laser beam. As with the bead-arrays, a 2-color mass-image is shown in FIG. 11j for the myelin imaging of the tissue, and again, the PC-MT (red) provides a much higher signal than the PC-MT-L (green), thereby dominating the image. Spectra from representative pixels are shown in FIGS. 11k and 11l, confirming this result. In this case, the PC-MT to PC-MT-L ratio of peak intensities was 6:1 for both 5 and 25 min pre-UV. Finally, 0 min pre-UV shows virtually no detectable PC-MT or PC-MT-L signal (see FIG. 11j). To quantify the effects of pre-UV, average spectra were generated from each of the entire regions of interest (see dotted outlines in FIG. 11j) for each tissue section. From these average spectra, monoisotopic peak intensities for the PC-MT were 2.5, 15.8 and 23.3 for 0, 5 and 25 min pre-UV, respectively. Importantly, this demonstrates that photocleavage in-line with the MALDI-MSI analysis using the instrument's laser beam (0 min pre-UV) is far less sensitive (by about 6 to 9-fold in this example) than pre-UV treatment for photocleavage.

Example 7

Fluorescent PC-MTs for Mass Spectrometry Based Immunohistochemistry

Mass Spectrometry Based Immunohistochemistry (MIHC)

MIHC on mouse brain sagittal tissue sections was performed as in Example 2 with the following exceptions: A recombinant anti-NeuN antibody (see Materials) was conjugated to a PC-MT which was configured as in FIG. 3 (with mass unit 1 from Table 1) but which additionally comprised a Sulfo-Cy5 fluorescent label attached to the ε-amine of a lysine amino acid added to the spacer unit. Thus, the full sequence of this fluorescent PC-MT with mass unit 1, referred to as Fluor-PC-MT1, was as follows (from N-terminal to C-terminal): Acetyl-APRLRFYSL-[PC-Linker]-GS[K-Sulfo-Cy5]GG-[K-NHS]-COOH. The resultant antibody probe, referred to as Anti-NeuN Fluor-PC-MT1, was used for MIHC.

As a negative control, a recombinant anti-Cas9 antibody (see materials) was conjugated also to Fluor-PC-MT1 (note Cas9 is a bacterial specific protein not present in mammals). The resultant antibody probe, referred to as Anti-Cas9 Fluor-PC-MT1, was used for MIHC.

Finally, as a positive control, the recombinant anti-NeuN antibody was conjugated only to a non-fluorescent PC-MT configured as in FIG. 3 except with mass unit 7 from Table 1, referred to as PC-MT7. The resultant antibody probe, referred to as Anti-NeuN PC-MT7, was used for MIHC.

Since Fluor-PC-MT1 contains a fluorophore, fluorescence imaging of the same tissue (on the gold coated slides) could be performed in addition to MALDI-MSI (fluorescence imaging performed just before pre-UV treatment for photocleavage, before matrix application and before MALDI-MSI analysis). Fluorescence imaging was performed as in Example 2.

Results

Fluorescence images of the mouse brain tissues are displayed as yellow in FIG. 12 (see "Fluorescence"). Strong and specific fluorescent signals are observed when the tissue is probed with Anti-NeuN Fluor-PC-MT1. In comparison, the tissue probed with the negative control Anti-Cas9 Fluor-PC-MT1 shows only weak background (Cas9 is a bacterial protein not present in mammals). The tissue probed with the non-fluorescent Anti-NeuN PC-MT7 shows only extremely weak background fluorescence corresponding to tissue autofluorescence.

MALDI-MS images of the mouse brain tissues are displayed as red (mass reporter from Fluor-PC-MT1) and green (mass reporter from PC-MT7) in FIG. 12 (see "MALDI-MSI"). The tissue probed with Anti-NeuN Fluor-PC-MT1 shows strong and specific MALDI-MSI signals in comparison to the tissue probed with the negative control Anti-Cas9 Fluor-PC-MT1, which again only produces weak background (see red color in "MALDI-MSI" panel of FIG. 12).

The Anti-NeuN Fluor-PC-MT1 "staining" pattern is similar in the fluorescence and MALDI-MS images in FIG. 12. Specifically, as in Example 2, anti-NeuN detects distinct features such as the hippocampus (blue arrows in FIG. 12) and the cerebellum (white arrows in FIG. 12). However, in MALDI-MSI, the non-fluorescent Anti-NeuN PC-MT7 probe produces a more distinct pattern (green color in "MALDI-MSI" panel of FIG. 12) than does the Anti-NeuN Fluor-PC-MT1 probe. Based on the inset spectra in FIG. 12, showing mass reporter peaks (black arrows in spectra) for Fluor-PC-MT1 and PC-MT7 from representative single pixels within the hippocampus (blue arrows in FIG. 12), the superiority of Anti-NeuN PC-MT7 probe does not appear to be due to higher peak intensity (same y-axis scaling in spectra). The superior results may be explained by less non-specific binding of the Anti-NeuN PC-MT7 probe compared to the Anti-NeuN Fluor-PC-MT1 probe (and thus less diffuse background). This might be solved by using different fluorophores to reduce non-specific binding. Furthermore, increasing the length of the spacer unit such that the fluorophore is at a greater distance from the probe-reactive moiety (the NHS-ester on the PC-MTs in this Example) may improve probe labeling efficiency.

Finally, note that the spectra shown for the negative control Anti-Cas9 Fluor-PC-MT1 probe shows no discernable mass reporter peak.

Example 8

Recombinant Versus Conventional Antibodies

PC-MT-Abs

The following PC-MT-Abs were prepared as in Example 1 (antibodies are non-recombinant unless otherwise specified—see Materials for antibodies) (note that the following numbers indicate the mass units from Table 1 used in a particular PC-MT): Recombinant Anti-Amyloid Beta (called rAnti-AB2); Recombinant Anti-Myelin Basic Protein (called rAnti-MBP1); Anti-Myelin Basic Protein (called Anti-MBP1); Recombinant Anti-NeuN (called rAnti-NeuN7); and Anti-NeuN (called Anti-NeuN7).

Bead-Arrays

Performed as in Example 6 with the following exceptions: 37 μm streptavidin coated PMMA beads were used for conjugation to PC-MTs (these PC-MTs are referred to as Bead ID-Tags). The beads were then used to capture the aforementioned PC-MT-Abs as follows: Beads were processed in Filter Devices as in Example 6. Each PC-MT bead species was processed separately unless otherwise noted. Beads were washed 4×400 μL with OBG Saline (see Example 6 for formulation). 200 μL of 100 μg/mL biotinylated protein G in OBG Saline was added to each bead pellet and mixed for 30 min. Beads were washed 8×400 μL with OBG Saline. 200 μL of a 1 μg/mL PC-MT-Ab solution in OBG Saline was added to the bead pellets and mixed for 30 min. Beads were washed 2×400 μL with OBG Saline and 2×400 μL with OBG Buffer (same as OBG Saline but without the NaCl). The different bead species were pooled at this stage. Next, bead-array formation, photocleavage, matrix application and MALDI-MSI was performed as in Example 6.

As a result of the procedures above, 2 pools of beads were created and separately analyzed in the bead-arrays by MALDI-MSI. Each bead species in a pool has a unique directly attached Bead ID-Tag as well as a bound PC-MT-Ab. All numbers below refer to the mass units listed in Table 1 used in a particular PC-MT:

Bead Pool 1:
Bead ID-Tag9/rAnti-MBP1
Bead ID-Tag10/Anti-MBP1
Bead ID-Tag15/rAnti-AB2
Bead Pool 2:
Bead ID-Tag9/rAnti-NeuN7
Bead ID-Tag 10/Anti-NeuN7
Bead ID-Tag15/rAnti-AB2
Mass Spectrometry Based Immunohistochemistry (MIHC)

MIHC on mouse brain sagittal tissue sections was performed as in Example 2 using the following aforementioned PC-MT-Abs: rAnti-NeuN7 and Anti-NeuN7.

Results

Figure 13A:
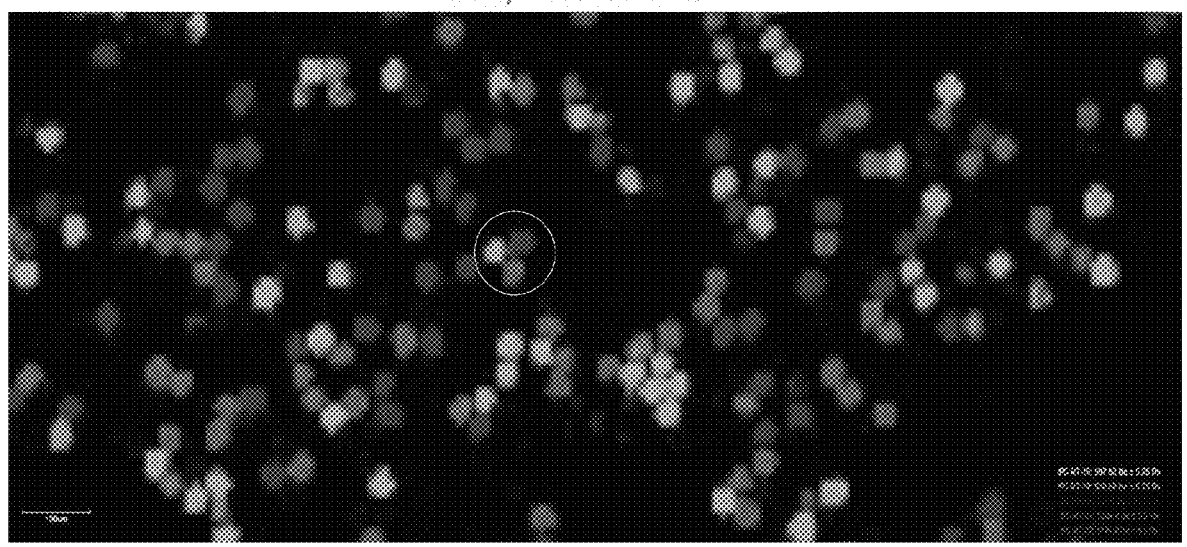
FIG. 13A-E. Recombinant versus Conventional Antibodies. 37 μm streptavidin PMMA beads were directly conjugated to PC-MTs (Bead ID-Tags) and then loaded with biotinylated protein G followed by binding specific PC-MT-Abs (each PC-MT-Ab species loaded separately to a specific bead species).
Figure 13B:
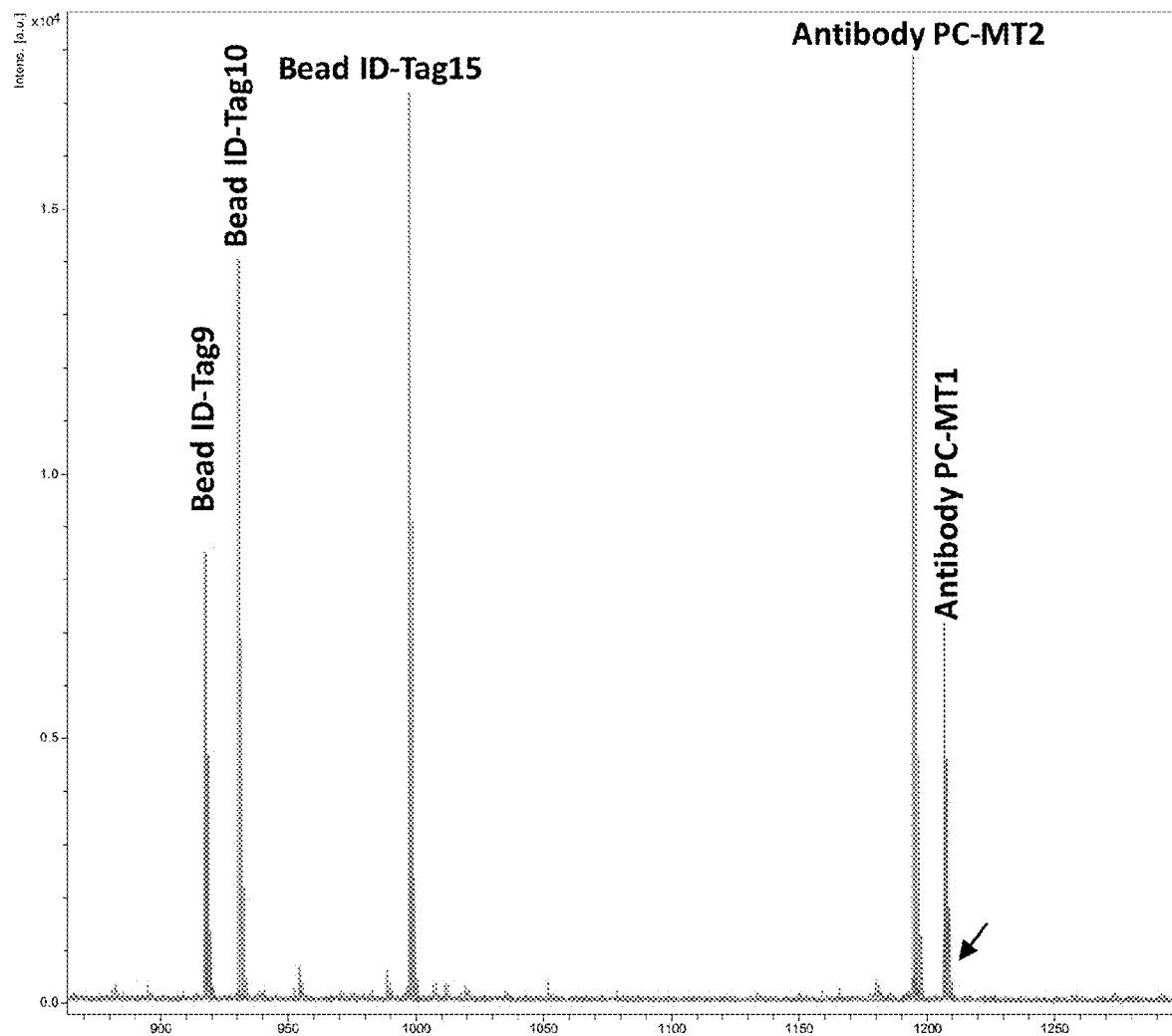

FIG. 13a shows a MALDI-MS mass-image of the bead-array for Bead Pool 1. The beads are color-coded in the image as blue, green and yellow for the mass spectral peak intensities for Bead ID-Tags 9, 10 and 15, which correspond to the beads loaded with rAnti-MBP1, Anti-MBP1 and rAnti-AB2, respectively. PC-MTs from the PC-MT-Abs are all color-coded red. Therefore, the co-localization (overlay) of the blue Bead ID-Tag9 and the bound red rAnti-MBP1 appears as a pink color in the mass-image. Conversely, while the green Bead ID-Tag10 is detected, little to no signal for the corresponding red Anti-MBP1 is observed, thus, these beads appear as primarily green. Finally, the co-localization (overlay) of the yellow Bead ID-Tag15 and the bound red rAnti-AB2 appears as an orange color in the mass-image. In conclusion, while both recombinant antibodies show a strong PC-MT-Ab signal on their respective beads (observed as pink and orange beads), the non-recombinant Anti-Myelin Basic Protein PC-MT-Ab (Anti-MBP1) is poorly detected. This is confirmed by the overlaid spectra shown in FIG. 13b. The 3 spectra correspond to 3 single pixels selected from the center of the 3 beads circled in FIG. 13a, and are color-coded according to the bead colors observed in FIG. 13a. The pink trace in FIG. 13b shows strong peaks for Bead ID-Tag9 and the corresponding Antibody PC-MT1 for the bound rAnti-MBP1. Conversely, the green trace in FIG. 13b shows a strong peak for Bead ID-Tag10, but only a weak peak (black arrow) for the corresponding Antibody PC-MT1 for the bound Anti-MBP1. Note that the Antibody PC-MT1 peak for the rAnti-MBP1 is 10-fold stronger than that for the (non-recombinant) Anti-MBP1. Finally, the orange trace in FIG. 13b shows strong peaks for Bead ID-Tag15 and the corresponding Antibody PC-MT2 for the bound rAnti-AB2.

Figure 13C:
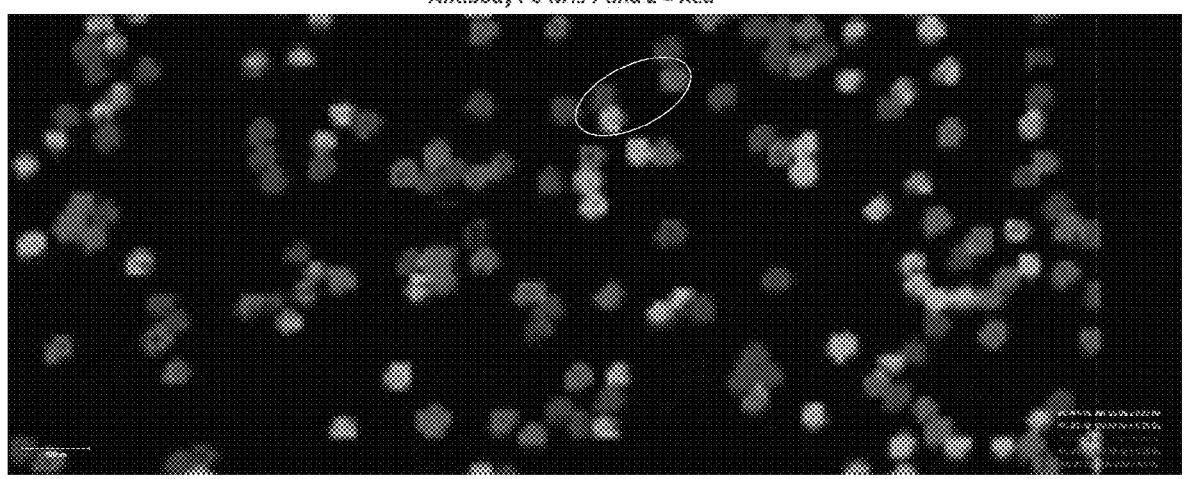
Figure 13D:
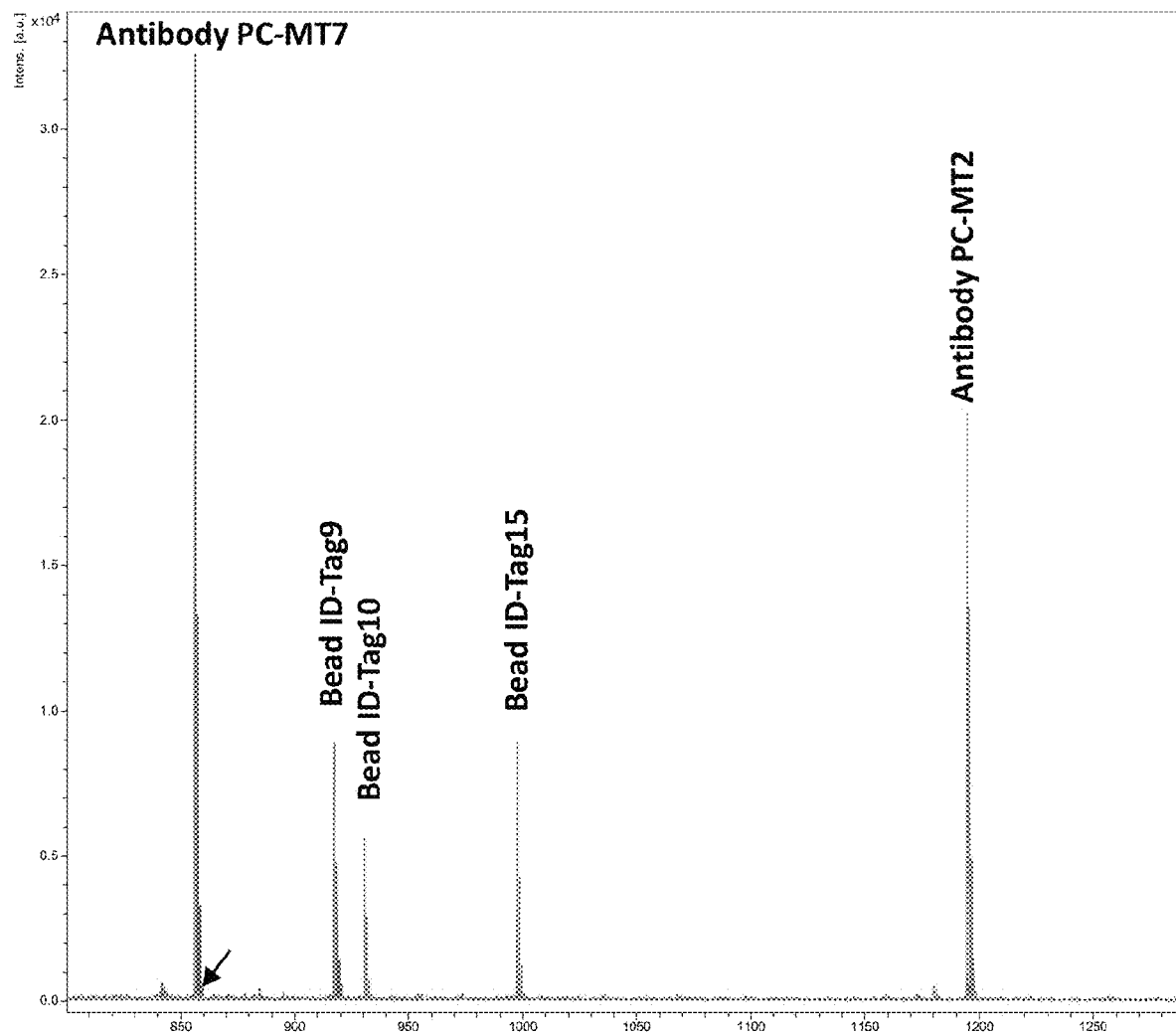

Bead Pool 2 shows a similar result. FIG. 13c shows a MALDI-MS mass-image of the bead-array for Bead Pool 2. The beads are color-coded in the image as blue, green and yellow for the mass spectral peak intensities for Bead ID-Tags 9, 10 and 15, which correspond to the beads loaded with rAnti-NeuN7, Anti-NeuN7 and rAnti-AB2, respectively. PC-MTs from the PC-MT-Abs are all color-coded red. Therefore, the co-localization (overlay) of the blue Bead ID-Tag9 and the bound red rAnti-NeuN7 appears as a pink color in the mass-image. Conversely, while the green Bead ID-Tag10 is detected, little to no signal for the corresponding red Anti-NeuN7 is observed, thus, these beads appear as primarily green. Finally, the co-localization (overlay) of the yellow Bead ID-Tag15 and the bound red rAnti-AB2 appears as an orange color in the mass-image. In conclusion, while both recombinant antibodies show a strong PC-MT-Ab signal on their respective beads (observed as pink and orange beads), the non-recombinant Anti-NeuN PC-MT-Ab (Anti-NeuN7) is poorly detected. This is confirmed by the overlaid spectra shown in FIG. 13d. The 3 spectra correspond to 3 single pixels selected from the center of the 3 beads circled in FIG. 13c, and are color-coded according to the bead colors observed in FIG. 13c. The pink trace in FIG. 13d shows strong peaks for Bead ID-Tag9 and the corresponding Antibody PC-MT7 for the bound rAnti-NeuN7. Conversely, the green trace in FIG. 13d shows a strong peak for Bead ID-Tag10, but only an extremely weak peak (black arrow) for the corresponding Antibody PC-MT7 for the bound Anti-NeuN7. Note that the Antibody PC-MT7 peak for the rAnti-NeuN7 is 60-fold stronger than that for the (non-recombinant) Anti-NeuN7. Finally, the orange trace in FIG. 13d shows strong peaks for Bead ID-Tag15 and the corresponding Antibody PC-MT2 for the bound rAnti-AB2.

Figure 13E:
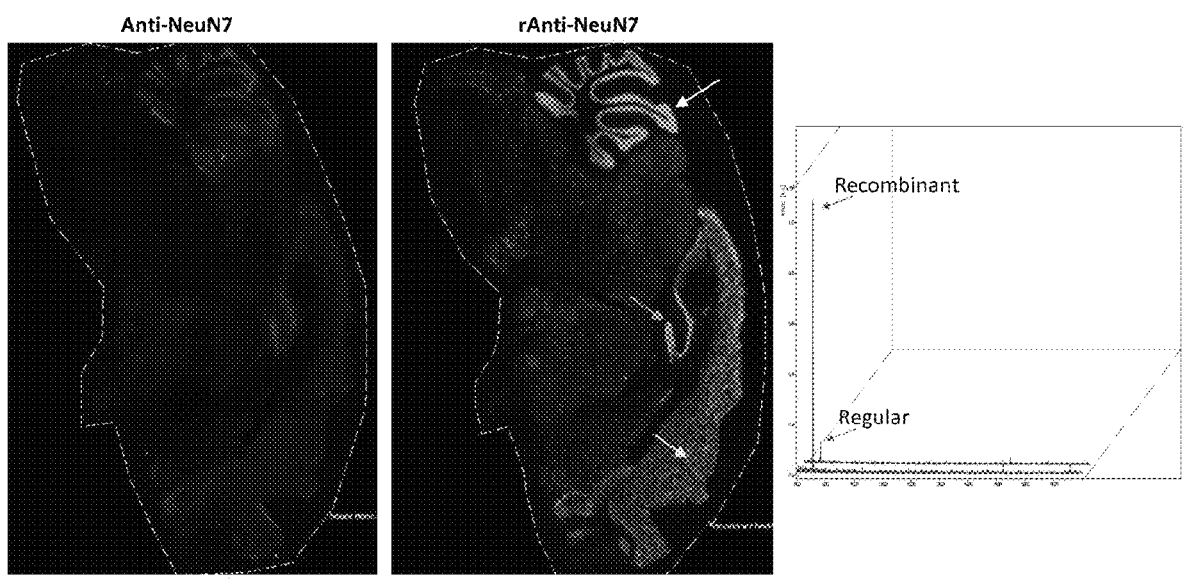

The superior performance of the recombinant PC-MT-Abs in the bead-arrays is recapitulated in mass spectrometry based immunohistochemistry (MIHC) on mouse brain sagittal tissue sections. FIG. 13e shows MALDI-MSI mass-images of tissues stained with Anti-NeuN7 and rAnti-NeuN7. The NeuN immunostaining shows the typical pattern for this biomarker, similar to as observed in Example 2. Of note, the hippocampus (blue arrow) and cerebellum (white arrow) stain strongly, and a speckling pattern characteristic of nuclear staining (NeuN is a neuronal nuclear biomarker) is observed (yellow arrow). The recombinant rAnti-NeuN7 however shows substantially greater sensitivity than the non-recombinant Anti-NeuN7, as is clear from the mass-images in FIG. 13e. This is confirmed by the spectra shown in FIG. 13e. The spectra are taken from the strongest pixels within the hippocampus for each image, whereby the peak from the "Recombinant" antibody (red trace) is approximately 7-fold stronger than that from the "Regular" non-recombinant antibody (blue trace).

Overall, it is believed that the superior performance of the recombinant antibodies stems from the generally greater purity of these antibodies, free of contaminating proteins, azide and amine containing buffers, which increases the PC-MT labeling efficiency.

Example 9

Demonstration of 12-Plex MIHC on FFPE Tonsil and Breast Cancer Tissue

Methods

Performed as in Example 2 except the following: FFPE human tonsil and breast cancer tissues were used. The antigen retrieval step was performed as follows: Basic antigen retrieval was achieved in 60 mL of 95° C. 1× Antigen Retrieval Reagent-Basic (see Materials) for 30 mins and followed by cooling in the same Coplin staining jar for 30 mins at room temperature. Moreover, 12 different PC-MT antibodies were used in this case (see Table 1 for PC-MT antibody assignments) and antibodies were used a 0.5 µg/mL for tissue probing. Finally, for dual-labeling of the pan-cytokeratin antibody (CK) with both a PC-MT and fluorescence, PC-MT antibody labeling was performed as in Example 1, except after addition of PC-MT labeling reagent and reaction for 1 hr, a DyLight 650 NHS Ester reagent was then added (15-fold molar excess added from 5 mM stock in DMF) and reacted for another 1 hr before proceeding with the remainder of the antibody labeling procedure detailed in Example 1.

Results

We constructed a 12-plex biomarker panel suitable for assessing the breast cancer tumor microenvironment, specifically: the breast cancer-related biomarkers [Mueller, Haymond et al. (2018) Expert Rev Proteomics 15: 131-152] estrogen receptor (ER), progesterone receptor (PR), human epidermal growth factor receptor 2 (HER2) and Ki67 (proliferation biomarker); biomarkers for tumor infiltrating lymphocytes (TILs) and other immune-related cells [Blom, Paavolainen et al. (2017) Sci Rep 7: 15580; Chistiakov, Killingsworth et al. (2017) Lab Invest 97: 4-13; Halse, Colebatch et al. (2018) Sci Rep 8: 11158; Poh and Ernst (2018) Front Oncol 8: 49] which included the T-cell subset biomarkers CD3 (T-cells), CD4 (T-helper), CD8 (cytotoxic T-cells), and CD45RO (memory T-cells), the B-cell biomarker CD20, and CD68, a biomarker for macrophages and other mononuclear phagocytes; and finally, a pan-cytokeratin (CK) antibody as a general epithelial cell biomarker [Karantza (2011) Oncogene 30: 127-38] and a histone H2A.X antibody as a nuclear biomarker [Rogakou, Pilch et al. (1998) J Biol Chem 273: 5858-68]. Importantly, it should be clarified that the purpose of these studies was not to validate any given biomarker for detection of any specific cell or cancer type nor to determine the validity of the biomarkers in the identification of any particular disease state. The goal was to demonstrate the functionality and utility of the new MIHC method presented here.

Each antibody was directly labeled with a unique PC-MT (see Table 1 for PC-MT assignments for each antibody and also for mass reporter masses). Notably, to eliminate bias from variable MALDI-MS ionization efficiency that would occur with different PC-MT amino acid sequences, 8 of the PC-MTs were comprised of either mass unit 1 (see Table 1 for all mass units) or the same sequence comprised of various stable isotopes (mass units Iso-1.1 to Iso-1.5, Iso-1.7 and Iso-1.8); the remaining 4 PC-MTs were also comprised of the core sequence of mass unit 1, but extended by 1-3 glycine and/or serine amino acids on the termini (mass units 1.2 to 1.5), which is not expected to significantly alter the MALDI-MS ionization efficiency.

Moreover, to enhance the MIHC procedure, the CK antibody was dual-labeled with a PC-MT and a fluorophore. The ability to combine conventional immunofluorescence with the PC-MT based MSI on the same tissue section would be extremely useful even if the immunofluorescence multiplexing were limited to less than 5-plex. First, such a combination would aid in method development and antibody probe validation. Furthermore, since MALDI-MSI spatial resolution does not yet match that of optical imaging, even a high-resolution non-multiplex co-registered fluorescence image could be used to assist in deconvolving the observed structures in a highly multiplex MALDI-MS image. While this could be achieved by staining adjacent tissues (one for fluorescence and one for MALDI-MSI) or by sequential procedures on the same tissue section, both methods are cumbersome as they introduce many added steps and also introduce variables which can make co-registration of the MALDI-MS images and fluorescence images inaccurate. To overcome this limitation, we sequentially labeled the CK antibody with two different amine-reactive NHS-ester-activated reagents, first with the PC-MT and second with the fluorescent reagent. The PC-MT labeling reagent was used at a 10-fold excess relative to the antibody on a molar basis and the fluorescent reagent at a 15-fold excess (note antibodies contain up to 80 available lysine amino acids for labeling with NHS-ester activated reagents [Mueller, Wrasidlo et al. (1988) Hybridoma 7: 453-6]). Using this dual-labeled antibody as part of the panel, the tissue section is stained once with the multiplex antibody mixture, followed by fluorescence imaging, PC-MT photocleavage, MALDI-MS matrix application and MALDI-MSI on the same tissue section.

Figure 14A:
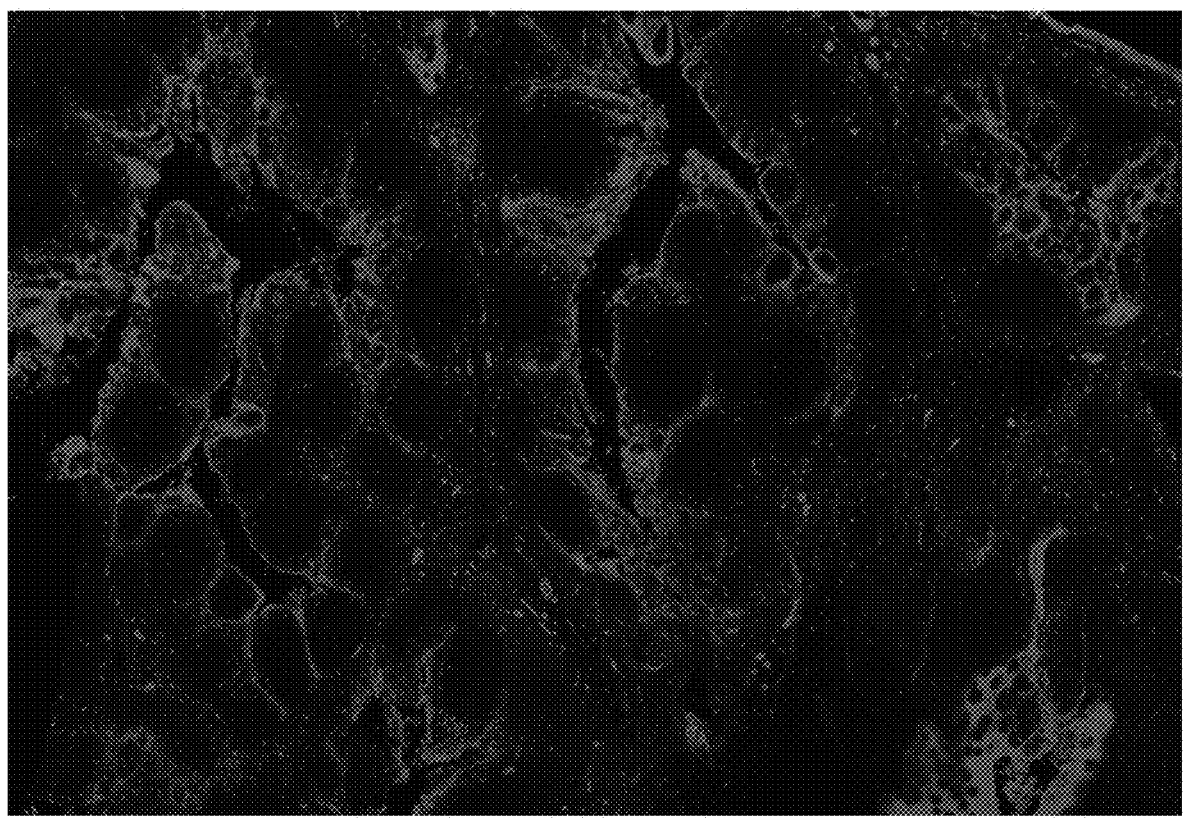
FIG. 14A-D. Multiplex Mass Spectrometry Based Immunohistochemistry (MIHC) on 12 Biomarkers in Human Tonsil FFPE Tissue Sections. MIHC was performed as in FIG. 7 except 12 different biomarkers were used (see Table 1 for PC-MT assignments for each antibody). Furthermore, the pan-cytokeratin antibody (CK) was labeled with both a PC-MT and fluorophore.
Figure 14B:
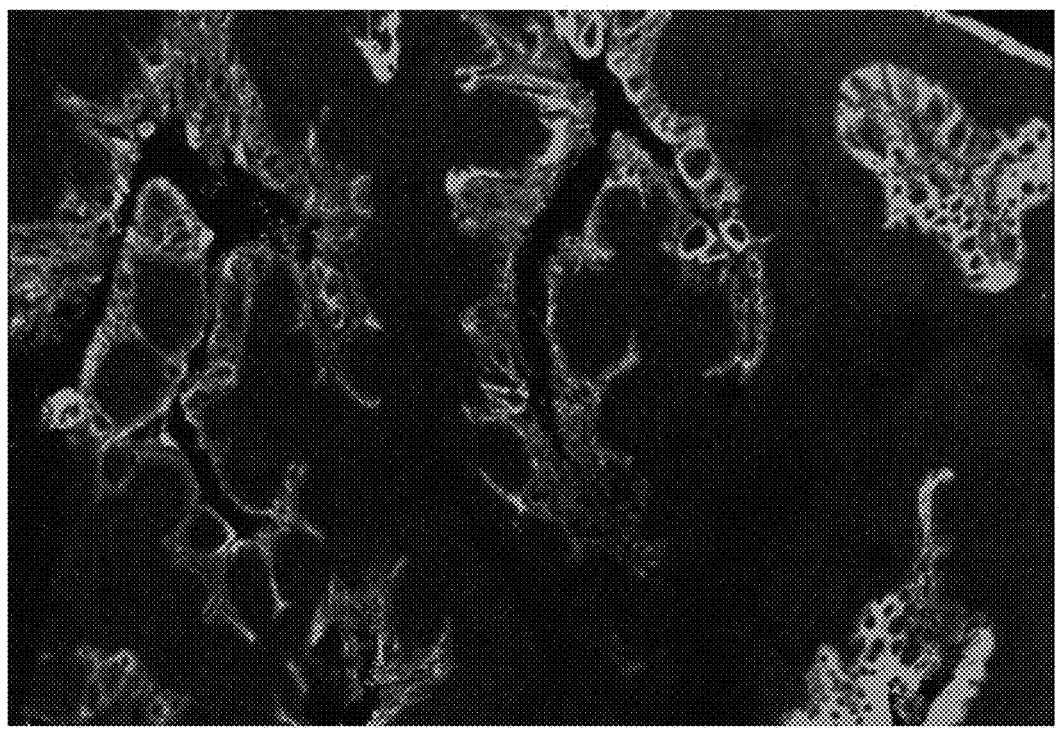

First we used human tonsil tissue to validate most of the antibodies in the 12-plex panel. Tonsil is frequently used as a positive control for immune cell CD markers [Kap, van Meurs et al. (2009) J Histochem Cytochem 57: 1159-67; Kalina, Fiser et al. (2019) Front Immunol 10: 2434] including for B-cells [Kalina, Fiser et al. (2019) Front Immunol 10: 2434] and T-cells [Sada-Ovalle, Talayero et al. (2012) Clin Exp Immunol 168: 200-6; Geissler, Markwart et al. (2017) PLoS One 12: e0183214], and is also known to be strongly positive for Ki67 [Hsu, Yang et al. (2013) Histopathology 63: 810-6]. FIG. 14a shows the CK immunofluorescence image of the whole tissue section (5 μm image resolution using a GenePix 4200A microarray scanner). The CK antibody selectively stains the squamous epithelial layer that covers the tonsil and lines its many invaginations and crypts, as expected. FIG. 14b shows the corresponding MALDI-MS image of the CK PC-MT on the same tissue section, producing an identical pattern (10 μm resolution used here which is the limit of the Bruker rapifleX instrument used for this work, although the Caprioli and Spengler groups have developed technologies which can achieve resolutions of ~1-2 μm [Zavalin, Todd et al. (2012) J Mass Spectrom 47: i; Kompauer, Heiles et al. (2017) Nat Methods 14: 90-96]).

Figure 14C:
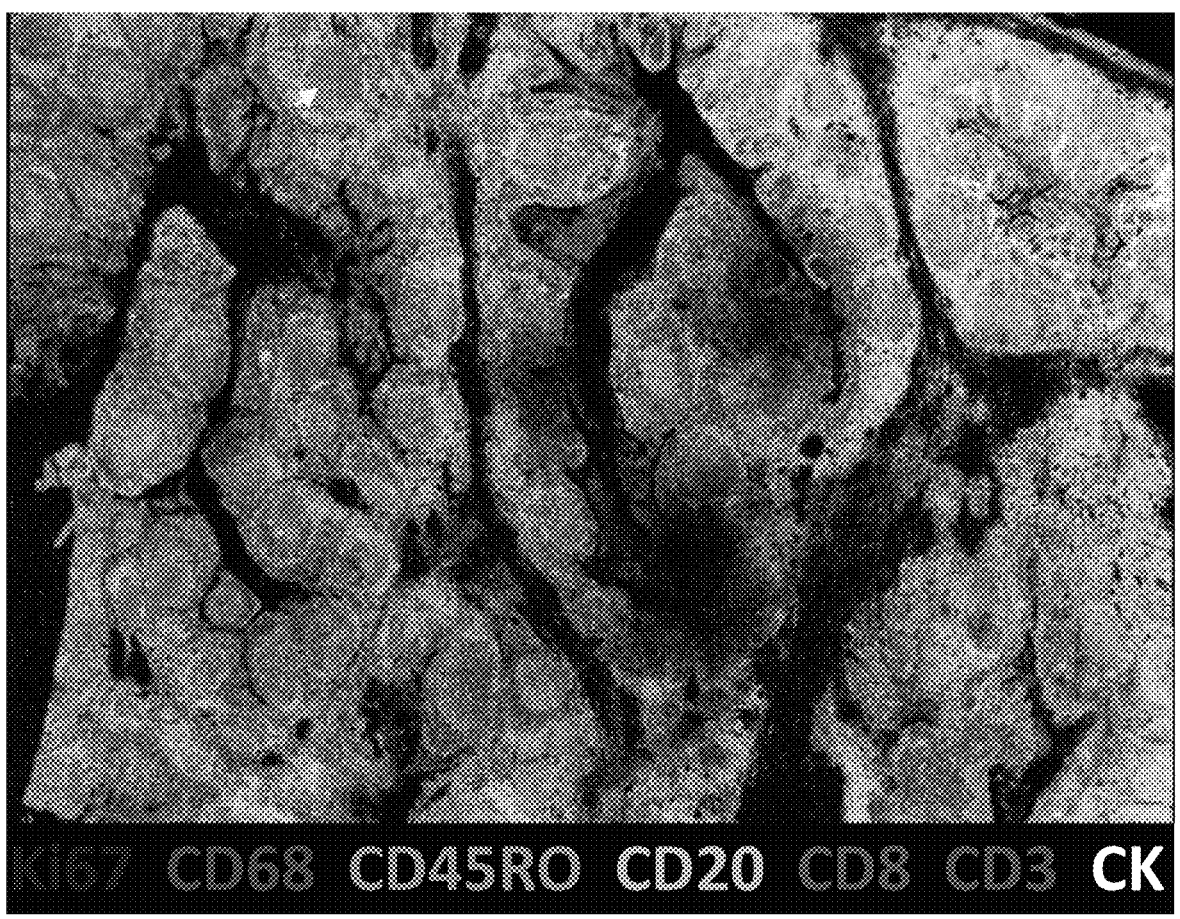
Figure 14D:
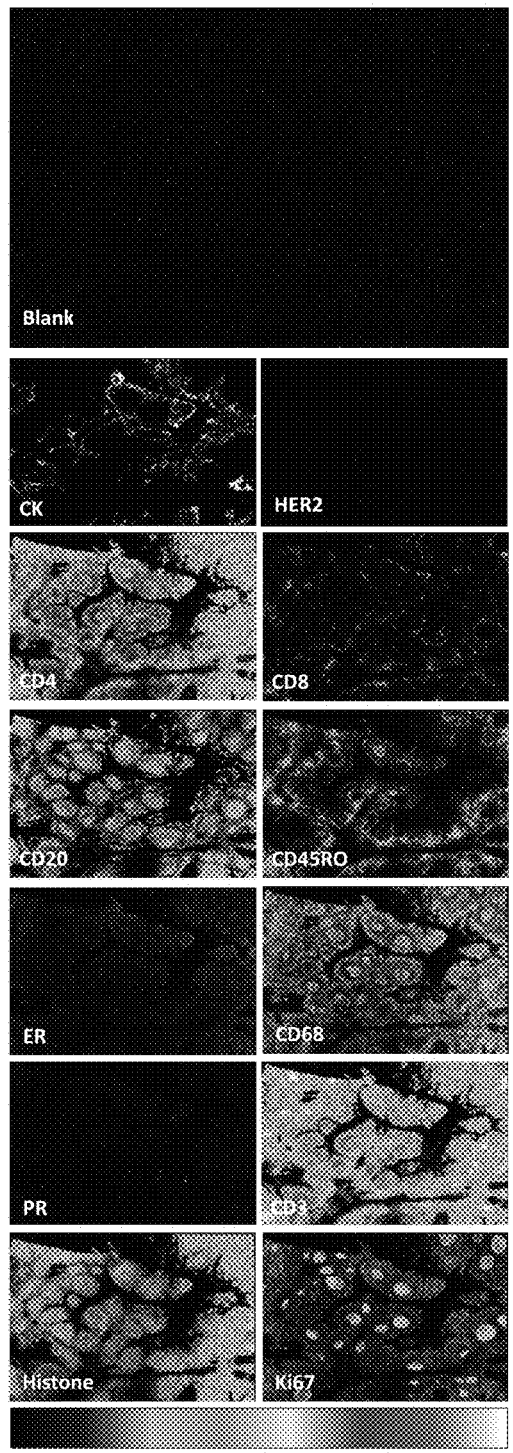

FIG. 14c shows a multi-color MALDI-MS image corresponding to PC-MTs from selected biomarkers (since it is not practical for the human eye to distinguish a large number of overlaid colors, selected biomarkers which produce differential patterns are shown here as an example; see instead FIG. 14d for all 12 biomarkers separately). Of note, the germinal centers (e.g., white arrow) within the lymphoid follicles are strongly positive for Ki67 (proliferation marker; blue in FIG. 14c) and CD20 (B-cell marker; cyan in FIG. 14c; see also CD20 in FIG. 14d for better visualization of this biomarker in the germinal centers). This is expected since the germinal centers are the sites known to contain proliferating B-cells [MacLennan (1994) Annu Rev Immunol 12: 117-39]. The strong Ki67 staining of the germinal centers also agrees with previously reported results using standard IHC [Hsu, Yang et al. (2013) Histopathology 63: 810-6]. In contrast, the T-cells (e.g., CD3 and CD45RO, red and orange respectively in FIG. 14c) are prevalent in the extra-follicular regions (as well as some staining in the follicles), also in agreement with previous reports [Nave, Gebert et al. (2001) Anat Embryol (Berl) 204: 367-73; Sada-Ovalle, Talayero et al. (2012) Clin Exp Immunol 168: 200-6]. Interestingly, the CD8+ cytotoxic T-cells were not widely distributed in the tissue, but were found in high concentration in discrete zones within the tonsillar crypts, in the peri- and intra-epithelial zones (green in FIG. 14c). This is logical since the tonsillar crypts are known to harbor or entrap microbes and pathogens [Jensen, Fago-Olsen et al. (2013) PLoS One 8: e56418; Rieth, Gill et al. (2018) JAMA Otolaryngol Head Neck Surg 144: 231-237]. FIG. 14d shows all 12 antibodies separately on a representative sub-region of the tissue section, using a gradient color scale. The "Blank" corresponds to PC-MT labeled isotype control IgG which was used to stain a separate but adjacent tissue section (same PC-MT as on CD3 antibody), and provides no detectable signal. Conversely, all of the CD antibodies are positive to varying degrees, as are the CK, Ki67 and histone antibodies as expected, with many showing different patterns. HER2 and PR are negative. While ER shows slight positivity, this is not unexpected based in previous reports using standard IHC [Shirasaki, Watanabe et al. (2003) International Congress Series 1257: 115-118], which showed ER was detected in all four of the tonsil tissues evaluated, while PR was found in none (it is also worth noting the tonsil presented in FIG. 14 was of female origin).

Figure 15A:
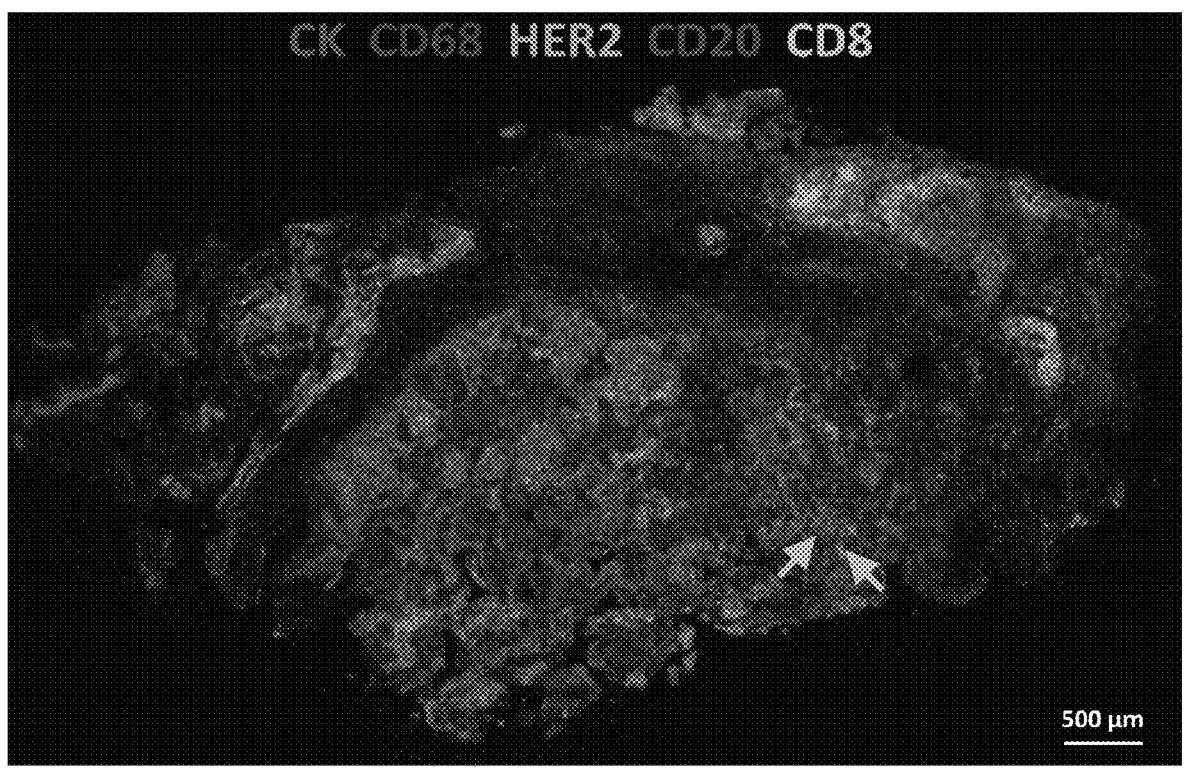
FIG. 15A-D. Multiplex Mass Spectrometry Based Immunohistochemistry (MIHC) on 12 Biomarkers in Human Breast Cancer FFPE Tissue Sections. MIHC was performed as in FIG. 14 (see Table 1 for PC-MT assignments for each antibody).

Next we applied the 12-plex antibody panel to breast cancer FFPE tissue sections to demonstrate utility and to further validate the PR, ER and HER2 antibodies which were generally negative on the tonsil tissue (except for light ER staining as discussed above). For the tissue presented in FIG. 15a-5c, the clinical annotations according to the pathology report provided by the biospecimen vendor (OriGene) were as follows: adenocarcinoma of breast (ductal), TNM staging of pT1cpN3apMX, minimum stage grouping IIIC, 75% tumor, and PR−/ER−/HER2+ according to traditional IHC. FIG. 15a again shows a multi-color MALDI-MS image overlay of selected biomarkers which display differential patterns. The tumor is identified by the regions staining positive for both CK (red; epithelial marker) and HER2 (light green), with the co-localization of the two colors often appearing yellow-orange. Discrete patches of CD20 B-cells (dark green) are observed in the extra- and peri-tumoral regions. The CD8+ cytotoxic T-cells (cyan) are again not widely distributed across the tissue, as with tonsil, but bright staining is observed in discrete zones, including infiltrated into the tumor (e.g., cyan arrows). The prevalence of CD8+ T-cells and their infiltration into the tumor have been reported as positive prognostic indicators for some forms of breast cancer [Vihervuori, Autere et al. (2019) J Cancer Res Clin Oncol 145: 3105-3114; Gao, Wang et al. (2020) BMC Cancer 20: 179; Jin and Hu (2020) Cancers (Basel) 12]. There is also a highly abundant CD68 staining (purple) in the extra- and peri-tumoral regions, indicative of macrophages (and other mononuclear phagocytes) [Chistiakov, Killingsworth et al. (2017) Lab Invest 97: 4-13]. The abundant CD68 staining is consistent with reports that macrophages can often comprise up to 50% of the tumor mass [Poh and Ernst (2018) Front Oncol 8: 49]. The presence of Tumor Associated Macrophages (TAMs) can indicate a positive or negative prognosis for a variety of solid tumors, although usually negative due to their tumor-promoting activities such as immunosuppression as well as promoting angiogenesis and inflammation (reviewed in Poh et al. [Poh and Ernst (2018) Front Oncol 8: 49] and Goswami et al. [Goswami, Ghosh et al. (2017) Cell Immunol 316: 1-10]).

Figure 15B:
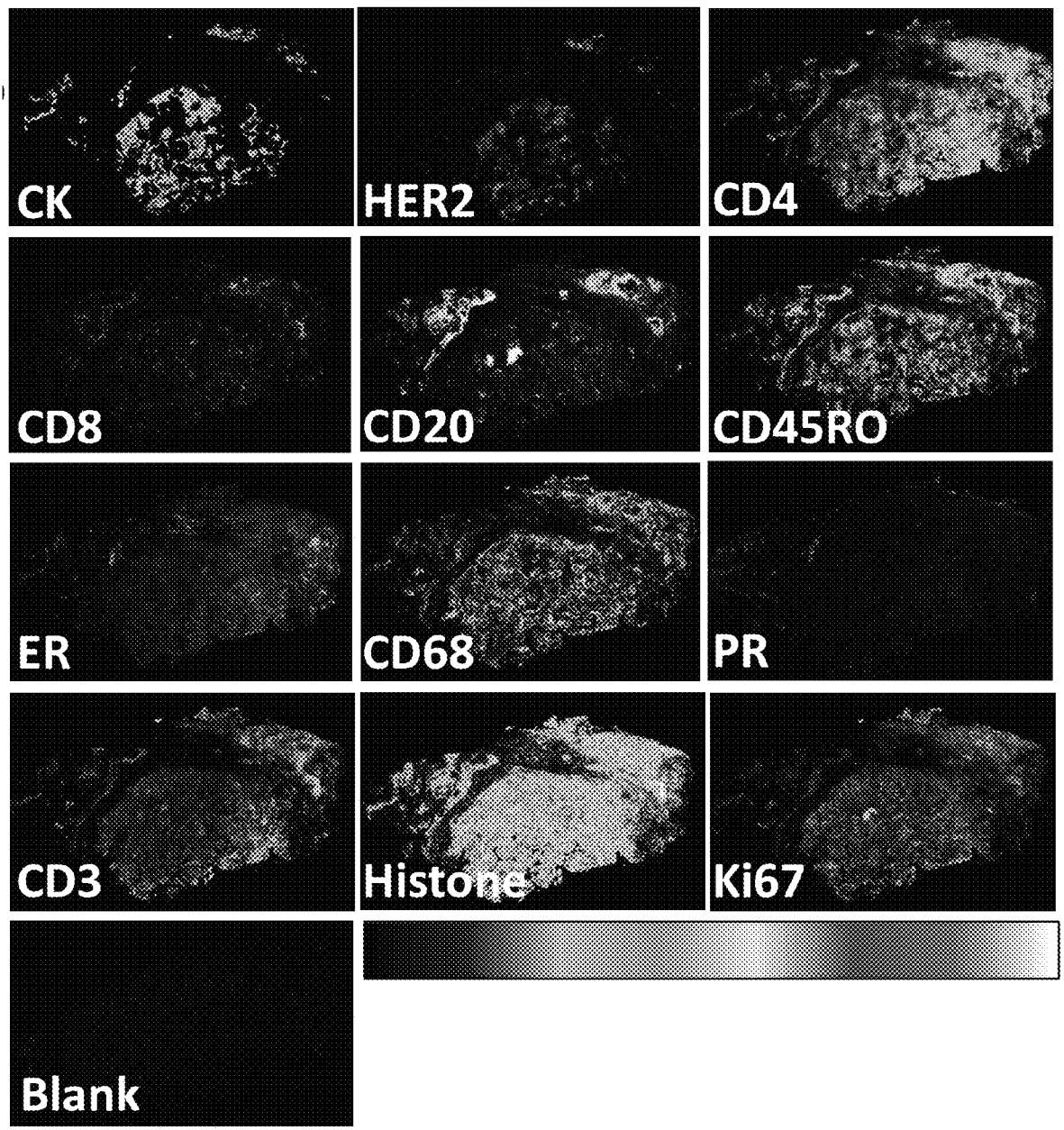
Figure 15C:
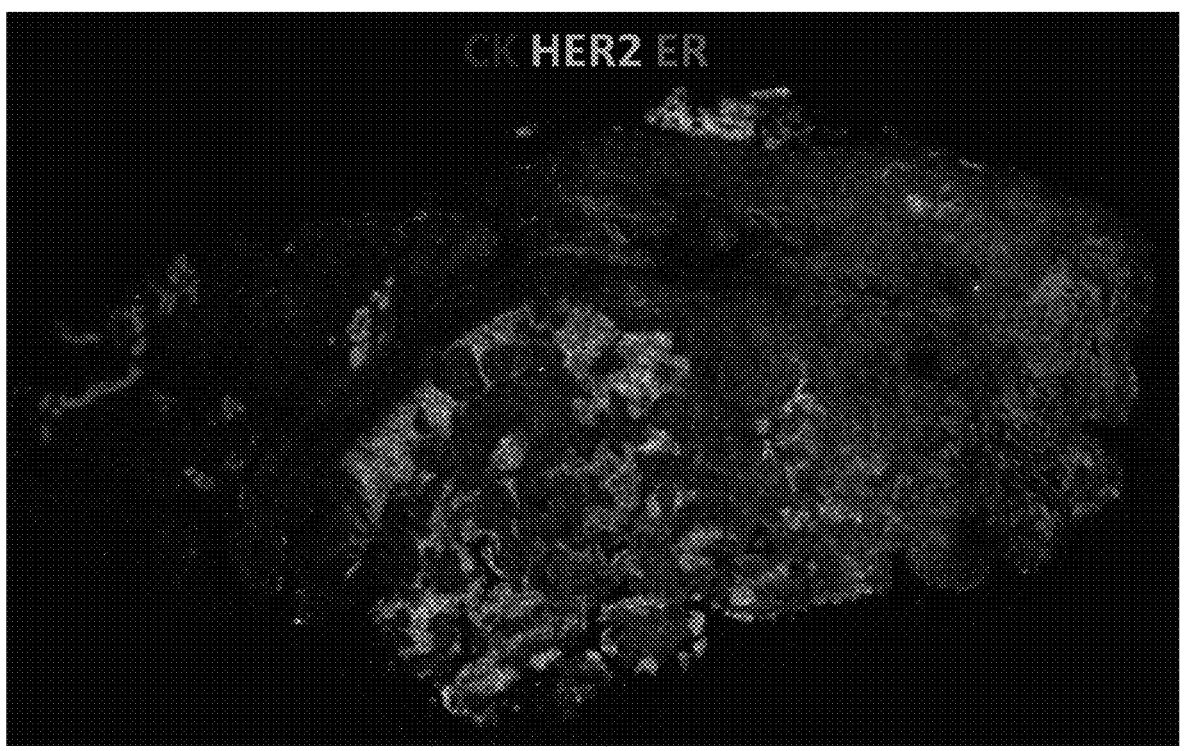

FIG. 15b again shows MALDI-MS images of all 12 antibodies separately, as well as the "Blank" which was done as described earlier (on an adjacent breast cancer tissue section in this case). While HER2 is positive as noted earlier, PR is negative, both agreeing with the biospecimen pathology report. ER shows positive staining, however, this is in the extra-tumoral regions, whereas the tumor itself is not ER+, again agreeing with the pathology report. To illustrate this, for simplicity FIG. 15c shows a multi-color overlay of only three biomarkers (CK, HER2, and ER) denoted with the primary colors. The tumor is indicated by the co-localized CK (colorized blue in this case) and HER2 (green) staining, however, ER staining (red) is almost exclusively restricted to the extra-tumoral regions of the tissue section.

Figure 15D:
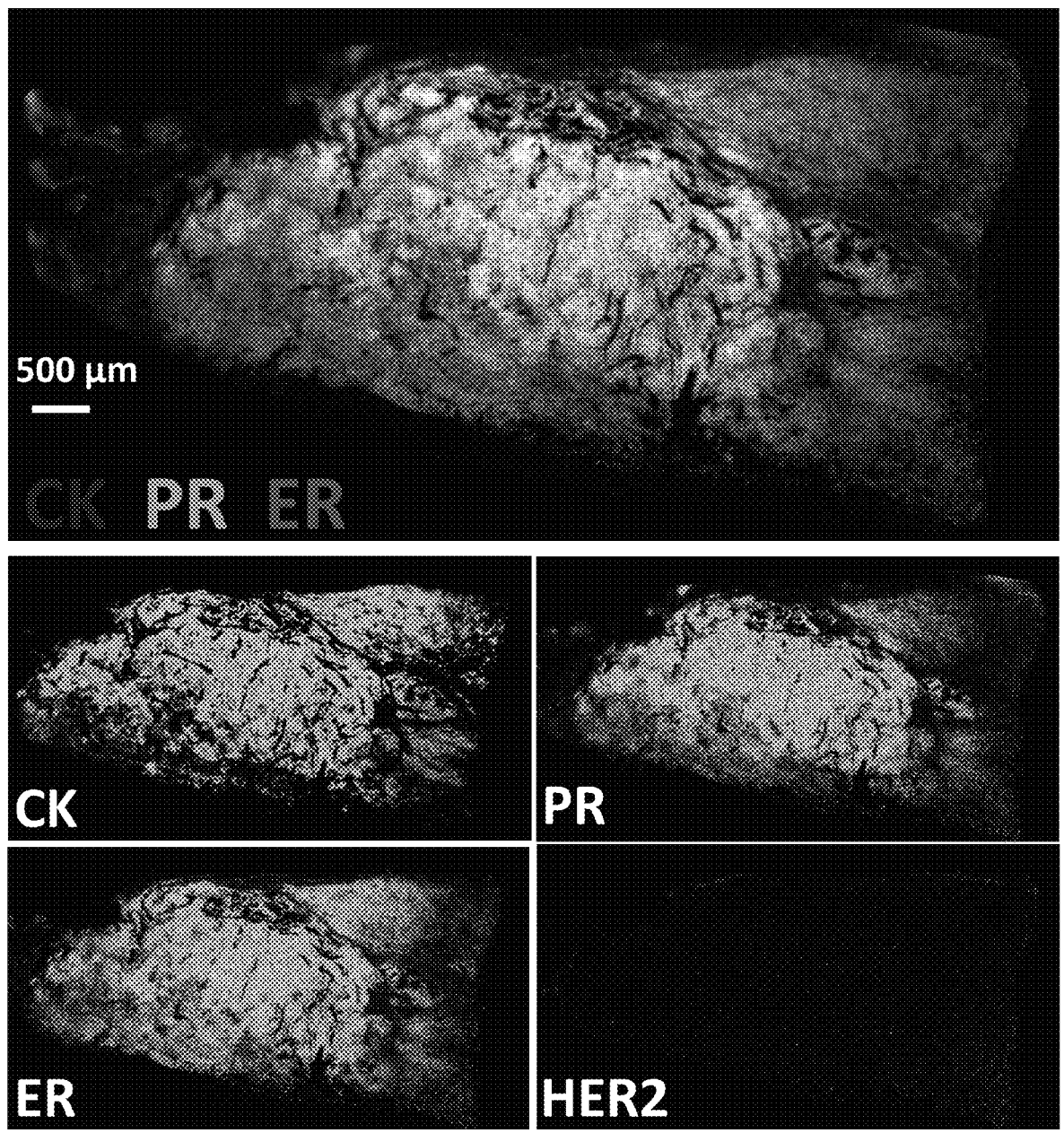

Finally, to further validate the PR, ER and HER2 antibodies, a second breast cancer tissue specimen was analyzed. In this case the clinical annotations according to the pathology report provided by the biospecimen vendor (OriGene) were as follows: adenocarcinoma of breast, ductal, lobular, metastatic, TNM staging of T2N2aMX, minimum stage grouping IIIA, 95% tumor, and PR+/ER+/HER2− according to traditional IHC (i.e., the PR/ER/HER2 profile is the inverse of the previous tissue). The MALDI-MS image in the top panel of FIG. 15d again shows a 3-color image overlay using the primary colors for simple visualization in this case of PR, ER and CK. PR (green) and ER (red) are both strongly positive and co-localization with the CK epithelial biomarker (blue) produces a white color in many areas (occurring when all 3 colors are of similar intensity). FIG. 15d (lower panels) also shows CK, PR, ER and HER2 separately, again with each as gradient color, indicating PR+/ER+/HER2− in full agreement with the pathology report.

Example 10

Gold-Coated Microscope Slides for Improved Tissue Adhesion in Mass Spectrometry Imaging Background Conductive slides are required for most forms of MSI, including most forms of MALDI-MSI. Indium Tin Oxide (ITO) coated glass slides are commonly used and gold coated slides are also used for their conductive properties, and in some cases because gold for example is amenable to chemical modification [Chaurand, Cornett et al. (2011) Mol Cell Proteomics 10: O110 004259; Yang and Caprioli (2014) J Mass Spectrom 49: 417-22]. However, these are used for direct MSI applications, whereby tissues are mounted, in some cases matrix compound applied (for MALDI-MS) and MSI performed. Therefore, there is little to no liquid-phase processing of the slides. In contrast, the methods of the Present Invention (mass spectrometry based immunohistochemistry and mass spectrometry based in situ hybridization, MIHC and MISH) are similar to conventional IHC or ISH, but with PC-MT probes instead of fluorogenic or chromogenic probes, and MSI (and the associated procedures) instead of optical microscopy (see FIG. 16 for comparison of IHC/ISH, direct MSI and MIHC/MISH protocols). Therefore, MIHC and MISH require the slides to both be conductive (unlike IHC and ISH) and to provide more robust tissue adhesion than is required for direct MSI. We have found this is best achieved with gold surfaces, and to our knowledge gold surfaces have not been previously reported for use with IHC-style and ISH-style procedures that use PC-MT probes and MSI.

Methods

Performed as in Example 2 except tissues were mounted on glass slides (standard microscope slide dimensions) with different conductive coatings. These were as follows: Indium Tin Oxide (ITO) slides (Bruker Daltonics, Billerica, MA), ITO slides silanized using (3-aminopropyl)triethoxysilane as a silanization reagent according to published protocols [Qin, Hou et al. (2007) Colloids Surf B Biointerfaces 60: 243-9], ITO slides coated with a Poly-L-Lysine Solution according to the manufacturer's instructions (0.01%, sterile-filtered, BioReagent, suitable for cell culture, Millipore-Sigma, St. Louis, MO), ITO slides coated with Chrome Alum Adhesive according to the manufacturer's instructions (American MasterTech Scientific Inc., Lodi, CA), ITO slides coated with BIOBOND Tissue Section Adhesive according to the manufacturer's instructions (Ted Pella, Inc., Redding, CA), commercially available silver coated slides (Platypus Technologies LLC, Madison, WI) and two kinds of gold coated slides (glass slides with a 10 nm gold layer and 2 nm titanium adhesion underlayer as from Platypus Technologies LLC, Madison, WI, or a 50 nm gold layer and 5 nm chromium adhesion underlayer as from Substrata Thin Film Solutions/Angstrom Engineering Inc., ON, Canada). Tissue damage or loss was visually assessed through to the end of the antigen retrieval step.

Results

Figure 17:
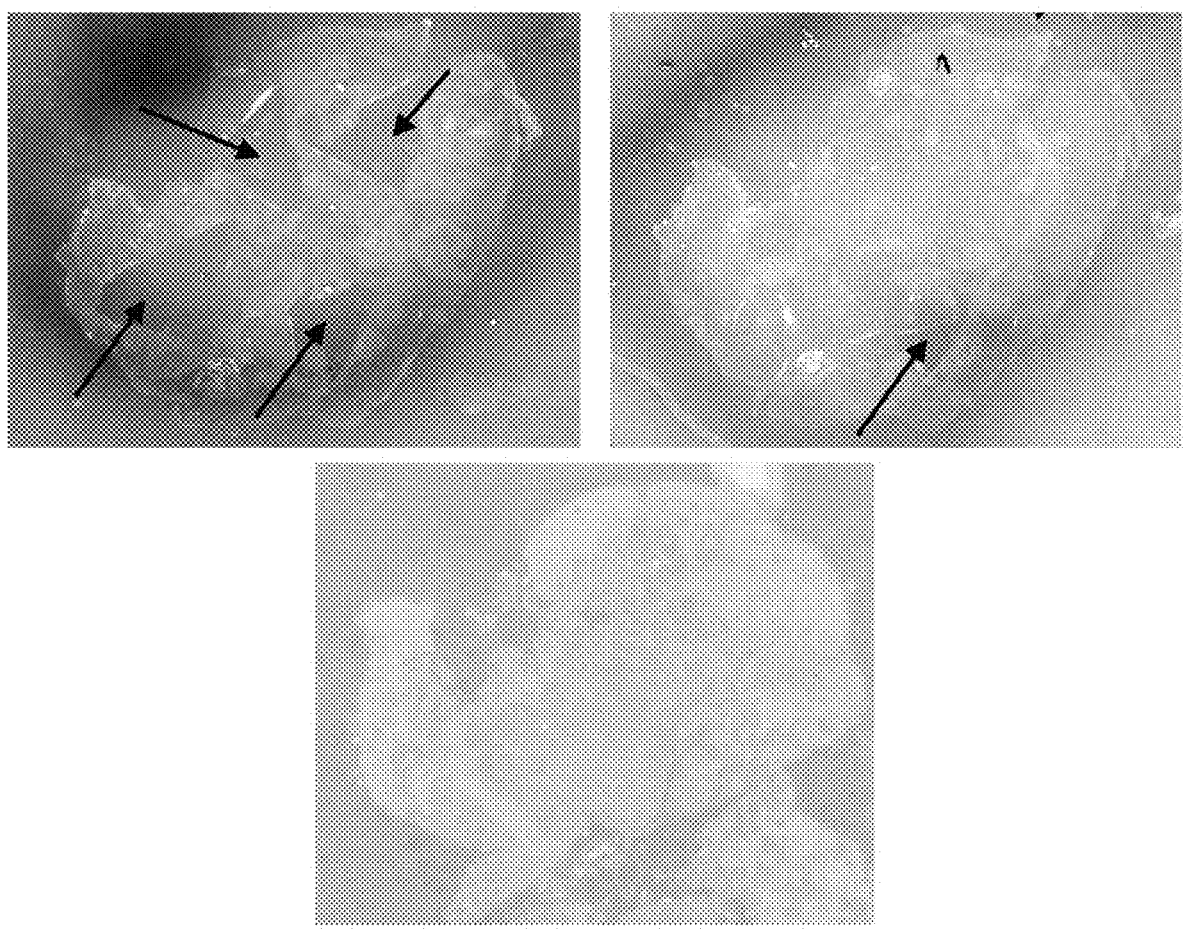
FIG. 17. Examples of Damage to Mouse Brain Tissue Sections on Indium Tin Oxide (ITO) Coated Glass Slides Subjected to the Mass Spectrometry Based Immunohistochemistry (MIHC) Procedures of the Present Invention. Top 2 images are on ITO coated glass slides and bottom image is on a gold coated glass slide. Tissue section loss or damage can be variable. Major sites of damage to the tissue section are indicated with the black arrows.

Heavy tissue damage or tissue loss was observed in all cases to varying degrees, except for both types of gold-coated slides for which little to no tissue damage was observed. Damage could occur at any of the liquid-phase processing steps but was more likely to occur or to initiate at the heat-mediated antigen retrieval step. FIG. 17 shows visible light images of damaged mouse brain tissue sections on ITO slides after processing, as well as an example of an intact tissue section on a gold slide.

Example 11

Matrix Sublimation and the Requirement for Subsequent Matrix Recrystallization in Mass Spectrometry Based Immunohistochemistry (MIHC)

Background

Those skilled in the art will recognize that analyte co-crystallization with an excess of exogenously added matrix compound is generally required for efficient analyte vaporization/ionization and detection in most forms of laser-based mass spectrometry (MALDI mass spectrometry), since it facilitates absorption of the mass spectrometer's laser energy and transfer to the analyte [Yao, Scott et al. (1998) J Am Soc Mass Spectrom 9: 805-13; Duenas, Carlucci et al. (2016) J Am Soc Mass Spectrom 27: 1575-8]. This is referred to as matrix-assisted laser desorption ionization mass spectrometry (MALDI-MS). Matrix-free LDI methods do exist, such as TAMSIM [Thiery, Shchepinov et al. (2007) Rapid Commun Mass Spectrom 21: 823-9] and DIOS [Trauger, Go et al. (2004) Anal Chem 76: 4484-9], but their use is generally restricted to niche applications (e.g., drug detection using DIOS, but non-laser-based methods are generally preferred for this). Furthermore, these matrix-free methods lack sensitivity. Many methods of matrix application in MALDI mass spectrometry imaging (MALDI-MSI) exist, including air brush, automated commercial sprayers and sublimation as some examples [Gemperline, Rawson et al. (2014) Anal Chem 86: 10030-5]. The goal is to maximize sensitivity while minimizing analyte diffusion/delocalization. While the Present Invention is not intended to be restricted to any one method of matrix application, or the requirement for matrix at all, a preferred embodiment uses matrix sublimation followed by recrystallization [Hankin, Barkley et al. (2007) J Am Soc Mass Spectrom 18: 1646-52; Duenas, Carlucci et al. (2016) J Am Soc Mass Spectrom 27: 1575-8]. This provides both excellent spatial resolution (i.e., provided by the sublimation which limits analyte delocalization during matrix application due to the lack of any liquid-phase) and high sensitivity (i.e., provided by the vapor-based recrystallization which allows the analytes [mass reporters of PC-MTs] to sufficiently co-crystallize with matrix, but without significant analyte delocalization).

Methods

Performed as in Example 2 except using the PC-MT anti-NeuN antibody only (1 μg/mL probing concentration), and a comparison between with and without recrystallization was made.

Results

MIHC with the PC-MT labeled anti-NeuN antibody using MALDI-MSI on mouse brain tissue sections is shown in FIG. 18 (colorized MALDI-MS images shown), using matrix (DHB) sublimation with and without recrystallization (see Examples 1-2 for methods). FIG. 18 shows that strong signals and the typical anti-NeuN pattern is observed on the mouse brain tissue sections (see Example 2) when re-crystallization is applied. Without recrystallization, no signal is visibly detected in the image. To quantify the effects of matrix recrystallization following sublimation, average spectra were generated from each of the entire regions of interest (see dotted outlines in FIG. 18) for each tissue section. From these average spectra, monoisotopic peak intensities for the PC-MT were 55.4 and 2.5 for with and without recrystallization, respectively. Importantly, this demonstrates that matrix recrystallization following sublimation, for the MALDI-MSI step of MIHC, is required for robust PC-MT signals.

Example 12

Mass Spectrometry Based Immunohistochemistry (MIHC) for Multiplex Imaging of Biomarkers Related to Anti-Cancer Immune Checkpoint Inhibitor Drugs Background The normal biological function of the immune checkpoint pathways is the maintenance of peripheral immune tolerance for example by suppression of T-cell responses. In evidence of this, mice deficient in key proteins of the immune checkpoint pathway (CTLA-4 or PD-1) develop autoimmune type disorders [Haanen and Robert (2015) Prog Tumor Res 42: 55-66]. It is now well-known that activation of T-cells induces the expression of immune checkpoints, such as PD-1 and CTLA-4 on the activated T-cells, which in turn suppresses T-cell signaling and activation as a form of negative feedback [Sharma and Allison (2015) Science 348: 56-61; Darvin, Toor et al. (2018) Exp Mol Med 50: 1-11; Wei, Duffy et al. (2018) Cancer Discov 8: 1069-1086]. However, this immune suppression can also block the beneficial anti-tumor immune response, and in some cases, the tumor itself can hijack the immune checkpoints to its advantage. For example, tumor cells can express the PD-L1 ligand which binds PD-1 on activated T-cells to suppress the anti-tumor immune response [Sharma and Allison (2015) Science 348: 56-61; Darvin, Toor et al. (2018) Exp Mol Med 50: 1-11; Wei, Duffy et al. (2018) Cancer Discov 8: 1069-1086]. Several antibody therapeutics now exist, for example pembrolizumab (marketed as Keytruda®, Merck, Kenilworth, NJ), which binds PD-1 and prevents its interaction with PD-L1/2 and thereby preventing immune suppression (likewise, therapeutic antibodies against PD-L1 for example also block this interaction) [Kwok, Yau et al. (2016) Hum Vaccin Immunother 12: 2777-2789; Wei, Duffy et al. (2018) Cancer Discov 8: 1069-1086]. Current FDA approved immune checkpoint inhibitor drugs include ipilimumab, specific for CTLA-4; nivolumab, pembrolizumab, and cemiplimab, specific for PD-1; and atezolizumab, avelumab, and durvalumab, specific for PD-L1 [Vaddepally, Kharel et al. (2020) Cancers (Basel) 12]. While these drugs have achieved breakthrough status [Darvin, Toor et al. (2018) Exp Mol Med 50: 1-11] and are effective on a range of cancers [Sharma and Allison (2015) Science 348: 56-61; Gorris, Halilovic et al. (2018) J Immunol 200: 347-354], durable responses are only achieved in 20-40% of patients [Gorris, Halilovic et al. (2018) J Immunol 200: 347-354]. Thus a problem remains in understanding and predicting which patients will respond, and to which of the range of available treatments. Therefore, it is critical to understand the expression of a range of known immune checkpoint and related molecules on both the tumor itself and the infiltrating immune cells within the tumor microenvironment [Gorris, Halilovic et al. (2018) J Immunol 200: 347-354]. Considering the large number of known immune checkpoint molecules, including PD-1, PD-L1, PD-L2, CTLA-4, OX40, CD27, and TIM3, a method for highly multiplex IHC, such as with the MIHC technology of the Present Invention, will be a vital clinical tool.

Methods

MIHC will be performed as in Examples 2 and 9 except the 12-plex antibody panel detailed in Example 9 for breast cancer biomarkers and biomarkers of infiltrating immune cells will be further expanded to include PC-MT antibodies to the following biomarkers related to immune checkpoints and checkpoint inhibitor drugs: PD-1, PD-L1, PD-L2, CTLA-4, OX40, CD27, CD28 and TIM3. So as not to overlap with other antibodies in the panel, these new antibodies will be labeled with PC-MTs containing mass units 7-14 (see Table 1) using the methods from Examples 1, 2 and 9, for a total 20-plex antibody panel.

Antibodies for PC-MT labeling will be commercially obtained from ABCAM (Cambridge, MA) and will be as follows: Recombinant Anti-PD1 antibody [CAL20]—BSA and Azide free (ab251613); Recombinant Anti-PD-L1 antibody [73-10]—BSA and Azide free (ab226766); Recombinant Anti-PD-L2 antibody [EPR1163(2)]—BSA and Azide free (ab215254); Recombinant Anti-CTLA4 antibody [CAL49]—BSA and Azide free (ab251599); Human OX40 Antibody Pair—BSA and Azide free (TNFRSF4) (ab244076) (both antibodies will be tested and the best chosen); Recombinant Anti-CD27 antibody [EPR8569]—BSA and Azide free (ab256583); Recombinant Anti-CD28 antibody [EPR22076]—BSA and Azide free (ab243557); Recombinant Anti-TIM3 antibody [EPR22241]—BSA and Azide free (ab242080).

MIHC will be performed on FFPE breast cancer tissues as an example, as described in Example 9, except using the full aforementioned 20-plex antibody panel. However, the Present Invention is applicable to any tumor type, and including but not limited to tissues prepared as FFPE (formalin fixed paraffin embedded) or FF (fresh frozen).

Results

It is anticipated that this approach will allow simultaneous multiplex imaging of cancer biomarkers, biomarkers of infiltrating immune cells and biomarkers of immune checkpoints (similar to Example 9 but with the aforementioned added biomarkers), to provide pathologists with vital information on cancer diagnosis, prognosis, and guiding therapies such as immune checkpoint inhibitors.

Example 13

PC-MT Lectins for Targeted Multiplex Mass Spectrometry Imaging of Glycans

Background

This Example describes the use of PC-MT labeled lectin probes for tissue MSI. Lectins are a type of carbohydrate-binding protein (discussed earlier) usually derived from plants. PC-MT labeled lectin probes can be used for MSI of N- and O-glycans in tissues, but are particularly important for O-glycans, whereby, unlike N-glycans, no suitable glycosidase exists for in situ tissue digestion followed by direct label-free MSI. Rather, O-glycans must be sequentially chemically degraded until only the core Gal-β(1→3)-GalNAc carbohydrates remain, at which point O-glycosidase may be used for core removal, but these procedures are not amenable to in situ digestion and direct label-free MSI of tissues [Poiroux, Barre et al. (2017) Int J Mol Sci 18; Wilkinson and Saldova (2020) J Proteome Res 19: 3890-3905]. PC-MT labeled lectin probes avoid this problem and thus facilitate targeted, highly multiplex, MSI of both N- and O-glycans in tissues. Importantly, not only do lectins exist to bind N- and O-glycans [Tsaneva and Van Damme (2020) Glycoconj J 37: 533-551], but for example Peanut (*Arachis hypogaea*) agglutinin lectin (PNA) is selective for the Gal-β(1→3)-GalNAc core of O-glycans [Chacko and Appukuttan (2001) Int J Biol Macromol 28: 365-71; Cummings, Darvill et al. (2015) Essentials of Glycobiology: 611-625] and could be used to distinguish O-glycans from N-glycans. Jacalin lectin from *Artocarpus integrifola* as well as the *Agaricus bisporus* lectin are also specific to the O-glycan T/Tn antigens [Poiroux, Barre et al. (2017) Int J Mol Sci 18]. O-glycans are especially important as O-glycan alteration has been repeatedly linked to cancer [Chacko and Appukuttan (2001) Int J Biol Macromol 28: 365-71; Poiroux, Bane et al. (2017) Int J Mol Sci 18]. Note, as discussed in the Detailed Description of the Invention, probes of various types may be combined such as lectins and antibodies, and PC-MT probes of all kinds may be combined with other "omic" MSI approaches (e.g., direct label-free metabolomic MSI).

Methods

Lectins were labeled with PC-MTs in the same manner as the antibodies in Example 1, with the following changes: The 10-fold molar ratio of PC-MT labeling reagent to probe was maintained, therefore, since the lectins have different molecular weights than antibodies, the amount of PC-MT labeling reagent was adjusted accordingly. Instead of using PD SpinTrap G-25 Columns, removal of unreacted PC-MT labeling reagent in this case was achieved by 6 cycles of washing with 450 µL of TBS using Amicon Ultra-0.5 Centrifugal Filter Units comprised of Ultracel Regenerated Cellulose Membrane (Millipore-Sigma), according to the manufacturer's instructions. The nominal molecular weight limit (NMWL) of the Filter Units was 10 kDa for the wheat germ agglutinin (WGA; from Millipore-Sigma) and *Phaseolus vulgaris* agglutinin (PHA-E4; from amsbio) lectins and 50 kDa for the peanut agglutinin (PNA; from Millipore-Sigma) and *Dolichos biflorus* agglutinin (DBA; from Millipore-Sigma) lectins. Each lectin was labeled with a unique PC-MT as follows: PC-MT Mass Unit IDs 1, Iso-1.2, Iso-1.3, and 1.2 (see Table 1 for details), for WGA, PNA, PHA-E4, and DBA lectins, respectively.

Subsequent tissue processing of sagittal mouse brain FFPE sections was performed as in Example 2 except the antigen retrieval step was omitted, as it was not necessary in this case. Thus, the processing steps performed were deparaffinization, hydration, blocking, probing/staining (with PC-MT lectins in this case), washing, drying, photocleavage, DHB matrix sublimation/recrystallization and MALDI-MSI (no immunofluorescence was performed). Note that antigen retrieval could still be used in cases where PC-MT lectin probes are combined with PC-MT antibody probes for example. All 4 aforementioned PC-MT labeled lectins were mixed together for multiplex probing/staining of the tissue sections and concentrations ranged from 1-20 µg/mL. In some cases, the PC-MT lectin probing/staining mixture was supplemented with the soluble sugar N,N',N"-Triacetylchitotriose (TCT; binds WGA lectin) at 1 mM concentration and pre-incubated for 30 min prior to tissue probing/staining (and the soluble sugar remained present during tissue probing/staining). This was to confirm specificity of PC-MT lectin (WGA) staining by competitive inhibition.

Results

Figure 19A:
FIG. 19A-C. MALDI-MSI of Sagittal Mouse Brain FFPE Tissue Sections Stained with PC-MT Labeled Lectin Probes.
Figure 19B:
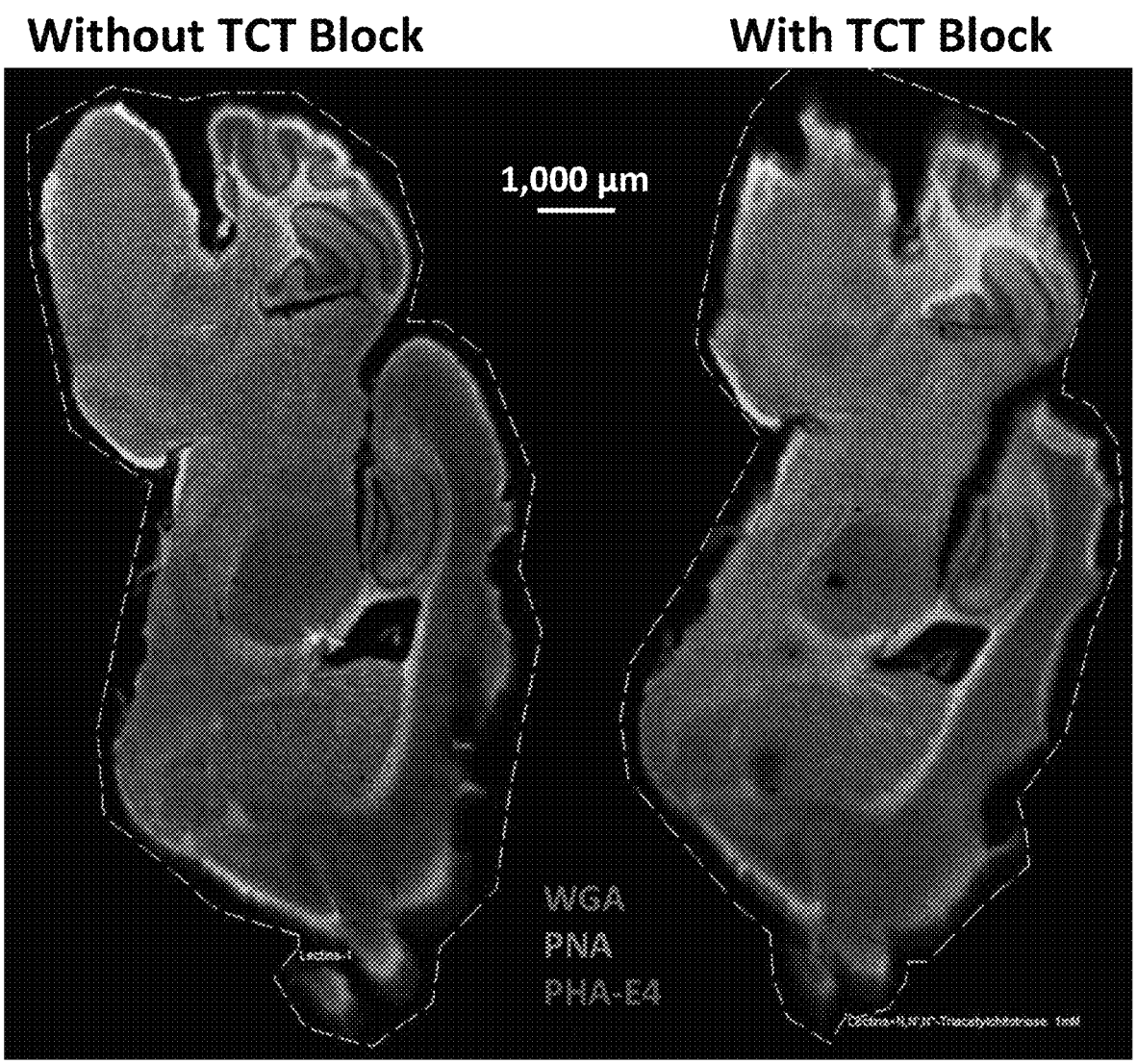

FIG. 19a is a colorized mass-image of the monoisotopic mass spectral peaks of the PC-MT reporters corresponding to 3 of the lectins, PHA-E4, PNA and WGA. Results agree with prior literature reports by Kitada et al. which stained mouse brain tissue sections with fluorescently labeled lectins [Kitada, Kuroda et al. (2011) Anat Rec (Hoboken) 294: 305-21]. Notably, in Kitada et al., PHA-E4 lectin staining was prevalent in the choroid plexus along with some WGA staining, as was observed here with the PC-MT lectins and MSI (choroid plexus is labeled in FIG. 19a; see also FIG. 19b). Whereas PNA lectin in Kitada et al. preferentially stained the white matter of the brain, i.e., the myelinated axons. Thus, PC-MT PNA lectin staining here (green in FIG. 19a) matches the PC-MT myelin antibody staining previously observed, as would be expected (see Example 2, FIG. 7a, red, for previous PC-MT myelin antibody staining).

Figure 19C:
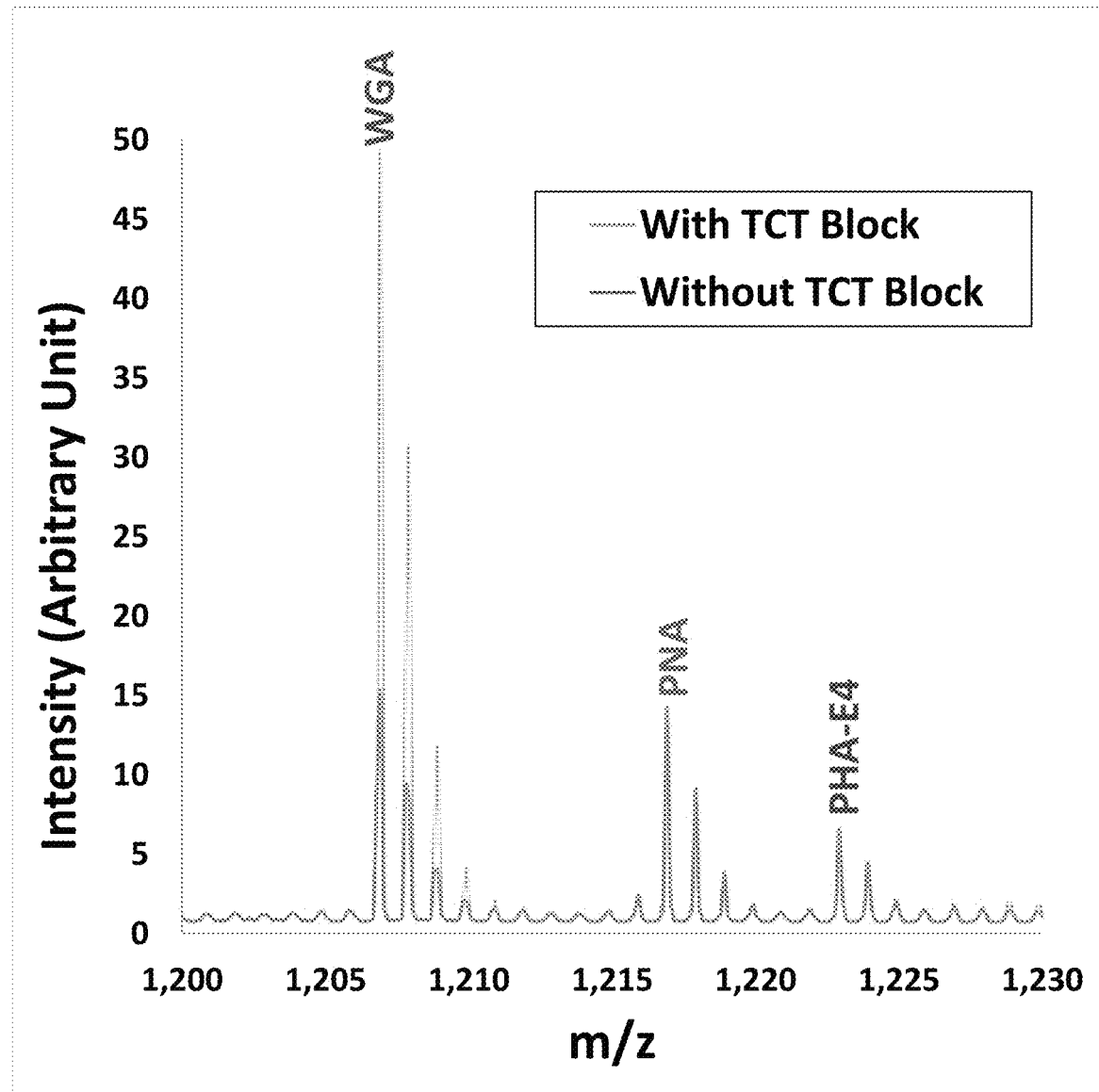

Finally, to demonstrate specificity of the PC-MT lectin binding to the tissue, the PC-MT lectin probing/staining mixture was pre-incubated with 1 mM of the soluble sugar N,N',N"-Triacetylchitotriose (TCT) and this sugar remained present during the tissue probing/staining steps for competitive inhibition (blocking) of WGA binding (since TCT specifically binds WGA [Damm, Mikkat et al. (2004) Pancreas 28: 31-7]). As observed in the PC-MT mass-images of FIG. 19b, when the TCT blocking was not used, a predominant WGA staining was observed (blue in FIG. 19b). When the TCT blocking was used, WGA staining was selectively inhibited while staining with the other lectins, PHA-E4 (red) and PNA (green), was still observed. To quantify this result, the overall average spectrum from the entirety of each tissue section, with and without TCT blocking, was obtained (FIG. 19c). When the TCT blocking was used (orange trace), WGA PC-MT signal intensity was reduced by 70% compared to without TCT blocking (purple trace), whereas the peak intensities of the other 2 lectins, PNA and PHA-E4, were virtually identical with and without the TCT blocking, thereby demonstrating specificity.

Example 14

Improved Multi-Omic MSI: Untargeted Label-Free MSI of Lipids and Targeted MIHC on the Same FF Tissue Section

Methods

This Example was performed the same as in Example 4 using FF sagittal mouse brain tissue sections except with some enhancements for better tissue fixation and better removal of unfixed small endogenous organic compounds after the initial direct label-free MALDI-MSI (of endogenous lipids in this case), before the subsequent MIHC steps with PC-MT labeled antibodies (PC-MT-Abs). Thus, after the initial direct label-free MALDI-MSI of endogenous lipids, the following was performed on the tissue sections (each treatment step in separate staining jars): Pre-wash 2× with −80° C. acetone for 3 min each (note, serves to remove any remaining matrix compound from the prior MALDI-MSI while providing solvent fixation) and vacuum dry for 10 min; 30 min fixation using 1% PFA in PBS, pH 7.4 (note this solution was prepared fresh by dissolving 1.0 g of PFA in 60 mL of PBS with 1.0 mL 1 M NaOH on a heating block at ~60° C. under constant stirring, followed by adjusting the pH to 7.4 with 1 M HCl [~1 mL] and adjusting the final volume to 100 mL with PBS); wash 1× with PBS for 10 min; wash 2×3 min each with RT acetone; and wash 1×3 min with Carnoy's Solution (6:3:1 EtOH/chloroform/acetic acid) for further fixation and to further remove unfixed endogenous organic compounds. The remaining steps for the subsequent PC-MT-Ab based MIHC were performed as in Example 2 starting with the antigen retrieval step to the end.

Results

Figure 20A:
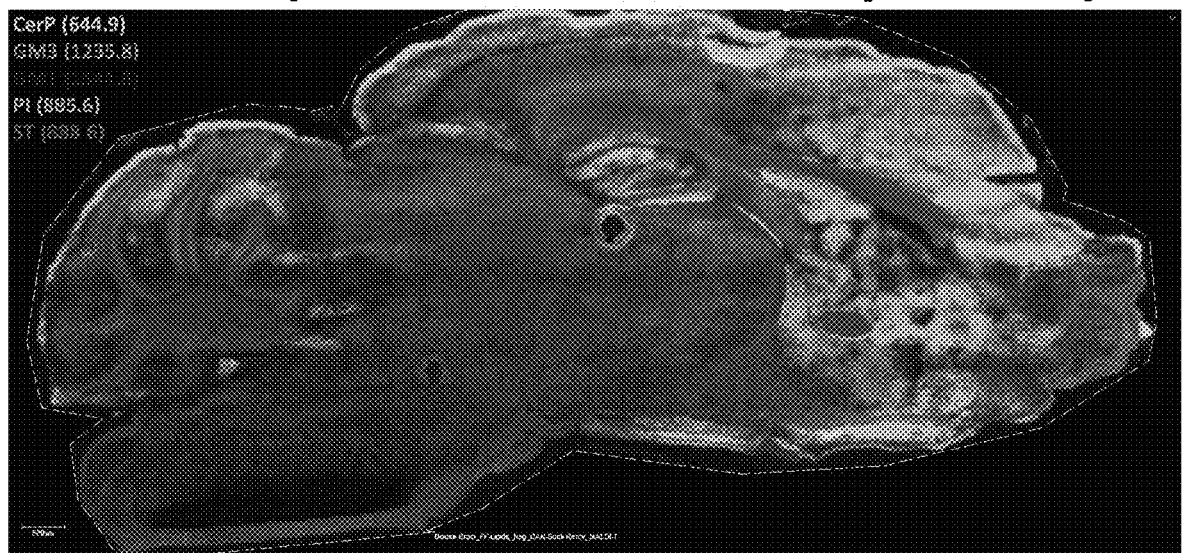
FIG. 20A-C. Direct Label-Free MALDI-MSI Followed by MIHC on the Same Tissue Section. FF sagittal mouse brain tissue sections were used. Mass-images of the directly detected lipids and the PC-MTs derived from the various antibodies are shown.
Figure 20B:
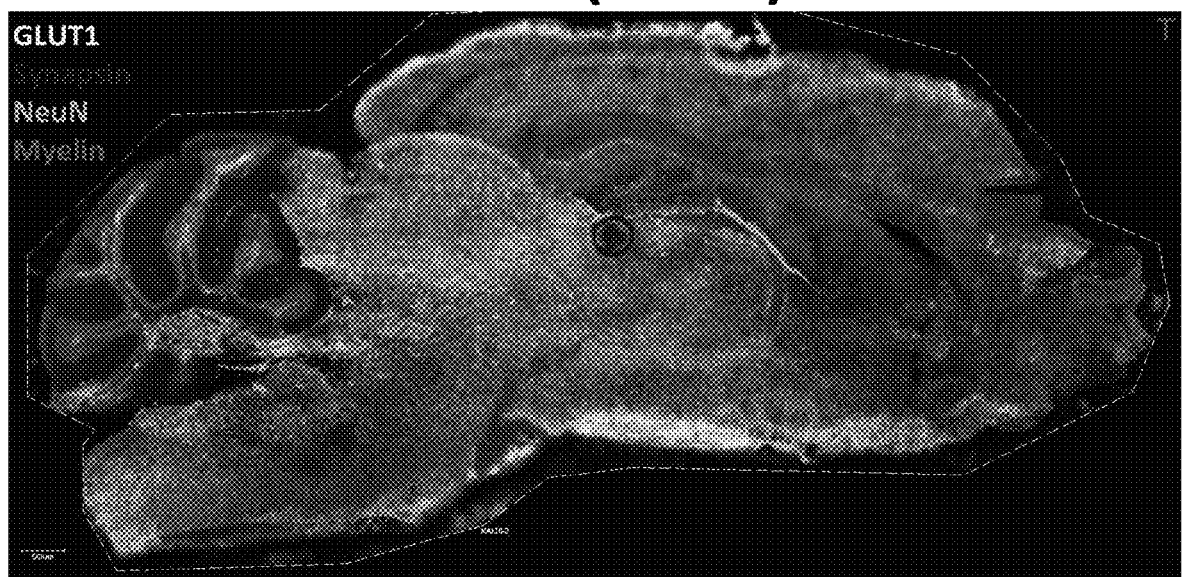
Figure 20C:
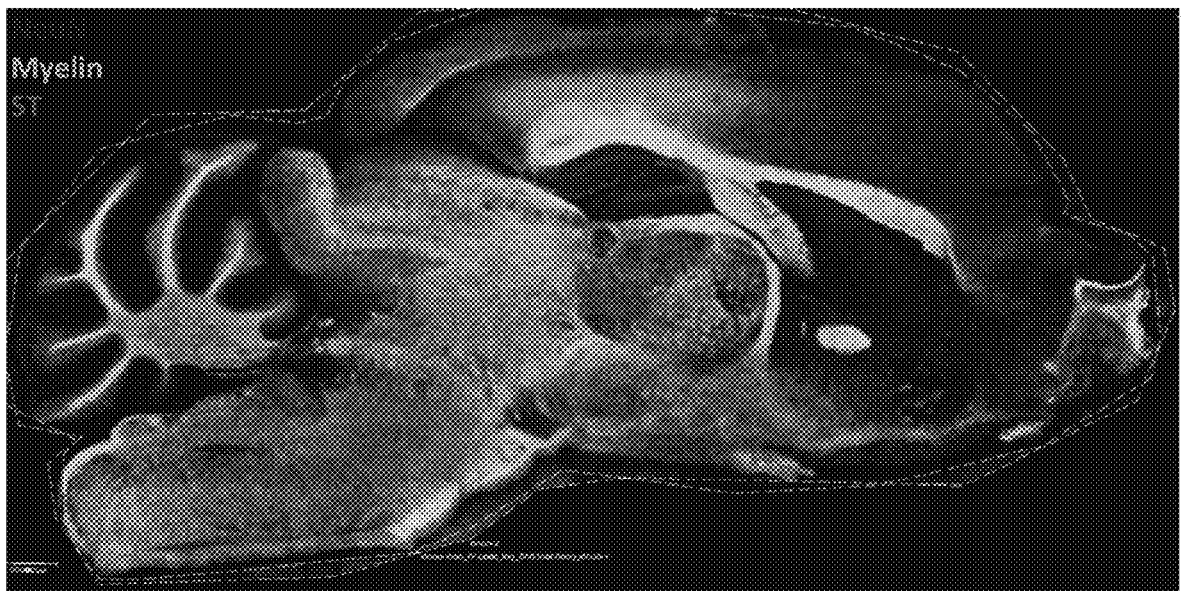

Mass-images are shown in FIG. 20. FIG. 20a is the initial direct label-free MALDI-MSI of endogenous lipids (see FIG. 20a for which example lipids are displayed); FIG. 20b is the subsequent MIHC, showing selected antibody PC-MTs (see FIG. 20b for which antibody PC-MTs are displayed), and FIG. 20c is an image merge between selected analytes from the initial direct label-free MALDI-MSI and subsequent MIHC (see FIG. 20c for which analytes). The expected co-localization of the lipid sulfatide (ST) with myelin but not between ST and NeuN is explained in Example 4.

Example 15

Multi-Omic Tissue Imaging: MIHC Combined with Bottom-Up Proteomic MSI

In the Detailed Description of Invention under the section headed "Multi-Omic Tissue Imaging using PC-MT-Probes", a wide range of permutations of multi-omic imaging approaches which incorporate the PC-MT probe technology are described. The following Example demonstrates some permutations of such approaches but is not intended to limit the scope of the Present Invention.

Methods

Breast cancer FFPE tissue sections will be used as in Example 9.

In one embodiment, in situ tissue glycan digestion with the glycosidase PNGase F followed by direct label-free MALDI-MSI of the liberated glycans will be performed according to Drake et al. [Drake, Powers et al. (2018) Curr Protoc Protein Sci 94: e68]. Next, after the MALDI-MSI, the MALDI-MS matrix will be removed by washing 2×3 min each with RT acetone (in staining jars) and the tissue will then be fully dried for 10 min under vacuum. Next, 12-plex MIHC will be performed as in Example 9 to detect macromolecular protein biomarkers for breast cancer as well as tumor infiltrating lymphocytes/immune cells (except the deparaffinization steps of Example 9 will be omitted since they will have already been done per the steps of Drake et al.).

In another embodiment, MIHC (targeted) will be performed first followed by in situ protease digestion of the tissue sections and direct, untargeted, label-free MALDI-MSI of the liberated proteolytic fragments (from the endogenous tissue proteins). See for example, FIG. 22. In this case, MIHC will again be performed as in Example 9, which includes as the last step MALDI-MSI. The MALDI-MS matrix will then be removed by washing 2×3 min each with RT acetone (in staining jars) and the tissue will then be fully dried for 10 min under vacuum. Subsequent in situ protease (trypsin) digestion and direct label-free MALDI-MSI of the liberated proteolytic fragments will be performed according to Lazova et al. [Lazova, Smoot et al. (2020) J Cutan Pathol 47: 226-240] except the deparaffinization and antigen retrieval steps will be omitted as they will already have been done per the MIHC process. Finally, in another embodiment, it may be desirable to remove the antibodies (and proteinaceous blocking agents) from the initial MIHC process before the in situ proteolytic digestion for the subsequent direct label-free MALDI-MSI (so that only proteolytic fragments from endogenous tissue proteins are detected). In this case, the MALDI-MS matrix from the final step in the MIHC process will again be removed by washing 2×3 min each with RT acetone (all steps in staining jars), however, the tissue will then be subjected to a denaturing treatment at 65° C. for 5 min in a solution of 1% (w/v) SDS detergent in 50 mM Tris, pH 7.4, containing 1 mM dithiothreitol (DTT). This denaturing treatment serves to detach the antibody probes (and proteinaceous blocking agents) from the tissue. This will be followed by washing 2×3 min each with plain 50 mM Tris, pH 7.4, and then 2×3 min each with RT acetone (which will further assist in complete removal of the SDS detergent from the tissue). The tissue will then be fully dried for 10 min under vacuum. Subsequent in situ protease (trypsin) digestion and direct label-free MALDI-MSI of the proteolytic fragments will be performed, again according to Lazova et al. [Lazova, Smoot et al. (2020) J Cutan Pathol 47: 226-240] (but again, the deparaffinization and antigen retrieval steps of Lazova et al. will be omitted as they will already have been done per the MIHC process).

Results

By combining the results of MIHC with bottom-up MSI approaches, a much greater spatial information content from the tissues will be obtained as compared to either approach alone. This is anticipated to lead to better biomarker "signatures", e.g. as determined by the machine learning statistical approaches of Lazova et al., which for example can be used in cancer on tumor tissues to diagnose, stage, prognose, sub-type, and predict optimal treatment paths for improved patient outcomes.

Example 16

PC-MT-Probes in Non-Imaging Mass Spectrometry Applications

Background

PC-MT-Probes are also not limited to mass spectrometric imaging applications but can be used in conjunction with non-imaging mass spectrometric (MS) applications. For example, a group of PC-MT-Probes can be applied to a heterogenous biological sample including but not limited to a tissue or excised portion of a tissue, tumor, cells derived from a tumor (or derived from any tissue), liquid biopsy, cell cultures, blood and other bodily fluids, bacterial cells and cultured infections pathogens in order to identify the presence of components of the heterogeneous sample. For example, pathogens present in a biological sample could be identified using one or more PC-MT antibody (PC-MT-Ab) probes which target antigens characteristic of the pathogen or multiple pathogens. Readout would be through detection of the photocleaved (photo-released) PC-MTs using non-imaging mass spectrometry methods including but not limited to MALDI-MS or ESI-MS, with or without liquid chromatography prior to mass spectrometric analysis (e.g., LC-MS), which will be recognized by those skilled in the art as sometimes necessary to further purify the analytes prior to the mass spectrometric analysis (e.g., desalting). In one embodiment, antigens/epitopes specific to particular variants of the SARS-CoV-2 virus responsible for causing the COVID-19 pandemic could be identified using PC-MT-Ab probes targeted to these antigens/epitopes, such as the Spike protein antigen and/or its epitopes. In a second embodiment, specific antigens/epitopes present on tumor infiltrating lymphocytes that are present in a tumor biopsy could be targeted with specific PC-MT-Ab probes and detected using non-imaging mass spectrometry, to determine the presence of various immune cell types in the tumor, which for example can provide prognostically and therapeutically useful information. While spatial information is lost due to this non-imaging approach, it is well known to those skilled in the art of immunodiagnostics, including ELISA and flow cytometry, that the positive binding of a particular combination of antibodies (or other probe types) to a biological sample can be used to identify the presence of particular components of the sample, such as bacterial cells or viruses in the case of infectious disease. This targeted approach which detects the presence of specific biomarkers in the sample can be combined with other mass spectrometric methods such as the untargeted detection of particular combinations of small molecules, lipids, metabolites and proteins to identify components of the sample (e.g., components of a biological mixture). In the Experimental Example presented below, binding of a PC-MT-Probe (PC-MT-Ab) to a surface, followed by PC-MT photo-release and non-imaging mass spectrometry analysis of the photo-released PC-MT, is demonstrated. While in this case the surface to which the PC-MT-Ab was bound was beads, ultimately, PC-MT-Probes of any kind can be bound to any sample such as exemplified above.

Methods

The PC-MT (mass unit Iso-1.1 in Table 1) and the PC-MT-Ab were prepared as in Example 1. Note, in this case, as a model PC-MT-Ab, purified rabbit IgG was used (see "Materials for Experimental Examples" section).

The resultant PC-MT-Ab was bound to Protein G agarose beads (Thermo Fisher Scientific, Waltham, MA), the beads then washed to remove unbound PC-MT-Ab, the PC-MT then photo-released from the bead-bound PC-MT-Ab, and non-imaging MALDI-MS analysis performed on the photo-released PC-MT present in the supernatant. The full procedure was as follows: Protein G agarose beads were processed in 0.5 mL Ultrafree-MC Centrifugal 0.45 μm Filter Devices (see "Materials for Experimental Examples" section) unless otherwise noted (note that washes were by brief vortex mixing of the beads in the wash solution, followed by brief spinning at 15,000 rpm in a standard micro-centrifuge, and then discarding the filtrate in the bottom chamber of the Filter Devices; while the washed beads are retained in the top chamber of the Filter Devices). 1 μL bead pellet volume was used for each sample (each sample processed in parallel in separate Filter Devices). Beads for each sample were first pre-washed 4×400 μL briefly with OBG-Saline (see Example 6 for formulation). Each washed bead pellet was then re-suspended in 100 μL of the PC-MT-Ab solution (prepared in OBG-Saline with PC-MT-Ab concentrations of 0.625, 1.25, 2.5, 5, 7.5 and 10 μg/mL). Beads were mixed gently for 30 min (protected from light) to allow binding of the PT-MT-Ab to the Protein G on the beads. Beads were then washed 4×400 μL briefly with OBG-Saline followed by 4×400 μL briefly with mass spectrometry grade waster (MS-Water) to remove unbound PC-MT-Ab.

Beads were then re-suspended and transferred to clear, thin-walled polypropylene PCR-type micro-centrifuge tubes in 100 μL MS-Water. Beads were then spun down briefly at 15,000 rpm in a standard micro-centrifuge followed by discarding ~80 μL of the supernatant, leaving ~20 μL of MS-Water in the tubes plus the bead pellets. Beads were re-suspended in the tubes by brief mixing and exposed to UV light for 5 min through the side-walls of the tubes (tubes placed on their sides) using a Honle LED Cube 100IC (Honle UV Technology, Marlboro, MA) at 25% power (30 mW/cm$^2$ at 360 nm). With the beads still in the tubes, 20 μL of the following solution was next added to each sample: 10 mg/mL alpha-cyano-4-hydroxycinnamic acid (CHCA; Sigma-Aldrich, St. Louis, MO), 80% acetonitrile, 0.2% (v/v) trifluoroacetic acid (TFA) and 25 femtomoles/μL of an unmodified control peptide having the sequence APRLRFYSL (custom synthesized by GenScript, Piscataway, NJ). Beads were then mixed for 15 min to allow full extraction of the photo-released PC-MT. Beads were spun down briefly at 15,000 rpm in a standard micro-centrifuge and then 2 μL of each sample supernatant (not including any beads) was spotted onto a standard steel MALDI-MS target for standard non-imaging MALDI-MS analysis on a rapifleX MALDI-TOF-MS instrument (Bruker Daltonics, Billerica, MA).

Results

Figure 21A:
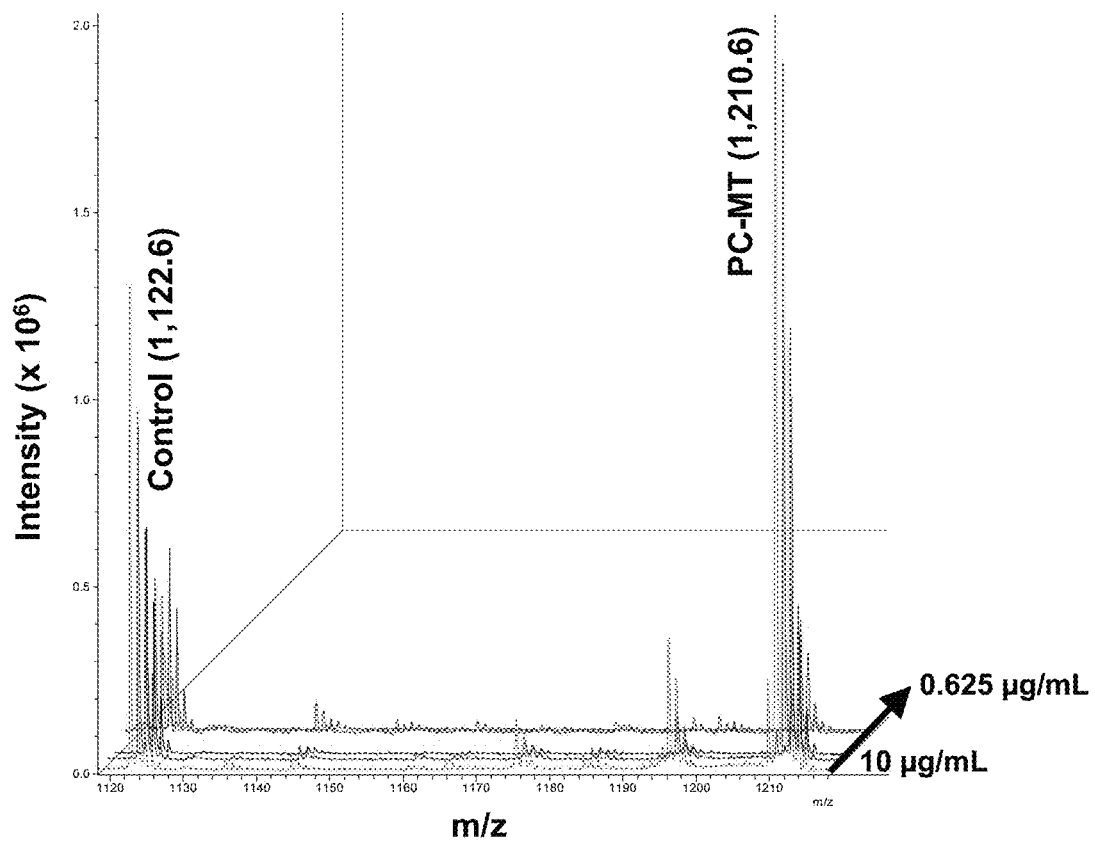
FIG. 21A-B. PC-MT-Probes in Non-Imaging Mass Spectrometry Applications. PC-MT-Ab was bound to Protein G agarose beads, the beads washed, the PC-MT photo-released from the bead-bound PC-MT-Ab, and the supernatant analyzed by non-imaging standard MALDI-MS (FIG. 21A) Stacked 3D projection of the MALDI-MS spectra from the 6 samples corresponding to the 6 different concentrations of PC-MT-Ab added to the Protein G beads (concentration range of the PC-MT-Ab added to the beads is indicated by the black arrow). The control peptide was included in the samples at a fixed concentration for data normalization purposes.
Figure 21B:
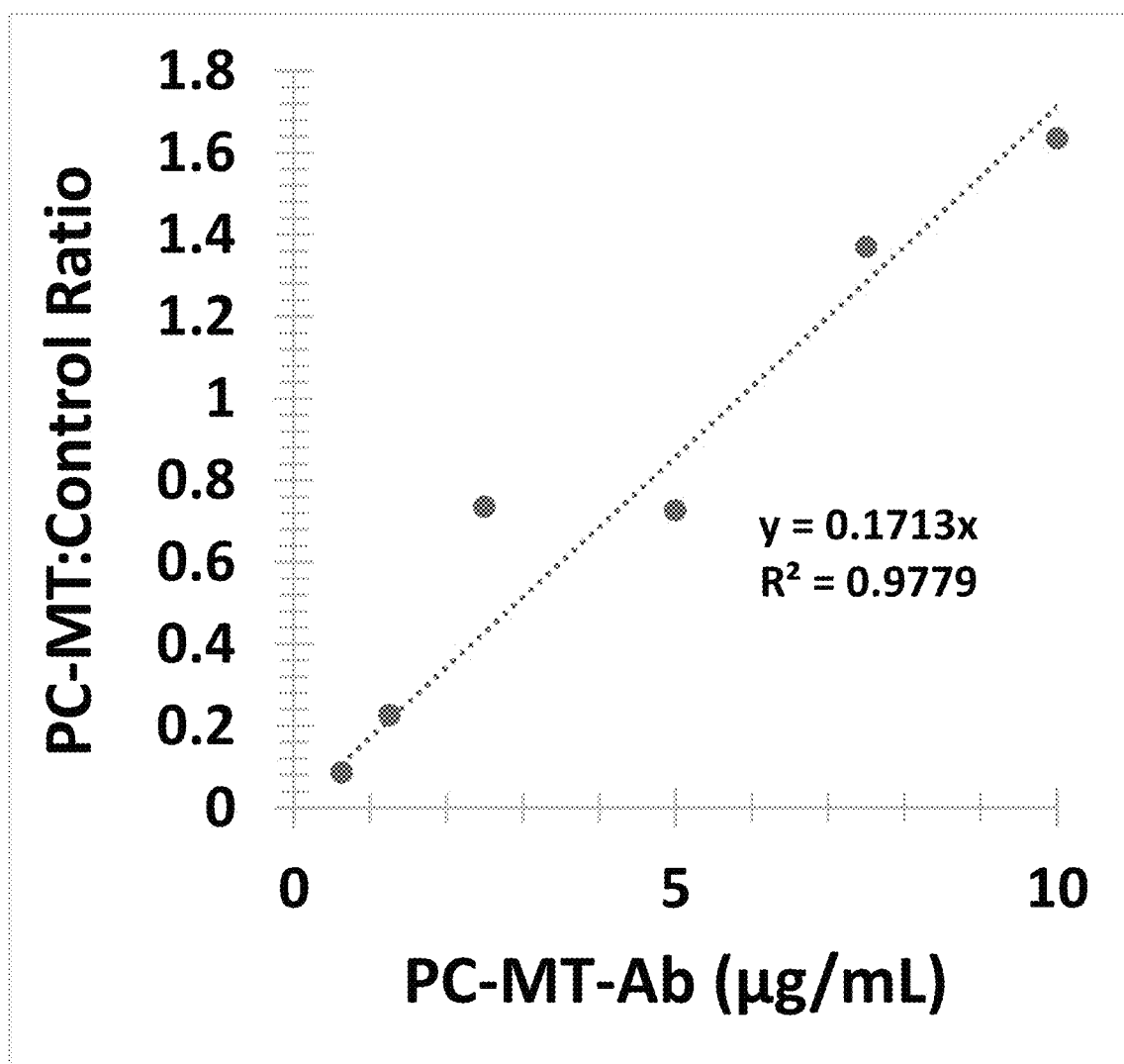

FIG. 21a shows spectra from the non-imaging MALDI-MS analysis of the photo-released PC-MT from the 6 samples corresponding to the 6 different concentrations of PC-MT-Ab added to the Protein G beads. The photo-released PC-MT (reporter) and control peptide monoisotopic peaks are observed at m/z 1,210.6 and 1,122.6, respectively, as expected. To quantify the results, the ratio of the monoisotopic peak intensity of the photo-released PC-MT to that of the control peptide (which was at a fixed concentration) was calculated and graphed in FIG. 21b. A linear response as a function of PC-MT-Ab concentration is observed ($R^2$=0.9779).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

What is claimed:

1. A multiplex method for co-detecting a plurality of different types of biomarkers in a tissue sample on a single slide, said method comprising:
   a) providing a tissue sample on a single slide;
   b) contacting said tissue sample with a plurality of different antibodies to effect binding of the antibodies to the tissue sample, each of said antibodies reactive with a different biomarker, and each of said antibodies conjugated to a unique photocleavable mass-tag;
   c) illuminating said photocleavable mass-tags with light so as to photocleave at least a portion of said mass-tags prior to step d); and
   d) detecting, using mass spectrometric imaging, said mass-tags, or fragments thereof, as molecular ions;
   where said antibodies conjugated to a mass-tags have the following general structure

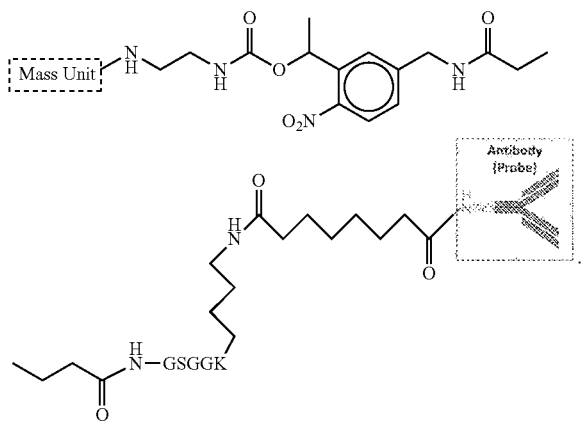

2. The method of claim 1, further comprising performing, after step a) but before step b), direct mass spectrometric imaging on said tissue sample.

3. The method of claim 1, wherein said plurality of different antibodies are in a mixture and said tissue sample in step b) is contacted with said mixture.

4. The method of claim 1, wherein said mass-tags are non-rare-earth-metal mass-tags.

5. The method of claim 1, wherein said mass-tags comprise a plurality of amino acids.

6. The method of claim 1, wherein said tissue sample is fresh frozen and thin-sectioned prior to being mounted on said single slide.

7. The method of claim 1, wherein said slide comprises gold.

8. The method of claim 7, wherein said slide is a glass slide with a gold layer.

9. The method of claim 1, wherein said tissue sample was formalin-fixed and paraffin embedded and thin-sectioned prior to being mounted on said single slide.

10. The method of claim 9, wherein the tissue sample is subjected to a treatment prior to the steps of contacting the sample with antibody, said treatment comprising deparaffinization.

11. The method of claim 10, wherein said deparaffinization is performed with xylene.

12. The method of claim 10, wherein the tissue sample is further subjected to a treatment, said treatment comprising rehydration.

13. The method of claim 12, wherein said rehydration is performed with a series of ethanol/water mixtures and aqueous saline buffers.

14. The method of claim 12, wherein the tissue sample is further subjected to a treatment, said treatment comprising antigen retrieval.

15. The method of claim 14, wherein said antigen retrieval is performed by heating in citrate buffer, pH 6.

16. The method of claim 14, wherein said antigen retrieval is performed with formic acid.

17. The method of claim 1, wherein a matrix compound is applied to said mass-tags before step d).

18. The method of claim 17, wherein said matrix compound is selected from the group consisting of alpha-cyano-4-hydroxycinnamic acid (CHCA), 2,5-Dihydroxybenzoic acid (DHB) and 3,5-Dimethoxy-4-hydroxycinnamic acid (sinapinic acid).

19. The method of claim 17, wherein said matrix compound is applied by sublimation.

20. The method of claim 17, wherein the tissue sample is subjected to a treatment after the steps of contacting the sample with a matrix compound, said treatment comprising matrix recrystallization.

21. The method of claim 1, wherein said tissue is from a tumor.

22. The method of claim 21, wherein said tumor is a breast tumor.

23. The method of claim 1, wherein at least one of said plurality of different antibodies comprises a fluorescent moiety in addition to said mass-tag.

24. The method of claim 1, wherein the number of said different antibodies is 8 or more.

25. The method of claim 24, wherein a subset of said different antibodies reacts with i) the estrogen receptor (ER), ii) the progesterone receptor (PR), iii) human epidermal growth factor receptor 2 (HER2), and iv) Ki67.

26. The method of claim 24, wherein a subset of said different antibodies reacts with T-cell biomarkers i) CD3 (T-cells), ii) CD4 (T-helper), iii) CDS (cytotoxic T-cells), and iv) CD45RO (memory T-cells).

27. The method of claim 24, wherein one of said different antibodies reacts with the B-cell biomarker CD20.

28. The method of claim 24, wherein one of said different antibodies reacts with the macrophage biomarker CD68.

29. The method of claim 24, wherein one of said plurality of different antibodies reacts with an immune checkpoint molecule.

30. The method of claim 29, wherein said immune checkpoint molecule is selected from the group consisting of PD-1, PD-L1, PD-L2, CTLA-4, OX40, CD27, and TIM3.

31. A conjugate, having the structure:
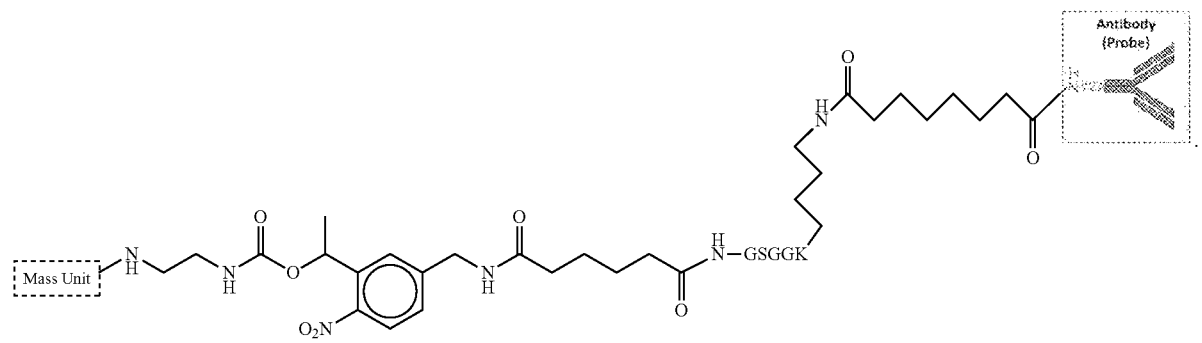

UNITED STATES PATENT AND TRADEMARK OFFICE
CERTIFICATE OF CORRECTION

| | | |
|---|---|---|
| PATENT NO. | : 11,906,527 B2 | Page 1 of 1 |
| APPLICATION NO. | : 17/399390 | |
| DATED | : February 20, 2024 | |
| INVENTOR(S) | : Mark J. Lim, Gargey Yagnik and Kenneth J. Rothschild | |

It is certified that error appears in the above-identified patent and that said Letters Patent is hereby corrected as shown below:

In the Specification

Column 1 Line 18, delete entire paragraph beginning with "This invention was" to and ending "rights in the invention." and insert the following paragraph:
--This invention was made with government support under CA236097 awarded by the National Institutes of Health. The government has certain rights in the invention.--

Signed and Sealed this
Fourth Day of June, 2024

*Katherine Kelly Vidal*

Katherine Kelly Vidal
*Director of the United States Patent and Trademark Office*